US010544220B2

(12) United States Patent
Engelberts et al.

(10) Patent No.: US 10,544,220 B2
(45) Date of Patent: *Jan. 28, 2020

(54) BISPECIFIC ANTIBODIES AGAINST CD3 AND CD20

(71) Applicant: GENMAB A/S, Copenhagen V (DK)

(72) Inventors: Patrick Engelberts, Utrecht (NL); Esther Breij, Utrecht (NL); Rik Rademaker, Utrecht (NL); Isil Altintas, Utrecht (NL); David Satijn, Utrecht (NL); Sandra Verploegen, Utrecht (NL); Riemke Van Dijkhuizen Radersma, Utrecht (NL); Edward Van Den Brink, Utrecht (NL); Janine Schuurman, Utrecht (NL); Paul Parren, Utrecht (NL)

(73) Assignee: GENMAB A/S, Copenhagen V (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/541,594

(22) PCT Filed: Jan. 8, 2016

(86) PCT No.: PCT/EP2016/050296

§ 371 (c)(1),
(2) Date: Jul. 5, 2017

(87) PCT Pub. No.: WO2016/110576

PCT Pub. Date: Jul. 14, 2016

(65) Prior Publication Data

US 2017/0355767 A1    Dec. 14, 2017

(30) Foreign Application Priority Data

| Jan. 8, 2015 | (WO) | PCT/EP2015/050276 |
| Jul. 15, 2015 | (DK) | 2015 00412 |
| Jul. 15, 2015 | (DK) | 2015 00413 |
| Jul. 16, 2015 | (DK) | 2015 00415 |
| Jul. 16, 2015 | (DK) | 2015 00416 |

(51) Int. Cl.

| C07K 16/28 | (2006.01) |
| C07K 16/30 | (2006.01) |
| A61K 39/395 | (2006.01) |
| A61K 39/00 | (2006.01) |

(52) U.S. Cl.
CPC .... *C07K 16/2809* (2013.01); *A61K 39/39558* (2013.01); *C07K 16/2887* (2013.01); *C07K 16/30* (2013.01); *A61K 2039/505* (2013.01); *C07K 2317/21* (2013.01); *C07K 2317/24* (2013.01); *C07K 2317/31* (2013.01); *C07K 2317/567* (2013.01); *C07K 2317/73* (2013.01); *C07K 2317/732* (2013.01); *C07K 2317/75* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 2011/0275787 A1* | 11/2011 | Kufer | C07K 16/2803 |
| | | | 530/324 |
| 2014/0088295 A1 | 3/2014 | Smith et al. | |
| 2015/0166661 A1* | 6/2015 | Chen | C07K 16/2809 |
| | | | 424/135.1 |
| 2015/0337049 A1 | 11/2015 | Labrijn et al. | |
| 2016/0168247 A1 | 6/2016 | Van Den Brink et al. | |
| 2016/0333095 A1 | 11/2016 | Van Den Brink et al. | |

FOREIGN PATENT DOCUMENTS

| WO | 2004/035607 A2 | 4/2004 | |
| WO | WO-2004035607 A2 * | 4/2004 | C07K 16/2887 |
| WO | 2007/042261 A2 | 4/2007 | |
| WO | 2011014659 A2 | 2/2011 | |
| WO | 2011/028952 A1 | 3/2011 | |
| WO | 2011090762 A1 | 7/2011 | |
| WO | WO-2011131746 A2 * | 10/2011 | C07K 16/1063 |
| WO | 2012/162067 A2 | 11/2012 | |
| WO | 2013/026833 A1 | 2/2013 | |
| WO | 2014/047231 A1 | 3/2014 | |
| WO | WO-2014108483 A1 * | 7/2014 | C07K 16/00 |
| WO | 2014/131694 A1 | 9/2014 | |
| WO | 2014/131711 A1 | 9/2014 | |
| WO | WO-2015006749 A2 * | 1/2015 | C07K 19/2803 |
| WO | 2015/143079 A1 | 9/2015 | |
| WO | 2016/081490 A1 | 5/2016 | |
| WO | 2017/210485 A1 | 12/2017 | |

OTHER PUBLICATIONS

Blinatumomab prescribing information and medication guide, Dec. 2014, pp. 1-20 and 1-4 (Year: 2014).*
Vajdos et al. (J Mol Biol. Jul. 5, 2002;320(2):415-28) (Year: 2002).*
Bedouelle et al. (FEBS J. Jan. 2006;273(1):34-46) (Year: 2006).*
Brown et al. (J Immunol. May 1, 1996;156(9):3285-91). (Year: 1996).*
Colman (Research in Immunology, 145:33-36, 1994) (Year: 1994).*
Rudikoff et al. (Proc. Natl. Acad. Sci. USA, 79: 1979-1983, Mar. 1982) (Year: 1982).*
Jabbour et al. (Blood, 122(21), 2664 (2013)) (Year: 2013).*
Bacac, M. et al, "CD20-TCB with obinutuzumab pretreatment as next generation treatment of hematological malignancies," Clin. Cancer Research,44 pages (2018) pii:clincanres.0455.2018. doi: 10.158/1078-0432. CCR-18-0455.

(Continued)

*Primary Examiner* — Zachary S Skelding
(74) *Attorney, Agent, or Firm* — Nelson Mullins Riley & Scarborough LLP; Jane E. Remillard, Esq.; Christopher L. Frank

(57) ABSTRACT

Bispecific antibodies directed to CD3 and CD20 and uses of such bispecific antibodies, in particular use thereof in the treatment of diseases in which specific targeting and T cell-mediated killing of cells that express CD20 is desired.

12 Claims, 32 Drawing Sheets

Specification includes a Sequence Listing.

(56) References Cited

OTHER PUBLICATIONS

Gall, J. et al., "T cells armed with anti-CD3 x anti-CD20 bispecific antibody enhance killing of CD20 malignant B cells and bypass complement-mediated rituximab resistance in vitro," Experimental Hematology, vol. 33: 452-459 (2005).
Perks, B. "Bispecific antibodies direct the immune system against blood cancers," The Pharmaceutical Journal, 2 pages (2015).
Smith, E., et al, "Anti-CD20/CD3 T cell-dependent bispecific antibody for the treatment of B cell malignancies," Scientific Reports, vol. 5 (17943):12 pages (2015) DOI: 10.1038/srep17943.
Stanglmaier, M. et al., "Bi20 (FBTA05), a novel trifunctional bispecific antibody (anti-CD20 3 anti-CD3), mediates efficient killing of B-cell lymphoma cells even with very low CD20 expression levels," Int. J. Cancer., vol. 123:1181-1189 (2008).
Sun, L. et al., "Anti-CD20/CD3 T cell-dependent bispecific antibody for the treatment of B cell malignancies,"Sci. Transl. Med., vol. 7(Issue 287): 287r70 11 pages (2015).
Wu, C. et al., "Simultaneous targeting of multiple disease mediators by a dual-variable-domain immunoglobulin," Nat Biotechnol., vol. 25: 1290-1297 (2007).
Chu, S. et al., "3111 Immunotherapy with Long-Lived Anti-CD20 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias," 56th ASH Annual Meeting and Exposition, San Francisco, CA • Dec. 6-9, 2014, Abstract No. 3111, 2 pages (2014).
Xiong, D. et al., "Efficient inhibition of human B-cell lymphoma xenografts with an anti-CD20 x anti-CD3 bispecific diabody," Cancer Letters, vol. 177:29-39 (2002).
U.S. Appl. No. 14/760,157, filed Jul. 9, 2015, Aran Frank Labrijn.
U.S. Appl. No. 14/902,757, filed Jan. 4, 2016, Edward Van Den Brink.
U.S. Appl. No. 15/110,414, filed Jul. 8, 2016, Edward Norbert Van Den Brink.
U.S. Appl. No. 15/744,317, filed Jan. 12, 2018, Rik Rademaker.
U.S. Appl. No. 14/760,157, filed Aug. 27, 2018, M. Natarajan.
U.S. Appl. No. 14/760,157, filed Apr. 9, 2018, M. Natarajan.
U.S. Appl. No. 14/760,157, filed Sep. 20, 2017, M. Natarajan.
U.S. Appl. No. 14/760,157, filed Feb. 17, 2017, M. Natarajan.
U.S. Appl. No. 14/902,757, filed Jul. 30, 2018, Z. Skelding.
U.S. Appl. No. 14/902,757, filed Dec. 18, 2017, Z. Skelding.
U.S. Appl. No. 15/110,414, filed May 24, 2018, Z. Skelding.

\* cited by examiner

- PBS
- bsIgG1- huCLB-T3/4-FEAL x b12-FEAR 0.5 mg/kg
- bsIgG1- huCLB-T3/4-FEAL x b12-FEAR 0.05 mg/kg
- bsIgG1-huCLB-T3/4-FEAL x CD20-7D8-FEAR 0.5 mg/kg
- bsIgG1-huCLB-T3/4-FEAL x CD20-7D8-FEAR 0.05 mg/kg

- PBS
- bsIgG1-huCD3-H1L1-FEAL x CD20-7D8-FEAR 0.5 mg/kg
- bsIgG1-huCD3-H1L1-FEAL x CD20-7D8-FEAR 0.05 mg/kg
- bsIgG1-huCD3-H1L1-FEAL x CD20-7D8-FEAR 0.005 mg/kg
- bsIgG1-huCD3-H1L1-FEAL x CD20-11B8-FEAR 0.5 mg/kg
- bsIgG1-huCD3-H1L1-FEAL x CD20-11B8-FEAR 0.05 mg/kg
- bsIgG1-huCD3-H1L1-FEAL x CD20-11B8-FEAR 0.005 mg/kg

BISPECIFIC ANTIBODIES AGAINST CD3 AND CD20

REFERENCE TO RELATED APPLICATIONS

This application is a 35 U.S.C. 371 national stage filing of International Application No. PCT/EP2016/050296, filed Jan. 8, 2016, which claims priority to International Application No. PCT/EP2015/050276, filed Jan. 8, 2015 and Danish Patent Application Nos. PA 2015 00412, filed Jul. 15, 2015; PA 2015 00413, filed Jul. 15, 2015; PA 2015 00415, filed Jul. 16, 2015; and PA 2015 00416, filed Jul. 16, 2015. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Jul. 5, 2017, is named GMI_147USE_Sequence_Listing.txt and is 83,657 bytes in size.

FIELD OF THE INVENTION

The present invention relates to bispecific antibodies directed to CD3 and CD20 and to uses of such bispecific antibodies, in particular use thereof in the treatment of diseases in which specific targeting and T cell-mediated killing of cells that express CD20 is desired.

BACKGROUND OF THE INVENTION

CD3 has been known for many years and therefore has been subject of interest in many aspects. Specifically antibodies raised against CD3 or the T-cell Receptor Complex, which CD3 is part of, are known. An in vitro characterization of five humanized OKT3 effector function variant antibodies has been described (Xu et al., 2000, Cell Immunol. 200(1):16-26).

Treatment with the anti-CD3 monoclonal antibody hOKT3gamma1(Ala-Ala) results in improved C-peptide responses and clinical parameters for at least 2 years after onset of type 1 diabetes in absence of continued immunosuppressive medications (Herold et al., 2005, Diabetes, 54(6):1763-9).

CD3 antibodies cross-reactive to cynomolgus and/or rhesus monkey CD3 have been described (WO2012162067, WO2008119567).

A promising approach to improve targeted antibody therapy is by delivering cytotoxic cells specifically to the antigen-expressing cancer cells. This concept of using T-cells for efficient killing of tumor cells has been described in Staerz, et. al., 1985, Nature 314:628-631). However, initial clinical studies were rather disappointing mainly due to low efficacy, severe adverse effects (cytokine storm) and immunogenicity of the bispecific antibodies (Muller and Kontermann, 2010, BioDrugs 24: 89-98). Advances in the design and application of bispecific antibodies have partially overcome the initial barrier of cytokine storm and improved clinical effectiveness without dose-limiting toxicities (Garber, 2014, Nat. Rev. Drug Discov. 13: 799-801; Lum and Thakur, 2011, BioDrugs 25: 365-379). Critical to overcome the initial barrier of cytokine storm as described for catumaxomab (Berek et al. 2014, Int. J. Gynecol. Cancer 24(9): 1583-1589; Mau-Sorensen et al. 2015, Cancer Chemother. Pharmacol. 75: 1065-1073), was the absence or silencing of the Fc domain.

The CD20 molecule (also called human B-lymphocyte-restricted differentiation antigen or Bp35) is a hydrophobic transmembrane protein with a molecular weight of approximately 35 kD located on pre-B and mature B lymphocytes (Valentine et al. (1989) J. Biol. Chem. 264(19):11282-11287; and Einfield et al., (1988) EMBO J. 7(3):711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson et al. (1984) Blood 63(6): 1424-1433), but is not found on hematopoietic stem cells, pro-B cells, normal plasma cells, or other normal tissues (Tedder et al. (1985) J. Immunol. 135(2):973-979).

Methods for treating cancer as well as autoimmune and immune diseases by targeting CD20 are known in the art. For example, the chimeric CD20 antibody rituximab has been used for or suggested for use in treating cancers such as non-Hodgkin's lymphoma (NHL), chronic lymphocytic leukemia (CLL) and small lymphocytic lymphoma (SLL). The human monoclonal CD20 antibody ofatumumab has been used for or suggested for use in treating among others various CLL indications, follicular lymphoma (FL), neuromyelitis optica (NMO), diffuse and relapsing-remitting multiple sclerosis (RRMS). The human monoclonal CD20 antibody obinutuzumab has been used for or suggested for use in treating CLL. Furthermore, the humanized CD20 antibody ocrelizumab is being developed for RRMS.

Gall et al. (2005 Experimental Hematology 33: 452) disclose the CD3×CD20 bispecific antibody CD20bi resulting from the chemical heteroconjugation of the CD20-specific chimeric antibody Rituximab (Rituxan) to anti-CD3 (Orthoclone OKT-3).

Stanglmaier et al. (2008 Int. J. Cancer: 123, 1181) describe the trifunctional bispecific anti-CD3×anti-CD20 antibody Bi20/FBTA05 combining a CD20-specific mouse IgG2a and a CD3-specific rat IgG2b.

Wu et al. (2007 Nat Biotechnol. 25: 1290-1297) and WO2011014659 describe a dual-specific (CD3 and CD20), tetravalent immunoglobulin G (dual-variable-domain immunoglobulin, DVD-Ig).

WO2011090762 describes the generation of a CD3×CD20 polypeptide heterodimer.

WO2011028952 describes amongst others the generation of CD3×CD20 bispecific molecules using Xencor's XmAb bispecific Fc domain technology.

WO2014047231 describes REGN1979 and other CD3×CD20 bispecific antibodies generated using the FcAAdp technology from Regeneron Pharmaceuticals.

Sun et al. (2015, Science Translational Medicine 7, 287ra70) describe a B cell-targeting anti-CD20/CD3 T cell-dependent bispecific antibody constructed using "knobs-into-holes" technology.

Bispecific antibodies that bind to both CD3 and CD20 may be useful in therapeutic settings in which specific targeting and T cell-mediated killing of cells that express CD20 is desired, and there is still a need for further efficient CD3×CD20 bispecific antibodies.

SUMMARY OF THE INVENTION

It is an object of the present invention to provide novel efficient bispecific antibodies comprising a first antigen-binding region derived from a CD3 antibody and a second antigen-binding region derived from a CD20 antibody.

The novel CD3×CD20 bispecific antibodies are useful in therapeutic settings in which specific targeting and T cell-mediated killing of cells that express CD20 is desired. The novel CD3×CD20 bispecific antibodies are highly efficient in killing CD20 expressing cells, including cells with low CD20 copy numbers, and have been shown to be highly potent in eradicating tumor cells in animal models. The novel CD3×CD20 bispecific antibodies are advantageous by inducing rapid and strong killing of cells at low dosing. The novel CD3×CD20 bispecific antibodies are furthermore capable of inducing cytotoxicity by both CD4$^+$ T cells and CD8$^+$ T cells which makes them suitable for engaging T cells for killing CD20 positive tumors and other diseases involving CD20 positive cells. In addition, the CD3×CD20 bispecific antibodies are efficient in depleting B cells from lymphoid structures. Accordingly, it is an object of the present invention to provide a bispecific CD3×CD20 antibody which is capable of inducing cytotoxicity by both CD4$^+$ T cells and CD8$^+$ T cells. It is a further object of the present invention to provide a bispecific CD3×CD20 antibody which is highly efficient in killing CD20 expressing cells such as CD20 expressing tumor cells. It is a further object of the present invention to provide a bispecific CD3×CD20 antibody which is highly efficient in killing CD20 expressing cancers.

These and other aspects of the invention are described in further detail below.

BRIEF DESCRIPTION OF THE DRAWINGS

(FIG. 1A) Binding of bsIgG1-huCD3-H1L1-FEAL×CD20-7D8-FEAR and IgG1-7D8, (FIG. 1B) Binding of bsIgG1-huCD3-H1L1-FEAL×CD20-2F2-FEAR and IgG1-2F2, (FIG. 1C) Binding of bsIgG1-huCD3-H1L1-FEAL×CD20-RTX-FEAR and IgG1-RTX, (FIG. 1D) Binding of bsIgG1-huCD3-H1L1-FEAL×CD20-11B8-FEAR and IgG1-11B8, (FIG. 1E) Binding of bsIgG1-huCD3-H1L1-FEAL×CD20-GA101-FEAR and IgG1-GA101, (FIG. 1F) Binding of bsIgG1-huCD3-H1L1-FEAL×CD20-2C6-FEAR (and IgG1-7D8). Data shown are geometric means of fluorescence intensity (geomean) (FIGS. 1A-1E) and median fluorescence intensity (FIG. 1F) of binding to Daudi cells, as determined by flow cytometry, for two representative experiments (FIGS. 1A-1E from one, FIG. 1F from the other). (FIG. 1G) Binding of bsIgG1-huCLB-T3/4-FEAL×CD20-7D8-FEAR (huCLB-T3/4×7D8), bsIgG1-huCLB-T3/4-FEAL×CD20-2F2-FEAR (huCLB-T3/4×2F2), bsIgG1-huCLB-T3/4-FEAL×CD20-GA101-FEAR (huCLB-T3/4×GA101), bsIgG1-huCLB-T3/4-FEAL×CD20-11B8-FEAR (huCLB-T3/4×11B8) and monospecific bivalent IgG1-7D8-FEAR to Daudi cells, (FIG. 1H) Binding of bsIgG1-huCD3-H1L1-FEAL×CD20-7D8-FEAR, bsIgG1-huCD3-H1L1-FEAL×CD20-2F2-FEAR, bsIgG1-huCD3-H1L1-FEAL×CD20-GA101-FEAR, bsIgG1-huCD3-H1L1-FEAL×CD20-RTX-FEAR, bsIgG1-huCD3-H1L1-FEAL×CD20-11B8-FEAR, bsIgG1-huCD3-H1L1-FEAL×CD20-2C6-FEAR, bsIgG1-huCD3-H1L1-FEAL×b12-FEAR and monospecific, bivalent IgG1-huCD3-H1L1-FEAL to Jurkat cells (FIG. 1I) Binding of bsIgG1-huCLB-T3/4-FEAL×CD20-7D8-FEAR, bsIgG1-huCLB-T3/4-FEAL×CD20-2F2-FEAR, bsIgG1-huCLB-T3/4-FEAL×CD20-GA101-FEAR, bsIgG1-huCLB-T3/4-FEAL×CD20-RTX-FEAR, bsIgG1-huCLB-T3/4-FEAL×CD20-11B8-FEAR, bsIgG1-huCLB-T3/4-FEAL×CD20-2C6-FEAR, bsIgG1-huCLB-T3/4-FEAL×b12-FEAR and monospecific, bivalent IgG1-huCLB-T3/4-FEAL to Jurkat cells. Data shown are median fluorescence intensity, as determined by flow cytometry, of one representative experiment.

(FIG. 3A) Daudi cells were incubated with bsIgG1-huCD3-H1L1-FEAL×CD20-7D8-FEAR (CD3×7D8), bsIgG1-huCD3-H1L1-FEAL×CD20-11B8-FEAR (CD3×11B8), the monospecific CD20 antibodies IgG1-7D8 (7D8), IgG1-7D8-FEAR (7D8-FEAR; with inactive Fc region), IgG1-11B8-F405L or IgG1-11B8-FEAR (11B8-FEAR; with inactive Fc region), and the bispecific control antibody bsIgG1-huCD3-H1L1-FEAL×b12-FEAR (CD3×b12) PBMCs were used as effector cells. [FIG. 3C]), 11B8 (BsIgG1-huCD3-H1L1-FEAL×CD20-11B8-FEAR and BsIgG1-huCLB-T3/4-FEAL×CD20-11B8-FEAR; [FIG. 3D]), GA101 (BsIgG1-huCD3-H1L1-FEAL×CD20-GA101-FEAR and BsIgG1-huCLB-T3/4-FEAL×CD20-GA101-FEAR; [FIG. 3E]) and 2F2 (BsIgG1-huCD3-H1L1-FEAL×CD20-2F2-FEAR and BsIgG1-huCLB-T3/4-FEAL×CD20-2F2-FEAR; [FIG. 3F]). (FIG. 3N) Daudi cells were incubated with bsIgG1-huCD3-H1L1-FEAL×CD20-7D8-FEAR (CD3×7D8), bsIgG1-huCD3-H1L1-FEAL×CD20-2C6-FEAR (CD3×2C6) and bsIgG1-huCD3-H1L1-FEAL×b12-FEAR (CD3×b12), purified T cells were used as effector cells. Data shown are mean percentages specific lysis±S.D of triplicate wells and data for each graph were obtained from one representative experiment.

(FIG. 7A) Average tumor size in mice that were treated with vehicle (PBS) or bsIgG1-huCD3-H1L1-FEALxCD20-7D8-FEAR at the indicated doses. Error bars indicate S.E.M. (FIG. 7B) Tumor size in individual mice after treatment with PBS or bsIgG1-huCD3-H1L1-FEALxCD20-7D8-FEAR on day 21 after tumor inoculation. Statistical analysis of data at day 21 was performed using Kruskal Wallis (Dunn's multiple comparison as post-test). $**p<0.01$ (FIG. 7C) Kaplan-Meier plots with tumorsize cut-off set at 600 mm$^3$. Statistical significance of differences in survival between the bsIgG1-huCD3-H1L1-FEALxCD20-7D8-FEAR-treated groups and the PBS-treated control group were assessed by Mantel Cox analysis. $*p<0.05$, $**p<0.01$, n.s. not significant (FIG. 7D) Average tumor size in mice that were treated with vehicle (PBS) or bsIgG1-huCLB-T3/4-FEALxCD20-7D8-FEAR at the indicated doses. Error bars indicate S.E.M. (FIG. 7E) Tumor size in individual mice in the different treatment groups on day 25 after tumor inoculation. Statistical analysis was performed using Kruskal Wallis test (Dunn's multiple comparison as post-test) (FIG. 7F) Kaplan-Meier plots with tumorsize cut-off set at 500 mm$^3$. Statistical significance of differences between treatment groups and the vehicle control group was analysed by Mantel Cox analysis. $*p<0.05$, $** p<0.01$, n.s. not significant. (FIG. 7G) Average tumor size in mice that were treated with vehicle (PBS), bsIgG1-huCD3-H1L1-FEALxCD20-7D8-FEAR or bsIgG1-huCD3-H1L1-FEALxCD20-11B8-FEAR at the indicated doses. Error bars indicate S.E.M. (FIG. 7H) Tumor size in individual mice after treatment with PBS, or bsIgG1-huCD3-H1L1-FEALxCD20-7D8-FEAR or bsIgG1-huCD3-H1L1-FEALxCD20-11B8-FEAR on day 20 after tumor inoculation. Statistical analysis of data at day 20 was performed using one-way ANOVA (Tukey's multiple comparison as post-test). $*p<0.05$, $**p<0.01$ (FIG. 7I) Kaplan-Meier plots with tumorsize cut-off set at 500 mm$^3$. Statistical significance of differences in survival between the bsIgG1-huCD3-H1L1-FEALxCD20-7D8-FEAR treated groups and the PBS-treated control group were assessed by Mantel Cox analysis. $*p<0.05$, $**p<0.01$, n.s. not significant.

(FIG. 8A) Average tumor size in the Daudi-luc xenograft model in BRGS-HIS mice after treatment with PBS (vehicle control), bsIgG1-huCD3-H1L1-FEALxCD20-7D8-FEAR (mAb2) or the control bispecific antibody bsIgG1-huCD3-H1L1-FEALxb12-FEAR (mAb1) at the indicated dose levels. Tumor burden was assessed by bioluminescence imaging. Error bars indicate S.E.M. (FIG. 8B) Statistical analysis was performed at day 21 (Kruskal Wallis test followed by Dunn's multiple comparison post-test) $** p<0.01$ (FIG. 8C) Characterization of peripheral blood leukocyte populations in Daudi-luc xenograft-bearing BRGS-HIS mice after treatment with bsIgG1-huCD3-H1L1-FEALxCD20-7D8-FEAR or the control bispecific antibody bsIgG1-huCD3-H1L1-FEALxb12-FEAR, as determined by flow cytometry at day 9. % hCD45$^+$ cells represents the total percentage of human leukocytes in mouse peripheral blood. % hCD19$^+$, % hCD3$^+$ and % hCD3$^+$ FSC$^{hi}$ represent the percentage of B cells, T cells and activated T cells, respectively, within the human leukocyte population.

Figure 1A:
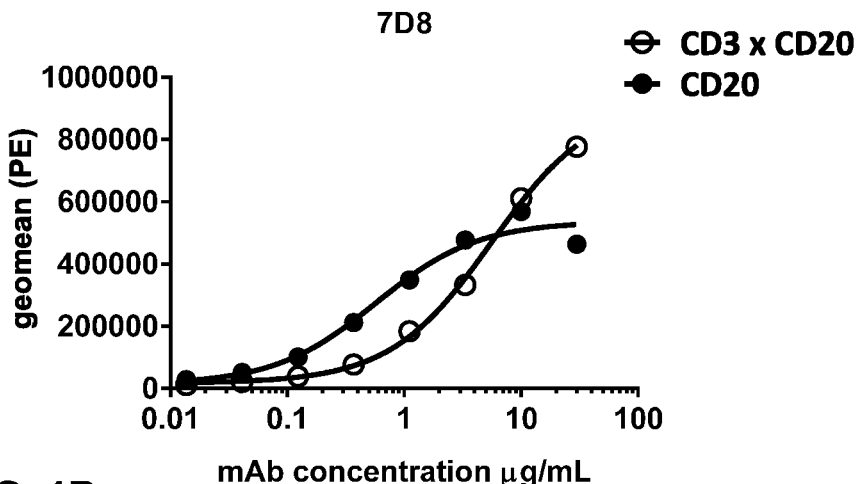
FIGS. 1A-1I: Binding of bispecific CD3×CD20 antibodies to Daudi (FIGS. 1A-1F) and Jurkat (FIGS. 1G-1I) cells.
Figure 1B:
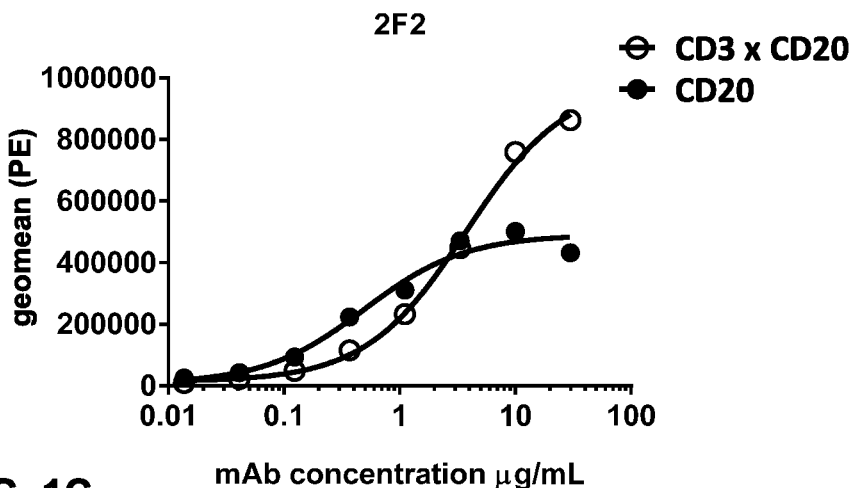
Figure 1C:
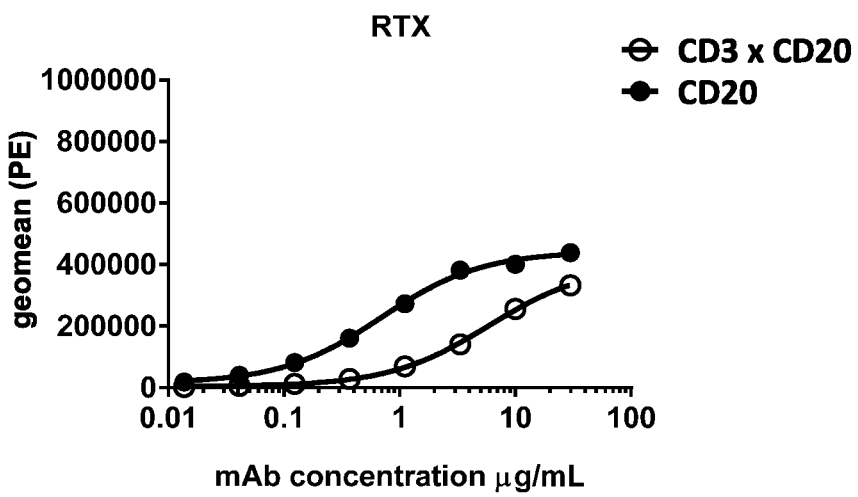
Figure 1D:
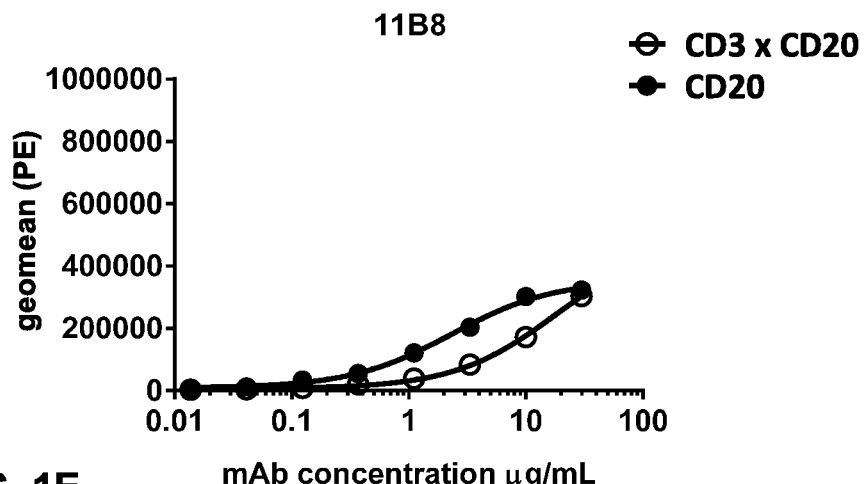
Figure 1E:
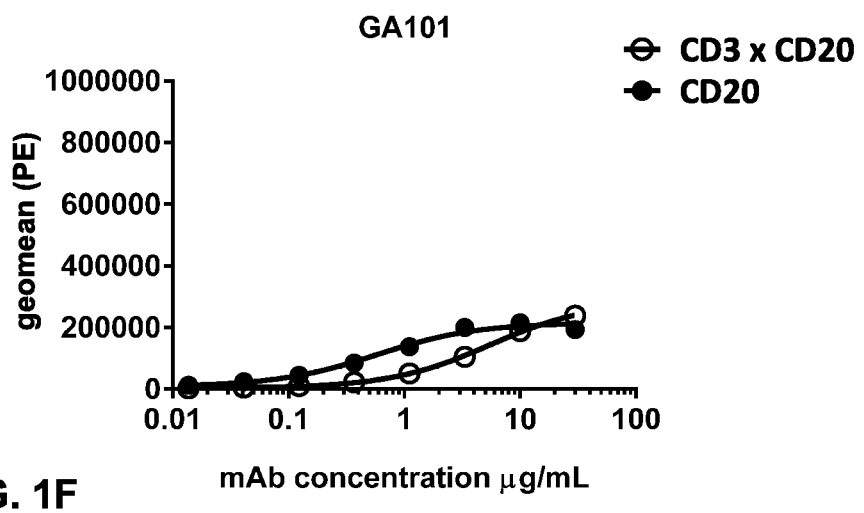
Figure 1F:
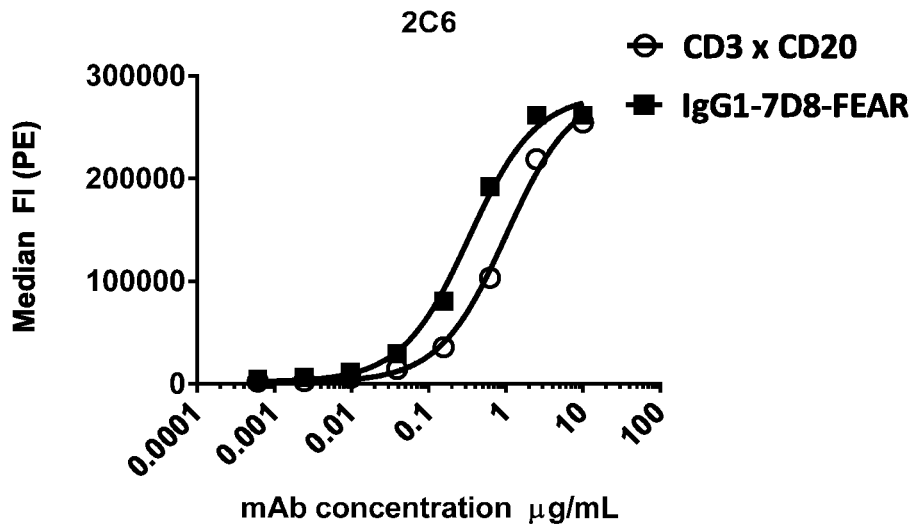

Healthy donor PBMC were incubated with bsIgG1-huCD3-H1L1-FEAL×CD20-7D8-FEAR or positive and negative control antibodies, and T cell activation was assessed by measuring CD69 expression within the T cell population (CD28+ cells). Experiments were performed with PBMC isolated from five healthy donors. Results for two representative donors are shown.

TABLE 1

| SEQ ID NO: | Clone name | Sequence |
|---|---|---|
| SEQ ID NO: 1 | huCD3 VH CDR1 | GFTFNTYA |
| SEQ ID NO: 2 | huCD3 VH CDR2 | IRSKYNNYAT |
| SEQ ID NO: 3 | huCD3 VH CDR3 | VRHGNFGNSYVSWFAY |
| SEQ ID NO: 4 | huCD3 VL CDR1 | TGAVTTSNY |
|  | huCD3 VL CDR2 | GTN |
| SEQ ID NO: 5 | huCD3 VL CDR3 | ALWYSNLWV |
| SEQ ID NO: 6 | huCD3 VH1 | EVKLVESGGGLVQPGGSLRLSCAAS<u>GFTFNTYA</u>MNWVRQA PGKGLEWVAR<u>IRSKYNNYAT</u>YYADSVKDRFTISRDDSKSSL YLQMNNLKTEDTAMYYC<u>VRHGNFGNSYVSWFAY</u>WGQGTL VTVSS |
| SEQ ID NO: 7 | huCD3 VH2 | EVKLVESGGGLVKPGRSLRLSCAAS<u>GFTFNTYA</u>MNWVRQA PGKGLEWVAR<u>IRSKYNNYAT</u>YYADSVKDRFTISRDDSKSIL YLQMNNLKTEDTAMYYC<u>VRHGNFGNSYVSWFAY</u>WGQGTL VTVSS |
| SEQ ID NO: 8 | huCD3 VH3 | EVKLVESGGGLVKPGRSLRLSCAAS<u>GFTFNTYA</u>MNWVRQA PGKGLEWVAR<u>IRSKYNNYAT</u>YYADSVKDRFTISRDDSKSIL YLQMNSLKTEDTAMYYC<u>VRHGNFGNSYVSWFAY</u>WGQGTL VTVSS |
| SEQ ID NO: 9 | huCD3 VH4 | EVKLVESGGGLVKPGRSLRLSCAAS<u>GFTFNTYA</u>MNWVRQA PGKGLEWVAR<u>IRSKYNNYAT</u>YYADSVKDRFTISRDDSKSIL YLQMNSLKTEDTAMYYC<u>VRHGNFGNSYVSWFAY</u>WGQGTM VTVSS |
| SEQ ID NO: 10 | huCD3 VL1 | QAVVTQEPSFSVSPGGTVTLTCRSS<u>TGAVTTSNY</u>ANWVQQ TPGQAFRGLIG<u>GTN</u>KRAPGVPARFSGSLIGDKAALTITGAQA DDESIYFC<u>ALWYSNLWV</u>FGGGTKLTVL |
| SEQ ID NO: 11 | huCD3 VL2 | QAVVTQEPSFSVSPGGTVTLTCRSS<u>TGAVTTSNY</u>ANWVQQ TPGQAFRGLIG<u>GTN</u>KRAPGVPARFSGSILGNKAALTITGAQA DDESIYFC<u>ALWYSNLWV</u>FGGGTKLTVL |
| SEQ ID NO: 12 | huCD3 VL3 | QAVVTQEPSFSVSPGGTVTLTCRSS<u>TGAVTTSNY</u>ANWVQQ TPGQAFRGLIG<u>GTN</u>KRAPGVPARFSGSILGNKAALTITGAQA DDESDYYC<u>ALWYSNLWV</u>FGGGTKLTVL |
| SEQ ID NO: 13 | Mature human CD3ε (epsilon) | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVCENCMEMDVMSVATIVIVDICITGGLL LLVYYWSKNRKAKAKPVTRGAGAGGRQRGQNKERPPPVPN PDYEPIRKGQRDLYSGLNQRRI |
| SEQ ID NO: 14 | Human CD3δ (delta) | FKIPIEELEDRVFVNCNTSITWVEGTVGTLLSDITRLDLGKRI LDPRGIYRCNGTDIYKDKESTVQVH YRMCQSCVELDPATVA GIIVTDVIATLLLALGVFCFAGHETGRLSGAADTQALLRNDQ VYQPLRDRDDAQYSHLGGNWARNK |
| SEQ ID NO: 15 | IgG1m(f) heavy chain constant region (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSKLTVDKSRWQQGNVFSCSVMHEALHNHYTQKSLSLSPGK |
| SEQ ID NO: 16 | IgG1m(f)-LFLEDA heavy chain constant region | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPE<u>FE</u>GGPSVF |

TABLE 1 -continued

| SEQ ID NO: | Clone name | Sequence |
|---|---|---|
| | (amino acids positions 118-447 according to EU numbering) | LFPPKPKDTLMISRTPEVTCVVVAVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSKLTVDKSRWQQGNVFSCSVMHEALHNHYTQKSLSLSPGK |
| SEQ ID NO: 17 | VH huCLB-T3/4 | EVQLVESGGGLVKPGGSLRLSCAAS<u>GFTFSSYGM</u>FWVRQA PGKGLEWVAT<u>ISRYSRYI</u>YYPDSVKGRFTISRDNAKNSLYLQ MNSLRAEDTAVYYC<u>ARRPLYGSSPDY</u>WGQGTLVTVSS |
| SEQ ID NO: 18 | VL huCLB-T3/4 | EIVLTQSPATLSLSPGERATLSCSA<u>SSSVTY</u>VHWYQQKPGQ APRLLIY<u>DTS</u>KLASGIPARFSGSGSGTDFTLTISSLEPEDFAV YYC<u>FQGSGYPLT</u>FGSGTKLEMR |
| SEQ ID NO: 19 | Mature cyno CD3ε (epsilon) | QDGNEEMGSITQTPYQVSISGTTVILTCSQHLGSEAQWQH NGKNKEDSGDRLFLPEFSEMEQSGYYVCYPRGSNPEDASH HLYLKARVCENCMEMDVMAVATIVIVDICITLGLLLLVYYWS KNRKAKAKPVTRGAGAGGRQRGQNKERPPPVPNPDYEPIR KGQQDLYSGLNQRRI |
| SEQ ID NO: 20 | Mature rhesus CD3ε (epsilon) | QDGNEEMGSITQTPYHVSISGTTVILTCSQHLGSEVQWQH NGKNKEDSGDRLFLPEFSEMEQSGYYVCYPRGSNPEDASH HLYLKARVCENCMEMDVMAVATIVIVDICITLGLLLLVYYWS KNRKAKAKPVTRGAGAGGRQRGQNKERPPPVPNPDYEPIR KGQQDLYSGLNQRRI |
| SEQ ID NO: 21 | IgG1m(f)-F405L (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFL LYSKLTVDKSRWQQGNVFSCSVMHEALHNHYTQKSLSLSP GK |
| SEQ ID NO: 22 | IgG1m(f)-K409R (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSRLTVDKSRWQQGNVFSCSVMHEALHNHYTQKSLSLSPGK |
| SEQ ID NO: 23 | IgG1m(f)-LFLEDA-F405L (FEAL) (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPSVF LFPPKPKDTLMISRTPEVTCVVVAVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFL LYSKLTVDKSRWQQGNVFSCSVMHEALHNHYTQKSLSLSPGK |
| SEQ ID NO: 24 | IgG1m(f)-LFLEDA-K409R (FEAR) (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPSVF LFPPKPKDTLMISRTPEVTCVVVAVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSRLTVDKSRWQQGNVFSCSVMHEALHNHYTQKSLSLSPGK |
| SEQ ID NO: 25 | Parent murine VH of SP34 | EVKLLESGGGLVQPKGSLKLSCAAS<u>GFTFNTYAMN</u>WVRQA PGKGLEWVAR<u>IRSKYNNYATY</u>YADSVKDRFTISRDDSQSIL YLQMNNLKTEDTAMYYC<u>VRHGNFGNSYVSWFAY</u>WGQGTL VTVSA |
| SEQ ID NO: 26 | Parent murine VL of SP34 | QAVVTQESALTTSPGETVTLTCRSS<u>TGAVTTSNY</u>ANWVQEK PDHLFTGLIG<u>GTN</u>KRAPGVPARFSGSLIGDKAALTITGAQTE DEAIYFC<u>ALWYSNLWV</u>FGGGTKLTVL |
| SEQ ID NO: 27 | VH CD20-7D8 | EVQLVESGGGLVQPDRSLRLSCAASGFTFHDYAMHWVRQA PGKGLEWVSTISWNSGTIGYADSVKGRFTISRDNAKNSLYL QMNSLRAEDTALYYCAKDIQYGNYYYGMD VWGQGTTVTVSS |

TABLE 1-continued

| SEQ ID NO: | Clone name | Sequence |
|---|---|---|
| SEQ ID NO: 28 | VL CD20-7D8 | EIVLTQSPATLSLSPGERATLSCRASQSVSSYLAWYQQKPG QAPRLLIYDASNRATGIPARFSGSGSGTDFTLTISSLEPEDFA VYYCQQRSNWPITFGQGTRLEIK |
| SEQ ID NO: 29 | Human IgLC2/IgLC3 constant domain | GQPKAAPSVTLFPPSSEELQANKATLVCLISDFYPGAVTVAW KADSSPVKAGVETTTPSKQSNNKYAASSYLSLTPEQWKSHR SYSCQVTHEGSTVEKTVAPTECS |
| SEQ ID NO: 30 | VL huCD3-LKNH | QAVVTQEPSLSVSPGGTVTLTCRSSTGAVTTSNYANWVQQ KPGQAFRGLIGGTNNRAPGVPARFSGSLIGDKAALTITGAQ ADDESIYFCALWYSNHWVFGGGTKLTVL |
| SEQ ID NO: 31 | VL huCD3-T41K | QAVVTQEPSFSVSPGGTVTLTCRSSTGAVTTSNYANWVQQ KPGQAFRGLIGGTNKRAPGVPARFSGSLIGDKAALTITGAQ ADDESIYFCALWYSNLWVFGGGTKLTVL |
| SEQ ID NO: 32 | VH CD20-7D8 CDR1 | GFTFHDYA |
| SEQ ID NO: 33 | VH CD20-7D8 CDR2 | ISWNSGTI |
| SEQ ID NO: 34 | VH CD20-7D8 CDR3 | AKDIQYGNYYYGMDV |
| SEQ ID NO: 35 | VL CD20-7D8 CDR1 | QSVSSY |
| | VL CD20-7D8 CDR2 | DAS |
| SEQ ID NO: 36 | VL CD20-7D8 CDR3 | QQRSNWPIT |
| SEQ ID NO: 37 | VH CD20-2F2 | EVQLVESGGGLVQPGRSLRLSCAASGFTFNDYAMHWVRQA PGKGLEWVSTISWNSGSIGYADSVKGRFTISRDNAKKSLYL QMNSLRAEDTALYYCAKDIQYGNYYYGMDVWGQGTTVTSS |
| SEQ ID NO: 28 | VL CD20-2F2 | EIVLTQSPATLSLSPGERATLSCRASQSVSSYLAWYQQKPG QAPRLLIYDASNRATGIPARFSGSGSGTDFTLTISSLEPEDFA VYYCQQRSNWPITFGQGTRLEIK |
| SEQ ID NO: 38 | VH CD20-2F2 CDR1 | GFTFNDYA |
| SEQ ID NO: 39 | VH CD20-2F2 CDR2 | ISWNSGSI |
| SEQ ID NO: 34 | VH CD20-2F2 CDR3 | AKDIQYGNYYYGMDV |
| SEQ ID NO: 35 | VL CD20-2F2 CDR1 | QSVSSY |
| | VL CD20-2F2 CDR2 | DAS |
| SEQ ID NO: 36 | VL CD20-2F2 CDR3 | QQRSNWPIT |
| SEQ ID NO: 40 | VH CD20-11B8 | EVQLVQSGGGLVHPGGSLRLSCTGSGFTFSYHAMHWVRQA PGKGLEWVSIIGTGGVTYYADSVKGRFTISRDNVKNSLYLQ MNSLRAEDMAVYYCARDYYGAGSFYDGLYGMDVWGQGTT VTVSS |
| SEQ ID NO: 41 | VL CD20-11B8 | EIVLTQSPATLSLSPGERATLSCRASQSVSSYLAWYQQKPG QAPRLLIYDASNRATGIPARFSGSGSGTDFTLTISSLEPEDFA VYYCQQRSDWPLTFGGGTKVEIK |
| SEQ ID NO: 42 | VH CD20-11B8 CDR1 | GFTFSYHA |
| SEQ ID NO: 43 | VH CD20-11B8 CDR2 | IGTGGVT |
| SEQ ID NO: 44 | VH CD20-11B8 CDR3 | ARDYYGAGSFYDGLYGMDV |

TABLE 1 -continued

| SEQ ID NO: | Clone name | Sequence |
|---|---|---|
| SEQ ID NO: 45 | VL CD20-11B8 CDR1 | QSVSSY |
| | VL CD20-11B8 CDR2 | DAS |
| SEQ ID NO: 46 | VL CD20-11B8 CDR3 | QQRSDWPLT |
| SEQ ID NO: 47 | VH CD20-2C6 | AVQLVESGGGLVQPGRSLRLSCAASGFTFGDYTMHWVRQA PGKGLEWVSGISWNSGSIGYADSVKGRFTISRDNAKNSLY LQMNSLRAEDTALYYCTKDNQYGSGSTYGLGVWGQGTLVT VSS |
| SEQ ID NO: 48 | VL CD20-2C6 | EIVLTQSPATLSLSPGERATLSCRASQSVSSYLAWYQQKPG QAPRLLIYDASNRATGIPARFSGSGSGTDFTLTISSLEPEDFA VYYCQQRSNWPLTFGGGTKVEIK |
| SEQ ID NO: 49 | VH CD20-2C6 CDR1 | GFTFGDYT |
| SEQ ID NO: 50 | VH CD20-2C6 CDR2 | ISWNSGSI |
| SEQ ID NO: 51 | VH CD20-2C6 CDR3 | TKDNQYGSGSTYGLGV |
| SEQ ID NO: 52 | VL CD20-2C6 CDR1 | QSVSSY |
| | VL CD20-2C6 CDR2 | DAS |
| SEQ ID NO: 53 | VL CD20-2C6 CDR3 | QQRSNWPLT |
| SEQ ID NO: 54 | VL huCD3-CDR3 L97H | ALWYSNHWV |
| SEQ ID NO: 55 | huCLB-T3/4 VH CDR1 | GFTFSSYG |
| SEQ ID NO: 56 | huCLB-T3/4 VH CDR2 | ISRYSRYI |
| SEQ ID NO: 57 | huCLB-T3/4 VH CDR3 | ARRPLYGSSPDY |
| SEQ ID NO: 58 | huCLB-T3/4 VL CDR1 | SSVTY |
| | huCLB-T3/4 VL CDR2 | DTS |
| SEQ ID NO: 59 | huCLB-T3/4 VL CDR3 | FQGSGYPLT |
| SEQ ID NO: 60 | IgG1m(a) CH3 region | GQPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSPGK |
| SEQ ID NO: 61 | IgG1m(f) CH3 region | GQPREPQVYTLPPSREEMTKNQVSLTCLVKGFYPSDIAVEW ESNGQPENNYKTTPPVLDSDGSFFLYSKLTVDKSRWQQGN VFSCSVMHEALHNHYTQKSLSLSPGK |
| SEQ ID NO: 62 | IgG1m(ax) CH3 region | GQPREPQVYTLPPSRDELTKNQVSLTCLVKGFYPSDIAVEWE SNGQPENNYKTTPPVLDSDGSFFLYSKLTVDKSRWQQGNV FSCSVMHEGLHNHYTQKSLSLSPGK |
| SEQ ID NO: 63 | IgG1 heavy chain constant region-WT (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSKLTVDKSRWQQGNVFSCSVMHEALHNHYTQKSLSLSPGK |

TABLE 1-continued

| SEQ ID NO: | Clone name | Sequence |
|---|---|---|
| SEQ ID NO: 64 | IgG1 heavy chain constant region-F405L (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFLL YSKLTVDKSRWQQGNVFSCSVMHEALHNHYTQKSLSLSPG |
| SEQ ID NO: 65 | IgG1 heavy chain constant region-K409R (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSRLTVDKSRWQQGNVFSCSVMHEALHNHYTQKSLSLSPGK |
| SEQ ID NO: 66 | IgG1 heavy chain constant region-N297Q (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYQSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSKLTVDKSRWQQGNVFSCSVMHEALHNHYTQKSLSLSPGK |
| SEQ ID NO: 67 | IgG1 heavy chain constant region-LFLEDANQPS (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPSVF LFPPKPKDTLMISRTPEVTCVVVAVSHEDPEVKFNWYVDGV EVHNAKTKPREEQYQSTYRVVSVLTVLHQDWLNGKEYKCK VSNKALPASIEKTISKAKGQPREPQVYTLPPSREEMTKNQVS LTCLVKGFYPSDIAVEWESNGQPENNYKTTPPVLDSDGSFFL YSKLTVDKSRWQQGNVFSCSVMHEALHNHYTQKSLSLSPGK |
| SEQ ID NO: 68 | IgG1 heavy chain constant region-F405L N297Q (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYQSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFLL YSKLTVDKSRWQQGNVFSCSVMHEALHNHYTQKSLSLSPGK |
| SEQ ID NO: 69 | IgG1 heavy chain constant region-K409R N297Q (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYQSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSRLTVDKSRWQQGNVFSCSVMHEALHNHYTQKSLSLSPGK |
| SEQ ID NO: 70 | IgG1 heavy chain constant region-F405L LFLEDANQPS (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPSVF LFPPKPKDTLMISRTPEVTCVVVAVSHEDPEVKFNWYVDGV EVHNAKTKPREEQYQSTYRVVSVLTVLHQDWLNGKEYKCK VSNKALPASIEKTISKAKGQPREPQVYTLPPSREEMTKNQVS LTCLVKGFYPSDIAVEWESNGQPENNYKTTPPVLDSDGSFLL YSKLTVDKSRWQQGNVFSCSVMHEALHNHYTQKSLSLSPGK |
| SEQ ID NO: 71 | IgG1 heavy chain constant region-K409R LFLEDANQPS (amino acids positions 118-447 according to EU numbering) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPSVF LFPPKPKDTLMISRTPEVTCVVVAVSHEDPEVKFNWYVDGV EVHNAKTKPREEQYQSTYRVVSVLTVLHQDWLNGKEYKCK VSNKALPASIEKTISKAKGQPREPQVYTLPPSREEMTKNQVS LTCLVKGFYPSDIAVEWESNGQPENNYKTTPPVLDSDGSFFL YSRLTVDKSRWQQGNVFSCSVMHEALHNHYTQKSLSLSPGK |
| SEQ ID NO: 72 | huCD3 VH CDR1 affinity variant | GFTFX$_1$TYA, wherein X$_1$ is selected from V, H, F, T, P, L, Q, D, K, W, S, G, A, C and R |

TABLE 1 -continued

| SEQ ID NO: | Clone name | Sequence |
|---|---|---|
| SEQ ID NO: 73 | huCD3 VH CDR1 affinity variant | GFTFNX$_2$YA, wherein X$_2$ is selected from S, N, G, A, K, V, R, H, Q, P, I, F, M, Y, L, W, D, E and C |
| SEQ ID NO: 74 | huCD3 VH CDR1 affinity variant | GFTFNTX$_3$A, wherein X$_3$ is selected from F, H, N, M, W, G, Q, V, T, S, L, P, I, A, K, R and C |
| SEQ ID NO: 75 | huCD3 VH CDR2 affinity variant | IRSKYNX$_4$YAT, wherein X$_4$ is selected from S, Y, Q, W, L, A, I, M, D, T, K, R, G, F, E, V, C and P |
| SEQ ID NO: 76 | huCD3 VH CDR2 affinity variant | IRSKYNNYX$_5$T, wherein X$_5$ is selected from N, L, Y, W, H, M, G, F, K, S, V, R, Q, D, C, E, P and T |
| SEQ ID NO: 77 | huCD3 VH CDR3 affinity variant | VRX$_6$GNFGNSYVSWFAY, wherein X$_6$ is selected from A, S, V, N, K, L, T, I, P, Q, C, G, Y, W, F, and R |
| SEQ ID NO: 78 | huCD3 VH CDR3 affinity variant | VRHGNFX$_7$NSYVSWFAY, wherein X$_7$ is selected from P, Q, A, Y, H, I, N, V, E, L, F, W, M, R, C, S and T |
| SEQ ID NO: 79 | huCD3 VH CDR3 affinity variant | VRHGNFGNSYVX$_8$WFAY, wherein X$_8$ is selected from A, T, G, L, N, C, P, F, Q, H, R, K, E, W, and Y |
| SEQ ID NO: 80 | huCD3 VH CDR3 affinity variant | VRHGNFGNSYVSWFAX$_9$, wherein X$_9$ is selected from H, S, F, N, W, T, C, A, I, L, Q, V, E, M, K, R, G and P |
| SEQ ID NO: 81 | huCD3 VL CDR1 affinity variant | TGAVTX$_{10}$SNY, wherein X$_{10}$ is selected from S, A, G, R, V, F, I, E, M, H, N, Y, P, Q, D, K and L |
| SEQ ID NO: 82 | huCD3 VL CDR3 affinity variant | AX$_{11}$WYSNLWV, wherein X$_{11}$ is selected from C, F, Y, I, T, V, M, A, S, N, G, W, E, K, P, R and D |
| SEQ ID NO: 83 | huCD3 VL CDR3 affinity variant | ALWYSNX$_{12}$WV, wherein X$_{12}$ is selected from D, K, Q, R, G, V, E, T, N, Y, S, P, W, F and M |

The CDR regions have been annotated according to the IMGT definitions.

DETAILED DESCRIPTION OF THE INVENTION

Definitions

The term "human CD3" or "CD3" as used herein, refers to the human Cluster of Differentiation 3 protein which is part of the T-cell co-receptor protein complex and is composed of four distinct chains. CD3 is also found in other species, and thus, the term "CD3" may be used herein and is not limited to human CD3 unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ (delta) chain (human CD3δ UniProtKB/Swiss-Prot No P04234, or cynomolgus monkey CD3δ UniProtKB/Swiss-Prot No Q95LI8), two CD3ε (epsilon) chains (human CD3ε UniProtKB/Swiss-Prot No P07766; cynomolgus CD3ε UniProtKB/Swiss-Prot No Q95LI5; or rhesus CD3ε UniProtKB/Swiss-Prot No G7NCB9), and a CD3ζ-chain (zeta) chain (human CD3ζ UniProtKB/Swiss-Prot No P20963, cynomolgus monkey CD3 UniProtKB/Swiss-Prot No Q09TKO). These chains associate with a molecule known as the T-cell receptor (TCR) and generate an activation signal in T lymphocytes. The TCR and CD3 molecules together comprise the TCR complex.

The term "human CD20" or "CD20" refers to human CD20 (UniProtKB/Swiss-Prot No P11836) and includes any variants, isoforms and species homologs of CD20 which are naturally expressed by cells, including tumor cells, or are expressed on cells transfected with the CD20 gene or cDNA. Species homologs include rhesus monkey CD20 (macaca mulatta; UniProtKB/Swiss-Prot No H9YXP1).

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "human antibody" as used herein, refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. Human monoclonal antibodies of the invention can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

A suitable animal system for preparing hybridomas that secrete human monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Human monoclonal antibodies can be generated using transgenic or transchromosomal mice carrying parts of the human immune system rather than the mouse system.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH or VH) and a heavy chain constant region (abbreviated herein as $C_H$ or CH). The heavy chain constant region typically is comprised of three domains, $C_H1$, $C_H2$, and $C_H3$. Each light chain typically is comprised of a light chain variable region (abbreviated herein as VL or VL) and a light chain constant region (abbreviated herein as $C_L$ or CL). The light chain constant region typically is comprised of one domain, $C_L$. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008; 36:W503-508 and Lefranc M P., Nucleic Acids Research 1999; 27:209-212; see also internet http address http://www.imgt.org/).

Unless otherwise stated or contradicted by context, reference to amino acid positions in the constant regions in the present invention is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the VH and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "bispecific antibody" in the context of the present invention refers to an antibody having two different antigen-binding regions defined by different antibody sequences.

When used herein, unless contradicted by context, the term "Fab-arm" or "arm" refers to one heavy chain-light chain pair and is used interchangeably with "half molecules" herein.

When used herein, unless contradicted by context, the term "Fc region" refers to an antibody region comprising at least a hinge region, a CH2 domain, and a CH3 domain.

As used herein, the term "isotype" refers to the immunoglobulin class (for instance IgG1, IgG2, IgG3, IgG4, IgD, IgA, IgE, or IgM) that is encoded by heavy chain constant region genes.

The term "monovalent antibody" means in the context of the present invention that an antibody molecule is capable of binding a single molecule of the antigen, and thus is not capable of antigen crosslinking.

A "CD20 antibody" or "anti-CD20 antibody" is an antibody as described above, which binds specifically to the antigen CD20.

A "CD3 antibody" or "anti-CD3 antibody" is an antibody as described above, which binds specifically to the antigen CD3, in particular human CD3ε (epsilon).

A "CD3×CD20 antibody" or "anti-CD3×CD20 antibody" is a bispecific antibody, which comprises two different antigen-binding regions, one of which binds specifically to the antigen CD20 and one of which binds specifically to CD3.

In a preferred embodiment, the bispecific antibody of the invention is isolated. An "isolated bispecific antibody," as used herein, is intended to refer to a bispecific antibody which is substantially free of other antibodies having different antigenic specificities (for instance an isolated bispecific antibody that specifically binds to CD20 and CD3 is substantially free of monospecific antibodies that specifically bind to CD20 or CD3).

The term "epitope" means a protein determinant capable of specific binding to an antibody. Epitopes usually consist of surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen binding peptide (in other words, the amino acid residue is within the footprint of the specifically antigen binding peptide).

The term "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" (sec$^{-1}$), as used herein, refers to the dissociation rate constant of a particular antibody-antigen interaction. Said value is also referred to as the $k_{off}$ value.

The term "$K_D$" (M), as used herein, refers to the dissociation equilibrium constant of a particular antibody-antigen interaction.

When used herein the term "heterodimeric interaction between the first and second CH3 regions" refers to the interaction between the first CH3 region and the second CH3 region in a first-CH3/second-CH3 heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

The term "reducing conditions" or "reducing environment" refers to a condition or an environment in which a substrate, here a cysteine residue in the hinge region of an antibody, is more likely to become reduced than oxidized.

The present invention also provides bispecific antibodies comprising functional variants of the VL regions, VH regions, or one or more CDRs of the bispecific antibodies of the examples. A functional variant of a VL, VH, or CDR used in the context of a bispecific antibody still allows each arm of the bispecific antibody to retain at least a substantial proportion (at least about 50%, 60%, 70%, 80%, 90%, 95% or more) of the affinity and/or the specificity/selectivity of the parent bispecific antibody and in some cases such a bispecific antibody may be associated with greater affinity, selectivity and/or specificity than the parent bispecific antibody.

Such functional variants typically retain significant sequence identity to the parent bispecific antibody. The percent identity between two sequences is a function of the number of identical positions shared by the sequences (i.e., % homology=# of identical positions/total # of positions× 100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

Exemplary variants include those which differ from VH and/or VL and/or CDR regions of the parent bispecific antibody sequences mainly by conservative substitutions; for instance 10, such as 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in the following table:
Amino acid residue classes for conservative substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Lysine with Arginine in position 409 is designated as: K409R, and the substitution of Lysine with any amino acid residue in position 409 is designated as K409X. In case of deletion of Lysine in position 409 it is indicated by K409*.

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO, CHO-S, HEK, HEK293, HEK-293F, Expi293F, PER.C6 or NS0 cells, and lymphocytic cells.

The term "treatment" refers to the administration of an effective amount of a therapeutically active bispecific antibody of the present invention with the purpose of easing, ameliorating, arresting or eradicating (curing) symptoms or disease states.

The term "effective amount" or "therapeutically effective amount" refers to an amount effective, at dosages and for periods of time necessary, to achieve a desired therapeutic result. A therapeutically effective amount of a bispecific antibody may vary according to factors such as the disease state, age, sex, and weight of the individual, and the ability of the bispecifc antibody to elicit a desired response in the individual. A therapeutically effective amount is also one in which any toxic or detrimental effects of the antibody or antibody portion are outweighed by the therapeutically beneficial effects.

The term "anti-idiotypic antibody" refers to an antibody which recognizes unique determinants generally associated with the antigen-binding site of an antibody.

Further Aspects and Embodiments of the Invention

As described above, the invention relates to a bispecific antibody comprising two different antigen-binding regions, one which has a binding specificity for CD3 and one which has a binding specificity for CD20.

Thus, the invention relates to a bispecific antibody comprising (i) a first binding arm comprising a first antigen-binding region binding to human CD3ε (epsilon), wherein said first antigen-binding region comprises
  a) heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:5, respectively;
  b) heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:54, respectively;
  c) heavy chain variable (VH) region CDR1, CDR2, and CDR3 having the sequences as set forth in SEQ ID NOs:73, 2, and 3, respectively, and light chain variable (VL) region CDR1, CDR2, and CDR3 having the sequences as set forth in SEQ ID NO:4, the sequence GTN, and the sequence as set forth in SEQ ID NO:5, wherein $X_2$ of SEQ ID NO:73 is selected from M and P, respectively;

d) heavy chain variable (VH) region CDR1, CDR2, and CDR3 having the sequences as set forth in SEQ ID NOs:74, 2, and 3, respectively, and light chain variable (VL) region CDR1, CDR2, and CDR3 having the sequences as set forth in SEQ ID NO:4, the sequence GTN, and the sequence as set forth in SEQ ID NO:5, wherein $X_3$ of SEQ ID NO:74 is A, respectively;

e) heavy chain variable (VH) region CDR1, CDR2, and CDR3 having the sequences as set forth in SEQ ID NOs:1, 75, and 3, respectively, and light chain variable (VL) region CDR1, CDR2, and CDR3 having the sequences as set forth in SEQ ID NO:4, the sequence GTN, and the sequence as set forth in SEQ ID NO:5, wherein $X_4$ of SEQ ID NO:75 is E, respectively;

f) heavy chain variable (VH) region CDR1, CDR2, and CDR3 having the sequences as set forth in SEQ ID NOs:1, 2, and 77, respectively, and light chain variable (VL) region CDR1, CDR2, and CDR3 having the sequences as set forth in SEQ ID NO:4, the sequence GTN, and the sequence as set forth in SEQ ID NO:5, wherein $X_6$ of SEQ ID NO:77 is selected from F, G, I, K, L and N, respectively;

g) heavy chain variable (VH) region CDR1, CDR2, and CDR3 having the sequences as set forth in SEQ ID NOs:1, 2, and 78, respectively, and light chain variable (VL) region CDR1, CDR2, and CDR3 having the sequences as set forth in SEQ ID NO:4, the sequence GTN, and the sequence as set forth in SEQ ID NO:5, wherein $X_7$ of SEQ ID NO:78 is P, respectively;

h) heavy chain variable (VH) region CDR1, CDR2, and CDR3 having the sequences as set forth in SEQ ID NOs:1, 2, and 79, respectively, and light chain variable (VL) region CDR1, CDR2, and CDR3 having the sequences as set forth in SEQ ID NO:4, the sequence GTN, and the sequence as set forth in SEQ ID NO:5, wherein $X_8$ of SEQ ID NO:79 is selected from A and G, respectively;

i) heavy chain variable (VH) region CDR1, CDR2, and CDR3 having the sequences as set forth in SEQ ID NOs:1, 2, and 80, respectively, and light chain variable (VL) region CDR1, CDR2, and CDR3 having the sequences as set forth in SEQ ID NO:4, the sequence GTN, and the sequence as set forth in SEQ ID NO:5, wherein $X_8$ of SEQ ID NO:80 is selected from M, R and V, respectively; or j) heavy chain variable (VH) region CDR1, CDR2, and CDR3 having the sequences as set forth in SEQ ID NOs:55, 56 and 57, respectively, and light chain variable (VL) region CDR1, CDR2, and CDR3 having the sequences as set forth in SEQ ID NO:58, the sequence DTS, and the sequence as set forth in SEQ ID NO:59, respectively, and (ii) a second binding arm comprising a second antigen-binding region binding to human CD20.

Hereby bispecific antibodies with varying binding affinities for CD3 epsilon are provided. In one embodiment it is preferred that the binding affinity for CD3 is lower than it is for the parent anti-CD3 binding arm. Experimental data have shown that bispecific CD3×CD20 antibodies as described above in c) to i) having an anti-CD3 binding arm with a substitution which lower the binding affinity for CD3 epsilon maintains the tumor killing potency of the parent bispecific anti-CD3×CD20 antibody.

In one embodiment, the invention relates to a bispecific antibody comprising (i) a first binding arm comprising a first antigen-binding region binding to human CD3ε (epsilon), wherein said first antigen-binding region comprises (a) heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:5 or SEQ ID NO:54, respectively, or (b) heavy chain variable (VH) region CDR1, CDR2, and CDR3 having the sequences as set forth in SEQ ID NOs:55, 56 and 57, respectively, and light chain variable (VL) region CDR1, CDR2, and CDR3 having the sequences as set forth in SEQ ID NO:58, the sequence DTS, and the sequence as set forth in SEQ ID NO:59, respectively, and (ii) a second binding arm comprising a second antigen-binding region binding to human CD20.

In one embodiment, the invention relates to a bispecific antibody comprising a first binding arm comprising a first antigen-binding region binding to human CD3ε (epsilon), wherein said first antigen-binding region comprises heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:5, respectively.

The term "binding arm comprising an antigen-binding region" means an antibody molecule or fragment that comprises an antigen-binding region. Thus, binding arm can be e.g. the six VH and VL CDR regions, the VH and VL sequences, the Fab fragment or a half-molecule antibody (i.e. comprising one heavy and one light chain).

In one embodiment, the first antigen-binding region comprises a first heavy chain variable sequence (VH), and a first light chain variable sequence (VL), and the second antigen-binding region comprises a second heavy chain variable sequence (VH), and a second light chain variable sequence (VL).

In one embodiment, the first binding arm comprises a first heavy chain comprising a first heavy chain variable sequence (VH) and a first heavy chain constant sequence (CH), and a first light chain comprising a first light chain variable sequence (VL) and a first light chain constant sequence (CL), and (ii) the second binding arm comprises a second heavy chain comprising a second heavy chain variable sequence (VH) and a second heavy chain constant sequence (CH), and a second light chain comprising a second light chain variable sequence (VL) and a second light chain constant sequence (CL).

In one embodiment, the bispecific antibody is a full length antibody, such as a full length IgG1 antibody, e.g. a full length IgG1, λ (lambda), κ (kappa) antibody or IgG1, κ (kappa), κ (kappa) antibody.

First Binding Arm

The first binding arm comprises a first antigen-binding region binding to human CD3ε (epsilon), wherein said first antigen-binding region comprises a) heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:5, respectively;

b) heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:54, respectively;

c) heavy chain variable (VH) region CDR1, CDR2, and CDR3 having the sequences as set forth in SEQ ID NOs:73, 2, and 3, respectively, and light chain variable (VL) region CDR1, CDR2, and CDR3 having the sequences as set forth in SEQ ID NO:4, the sequence GTN, and the sequence as set forth in SEQ ID NO:5, wherein $X_2$ of SEQ ID NO:73 is selected from M and P, respectively;

d) heavy chain variable (VH) region CDR1, CDR2, and CDR3 having the sequences as set forth in SEQ ID NOs:74, 2, and 3, respectively, and light chain variable (VL) region CDR1, CDR2, and CDR3 having the sequences as set forth in SEQ ID NO:4, the sequence GTN, and the sequence as set forth in SEQ ID NO:5, wherein $X_3$ of SEQ ID NO:74 is A;

e) heavy chain variable (VH) region CDR1, CDR2, and CDR3 having the sequences as set forth in SEQ ID NOs:1, 75, and 3, respectively, and light chain variable (VL) region CDR1, CDR2, and CDR3 having the sequences as set forth in SEQ ID NO:4, the sequence GTN, and the sequence as set forth in SEQ ID NO:5, wherein $X_4$ of SEQ ID NO:75 is E;

f) heavy chain variable (VH) region CDR1, CDR2, and CDR3 having the sequences as set forth in SEQ ID NOs:1, 2, and 77, respectively, and light chain variable (VL) region CDR1, CDR2, and CDR3 having the sequences as set forth in SEQ ID NO:4, the sequence GTN, and the sequence as set forth in SEQ ID NO:5, wherein $X_6$ of SEQ ID NO:77 is selected from F, G, I, K, L and N, respectively;

g) heavy chain variable (VH) region CDR1, CDR2, and CDR3 having the sequences as set forth in SEQ ID NOs:1, 2, and 78, respectively, and light chain variable (VL) region CDR1, CDR2, and CDR3 having the sequences as set forth in SEQ ID NO:4, the sequence GTN, and the sequence as set forth in SEQ ID NO:5, wherein $X_7$ of SEQ ID NO:78 is P;

h) heavy chain variable (VH) region CDR1, CDR2, and CDR3 having the sequences as set forth in SEQ ID NOs:1, 2, and 79, respectively, and light chain variable (VL) region CDR1, CDR2, and CDR3 having the sequences as set forth in SEQ ID NO:4, the sequence GTN, and the sequence as set forth in SEQ ID NO:5, wherein $X_8$ of SEQ ID NO:79 is selected from A and G, respectively;

i) heavy chain variable (VH) region CDR1, CDR2, and CDR3 having the sequences as set forth in SEQ ID NOs:1, 2, and 80, respectively, and light chain variable (VL) region CDR1, CDR2, and CDR3 having the sequences as set forth in SEQ ID NO:4, the sequence GTN, and the sequence as set forth in SEQ ID NO:5, wherein $X_8$ of SEQ ID NO:80 is selected from M, R and V, respectively; or j) heavy chain variable (VH) region CDR1, CDR2, and CDR3 having the sequences as set forth in SEQ ID NOs:55, 56 and 57, respectively, and light chain variable (VL) region CDR1, CDR2, and CDR3 having the sequences as set forth in SEQ ID NO:58, the sequence DTS, and the sequence as set forth in SEQ ID NO:59, respectively.

In one embodiment, the first binding arm comprises a first antigen-binding region binding to human CD3ε (epsilon), wherein said first antigen-binding region comprises (a) heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:5 or SEQ ID NO:54, respectively, or (b) heavy chain variable (VH) region CDR1, CDR2, and CDR3 having the sequences as set forth in SEQ ID NOs:55, 56 and 57, respectively, and light chain variable (VL) region CDR1, CDR2, and CDR3 having the sequences as set forth in SEQ ID NO:58, the sequence DTS, and the sequence as set forth in SEQ ID NO:59, respectively.

In one embodiment, the first binding arm comprises a first antigen-binding region binding to human CD3ε (epsilon), wherein said first antigen-binding region comprises heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:5, respectively.

The six CDR sequences as defined in (a) above are derived from a mouse antibody denoted SP34. Humanized versions of this antibody have been generated, and the humanized antibodies are denoted huCD3 herein and are further disclosed in WO2015001085 (Genmab).

The six CDR sequences as defined in (b) above are derived from huCLB-T3/4. huCLB-T3/4 is a humanized version of the murine CD3 antibody CLB-T3/4 (Parren et al., Res Immunol. 1991, 142(9):749-63, hereby incorporated by reference in its entirety, including sequence disclosures). Briefly, the CLB-T3/4 murine VH and VL sequences as published in Parren et al. (1991) were aligned to the human VH and VL repertoires using the IMGT's V-QUEST. The closest human germlines that were found were IGHV3-21*01 for the VH gene and IGKV3-11*01(+IGKJ4*02) for the VL gene. All amino acid residues in the murine VH and VL sequences that differed were replaced by the human equivalent, except for those within the CDR regions of CLB-T3/4. As no related J-region was found for the VH sequence, the common WGQGTLVTVSS sequence was used for the FR4 region of the heavy chain. Both sequences were cloned into the relevant expression vectors and expressed by cotransfection in HEK293F cells. huCLB-T3/4 has a VH region comprising the sequence set forth in SEQ ID NO:17 (VH huCLB-T3/4) and a VL region comprising the sequence set forth in SEQ ID NO:18 (VL huCLB-T3/4). huCLB-T3/4 has the VH CDR1, CDR2 and CDR3 sequences set forth in SEQ ID NOs:55, 56 and 57, respectively, and the VL CDR1, CDR2 and CDR3 sequences set forth in SEQ ID NO:58, the sequence DTS, and the sequence set forth in SEQ ID NO:59, respectively.

The various humanized huCD3 antibodies and huCLB-T3/4 bind to human CD3ε (epsilon).

In one embodiment, the bispecific antibody as defined in any of the embodiments disclosed herein comprises a first heavy chain variable sequence (VH), wherein said VH sequence has at least 90%, at least 95%, at least 97%, or at least 99% amino acid sequence identity to the amino acid sequence as set forth in the VH sequences selected from the group consisting of:

a) a VH sequence as set forth in SEQ ID NO:6;
b) a VH sequence as set forth in SEQ ID NO:7;
c) a VH sequence as set forth in SEQ ID NO:8;

d) a VH sequence as set forth in SEQ ID NO:9; and
e) a VH sequence as set forth in SEQ ID NO:17.

In one embodiment, the VH sequence of the first antigen-binding region is selected from the group consisting of:
a) a VH sequence as set forth in SEQ ID NO:6;
b) a VH sequence as set forth in SEQ ID NO:7;
c) a VH sequence as set forth in SEQ ID NO:8;
d) a VH sequence as set forth in SEQ ID NO:9;
e) a VH sequence as set forth in SEQ ID NO:17.

In one embodiment, the bispecific antibody as defined in any of the embodiments disclosed herein comprises a first VL sequence of the first antigen-binding region, wherein said VL sequence has at least 90%, at least 95%, at least 97%, or at least 99% amino acid sequence identity to the amino acid sequence as set forth in the VL sequences selected from the group consisting of:
a) a VL sequence as set forth in SEQ ID NO: 10;
b) a VL sequence as set forth in SEQ ID NO:11;
c) a VL sequence as set forth in SEQ ID NO: 12; and
d) a VL sequence as set forth in SEQ ID NO: 18.

In one embodiment, the VL sequence of the first antigen-binding region is selected from the group consisting of:
a VL sequence as set forth in SEQ ID NO: 10;
a) a VL sequence as set forth in SEQ ID NO:11;
b) a VL sequence as set forth in SEQ ID NO: 12; and
c) a VL sequence as set forth in SEQ ID NO: 18.

In one embodiment, the bispecific antibody as defined in any of the embodiments disclosed herein comprises first VH and VL sequences, wherein said VH and VL sequences of the first antigen-binding region are selected from the group consisting of:
a) a VH sequence as set forth in SEQ ID NO:6, and a VL sequence as set forth in SEQ ID NO:10;
b) a VH sequence as set forth in SEQ ID NO:8, and a VL sequence as set forth in SEQ ID NO:10;
c) a VH sequence as set forth in SEQ ID NO:9, and a VL sequence as set forth in SEQ ID NO:10;
d) a VH sequence as set forth in SEQ ID NO:6, and a VL sequence as set forth in SEQ ID NO:11;
e) a VH sequence as set forth in SEQ ID NO:6, and a VL sequence as set forth in SEQ ID NO:12;
f) a VH sequence as set forth in SEQ ID NO:7, and a VL sequence as set forth in SEQ ID NO:10;
g) a VH sequence as set forth in SEQ ID NO:7, and a VL sequence as set forth in SEQ ID NO:11;
h) a VH sequence as set forth in SEQ ID NO:7, and a VL sequence as set forth in SEQ ID NO:12;
i) a VH sequence as set forth in SEQ ID NO:8, and a VL sequence as set forth in SEQ ID NO:11;
j) a VH sequence as set forth in SEQ ID NO:8, and a VL sequence as set forth in SEQ ID NO:12;
k) a VH sequence as set forth in SEQ ID NO:9, and a VL sequence as set forth in SEQ ID NO:11;
l) a VH sequence as set forth in SEQ ID NO:9, and a VL sequence as set forth in SEQ ID NO:12; and
m) a VH sequence as set forth in SEQ ID NO:17, and a VL sequence as set forth in SEQ ID NO:18.

In one embodiment, the bispecific antibody as defined in any of the embodiments disclosed herein comprises first VH and VL sequences, wherein said VH and VL sequences of the first antigen-binding region are selected from the group consisting of:
a) a VH sequence as set forth in SEQ ID NO:6, and a VL sequence as set forth in SEQ ID NO:10;
b) a VH sequence as set forth in SEQ ID NO:17, and a VL sequence as set forth in SEQ ID NO:18 In one embodiment, the bispecific antibody as defined in any of the embodiments disclosed herein comprises first VH and VL sequences as set forth in SEQ ID Nos: 17 and 18.

In one embodiment, the bispecific antibody as defined in any of the embodiments disclosed comprises a first antigen-binding region having at least 90% sequence identity to the VH sequence is as set forth in SEQ ID NO:6, and at least 90% sequence identity to the VL sequence is as set forth in SEQ ID NO:10. In one embodiment the sequence deviations are in the framework sequences and not in the CDR sequences. Accordingly, in one embodiment, the invention relates to a bispecific antibody comprising a first antigen-binding region having at least 90% sequence identity to the VH sequence is as set forth in SEQ ID NO:6, and at least 90% sequence identity to the VL sequence is as set forth in SEQ ID NO:10 wherein the CDR sequences are as set forth in SEQ ID NOs:1, 2, and 3, for the heavy chain and as set forth in SEQ ID NO:4, the sequence GTN, and the sequence as set forth in SEQ ID NO:5 for the light chain so that the CDR sequences are unmutated.

In one embodiment, the bispecific antibody as defined in any of the embodiments disclosed comprises a first antigen-binding region having at least 95% sequence identity to the VH sequence is as set forth in SEQ ID NO:6, and at least 95% sequence identity to the VL sequence is as set forth in SEQ ID NO:10. In one embodiment, the invention relates to a bispecific antibody comprising a first antigen-binding region having at least 95% sequence identity to the VH sequence is as set forth in SEQ ID NO:6, and at least 95% sequence identity to the VL sequence is as set forth in SEQ ID NO:10 wherein the CDR sequences are as set forth in SEQ ID NOs: 1, 2, and 3, for the heavy chain and as set forth in SEQ ID NO:4, the sequence GTN, and the sequence as set forth in SEQ ID NO:5 for the light chain so that the CDR sequences are unmutated.

In one embodiment of the bispecific antibody as defined in any of the embodiments disclosed comprises a first antigen-binding region having at least 97% sequence identity to the VH sequence is as set forth in SEQ ID NO:6, and at least 97% sequence identity to the VL sequence is as set forth in SEQ ID NO:10. In one embodiment, the invention relates to a bispecific antibody comprising a first antigen-binding region having at least 97% sequence identity to the VH sequence is as set forth in SEQ ID NO:6, and at least 97% sequence identity to the VL sequence is as set forth in SEQ ID NO:10 wherein the CDR sequences are as set forth in SEQ ID NOs: 1, 2, and 3, for the heavy chain and as set forth in SEQ ID NO:4, the sequence GTN, and the sequence as set forth in SEQ ID NO:5 for the light chain so that the CDR sequences are unmutated.

In one embodiment of the bispecific antibody as defined in any of the embodiments disclosed comprises a first antigen-binding region having at least 98% sequence identity to the VH sequence is as set forth in SEQ ID NO:6, and at least 98% sequence identity to the VL sequence is as set forth in SEQ ID NO:10. In one embodiment, the invention relates to a bispecific antibody comprising a first antigen-binding region having at least 98% sequence identity to the VH sequence is as set forth in SEQ ID NO:6, and at least 98% sequence identity to the VL sequence is as set forth in SEQ ID NO:10 wherein the CDR sequences are as set forth in SEQ ID NOs: 1, 2, and 3, for the heavy chain and as set forth in SEQ ID NO:4, the sequence GTN, and the sequence as set forth in SEQ ID NO:5 for the light chain so that the CDR sequences are unmutated.

In one embodiment of the bispecific antibody as defined in any of the embodiments disclosed comprises a first antigen-binding region having at least 99% sequence identity to the VH sequence is as set forth in SEQ ID NO:6, and at least 99% sequence identity to the VL sequence is as set forth in SEQ ID NO:10. In one embodiment, the invention relates to a bispecific antibody comprising a first antigen-binding region having at least 99% sequence identity to the VH sequence is as set forth in SEQ ID NO:6, and at least 99% sequence identity to the VL sequence is as set forth in SEQ ID NO:10 wherein the CDR sequences are as set forth in SEQ ID NOs: 1, 2, and 3, for the heavy chain and as set forth in SEQ ID NO:4, the sequence GTN, and the sequence as set forth in SEQ ID NO:5 for the light chain so that the CDR sequences are unmutated.

Hereby bispecific antibodies of the invention are provided wherein the VH and VL sequences may vary within at least 90% sequence identity to the parent sequences. It is preferred that the variants have the same properties as the parent antibodies. In certain embodiments the sequences only vary in the framework sequences so that the CDR sequences are identical to the parent CDR sequences.

In one embodiment of the bispecific antibody as defined in any of the embodiments disclosed herein the first antigen-binding region comprises the VH sequence is as set forth in SEQ ID NO:6, and the VL sequence is as set forth in SEQ ID NO:10.

In one embodiment, the first binding arm of the bispecific antibody as defined in any of the embodiments disclosed herein is derived from a mouse antibody.

In one embodiment, the first binding arm of the bispecific antibody as defined in any of the embodiments disclosed herein is derived from a humanized antibody.

In one embodiment, the first binding arm of the bispecific antibody as defined in any of the embodiments disclosed herein is derived from a full-length antibody antibody.

In one embodiment, the first binding arm of the bispecific antibody as defined in any of the embodiments disclosed herein is derived from a full-length IgG1, λ (lambda) or IgG1, κ (kappa) antibody.

Second Binding Arm

Suitable CD20 antibodies for use as the second binding arm in the bispecific antibodies according to the invention are CD20 antibodies, which bind to an epitope on human CD20, which does not comprise or require the amino acid residues alanine at position 170 or proline at position 172, but which comprises or requires the amino acid residues asparagine at position 163 and asparagine at position 166. Examples of such antibodies are the antibodies denoted 2F2 and 7D8 as disclosed in WO2004035607 (Genmab) and the antibody denoted 2C6 as disclosed in WO2005103081 (Genmab). The CDR sequences of 2F2, 7D8 and 2C6 are disclosed in Table 1.

Further suitable CD20 antibodies for use as the second binding arm in the bispecific antibodies according to the invention are CD20 antibodies, which bind to an epitope on human CD20, which does not comprise or require the amino acid residues alanine at position 170 or proline at position 172. An example of such an antibody is 11B8 as disclosed in WO2004035607 (Genmab). The CDR sequences of 11B8 are disclosed in Table 1.

Further suitable CD20 antibodies for use as the second antigen-binding region in the bispecific antibodies according to the invention are CD20 antibodies with a low functional off-rate meaning that the antibodies are slowly dissociated from CD20 upon binding.

The $k_d$ dissociation constant or $k_{off}$ rate may be determined by the method described under the heading "Dissociation rates of anti-CD20 F(ab)$_2$ fragments" in Example 5 of WO2004035607. Thus, in one embodiment, the CD20 antibodies have a $k_d$ dissociation constant of $1.0 \times^{-4}$ sec$^{-1}$ or below, such as of $8.0 \times 10^{-5}$ sec$^{-1}$ or below, such as in the range of $8.0 \times 10^{-5}$ sec$^{-1}$ to $4.0 \times 10^{-5}$ sec$^{-1}$ as determined by the above method.

Further suitable CD20 antibodies for use as the second binding arm in the bispecific antibodies according to the invention are CD20 antibodies having the six CDR sequences of the antibody denoted 11B8 as disclosed in WO2004035607. The CDR sequences of 11B8 are disclosed in Table 1.

In one embodiment, the bispecific antibody as defined in any of the embodiments disclosed herein comprises a second antigen-binding region which binds to human CD20, which second antigen-binding region comprises heavy chain variable (VH) region CDR1, CDR2, and CDR3 having the sequences selected from:
  (i) the VH CDR1 region of SEQ ID NO:32, the VH CDR2 region of SEQ ID NO:33, the VH CDR3 region of SEQ ID NO:34,
  (ii) the VH CDR1 region of SEQ ID NO:38, the VH CDR2 region of SEQ ID NO:39, the VH CDR3 region of SEQ ID NO:34,
  (iii) the VH CDR1 region of SEQ ID NO:42, the VH CDR2 region of SEQ ID NO:43, the VH CDR3 region of SEQ ID NO:44, or
  (iv) the VH CDR1 region of SEQ ID NO:49, the VH CDR2 region of SEQ ID NO:50, the VH CDR3 region of SEQ ID NO:51.

In a preferred embodiment, the bispecific antibody as defined in any of the embodiments disclosed herein comprises a second antigen-binding region comprising the VH CDR1 region of SEQ ID NO:32, the VH CDR2 region of SEQ ID NO:33, and the VH CDR3 region of SEQ ID NO:34.

In one embodiment, the bispecific antibody as defined in any of the embodiments disclosed herein comprises a second antigen-binding region which binds to human CD20, which second antigen-binding region comprises heavy chain variable (VH) region CDR1, CDR2, and CDR3 and chain variable (LH) region CDR1, CDR2, and CDR3 sequences selected from:
  (i) the VH CDR1 region of SEQ ID NO:32, the VH CDR2 region of SEQ ID NO:33, the VH CDR3 region of SEQ ID NO:34, the VL CDR1 region of SEQ ID NO:35, the VL CDR2 region of DAS, and the VL CDR3 region of SEQ ID NO:36,
  (ii) the VH CDR1 region of SEQ ID NO:38, the VH CDR2 region of SEQ ID NO:39, the VH CDR3 region of SEQ ID NO:34, the VL CDR1 region of SEQ ID NO:35, the VL CDR2 region of DAS, and the VL CDR3 region of SEQ ID NO:36,
  (iii) the VH CDR1 region of SEQ ID NO:42, the VH CDR2 region of SEQ ID NO:43, the VH CDR3 region of SEQ ID NO:44, the VL CDR1 region of SEQ ID NO:45, the VL CDR2 region of DAS, and the VL CDR3 region of SEQ ID NO:46,
  (iv) the VH CDR1 region of SEQ ID NO:49, the VH CDR2 region of SEQ ID NO:50, the VH CDR3 region of SEQ ID NO:51, the VL CDR1 region of SEQ ID NO:52, the VL CDR2 region of DAS, and the VL CDR3 region of SEQ ID NO:53,
  (v) the VH CDR1 region of SEQ ID NO:32, the VH CDR2 region of SEQ ID NO:33, the VH CDR3 region of SEQ ID NO:34, the VL CDR1 region of SEQ ID NO:45, the VL CDR2 region of DAS, and the VL CDR3 region of SEQ ID NO:46, (vi) the VH CDR1 region of SEQ ID NO:32, the VH CDR2 region of SEQ ID NO:33, the VH CDR3 region of SEQ ID NO:34, the VL CDR1 region of SEQ ID NO:52, the VL CDR2 region of DAS, and the VL CDR3 region of SEQ ID NO:53, (vii) the VH CDR1 region of SEQ ID NO:38, the VH CDR2 region of SEQ ID NO:39, the VH CDR3 region of SEQ ID NO:34, the VL CDR1 region of SEQ ID NO:45, the VL CDR2 region of DAS, and the VL CDR3 region of SEQ ID NO:46, (viii) the VH CDR1 region of SEQ ID NO:38, the VH CDR2 region of SEQ ID NO:39, the VH CDR3 region of SEQ ID NO:34, the VL CDR1 region of SEQ ID NO:52, the VL CDR2 region of DAS, and the VL CDR3 region of SEQ ID NO:53, (ix) the VH CDR1 region of SEQ ID NO:42, the VH CDR2 region of SEQ ID NO:43, the VH CDR3 region of SEQ ID NO:44, the VL CDR1 region of SEQ ID NO:35, the VL CDR2 region of DAS, and the VL CDR3 region of SEQ ID NO:36, (x) the VH CDR1 region of SEQ ID NO:42, the VH CDR2 region of SEQ ID NO:43, the VH CDR3 region of SEQ ID NO:44, the VL CDR1 region of SEQ ID NO:52, the VL CDR2 region of DAS, and the VL CDR3 region of SEQ ID NO:53, (xi) the VH CDR1 region of SEQ ID NO:49, the VH CDR2 region of SEQ ID NO:50, the VH CDR3 region of SEQ ID NO:51, the VL CDR1 region of SEQ ID NO:35, the VL CDR2 region of DAS, and the VL CDR3 region of SEQ ID NO:36, or (xii) the VH CDR1 region of SEQ ID NO:49, the VH CDR2 region of SEQ ID NO:50, the VH CDR3 region of SEQ ID NO:51, the VL CDR1 region of SEQ ID NO:45, the VL CDR2 region of DAS, and the VL CDR3 region of SEQ ID NO:46.

In a preferred embodiment, the bispecific antibody as defined in any of the embodiments as disclosed herein comprises a second antigen-binding region comprising the VH CDR1 region of SEQ ID NO:32, the VH CDR2 region of SEQ ID NO:33, the VH CDR3 region of SEQ ID NO:34, the VL CDR1 region of SEQ ID NO:35, the VL CDR2 region of DAS, and the VL CDR3 region of SEQ ID NO:36.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:27, and a VL sequence which has at least 90%, at least 95%, at least 97%, or at least 99% amino acid sequence identity to the amino acid sequence as set forth in SEQ ID NO:28.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:37, and a VL sequence which has at least 90%, at least 95%, at least 97%, or at least 99% amino acid sequence identity to the amino acid sequence as set forth in SEQ ID NO:28.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:40, and a VL sequence which has at least 90%, at least 95%, at least 97%, or at least 99% amino acid sequence identity to the amino acid sequence as set forth in SEQ ID NO:41.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:47, and a VL sequence which has at least 90%, at least 95%, at least 97%, or at least 99% amino acid sequence identity to the amino acid sequence as set forth in SEQ ID NO:48.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:27, and a VL sequence which has at least 90%, at least 95%, at least 97%, or at least 99% amino acid sequence identity to the amino acid sequence as set forth in SEQ ID NO:41.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:27, and a VL sequence which has at least 90%, at least 95%, at least 97%, or at least 99% amino acid sequence identity to the amino acid sequence as set forth in SEQ ID NO:48.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:37, and a VL sequence which has at least 90%, at least 95%, at least 97%, or at least 99% amino acid sequence identity to the amino acid sequence as set forth in SEQ ID NO:41.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:37, and a a VL sequence which has at least 90%, at least 95%, at least 97%, or at least 99% amino acid sequence identity to the amino acid sequence as set forth in SEQ ID NO:48.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:40, and a VL sequence which has at least 90%, at least 95%, at least 97%, or at least 99% amino acid sequence identity to the amino acid sequence as set forth in SEQ ID NO:28.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:40, and a VL sequence which has at least 90%, at least 95%, at least 97%, or at least 99% amino acid sequence identity to the amino acid sequence as set forth in SEQ ID NO:48.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:47, and a VL sequence which has at least 90%, at least 95%, at least 97%, or at least 99% amino acid sequence identity to the amino acid sequence as set forth in SEQ ID NO:28.

In one embodiment, the bispecific antibody as defined in any of the embodiments disclosed herein comprises a VH sequence which has at least 90%, at least 95%, at least 97%, or at least 99% amino acid sequence identity to the amino acid sequence as set forth in SEQ ID NO:47, and a a VL sequence which has at least 90%, at least 95%, at least 97%, or at least 99% amino acid sequence identity to the amino acid sequence as set forth in SEQ ID NO:41.

In one embodiment, the bispecific antibody as defined in any of the embodiments disclosed herein comprises second VH and VL sequences, wherein said VH and VL sequences of the second antigen-binding region are selected from the group consisting of:

(i) the VH sequence of SEQ ID NO:27, and the VL sequence of SEQ ID NO:28, (ii) the VH sequence of SEQ ID NO:37, and the VL sequence of SEQ ID NO:28, (iii) the VH sequence of SEQ ID NO:40, and the VL sequence of SEQ ID NO:41, (iv) the VH sequence of SEQ ID NO:47, and the VL sequence of SEQ ID NO:48, (v) the VH sequence of SEQ ID NO:27, and the VL sequence of SEQ ID NO:41, (vi) the VH sequence of SEQ ID NO:27, and the VL sequence of SEQ ID NO:48, (vii) the VH sequence of SEQ ID NO:37, and the VL sequence of SEQ ID NO:41, (viii) the VH sequence of SEQ ID NO:37, and the VL sequence of SEQ ID NO:48, (ix) the VH sequence of SEQ ID NO:40, and the VL sequence of SEQ ID NO:28, (x) the VH sequence of SEQ ID NO:40, and the VL sequence of SEQ ID NO:48, (xi) the VH sequence of SEQ ID NO:47, and the VL sequence of SEQ ID NO:28, or (xii) the VH sequence of SEQ ID NO:47, and the VL sequence of SEQ ID NO:41.

In one embodiment of the bispecific antibody as defined in any of the embodiments disclosed herein the second antigen-binding region comprises the VH sequence of SEQ ID NO:27, and the VL sequence of SEQ ID NO:28.

In one embodiment, the second binding arm of the bispecific antibody as defined in any of the embodiments disclosed herein is derived from a human antibody.

In one embodiment, the second binding arm of the bispecific antibody as defined in any of the embodiments disclosed herein is derived from a full-length antibody antibody.

In one embodiment, the second binding arm of the bispecific antibody as defined in any of the embodiments disclosed herein is derived from a IgG1, K (kappa) antibody.

Bispecific Antibody Formats

The present invention provides bispecific CD3×CD20 antibodies which efficiently promote T cell-mediated killing of CD20-expressing tumor cells. Depending on the desired functional properties for a particular use, particular antigen-binding regions can be selected from the set of antibodies or antigen-binding regions provided by the present invention. Many different formats and uses of bispecific antibodies are known in the art, and were reviewed by Kontermann; Drug Discov Today, 2015 July; 20(7):838-47 and; MAbs, 2012 March-April; 4(2):182-97.

A bispecific antibody according to the present invention is not limited to any particular bispecific format or method of producing it.

Examples of bispecific antibody molecules which may be used in the present invention comprise (i) a single antibody that has two arms comprising different antigen-binding regions; (ii) a single chain antibody that has specificity to two different epitopes, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')$_2$ fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, or a bispecific antibody obtained via a controlled Fab-arm exchange (such as described in WO2011131746 (Genmab)).

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc-regions or parts thereof.

Examples of IgG-like molecules with complementary CH3 domain molecules include but are not limited to the Triomab/Quadroma molecules (Trion Pharma/Fresenius Biotech; Roche, WO2011069104), the so-called Knobs-into-Holes molecules (Genentech, WO9850431), Cross-MAbs (Roche, WO2011117329) and the electrostatically-matched molecules (Amgen, EP1870459 and WO2009089004; Chugai, US201000155133; Oncomed, WO2010129304), the LUZ-Y molecules (Genentech, Wranik et al. J. Biol. Chem. 2012, 287(52): 43331-9, doi: 10.1074/jbc.M112.397869. Epub 2012 Nov. 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcAAdp molecules (Regeneron, WO201015792), bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab A/S, WO2011131746).

Examples of recombinant IgG-like dual targeting molecules include but are not limited to Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2):208-18), approaches with common light chain (Crucell/Merus, U.S. Pat. No. 7,262,028), KABodies (NovImmune, WO2012023053) and CovX-body (CovX/Pfizer; Doppalapudi, V. R., et al 2007. Bioorg. Med. Chem. Lett. 17, 501-506.).

Examples of IgG fusion molecules include but are not limited to Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2):191-8), Ts2Ab (MedImmune/AZ; Dimasi et al. J Mol Biol. 2009 Oct. 30; 393(3):672-92) and BsAb molecules (Zymogenetics, WO2010111625), HERCULES molecules (Biogen Idec, U.S. 007951918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include but are not limited to ScFv/Fc Fusions (Pearce et al., Biochem Mol Biol Int. 1997 September; 42(6):1179-88), SCORPION molecules (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-DART) molecules (MacroGenics, WO2008157379, WO2010080538) and Dual(ScFv)2-Fab molecules (National Research Center for Antibody Medicine—China).

Examples of Fab fusion bispecific antibodies include but are not limited to F(ab)2 molecules (Medarex/AMGEN; Deo et al J Immunol. 1998 Feb. 15; 160(4):1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, J Immunol. 2000 Dec. 15; 165(12):7050-7.) and Fab-Fv molecules (UCB-Celltech, WO 2009040562 A1).

Examples of ScFv-, diabody-based and domain antibodies include but are not limited to Bispecific T Cell Engager (BiTE) molecules (Micromet, WO2005061547), Tandem Diabody molecules (TandAb) (Affimed) Le Gall et al., Protein Eng Des Sel. 2004 April; 17(4):357-66.), Dual Affinity Retargeting Technology (DART) molecules (MacroGenics, WO2008157379, WO2010080538), Single-chain Diabody molecules (Lawrence, FEBS Lett. 1998 Apr. 3; 425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August; 88(6): 667-75.), dual targeting nanobodies (Ablynx, Hmila et al., FASEB J. 2010) and dual targeting heavy chain only domain antibodies.

In one aspect, the bispecific antibody of the invention comprises a first Fc-region comprising a first CH3 region, and a second Fc-region comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference.

As described further herein, a stable bispecific CD3× CD20 antibody can be obtained at high yield using a particular method on the basis of one homodimeric starting CD20 antibody and one homodimeric starting CD3 antibody containing only a few, fairly conservative, asymmetrical mutations in the CH3 regions. Asymmetrical mutations mean that the sequences of said first and second CH3 regions contain amino acid substitutions at non-identical positions.

In one aspect, the bispecific antibody as defined in any of the embodiments disclosed herein comprises first and second heavy chains, wherein each of said first and second heavy chain comprises at least a hinge region, a CH2 and CH3 region, wherein in said first heavy chain at least one of the amino acids in the positions corresponding to a positions selected from the group consisting of T366, L368, K370, D399, F405, Y407, and K409 in a human IgG1 heavy chain has been substituted, and in said second heavy chain at least one of the amino acids in the positions corresponding to a position selected from the group consisting of T366, L368, K370, D399, F405, Y407, and K409 in a human IgG1 heavy chain has been substituted, and wherein said first and said second heavy chains are not substituted in the same positions.

In one embodiment, the bispecific antibody as defined in any of the embodiments disclosed herein comprises first and second heavy chains, wherein (i) the amino acid in the position corresponding to F405 in a human IgG1 heavy chain is L in said first heavy chain, and the amino acid in the position corresponding to K409 in a human IgG1 heavy chain is R in said second heavy chain, or (ii) the amino acid in the position corresponding to K409 in a human IgG1 heavy chain is R in said first heavy chain, and the amino acid in the position corresponding to F405 in a human IgG1 heavy chain is L in said second heavy chain.

In one embodiment of the bispecific antibody as defined in any of the embodiments disclosed herein, the first Fc-region has an amino acid substitution at a position selected from the group consisting of: 366, 368, 370, 399, 405, 407 and 409, and the second Fc-region has an amino acid substitution at a position selected from the group consisting of: 366, 368, 370, 399, 405, 407 and 409, and wherein the first and second Fc-regions are not substituted in the same positions.

In one embodiment of the bispecific antibody as defined in any of the embodiments disclosed herein, the first Fc-region has an amino acid substitution at position 366, and said second Fc-region has an amino acid substitution at a position selected from the group consisting of: 368, 370, 399, 405, 407 and 409. In one embodiment the amino acid at position 366 is selected from Ala, Asp, Glu, His, Asn, Val, or Gln.

In one embodiment of the bispecific antibody as defined in any of the embodiments disclosed herein, the first Fc-region has an amino acid substitution at position 368, and said second Fc-region has an amino acid substitution at a position selected from the group consisting of: 366, 370, 399, 405, 407 and 409.

In one embodiment of the bispecific antibody as defined in any of the embodiments disclosed herein, the first Fc-region has an amino acid substitution at position 370, and said second Fc-region has an amino acid substitution at a position selected from the group consisting of: 366, 368, 399, 405, 407 and 409.

In one embodiment of the bispecific antibody as defined in any of the embodiments disclosed herein, the first Fc-region has an amino acid substitution at position 399, and said second Fc-region has an amino acid substitution at a position selected from the group consisting of: 366, 368, 370, 405, 407 and 409.

In one embodiment of the bispecific antibody as defined in any of the embodiments disclosed herein, the first Fc-region has an amino acid substitution at position 405, and said second Fc-region has an amino acid substitution at a position selected from the group consisting of: 366, 368, 370, 399, 407 and 409.

In one embodiment of the bispecific antibody as defined in any of the embodiments disclosed herein, the first Fc-region has an amino acid substitution at position 407, and said second Fc-region has an amino acid substitution at a position selected from the group consisting of: 366, 368, 370, 399, 405, and 409.

In one embodiment of the bispecific antibody as defined in any of the embodiments disclosed herein, the first Fc-region has an amino acid substitution at position 409, and said second Fc-region has an amino acid substitution at a position selected from the group consisting of: 366, 368, 370, 399, 405, and 407.

Accordingly, in one embodiment of the bispecific antibody as defined in any of the embodiments disclosed herein, the sequences of said first and second CH3 regions contain asymmetrical mutations, i.e. mutations at different positions in the two CH3 regions, e.g. a mutation at position 405 in one of the CH3 regions and a mutation at position 409 in the other CH3 region.

In one embodiment of the bispecific antibody as defined in any of the embodiments disclosed herein, the first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino-acid substitution at a position selected from the group consisting of: 366, 368, 370, 399, 405 and 407. In one such embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Phe, e.g. Gly, Ala, Val, Ile, Ser, Thr, Lys, Arg, His, Asp, Asn, Glu, Gln, Pro, Trp, Tyr, Cys, Lys, or Leu, at position 405. In a further embodiment hereof, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405.

In another embodiment of the bispecific antibody as defined in any of the embodiments disclosed herein, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises an amino acid other than Phe, e.g. Gly, Ala, Val, Ile, Ser, Thr, Lys, Arg, His, Asp, Asn, Glu, Gln, Pro, Trp, Tyr, Leu, Met, or Cys, at position 405 and a Lys at position 409. In a further embodiment hereof, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405 and a Lys at position 409.

In another embodiment of the bispecific antibody as defined in any of the embodiments disclosed herein, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Leu at position 405 and a Lys at position 409. In a further embodiment hereof, said first Fc-region comprises a Phe at position 405 and an Arg at position 409 and said second Fc-region comprises an amino acid other than Phe, Arg or Gly, e.g. Leu, Ala, Val, Ile, Ser, Thr, Lys, Met, His, Asp, Asn, Glu, Gln, Pro, Trp, Tyr, or Cys, at position 405 and a Lys at position 409. In another embodiment, said first Fc-region comprises Phe at position 405 and an Arg at position 409 and said second Fc-region comprises a Leu at position 405 and a Lys at position 409.

In a further embodiment of the bispecific antibody as defined in any of the embodiments disclosed herein, said first Fc-region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Lys at position 409, a Thr at position 370 and a Leu at position 405. In a further embodiment, said first Fc-region comprises an Arg at position 409 and said second Fc-region comprises a Lys at position 409, a Thr at position 370 and a Leu at position 405.

In an even further embodiment of the bispecific antibody as defined in any of the embodiments disclosed herein, said first Fc-region comprises a Lys at position 370, a Phe at position 405 and an Arg at position 409 and said second Fc-region comprises a Lys at position 409, a Thr at position 370 and a Leu at position 405.

In another embodiment of the bispecific antibody as defined in any of the embodiments disclosed herein, said first Fc-region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first Fc-region comprises an Arg at position 409 and said second Fc region comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first Fc-region comprises a Thr at position 350, a Lys at position 370, a Phe at position 405 and an Arg at position 409 and said second Fc region comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first Fc-region comprises a Thr at position 350, a Lys at position 370, a Phe at position 405 and an Arg at position 409 and said second Fc-region comprises an Ile at position 350, a Thr at position 370, a Leu at position 405 and a Lys at position 409.

In one embodiment of the bispecific antibody as defined in any of the embodiments disclosed herein, said first Fc-region has an amino acid other than Lys, Leu or Met at position 409 and said second Fc-region has an amino acid other than Phe at position 405, such as other than Phe, Arg or Gly at position 405; or said first CH3 region has an amino acid other than Lys, Leu or Met at position 409 and said second CH3 region has an amino acid other than Tyr, Asp, Glu, Phe, Lys, Gin, Arg, Ser or Thr at position 407.

In one embodiment, the bispecific antibody as defined in any of the embodiments disclosed herein comprises a first Fc-region having an amino acid other than Lys, Leu or Met at position 409 and a second Fc-region having an amino acid other than Tyr, Asp, Glu, Phe, Lys, Gin, Arg, Ser or Thr at position 407.

In one embodiment, the bispecific antibody as defined in any of the embodiments disclosed herein comprises a first Fc-region having a Tyr at position 407 and an amino acid other than Lys, Leu or Met at position 409 and a second Fc-region having an amino acid other than Tyr, Asp, Glu, Phe, Lys, Gin, Arg, Ser or Thr at position 407 and a Lys at position 409.

In one embodiment, the bispecific antibody as defined in any of the embodiments disclosed herein comprises a first Fc-region having a Tyr at position 407 and an Arg at position 409 and a second Fc-region having an amino acid other than Tyr, Asp, Glu, Phe, Lys, Gin, Arg, Ser or Thr at position 407 and a Lys at position 409.

In another embodiment, said first Fc-region has an amino acid other than Lys, Leu or Met, e.g. Gly, Ala, Val, Ile, Ser, Thr, Phe, Arg, His, Asp, Asn, Glu, Gin, Pro, Trp, Tyr, or Cys, at position 409 and said second Fc-region has an amino acid other than Tyr, Asp, Glu, Phe, Lys, Gin, Arg, Ser or Thr, e.g. Leu, Met, Gly, Ala, Val, Ile, His, Asn, Pro, Trp, or Cys, at position 407. In another embodiment, said first Fc-region has an amino acid other than Lys, Leu or Met, e.g. Gly, Ala, Val, Ile, Ser, Thr, Phe, Arg, His, Asp, Asn, Glu, Gin, Pro, Trp, Tyr, or Cys, at position 409 and said second Fc-region has an Ala, Gly, His, Ile, Leu, Met, Asn, Val or Trp at position 407.

In another embodiment of the bispecific antibody as defined in any of the embodiments disclosed herein, said first Fc-region has an amino acid other than Lys, Leu or Met, e.g. Gly, Ala, Val, Ile, Ser, Thr, Phe, Arg, His, Asp, Asn, Glu, Gin, Pro, Trp, Tyr, or Cys, at position 409 and said second Fc-region has a Gly, Leu, Met, Asn or Trp at position 407.

In another embodiment of the bispecific antibody as defined in any of the embodiments disclosed herein, said first Fc-region has a Tyr at position 407 and an amino acid other than Lys, Leu or Met, e.g. Gly, Ala, Val, Ile, Ser, Thr, Phe, Arg, His, Asp, Asn, Glu, Gin, Pro, Trp, Tyr, or Cys, at position 409 and said second Fc-region has an amino acid other than Tyr, Asp, Glu, Phe, Lys, Gin, Arg, Ser or Thr, e.g. Leu, Met, Gly, Ala, Val, Ile, His, Asn, Pro, Trp, or Cys, at position 407 and a Lys at position 409.

In another embodiment of the bispecific antibody as defined in any of the embodiments disclosed herein, said first Fc-region has a Tyr at position 407 and an amino acid other than Lys, Leu or Met, e.g. Gly, Ala, Val, Ile, Ser, Thr, Phe, Arg, His, Asp, Asn, Glu, Gin, Pro, Trp, Tyr, or Cys, at position 409 and said second Fc-region has an Ala, Gly, His, Ile, Leu, Met, Asn, Val or Trp at position 407 and a Lys at position 409.

In another embodiment of the bispecific antibody as defined in any of the embodiments disclosed herein, said first Fc-region has a Tyr at position 407 and an amino acid other than Lys, Leu or Met, e.g. Gly, Ala, Val, Ile, Ser, Thr, Phe, Arg, His, Asp, Asn, Glu, Gin, Pro, Trp, Tyr, or Cys, at position 409 and said second Fc-region has a Gly, Leu, Met, Asn or Trp at position 407 and a Lys at position 409.

In another embodiment of the bispecific antibody as defined in any of the embodiments disclosed herein, said first Fc-region has a Tyr at position 407 and an Arg at position 409 and said second Fc-region has an amino acid other than Tyr, Asp, Glu, Phe, Lys, Gin, Arg, Ser or Thr, e.g. Leu, Met, Gly, Ala, Val, Ile, His, Asn, Pro, Trp, or Cys, at position 407 and a Lys at position 409.

In another embodiment of the bispecific antibody as defined in any of the embodiments disclosed herein, said first Fc-region has a Tyr at position 407 and an Arg at position 409 and said second Fc-region has an Ala, Gly, His, Ile, Leu, Met, Asn, Val or Trp at position 407 and a Lys at position 409.

In another embodiment of the bispecific antibody as defined in any of the embodiments disclosed herein, said first Fc-region has a Tyr at position 407 and an Arg at position 409 and said second Fc-region has a Gly, Leu, Met, Asn or Trp at position 407 and a Lys at position 409.

In another embodiment of the bispecific antibody as defined in any of the embodiments disclosed herein, the first Fc-region has an amino acid other than Lys, Leu or Met, e.g. Gly, Ala, Val, Ile, Ser, Thr, Phe, Arg, His, Asp, Asn, Glu, Gin, Pro, Trp, Tyr, or Cys, at position 409, and the second Fc-region has
(i) an amino acid other than Phe, Leu and Met, e.g. Gly, Ala, Val, Ile, Ser, Thr, Lys, Arg, His, Asp, Asn, Glu, Gin, Pro, Trp, Tyr, or Cys, at position 368, or
(ii) a Trp at position 370, or
(iii) an amino acid other than Asp, Cys, Pro, Glu or Gin, e.g. Phe, Leu, Met, Gly, Ala, Val, Ile, Ser, Thr, Lys, Arg, His, Asn, Trp, Tyr, or Cys, at position 399 or
(iv) an amino acid other than Lys, Arg, Ser, Thr, or Trp, e.g. Phe, Leu, Met, Ala, Val, Gly, Ile, Asn, His, Asp, Glu, Gin, Pro, Tyr, or Cys, at position 366.

In one embodiment, the first Fc-region has an Arg, Ala, His or Gly at position 409, and the second Fc region has
(i) a Lys, Gin, Ala, Asp, Glu, Gly, His, Ile, Asn, Arg, Ser, Thr, Val, or Trp at position 368, or
(ii) a Trp at position 370, or
(iii) an Ala, Gly, Ile, Leu, Met, Asn, Ser, Thr, Trp, Phe, His, Lys, Arg or Tyr at position 399, or
(iv) an Ala, Asp, Glu, His, Asn, Val, Gin, Phe, Gly, Ile, Leu, Met, or Tyr at position 366.

In one embodiment, the first Fc-region has an Arg at position 409, and the second Fc region has
(i) an Asp, Glu, Gly, Asn, Arg, Ser, Thr, Val, or Trp at position 368, or
(ii) a Trp at position 370, or
(iii) a Phe, His, Lys, Arg or Tyr at position 399, or
(iv) an Ala, Asp, Glu, His, Asn, Val, Gin at position 366.

In addition to the above-specified amino-acid substitutions, said first and second Fc regions may contain further amino-acid substitutions, deletion or insertions relative to wild-type Fc sequences.

In a further embodiment, said first and second Fab-arms (or heavy chain constant domains) comprising the first and second Fc regions comprise, except for the specified mutations, a CH3 sequence independently selected from the following: (IgG1m(a)) (SEQ ID NO:60), (IgG1m(f)) (SEQ ID NO:61), and (IgG1m(ax)) (SEQ ID NO:62).

In one embodiment, neither said first nor said second Fc-region comprises a Cys-Pro-Ser-Cys sequence in the (core) hinge region.

In a further embodiment, both said first and said second Fc-region comprise a Cys-Pro-Pro-Cys sequence in the (core) hinge region.

In separate and specific embodiments, one or both Fab arms comprise a heavy-chain constant region sequence independently selected from SEQ ID NO:63, 64, 65, 66, 67, 68, 69, 70, and 71 (see Table 1).

In one embodiment of the bispecific antibody according to any of the embodiments as disclosed herein, (a) the first antigen-binding region comprises heavy chain variable (VH) region CDR1, CDR2, and CDR3 having the sequences as set forth in SEQ ID NOs:1, 2, and 3, respectively, and light chain variable (VL) region CDR1, CDR2, and CDR3 having the sequences as set forth in SEQ ID NO:4, the sequence GTN, and the sequence as set forth in SEQ ID NO:5, respectively, and (b) the second antigen-binding region which binds to human CD20 comprises the VH CDR1 region of SEQ ID NO:32, the VH CDR2 region of SEQ ID NO:33, the VH CDR3 region of SEQ ID NO:34, the VL CDR1 region of SEQ ID NO:35, the VL CDR2 region of DAS, and the VL CDR3 region of SEQ ID NO:36, respectively.

In one embodiment of the bispecific antibody according to any of the embodiments as disclosed herein, (a) the first antigen-binding region comprises the VH sequence as set forth in SEQ ID NO:6, and a VL sequence as set forth in SEQ ID NO:10, and (b) the second antigen-binding region comprises the VH sequence as set forth in SEQ ID NO:27, and the VL sequence as set forth in SEQ ID NO:28.

In one embodiment of the bispecific antibody as defined in any of the embodiments disclosed herein the first antigen-binding region is a Fab arm derived from IgG1-huCD3-H1L1-FEAL, and the second antigen-binding region is a Fab arm derived from IgG1-7D8-FEAR.

In one embodiment of the bispecific antibody as defined in any of the embodiments disclosed herein the first binding arm is a half-molecule antibody (i.e. comprising one heavy and one light chain) derived from IgG1-huCD3-H1L1-FEAL, and the second binding arm is a half-molecule antibody derived from IgG1-7D8-FEAR.

In one embodiment of the bispecific antibody as defined in any of the embodiments disclosed herein the first binding arm is a half-molecule antibody derived from IgG1-huCD3-H1L1-FEAR, and the second binding arm is a half-molecule antibody derived from IgG1-7D8-FEAL.

Methods of Preparing Bispecific Antibodies

Traditional methods such as the hybrid hybridoma and chemical conjugation methods (Marvin and Zhu (2005) Acta Pharmacol Sin 26:649) can be used in the preparation of the bispecific antibodies of the invention. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific, product, upon co-expression of different antibody constructs can also be used, e.g., the method described by Lindhofer et al. (1995 J Immunol 155:219). Fusion of rat and mouse hydridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing the bispecific CD3×CD20 antibodies of the present invention includes the methods described in WO2011131746 and WO13060867 (Genmab) comprising the following steps:

a) providing a first antibody comprising an Fc region, said Fc region comprising a first CH3 region;

b) providing a second antibody comprising a second Fc region, said Fc region comprising a second CH3 region, wherein the first antibody is a CD3 antibody and the second antibody is a CD20 antibody, or vice versa; wherein the sequences of said first and second CH3 regions are different and are such that the heterodimeric interaction between said first and second CH3 regions is stronger than each of the homodimeric interactions of said first and second CH3 regions;

c) incubating said first antibody together with said second antibody under reducing conditions; and d) obtaining said bispecific CD3×CD20 antibody.

In one embodiment, the said first antibody together with said second antibody are incubated under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies are reduced and the resulting cysteines are then able to form inter heavy-chain disulfide bond with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a further embodiment, step c) comprises restoring the conditions to become non-reducing or less reducing, for example by removal of a reducing agent, e.g. by desalting.

For this method any of the CD3 and CD20 antibodies described above may be used including first and second CD3 and CD20 antibodies, respectively, comprising a first and/or second Fc region. Examples of such first and second Fc regions, including combination of such first and second Fc regions may include any of those described above. In a particular embodiment the first and second CD3 and CD20 antibodies, respectively, may be chosen so as to obtain a bispecific antibody as described herein.

In one embodiment of this method, said first and/or second antibodies are full-length antibodies.

The Fc regions of the first and second antibodies may be of any isotype, including, but not limited to, IgG1, IgG2, IgG3 or IgG4. In one embodiment of this method, the Fc regions of both said first and said second antibodies are of the IgG1 isotype. In another embodiment, one of the Fc regions of said antibodies is of the IgG1 isotype and the other of the IgG4 isotype. In the latter embodiment, the resulting bispecific antibody comprises an Fc region of an IgG1 and an Fc region of IgG4 and may thus have interesting intermediate properties with respect to activation of effector functions.

In a further embodiment, one of the antibody starting proteins has been engineered to not bind Protein A, thus allowing to separate the heterodimeric protein from said homodimeric starting protein by passing the product over a protein A column.

As described above, the sequences of the first and second CH3 regions of the homodimeric starting antibodies are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference in their entirety.

In particular, a stable bispecific CD3×CD20 antibody can be obtained at high yield using the above method of the invention on the basis of two homodimeric starting antibodies which bind CD3 and CD20, respectively, and contain only a few, fairly conservative, asymmetrical mutations in the CH3 regions. Asymmetrical mutations mean that the sequences of said first and second CH3 regions contain amino acid substitutions at non-identical positions.

The bispecific antibodies of the invention may also be obtained by co-expression of constructs encoding the first and second polypeptides in a single cell. Thus, in a further aspect, the invention relates to a method for producing a bispecific antibody, said method comprising the following steps:

a) providing a first nucleic-acid construct encoding a first polypeptide comprising a first Fc region and a first antigen-binding region of a first antibody heavy chain, said first Fc region comprising a first CH3 region, b) providing a second nucleic-acid construct encoding a second polypeptide comprising a second Fc region and a second antigen-binding region of a second antibody heavy chain, said second Fc region comprising a second CH3 region, wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407, optionally wherein said first and second nucleic acid constructs encode light chain sequences of said first and second antibodies c) co-expressing said first and second nucleic-acid constructs in a host cell, and d) obtaining said heterodimeric protein from the cell culture.

Thus, the present invention also relates to a recombinant eukaryotic or prokaryotic host cell which produces a bispecific antibody of the present invention.

In one embodiment of the present invention, the bispecific antibody is obtained by any of the methods according to the present invention.

Suitable expression vectors, including promoters, enhancers, etc., and suitable host cells for the production of antibodies are well-known in the art. Examples of host cells include yeast, bacterial and mammalian cells, such as CHO or HEK cells.

In one embodiment, the bispecific antibody as defined in any of the embodiments disclosed herein comprises first and second CH3 regions, except for the specified mutations, comprising the sequence of SEQ ID NO:60 (IgG1m(a)).

In one embodiment, the bispecific antibody as defined in any of the embodiments disclosed herein comprises a first Fc-region and a second Fc-region, wherein neither said first nor said second Fc-region comprises a Cys-Pro-Ser-Cys sequence in the hinge region.

In one embodiment, the bispecific antibody as defined in any of the embodiments disclosed herein comprises a first Fc-region and a second Fc-region, wherein both of said first and said second Fc-region comprise a Cys-Pro-Pro-Cys sequence in the hinge region.

In one embodiment, the bispecific antibody as defined in any of the embodiments disclosed herein comprises a first Fc-region and a second Fc-region, wherein the first and second Fc-regions are human antibody Fc-regions.

In one embodiment, the bispecific antibody as defined in any of the embodiments disclosed herein comprises a first Fc-region and a second Fc-region, wherein said first and second Fc region, except for the specified mutations, comprise a sequence independently selected from the group consisting of SEQ ID NOS:63, 64, 65, 66, 67, 68, 69, 70, and 71.

In one embodiment, the bispecific antibody as defined in any of the embodiments disclosed herein comprises a first Fc-region and a second Fc-region, wherein the first and second antigen-binding regions comprise human antibody VH sequences and, optionally, human antibody VL sequences.

In one embodiment, the bispecific antibody as defined in any of the embodiments disclosed herein comprises a first Fc-region and a second Fc-region, wherein the first and second antigen-binding regions are from heavy-chain antibodies.

In one embodiment, the bispecific antibody as defined in any of the embodiments disclosed herein comprises a first Fc-region and a second Fc-region, wherein the first and second antigen-binding regions comprise a first and second light chain.

In further embodiments, the co-expression method according to the invention comprises any of the further features described under the in vitro method above.

In a further aspect, the invention relates to an expression vector comprising the first and second nucleic-acid constructs specified herein above. In a further embodiment, the expression vector further comprises a nucleotide sequence encoding the constant region of a light chain, a heavy chain or both light and heavy chains of an antibody, e.g. a human antibody.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a CD20 or a CD3 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaP04-precipitated construct (as described in for instance WO200046147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the CD20 antibody and/or the CD3 antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

The expression vector may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the CD20 and/or CD3 antibody-encoding expression vector may be positioned in and/or delivered to the host cell or host animal via a viral vector.

In an even further aspect, the invention relates to a host cell comprising the first and second nucleic-acid constructs specified herein above.

Thus the present invention also relates to a recombinant eukaryotic or prokaryotic host cell which produces a bispecific antibody of the present invention, such as a transfectoma.

The first CD20-specific antibody may be expressed in a recombinant eukaryotic or prokaryotic host cell, such as a transfectoma, which produces an antibody of the invention as defined herein or a bispecific antibody of the invention as defined herein. The CD3-specific antibody may likewise be expressed in a recombinant eukaryotic or prokaryotic host cell, such as a transfectoma, which produces an antibody of the invention as defined herein or a bispecific antibody of the invention as defined herein.

Examples of host cells include yeast, bacterial, plant and mammalian cells, such as CHO, CHO-S, HEK, HEK293, HEK-293F, Expi293F, PER.C6 or NS0 cells or lymphocytic cells.

For example, in one embodiment, the host cell may comprise a first and second nucleic acid construct stably integrated into the cellular genome. In another embodiment, the present invention provides a cell comprising a non-integrated nucleic acid, such as a plasmid, cosmid, phagemid, or linear expression element, which comprises a first and second nucleic acid construct as specified above.

In an even further aspect, the invention relates to a transgenic non-human animal or plant comprising nucleic acids encoding one or two sets of a human heavy chain and a human light chain, wherein the animal or plant produces a bispecific antibody of the invention.

In a further aspect, the invention relates to a hybridoma which produces an antibody for use in a bispecific antibody of the invention as defined herein. In an even further aspect, the invention relates to a transgenic non-human animal or plant comprising nucleic acids encoding one or two sets of a human heavy chain and a human light chain, wherein the animal or plant produces an antibody for use in a bispecific antibody or a bispecific antibody of the invention.

In one aspect, the invention relates to a nucleic acid construct encoding one or more amino acid sequences set out in Table 1.

In one aspect, the invention relates to an expression vector comprising
  (i) a nucleic acid sequence encoding a heavy chain sequence of a first binding arm according to any one of the embodiments disclosed herein;
  (ii) a nucleic acid sequence encoding a light chain sequence of a first binding arm according to any one of the embodiments disclosed herein;
  (iii) a nucleic acid sequence encoding a heavy chain sequence of a second binding arm according to any one of the embodiments disclosed herein;
  (iv) a nucleic acid sequence encoding a light chain sequence of a second binding arm according to any one of the of the embodiments disclosed herein;
  (v) the nucleic acid set forth in (i) and the nucleic acid set forth in (ii);
  (vi) the nucleic acid set forth in (iii) and the nucleic acid set forth in (iv).
  (vii) the nucleic acid set forth in (i), (ii), (iii) and (iv).

In one aspect, the invention relates to a method for producing a bispecific antibody according to any one of the embodiments as disclosed herein, comprising the steps of
  a) culturing a host cell as disclosed herein comprising an expression vector as disclosed herein expressing the first antibody as disclosed herein and purifying said antibody from the culture media;
  b) culturing a host cell as disclosed herein comprising an expression vector as disclosed herein expressing the second antibody as disclosed herein and purifying said antibody from the culture media;
  c) incubating said first antibody together with said second antibody under reducing conditions sufficient to allow the cysteines in the hinge region to undergo disulfide-bond isomerization, and
  d) obtaining said bispecific antibody.

In one aspect, the invention relates to a host cell comprising an expression vector as defined above. In one embodiment, the host cell is a recombinant eukaryotic, recombinant prokaryotic, or recombinant microbial host cell.

Fc Regions

In one aspect of the present invention, the bispecific CD3×CD20 antibody according to the present invention further comprises a first Fc region and a second Fc region which may be comprised in a first and a second Fab-arm which respectively further comprise the first and second antigen-binding regions described above (or vice versa).

In another aspect of the present invention, the bispecific CD3×CD20 antibody comprises a first and a second Fab-arm comprising a first and a second antigen-binding region, respectively. The bispecific CD3×CD20 antibody further comprises a first and a second Fc region. In one aspect of the present invention, the bispecific CD3×CD20 antibody comprises the first Fab-arm comprising the first antigen-binding region and the first Fc region, and the second Fab-arm comprising the second antigen-binding region and the second Fc region.

In another aspect of the present invention, the bispecific CD3×CD20 antibody comprises the second Fab-arm comprising the second antigen-binding region and the first Fc region, and the first Fab-arm comprising the first antigen-binding region and the second Fc region.

The first and second Fc-regions may each be of any isotype, including, but not limited to, IgG1, IgG2, IgG3 and IgG4, and may comprise one or more mutations or modifications. In one embodiment, each of the first and second Fc regions is of the IgG4 isotype or derived therefrom, optionally with one or more mutations or modifications. In one embodiment, each of the first and second Fc regions is of the IgG1 isotype or derived therefrom, optionally with one or more mutations or modifications. In another embodiment, one of the Fc regions is of the IgG1 isotype and the other of the IgG4 isotype, or is derived from such respective isotypes, optionally with one or more mutations or modifications.

In one embodiment, one or both of the Fc regions comprise a mutation removing the acceptor site for Asn-linked glycosylation or is otherwise manipulated to change the glycosylation properties. For example, in an IgG1 Fc-region, an N297Q mutation can be used to remove an Asn-linked glycosylation site. Accordingly, in a specific embodiment, one or both Fc-regions comprise an IgG1 wildtype sequence with an N297Q mutation (SEQ ID NO:66, see Table 1).

In one embodiment, one or both Fc-regions are effector-function-deficient. For example, the Fc-region(s) may be of an IgG4 isotype, or a non-IgG4 type, e.g. IgG1, IgG2 or IgG3, which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24):12161-12168 (2001). In one embodiment, one or both Fc-regions comprise an IgG1 wildtype sequence (SEQ ID NO:63, see Table 1).

The bispecific antibody according to the present invention may comprise modifications in the Fc region. When a bispecific antibody comprises such modifications it may become an inert, or non-activating, bispecific antibody. The term "inertness", "inert" or "non-activating" as used herein, refers to an Fc region which is at least not able to bind any Fcγ receptors, induce Fc-mediated cross-linking of FcRs, or induce FcR-mediated cross-linking of target antigens via two Fc regions of individual antibodies, or is not able to bind C1q. The inertness of an Fc region of a humanized or chimeric CD3 antibody is advantageously tested using the antibody in a monospecific format.

Several variants can be constructed to make the Fc region of an antibody inactive for interactions with Fcγ (gamma) receptors and C1q for therapeutic antibody development. Examples of such variants are described herein.

Thus, in one embodiment, the antibody comprises an Fc region which has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

Thus, amino acids in the Fc region that play a dominant role in the interactions with C1q and the Fcγ receptors may be modified. Examples of amino acid positions that may be modified include positions L234, L235 and P331. Combinations thereof, such as L234F/L235E/P331S, can cause a profound decrease in binding to human CD64, CD32A, CD16 and C1q.

Hence, in one embodiment, the amino acid in at least one position corresponding to L234, L235 and P331, may be A, A and S, respectively (Xu et al., 2000, Cell Immunol. 200(1):16-26; Oganesyan et al., 2008, Acta Cryst. (D64): 700-4). Also, L234F and L235E amino acid substitutions can result in Fc regions with abrogated interactions with Fcγ receptors and C1q (Canfield et al., 1991, J. Exp. Med. (173):1483-91; Duncan et al., 1988, Nature (332):738-40). Hence, in one embodiment, the amino acids in the positions corresponding to L234 and L235, may be F and E, respectively. A D265A amino acid substitution can decrease binding to all Fc gamma Receptors and prevent ADCC (Shields et al., 2001, J. Biol. Chem. (276):6591-604). Hence, in one embodiment, the amino acid in the position corresponding to D265 may be A. Binding to C1q can be abrogated by mutating positions D270, K322, P329, and P331. Mutating these positions to either D270A or K322A or P329A or P331A can make the antibody deficient in CDC activity Idusogie E E, et al., 2000, J Immunol. 164: 4178-84). Hence, in one embodiment, the amino acids in at least one position corresponding to D270, K322, P329 and P331, may be A, A, A, and A, respectively.

An alternative approach to minimize the interaction of the Fc region with Fcγ receptors and C1q is by removal of the glycosylation site of an antibody. Mutating position N297 to e.g. Q, A, or E removes a glycosylation site which is critical for IgG-Fc gamma Receptor interactions. Hence, in one embodiment, the amino acid in a position corresponding to N297, may be G, Q, A or E Leabman et al., 2013, MAbs;

5(6):896-903). Another alternative approach to minimize interaction of the Fc region with Fcγ receptors may be obtained by the following mutations; P238A, A327Q, P329A or E233P/L234V/L235A/G236del (Shields et al., 2001, J. Biol. Chem. (276):6591-604).

Alternatively, human IgG2 and IgG4 subclasses are considered naturally compromised in their interactions with C1q and Fc gamma Receptors although interactions with Fcγ receptors were reported (Parren et al., 1992, J. Clin Invest. 90: 1537-1546; Bruhns et al., 2009, Blood 113: 3716-3725). Mutations abrogating these residual interactions can be made in both isotypes, resulting in reduction of unwanted side-effects associated with FcR binding. For IgG2, these include L234A and G237A, and for IgG4, L235E. Hence, in one embodiment, the amino acid in a position corresponding to L234 and G237 in a human IgG2 heavy chain, may be A and A, respectively. In one embodiment, the amino acid in a position corresponding to L235 in a human IgG4 heavy chain, may be E.

Other approaches to further minimize the interaction with Fc gamma Receptors and C1q in IgG2 antibodies include those described in WO2011066501 and Lightle, S., et al., 2010, Protein Science (19):753-62.

The hinge region of the antibody can also be of importance with respect to interactions with Fcγ receptors and complement (Brekke et al., 2006, J Immunol 177:1129-1138; Dall'Acqua W F, et al., 2006, J Immunol 177:1129-1138). Accordingly, mutations in or deletion of the hinge region can influence effector functions of an antibody.

The term "cross-linking" as used herein, refers to the indirect bridging of antibody Fab arm(s) (monovalently or bivalently) bound to the target antigen by an FcR-bearing cell through binding to the antibody Fc region. Thus, an antibody which binds its target antigen on target antigen-bearing cells may cross-link that cell with another cell expressing FcRs.

The term "unspecific killing" as used herein, refers to the killing of cells by the cytotoxic function of T cells or other effector cells, through tumor target antigen-independent activation of said cells. Thus, by unspecific killing is meant that effector cells, e.g. cytotoxic T cells, are activated and induce cytotoxicity independent of tumor target binding, for example by binding of the antibody to CD3 and an FcγR.

Thus, in one embodiment, the bispecific antibody comprises a first and a second immunoglobulin heavy chain, wherein in at least one of said first and second immunoglobulin heavy chains one or more amino acids in the positions corresponding to positions L234, L235, D265, N297, and P331 in a human IgG1 heavy chain, are not L, L, D, N, and P, respectively.

In one embodiment, in both the first and second heavy chains one or more amino acids in the position corresponding to positions L234, L235, D265, N297, and P331 in a human IgG1 heavy chain, are not L, L, D, N, and P, respectively.

In another embodiment, in at least one of the first and second heavy chains one or more amino acids in the positions corresponding to positions L234, L235 and D265 in a human IgG1 heavy chain, are not L, L and D, respectively, and the amino acids in the positions corresponding to N297 and P331 in a human IgG1 heavy chain, are N and P, respectively.

The term "amino acid corresponding to positions" as used herein refers to an amino acid position number in a human IgG1 heavy chain. Corresponding amino acid positions in other immunoglobulins may be found by alignment with human IgG1. Unless otherwise stated or contradicted by context, the amino acids of the constant region sequences are herein numbered according to the EU-index of numbering (described in Kabat, E. A. et al., 1991, Sequences of proteins of immunological interest. 5th Edition—US Department of Health and Human Services, NIH publication No. 91-3242, pp 662, 680, 689). Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

In the context of the present invention, the amino acid may be defined as described above.

The term "the amino acid is not" or similar wording when referring to amino acids in a heavy chain is to be understood to mean that the amino acid is any other amino acid than the specific amino acid mentioned. For example, the amino acid in the position corresponding to L234 in a human IgG1 heavy chain is not L, means that the amino acid may be any of the other naturally or non-naturally occurring amino acids than L.

In one embodiment, in at least one of said first and second heavy chains the amino acid in the position corresponding to position D265 in a human IgG1 heavy chain, is not D.

In one embodiment, in at least one of the first and second heavy chains the amino acid in the position corresponding to D265 in a human IgG1 heavy chain, is not D, and the amino acids in the positions corresponding to positions N297 and P331 in a human IgG1 heavy chain, are N and P, respectively.

In one embodiment, in at least one of said first and second heavy chains the amino acids in the positions corresponding to position D265 in a human IgG1 heavy chain is hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second heavy chains the amino acid in the position corresponding to position D265 in a human IgG1 heavy chain is selected from the group of amino acids consisting of; A, C, F, G, H, I, L, M, R, T, V, W and Y.

The term "polar" as used herein in relation to amino acid residues, refers to any amino acid residue selected from the group consisting of; C, D, E, H, K, N, Q, R, S, and T. Thus, in one embodiment, in at least one of said first and second heavy chains the amino acid in the position corresponding to position D265 in a human heavy chain is selected from the group consisting of; C, E, H, K, N, Q, R, S, and T.

In another embodiment, in at least one of said first and second heavy chains the amino acid in the position corresponding to position D265 in a human IgG1 heavy chain is an aliphatic uncharged, aromatic or acidic amino acid.

The term "aliphatic uncharged" as used herein in relation to amino acid residues, refers to any amino acid residue selected from the group consisting of: A, G, I, L, and V. Thus, in one embodiment, in at least one of said first and second heavy chains the amino acid in the position corresponding to position D265 in a human IgG1 heavy chain is selected from the group consisting of; A, G, I, L, and V.

The term "aromatic" as used herein in relation to amino acid residues, refers to any amino acid residue selected from the group consisting of: F, T, and W. Thus, in one embodiment, in at least one of said first and second heavy chains the amino acid in the position corresponding to position D265 in a human IgG1 heavy chain is selected from the group consisting of; F, T, and W.

The term "acidic" as used herein in relation to amino acid residues, refers to any amino acid residue chosen from the group consisting of: D and E. Thus, in one embodiment, in at least one of said first and second heavy chains the amino acid in the position corresponding to position D265 in a human IgG1 heavy chain is selected from the group consisting of; D and E.

In a particular embodiment, in at least one of said first and second heavy chains the amino acid in the position corresponding to position D265 in a human IgG1 heavy chain is selected from the group consisting of; A, E, F, G, I, L, T, V, and W.

In one embodiment, in both said first and second heavy chains the amino acid in the position corresponding to position D265 in a human IgG1 heavy chain, is not D.

In one embodiment, in both the first and second heavy chains the amino acid in the position corresponding to D265 in a human IgG1 heavy chain, is not D, and the amino acids in the positions corresponding to positions N297 and P331 in a human IgG1 heavy chain, are N and P, respectively.

In one embodiment, in both said first and second heavy chains the amino acid in the position corresponding to position D265 in a human IgG1 heavy chain is hydrophobic or polar amino acid.

Thus, in one embodiment, in both said first and second heavy chains the amino acid in the position corresponding to position D265 in a human IgG1 heavy chain is selected from the group of amino acids consisting of; A, C, F, G, H, I, L, M, R, T, V, W and Y.

Thus, in one embodiment, in both said first and second heavy chains the amino acid in the position corresponding to position D265 in a human heavy chain is selected from the group consisting of; C, E, H, K, N, Q, R, S, and T. In one embodiment, in both said first and second heavy chains the amino acid in the position corresponding to position D265 in a human IgG1 heavy chain is selected from the group of amino acids consisting of; A, C, F, G, H, I, L, M, R, T, V, W and Y.

In one embodiment, in both said first and second heavy chains the amino acids in the positions corresponding to position D265 in a human heavy chain is selected from the group consisting of; C, E, H, K, N, Q, R, S, and T.

In another embodiment, in both said first and second heavy chains the amino acid in the position corresponding to position D265 in a human IgG1 heavy chain is aliphatic uncharged, aromatic or acidic amino acids.

Thus, in one embodiment, in both said first and second heavy chains the amino acid in the position corresponding to position D265 in a human IgG1 heavy chain is selected from the group consisting of; A, G, I, L, and V.

Thus, in one embodiment, in both said first and second heavy chains the amino acid in the position corresponding to position D265 in a human IgG1 heavy chain is selected from the group consisting of; F, T, and W.

Thus, in one embodiment, in both said first and second heavy chains the amino acid in the position corresponding to position D265 in a human IgG1 heavy chain are selected from the group consisting of; D and E.

In a particular embodiment, in both said first and second heavy chains the amino acid in the position corresponding to position D265 in a human IgG1 heavy chain is selected from the group consisting of; A, E, F, G, I, L, T, V, and W.

In further embodiment, in at least one of said first and second heavy chains the amino acid in the position corresponding to position N297 in a human IgG1 heavy chain, is not N.

In one embodiment, in at least one of the first and second heavy chains the amino acid in the position corresponding to N297 in a human IgG1 heavy chain, is not N, and the amino acid in the position corresponding to position P331 in a human IgG1 heavy chain, is P.

In one embodiment, in both said first and second heavy chains the amino acid in the position corresponding to positions N297 in a human IgG1 heavy chain, is not N.

In one embodiment, in both the first and second heavy chains the amino acid in the position corresponding to N297 in a human IgG1 heavy chain, is not N, and the amino acid in the position corresponding to position P331 in a human IgG1 heavy chain, is P.

In further embodiment, in at least one of said first and second heavy chains the amino acids in the positions corresponding to positions L234 and L235 in a human IgG1 heavy chain, are not L and L, respectively.

In one embodiment, in at least one of the first and second heavy chains the amino acids in the positions corresponding to L234 and L235 in a human IgG1 heavy chain, are not L and L, respectively, and the amino acids in the positions corresponding to positions N297 and P331 in a human IgG1 heavy chain, are N and P, respectively.

In one embodiment, in at least one of said first and second heavy chains the amino acids corresponding to positions L234 and L235 in a human IgG1 heavy chain are selected from the group consisting of; A, C, D, E, F, G, H, I, K, M, N, P, Q, R, S, T, Y, V.

In one embodiment, in at least one of said first and second heavy chains the amino acids in the positions corresponding to positions L234 and L235 in a human IgG1 heavy chain are hydrophobic or polar amino acids.

Thus, in one embodiment, in at least one of said first and second heavy chains the amino acids in the positions corresponding to positions L234 and L235 in a human IgG1 heavy chain are each selected from the group consisting of; A, C, F, G, H, I, M, R, T, V, W, and Y.

Thus, in one embodiment, in at least one of said first and second heavy chains the amino acids in the positions corresponding to positions L234 and L235 in a human IgG1 heavy chain are each selected from the group of amino acids consisting of; C, D, E, H, K, N, Q, R, S, and T.

In a particular embodiment, in at least one of said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y.

In one embodiment, in both said first and second heavy chains the amino acids in the positions corresponding to positions L234 and L235 in a human IgG1 heavy chain, are not L and L, respectively.

In one embodiment, in both the first and second heavy chains the amino acids in the positions corresponding to L234 and L235 in a human IgG1 heavy chain, are not L and L, respectively, and the amino acids in the positions corresponding to positions N297 and P331 in a human IgG1 heavy chain, are N and P, respectively.

In one embodiment, in both said first and second heavy chains the amino acids in the positions corresponding to L234 and L235 in a human IgG1 heavy chain are hydrophobic or polar amino acids.

In one embodiment, in both said first and second heavy chains the amino acids in the positions corresponding to positions L234 and L235 in a human IgG1 heavy chain are each selected from the group consisting of; A, C, F, G, H, I, M, R, T, V, W, and Y.

In one embodiment, in both said first and second heavy chains the amino acids in the positions corresponding to positions L234 and L235 in a human IgG1 heavy chain are each selected from the group of amino acids consisting of; C, D, E, H, K, N, Q, R, S, and T.

In a particular embodiment, in both said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y.

In another embodiment, in at least one of said first and second heavy chains the amino acids in the positions corresponding to positions L234 and L235 in a human IgG1 heavy chain are aliphatic uncharged, aromatic or acidic amino acids.

Thus, in one embodiment, in at least one of said first and second heavy chains the amino acids in the positions corresponding to positions L234 and L235 in a human IgG1 heavy chain are each selected from the group consisting of; A, G, I, and V.

Thus, in one embodiment, in at least one of said first and second heavy chains the amino acids in the positions corresponding to positions L234 and L235 in a human IgG1 heavy chain are each selected from the group consisting of; F, T, and W.

Thus, in one embodiment, in at least one of said first and second heavy chains the amino acids in the positions corresponding to positions L234 and L235 in a human IgG1 heavy chain are each selected from the group consisting of; D and E.

In a particular embodiment, in at least one of said first and second heavy chains the amino acids in the positions corresponding to L234 and L235 are each selected from the group consisting of; A, D, E, F, G, I, T, V, and W.

In one embodiment, in at least one of said first and second heavy chains the amino acids in the positions corresponding to positions L234 and L235 in a human IgG1 heavy chain, are F and E; or A and A, respectively.

In one embodiment, in at least one of the first and second heavy chains the amino acids in the positions corresponding to L234 and L235 in a human IgG1 heavy chain, are F and E; or A and A, respectively, and the amino acids in the positions corresponding to positions N297 and P331 in a human IgG1 heavy chain, are N and P, respectively.

In one embodiment, in both said first and second heavy chains the amino acids in the positions corresponding to positions L234 and L235 in a human IgG1 heavy chain, are F and E; or A and A, respectively.

In one embodiment, in both the first and second heavy chains the amino acids in the positions corresponding to L234 and L235 in a human IgG1 heavy chain, are F and E; or A and A, respectively, and the amino acids in the positions corresponding to positions N297 and P331 in a human IgG1 heavy chain, are N and P, respectively.

In a particular embodiment, in at least one of said first and second heavy chains the amino acids in the positions corresponding to positions L234 and L235 in a human IgG1 heavy chain, are F and E, respectively.

In one embodiment, in both said first and second heavy chains the amino acids in the positions corresponding to positions L234 and L235 in a human IgG1 heavy chain, are F and E, respectively.

In one embodiment, in at least one of said first and second heavy chains at least the amino acids in the positions corresponding to positions L234 and L235 in a human IgG1 heavy chain, are A and A, respectively.

In one embodiment, in both said first and second heavy chains at least the amino acids in the positions corresponding to positions L234 and L235 in a human IgG1 heavy chain, are A and A, respectively.

In one embodiment, in at least one of said first and second heavy chains the amino acids in the positions corresponding to positions L234, L235, and D265 in a human IgG1 heavy chain, are not L, L, and D, respectively.

In one embodiment, in at least one of the first and second heavy chains the amino acids in the positions corresponding to L234, L235, and D265 in a human IgG1 heavy chain, are not L, L and D, respectively, and the amino acids in the positions corresponding to positions N297 and P331 in a human IgG1 heavy chain, are N and P, respectively.

In one embodiment, in at least one of said first and second heavy chains the amino acids corresponding to positions L234 and L235 in a human IgG1 heavy chain are selected from the group consisting of; A, C, D, E, F, G, H, I, K, M, N, P, Q, R, S, T, Y, V, and W, and the amino acid corresponding to position D265 is selected from the group consisting of; A, C, E, F, G, H, I, K, L, M, N, P, Q, R, S, T, Y, V, and W.

In one embodiment, in at least one of said first and second heavy chains the amino acids in the positions corresponding to positions L234, L235 and D265 in a human IgG1 heavy chain are hydrophobic or polar amino acids.

Thus, in one embodiment, in at least one of said first and second heavy chains the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

Thus, in one embodiment, in at least one of said first and second heavy chains the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in at least one of said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 in a human IgG1 heavy chain is selected from the group consisting of; A, C, E, F, G, H, I, K, L, M, N, Q, R, S, T, V, W, and Y.

In one embodiment, in both said first and second heavy chains the amino acids in the positions corresponding to L234, L235, and D265 in a human IgG1 heavy chain are hydrophobic or polar amino acids.

In one embodiment, in both said first and second heavy chains the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

In one embodiment, in both said first and second heavy chains the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in both said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 in a human IgG1 heavy chain is selected from the group consisting of; A, C, E, F, G, H, I, K, L, M, N, Q, R, S, T, V, W, and Y.

In another embodiment, in at least one of said first and second heavy chains the amino acids in the positions corresponding to positions L234, L235 and D265 in a human IgG1 heavy chain are aliphatic uncharged, aromatic or acidic amino acids.

Thus, in one embodiment, in at least one of said first and second heavy chains the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

Thus, in one embodiment, in at least one of said first and second heavy chains the amino acids in the positions corresponding to positions L234, L235 and D265 in a human IgG1 heavy chain are each selected from the group consisting of; F, T, and W.

Thus, in one embodiment, in at least one of said first and second heavy chains the amino acids in the positions corresponding to positions L234, L235, and D265 in a human IgG1 heavy chain are each selected from the group consisting of; D and E.

In a particular embodiment, in at least one of said first and second heavy chains the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In one embodiment, in both said first and second heavy chains the amino acids in the positions corresponding to positions L234, L235 and D265 in a human IgG1 heavy chain, are not L, L, and D, respectively.

In one embodiment, in both the first and second heavy chains the amino acids in the positions corresponding to L234, L235, and D265 in a human IgG1 heavy chain, are not L, L, and D, respectively, and the amino acids in the positions corresponding to positions N297 and P331 in a human IgG1 heavy chain, are N and P, respectively.

In one embodiment, in both said first and second heavy chains the amino acids in the positions corresponding to L234, L235, and D265 in a human IgG1 heavy chain are aliphatic uncharged, aromatic or acidic amino acids.

In one embodiment, in both said first and second heavy chains the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

In one embodiment, in both said first and second heavy chains the amino acids in the positions corresponding to positions L234, L235, and D265 in a human IgG1 heavy chain are each selected from the group consisting of; D and E.

In a particular embodiment, in both said first and second heavy chains the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In one embodiment, in at least one of said first and second heavy chains the amino acids in the positions corresponding to positions L234, L235, and D265 in a human IgG1 heavy chain, are F, E, and A; or A, A, and A, respectively.

In one embodiment, in at least one of the first and second heavy chains the amino acids in the positions corresponding to L234, L235, and D265 in a human IgG1 heavy chain, are F, E, and A; or A, A, and A, respectively, and the amino acids in the positions corresponding to positions N297 and P331 in a human IgG1 heavy chain, are N and P, respectively.

In one embodiment, in both said first and second heavy chains the amino acids in the positions corresponding to positions L234, L235, and D265 in a human IgG1 heavy chain, are F, E, and A; or A, A, and A, respectively.

In one embodiment, in both the first and second heavy chains the amino acids in the positions corresponding to L234, L235, and D265 in a human IgG1 heavy chain, are F, E, and A; or A, A, and A, respectively, and the amino acids in the positions corresponding to positions N297 and P331 in a human IgG1 heavy chain, are N and P, respectively.

In a particular embodiment, in at least one of said first and second heavy chains the amino acids in the positions corresponding to positions L234, L235, and D265 in a human IgG1 heavy chain, are F, E, and A, respectively.

In a particular preferred embodiment, in both said first and second heavy chains the amino acids in the positions corresponding to positions L234, L235, and D265 in a human IgG1 heavy chain, are F, E, and A, respectively.

In one embodiment, in at least one of said first and second heavy chains the amino acids in the positions corresponding to positions L234, L235, and D265 in a human IgG1 heavy chain, are A, A, and A, respectively.

In one embodiment, in both said first and second heavy chains the amino acids in the positions corresponding to positions L234, L235, and D265 in a human IgG1 heavy chain, are A, A, and A, respectively.

In another embodiment, in at least one of said first and second heavy chains the amino acids in the positions corresponding to positions L234, L235, D265, N297, and P331 in a human IgG1 heavy chain, are F, E, A, Q, and S, respectively.

In one embodiment, in both said first and second heavy chains the amino acids in the positions corresponding to positions L234, L235, D265, N297, and P331 in a human IgG1 heavy chain, are F, E, A, Q, and S, respectively.

In a particular embodiment, the antibody according to the invention, comprises a VH sequence as set out in SEQ ID NO:8, a VL sequence as set out in SEQ ID NO:10, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:8, a VL sequence as set out in SEQ ID NO:12, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:6, a VL sequence as set out in SEQ ID NO:10, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:6, a VL sequence as set out in SEQ ID NO:12, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:9, a VL sequence as set out in SEQ ID NO:10, and in at least one of the heavy chains the amino acids in positions corresponding to positions L234, L235, and D265 in a human IgG1 heavy chain, are F, E, and A, respectively. In another embodiment, the antibody according to the invention, comprises a VH sequence as set out in SEQ ID NO:9, a VL sequence as set out in SEQ ID NO:12, and in at least one of the heavy chains the amino acids in positions corresponding to positions L234, L235, and D265 in a human IgG1 heavy chain, are F, E, and A, respectively.

In one aspect, the bispecific antibody according to the invention comprises the human IgLC2/IgLC3 constant domain lambda light chain of SEQ ID NO:29.

Several antibody variants were generated with one or more amino acid substitutions in the Fc region. A non-activating Fc region prevents the antibody from interacting with Fc-receptors present on blood cells, such as monocytes, or with C1q to activate the classical complement pathway. Reduction of the Fc activity was tested in antibody variants that contain different combinations of amino acid substitutions in the Fc region. Maximally five amino acid substitutions were introduced, which include the mutations N297Q, L234A, L235A, L234F, L235E, D265A, and P331S. Substitutions in one or more of these five amino acid positions were introduced in the K409R and/or F405L IgG1 backbone. The following Fc region variants of the huCLB-T3/4 antibody were generated: N297Q (refers to the N297Q substitution, termed IgG1-huCLB-T3/4-N297Q), LFLE (refers to the L234F/L235E substitutions, termed IgG1-huCLB-T3/4-LFLE), LALA (refers to the L234A/L235A substitutions, termed IgG1-huCLB-T3/4-LALA), LFLENQ (refers to the L234F/L235E/N297Q substitutions, termed IgG1-huCLB-T3/4-LFLENQ), LFLEDA (refers to the L234F/L235E/D265A substitutions, termed IgG1-huCLB-T3/4-LFLEDA), DA (refers to the D265A substitution, termed IgG1-huCLB-T3/4-DA), DAPS (refers to the D265A/P331S substitutions, termed IgG1-huCLB-T3/4-DAPS), DANQ (refers to the D265A/N297Q substitutions, termed IgG1-huCLB-T3/4-DANQ), LFLEPS (refers to the L234F/L235E/P331S substitutions, termed IgG1-huCLB-T3/4-LFLEPS), and LFLEDANQPS (refers to the L234F/L235E/D265A/N297Q/P331S substitutions, termed IgG1-huCLB-T3/4-LFLEDANQPS).

In particular, in the IgG1-huCD3 antibody variants a combination of three amino acid substitutions, which include the mutations L234F, L235E and D265A and is referred to as LFLEDA or FEA, were introduced in the K409R and F405L IgG1 backbones to generate antibodies with a non-activating Fc region. The resulting non-activating antibody variant is termed with the suffix "FEAR" or "FEAL", respectively.

In one aspect, the bispecific antibodies according to the invention may be modified in the light chain and/or heavy chain to increase the expression level and/or production yield. In one embodiment, the antibodies according to the invention may be modified in the light chain. Such modifications are known in the art and may be performed according to the methods described in e.g. Zheng, L., Goddard, J.-P., Baumann, U., & Reymond, J.-L. (2004). Expression improvement and mechanistic study of the retro-Diels-Alderase catalytic antibody 10F11 by site-directed mutagenesis. Journal of Molecular Biology, 341(3), 807-14.

In one embodiment, the bispecific antibody as defined in any of the embodiments disclosed herein comprises a first heavy chain and first light chain, wherein the amino acid in the position corresponding to position T41 in the lambda light chain of SEQ ID NO:10 of the first light chain is not T.

In one embodiment the bispecific antibody as defined in any of the embodiments disclosed herein, the amino acid in the position corresponding to position T41 in the lambda light chain of SEQ ID NO: 10 is selected from H, I, K, L, Q, R and V.

In one embodiment the bispecific antibody as defined in any of the embodiments disclosed herein, the amino acid in the position corresponding to position T41 in the lambda light chain of SEQ ID NO: 10 is H, K or R.

In one embodiment of the bispecific antibody as defined in any of the embodiments disclosed herein, the amino acid in the position corresponding to position T41 in the lambda light chain of SEQ ID NO: 10 of the first light chain is K.

In one embodiment of the bispecific antibody as defined in any of the embodiments disclosed herein, the amino acid in the position corresponding to position F10 in the lambda light chain of SEQ ID NO: 10 of the first light chain is not F, and one or more of the amino acid positions corresponding to the positions T41, K55, and L97 in the lambda light chain of SEQ ID NO: 10 of the first light chain are not T, K and L, respectively.

In one embodiment of the bispecific antibody as defined in any of the embodiments disclosed herein, the amino acids in the positions corresponding to positions F10, T41, K55, and L97 in the lambda light chain of SEQ ID NO:10 of the first light chain are not F, T, K and L, respectively.

In one embodiment of the bispecific antibody as defined in any of the embodiments disclosed herein, the amino acids in the positions corresponding to positions F10, T41, K55, and L97 in the lambda light chain of SEQ ID NO: 10 of the first light chain are L, K, N, and H, respectively.

In one embodiment of the bispecific antibody as defined in any of the embodiments disclosed herein, the amino acids in the positions corresponding to positions R23 and A35 in the lambda light chain of SEQ ID NO: 10 of the first light chain are not R and A, respectively.

In one embodiment of the bispecific antibody as defined in any of the embodiments disclosed herein, the amino acids in the positions corresponding to positions R23 and A35 in the lambda light chain of SEQ ID NO: 10 of the first light chain are A and P, respectively.

In one embodiment of the bispecific antibody as defined in any of the embodiments disclosed herein, the amino acids in the positions corresponding to positions F10, R23, A35, R47, D71, A82, D83, S86, I87, and F89 in the lambda light chain of SEQ ID NO:10 of the first light chain are not F, R, A, R, D, A, D, S, I, and F, respectively.

In one embodiment of the bispecific antibody as defined in any of the embodiments disclosed herein, the amino acids in the positions corresponding to positions F10, R23, A35, R47, D71, A82, D83, S86, I87, and F89 in the lambda light chain of SEQ ID NO:10 of the first light chain are L, A, P, T, G, P, E, A, E, and Y, respectively.

In one embodiment of the bispecific antibody as defined in any of the embodiments disclosed herein, (i) the amino acid in the position corresponding to position F10 in the lambda light chain of SEQ ID NO: 10 of the first light chain is not F, or (ii) the amino acid in the position corresponding to position K55 in the lambda light chain of SEQ ID NO: 10 of the first light chain is not K, or (iii) the amino acid in the position corresponding to position F10 in the lambda light chain of SEQ ID NO:10 of the first light chain is not F, and the amino acid in the position corresponding to position K55 in the lambda light chain of SEQ ID NO:10 of the first light chain is not K.

In one embodiment of the bispecific antibody as defined in any of the embodiments disclosed herein, (i) the amino acid in the position corresponding to position F10 in the lambda light chain of SEQ ID NO: 10 of the first light chain is L, or (ii) the amino acid in the position corresponding to position K55 in the lambda light chain of SEQ ID NO: 10 of the first light chain is N, or (iii) the amino acid in the position corresponding to position F10 in the lambda light chain of SEQ ID NO:10 of the first light chain is L, and the amino acid in the position corresponding to position K55 in the lambda light chain of SEQ ID NO:10 of the first light chain is N.

In one embodiment, the bispecific antibody according to the invention comprises a first light chain, wherein the amino acid in the position corresponding to position T41 is selected from H, I, K, L, Q, R or V, such as selected from H, K and R, such as K. In one embodiment, the bispecific antibody according to the invention comprises a first light chain having the amino acids L, K, N, and H, respectively, in the positions corresponding to positions F10, T41, K55, and L97 in the lambda light chain of SEQ ID NO:10. In one embodiment, the bispecific antibody according to the invention comprises a first light chain, wherein the amino acid in the position corresponding to position R23 is selected from A, G, H, K, Q, S, and T, such as from A and G, and wherein the amino acid in the position corresponding to A35 is selected from I, L, M, P, V, G, F and W, such as from I, L, M, P, and V.

In one embodiment, the bispecific antibody according to the invention comprises a first light chain, wherein the amino acid in the position corresponding to position R23 is A or G, such as A, and the amino acid in the position corresponding to position A35 is P.

In one embodiment, the bispecific antibody according to the invention comprises a first light chain, wherein the amino acids in the positions corresponding to positions F10, R23, A35, R47, D71, A82, D83, 586, 187, and F89 in the lambda light chain of SEQ ID NO:10 are not F, R, A, R, D, A, D, S, I, and F, respectively.

In one embodiment, the bispecific antibody according to the invention comprises a first light chain, wherein the amino acid in the position corresponding to position R23 is selected from A, G, H, K, Q, S, and T, such as from A and G, wherein the amino acid in the position corresponding to A35 is selected from I, L, M, P, V, G, F and W, such as from I, L, M, P, and wherein the amino acids in the positions corresponding to positions F10, R47, D71, A82, D83, 586, 187, and F89 in the lambda light chain of SEQ ID NO: 10 are L, T, G, P, E, A, E, and Y, respectively.

In one embodiment, the bispecific antibody according to the invention comprises a first light chain, wherein the amino acid in the position corresponding to position R23 is A or G, and wherein the amino acids in the positions corresponding to positions F10, A35, R47, D71, A82, D83, 586, 187, and F89 in the lambda light chain of SEQ ID NO: 10 are L, P, T, G, P, E, A, E, and Y, respectively.

In one aspect, the bispecific antibodies according to the invention may be modified in the first and/or second light chains to increase the affinity of the antibodies.

In one aspect, the bispecific antibodies according to the invention may be modified in the light chain of the first and/or second binding arm to reduce the affinity of the antibodies. This may be advantageous in some settings and lead to increased efficacy. In particular low affinity of the first binding arm (binding to human CD3ε (epsilon)) may have an impact on the motility of T cells in circulation and at tumor site thus leading to better engagement of T cells with tumor cells, cf. Mølhøj et al., Molecular Immunology 44 (2007). In particular this may be useful in bispecific formats, in which the CD3 antibodies are used as one of the binding arms. Modifications that lead to reduced antibody affinity are known in the art, see for example Webster et al. Int J Cancer Suppl. 1988; 3:13-6.

In one embodiment, the bispecific antibody according to the invention comprises a first light chain, wherein (i) the amino acid in the position corresponding to position F10 in the lambda light chain of SEQ ID NO: 10 is not F, or (ii) the amino acid in the position corresponding to position K55 in the lambda light chain of SEQ ID NO: 10 is not K, or (iii) the amino acid in the position corresponding to position F10 in the lambda light chain of SEQ ID NO: 10 is not F, and the amino acid in the position corresponding to position K55 in the lambda light chain of SEQ ID NO: 10 is not K.

In one embodiment, the antibody according to the invention comprises a constant light chain (LC), wherein (i) the amino acid in the position corresponding to position F10 in the lambda light chain of SEQ ID NO: 10 is L, or (ii) the amino acid in the position corresponding to position K55 in the lambda light chain of SEQ ID NO: 10 is N, or (iii) the amino acid in the position corresponding to position F10 in the lambda light chain of SEQ ID NO:10 is L, and the amino acid in the position corresponding to position K55 in the lambda light chain of SEQ ID NO: 10 is N.

In one embodiment, the bispecific antibody according to the invention comprises a light chain, wherein the amino acids in the positions corresponding to positions F10, T41, K55, and L97 in the lambda light chain of SEQ ID NO:10 are not F, T, K and L, respectively. Such modifications serve both to increase the expression level and to reduce the affinity.

In one embodiment, the bispecific antibody according to the invention comprises a first light chain, wherein the amino acids in the positions corresponding to positions F10, T41, K55, and L97 in the lambda light chain of SEQ ID NO:10 are L, K, N, and H, respectively. Such modifications serve both to increase the expression level and to reduce the affinity.

In a further aspect of the invention, mutations in the CDR regions of huCD3 have been made to optimize the binding affinity of the CD3 binding arm, such as to reduce the binding affinity of the CD3 arm.

Thus, in one embodiment, the CD3 binding arm of the bispecific antibody according to the invention comprises the six CDR sequences selected from the CDR sequences set forth in the the below Table 2.

and VH4, and VL1, VL2 and VL3, respectively, replacing the CDR sequences of huCD3. In one embodiment, the six CDR sequences are inserted in the huCD3 framework sequences VH1 and VL1. In a further embodiment, the six

TABLE 2

| VH CDR1 (SEQ ID NO) | VH CDR2 (SEQ ID NO) | VH CDR3 (SEQ ID NO) | VL CDR1 (SEQ ID NO) | VL CDR2 | VL CDR3 (SEQ ID NO) |
|---|---|---|---|---|---|
| 72 | 2 | 3 | 4 | GTN | 5 |
| 72 | 2 | 3 | 81 | GTN | 5 |
| 72 | 2 | 3 | 4 | GTN | 82 |
| 72 | 2 | 3 | 4 | GTN | 83 |
| 73 | 2 | 3 | 4 | GTN | 5 |
| 73 | 2 | 3 | 81 | GTN | 5 |
| 73 | 2 | 3 | 4 | GTN | 82 |
| 73 | 2 | 3 | 4 | GTN | 83 |
| 74 | 2 | 3 | 4 | GTN | 5 |
| 74 | 2 | 3 | 81 | GTN | 5 |
| 74 | 2 | 3 | 4 | GTN | 82 |
| 74 | 2 | 3 | 4 | GTN | 83 |
| 1 | 75 | 3 | 4 | GTN | 5 |
| 1 | 75 | 3 | 81 | GTN | 5 |
| 1 | 75 | 3 | 4 | GTN | 82 |
| 1 | 75 | 3 | 4 | GTN | 83 |
| 1 | 76 | 3 | 4 | GTN | 5 |
| 1 | 76 | 3 | 81 | GTN | 5 |
| 1 | 76 | 3 | 4 | GTN | 82 |
| 1 | 76 | 3 | 4 | GTN | 83 |
| 1 | 2 | 77 | 4 | GTN | 5 |
| 1 | 2 | 77 | 81 | GTN | 5 |
| 1 | 2 | 77 | 4 | GTN | 82 |
| 1 | 2 | 77 | 4 | GTN | 83 |
| 1 | 2 | 78 | 4 | GTN | 5 |
| 1 | 2 | 78 | 81 | GTN | 5 |
| 1 | 2 | 78 | 4 | GTN | 82 |
| 1 | 2 | 78 | 4 | GTN | 83 |
| 1 | 2 | 79 | 4 | GTN | 5 |
| 1 | 2 | 79 | 81 | GTN | 5 |
| 1 | 2 | 79 | 4 | GTN | 82 |
| 1 | 2 | 79 | 4 | GTN | 83 |
| 1 | 2 | 80 | 4 | GTN | 5 |
| 1 | 2 | 80 | 81 | GTN | 5 |
| 1 | 2 | 80 | 4 | GTN | 82 |
| 1 | 2 | 80 | 4 | GTN | 83 |
| 1 | 2 | 3 | 81 | GTN | 5 |
| 1 | 2 | 3 | 4 | GTN | 82 |
| 1 | 2 | 3 | 4 | GTN | 83 |

In one embodiment, the six CDR sequences may be inserted in any one of the huCD3 VH and VL framework sequences VH1, VH2, VH3 and VH4, and VL1, VL2, and VL3, respectively, replacing the CDR sequences of huCD3. In one embodiment, the six CDR sequences are inserted in the huCD3 framework sequences VH1 and VL1.

In a further embodiment, the CD3 binding arm comprises the six CDR sequences selected from the Table 2, wherein $X_1$ of SEQ ID NO:72 is selected from V, H, F, T, P, L, Q, D, K, W, G, A, C and R;

$X_2$ of SEQ ID NO:73 is selected from N, A, H, Q, P, F, M, Y, L, W, D, E and C;

$X_4$ of SEQ ID NO:75 is selected from Y, Q, W, L, A, I, M, D, T, K, R, G, F, E, V, C and P;

$X_5$ of SEQ ID NO:76 is selected from N, L, Y, W, H, M, G, F, K, S, V, R, Q, D, C, E and P;

$X_{10}$ of SEQ ID NO:81 is selected from A, G, R, V, F, E, M, H, N, Y, P, Q, D, K and L;

$X_{12}$ of SEQ ID NO:83 is selected from D, K, Q, G, V, E, T, N, Y, S, P, W, F and M.

Such huCD3 CDR variant sequences have reduced binding affinity compared to huCD3 wildtype CDR sequences. The six CDR sequences may be inserted in any of the huCD3 VH and VL framework sequences VH1, VH2, VH3 and VH4, and VL1, VL2 and VL3, respectively, replacing the CDR sequences of huCD3. In one embodiment, the six CDR sequences have been inserted in the huCD3 framework sequences VH1 and VL1, wherein the amino acid T in position 41 of VL1 (SEQ ID NO:10) has been mutated to K.

In a further embodiment, the CD3 binding arm comprises the six CDR sequences selected from the Table 2, wherein $X_1$ of SEQ ID NO:72 is selected from L, P, Q, D, K, W, S, G, A, C and R;

$X_2$ of SEQ ID NO:73 is selected from S, N, G, A, K, V, R, H, Q, P, I, F, M, Y, L, W, D, E and C;

$X_3$ of SEQ ID NO:74 is selected from M, W, G, Q, V, T, S, L, P, I, A, K, R and C;

$X_4$ of SEQ ID NO:75 is selected from W, L, A, I, M, D, T, K, R, G, F, E, V, C and P;

$X_5$ of SEQ ID NO:76 is selected from C, E, P and T:

$X_6$ of SEQ ID NO:77 is selected from A, S, V, N, K, L, T, I, P, Q, C, G, Y, W, F, and R;

$X_7$ of SEQ ID NO:78 is selected from P, C, S, and T;

$X_8$ of SEQ ID NO:79 is selected from A, T, G, L, N, C, P, F, Q, H, R, K, E, W, and Y;

$X_9$ of SEQ ID NO:80 is selected from P, L, T, C, A, I, L, Q, V, E, M, K, R, G and P;

$X_{10}$ of SEQ ID NO:81 is selected from E, H, I, M, N, Y, P, Q, D, K and L;

$X_{11}$ of SEQ ID NO:82 is selected from F, Y, I, T, V, M, A, S, N, G, W, E, K, P, R and D; and X₁₂ of SEQ ID NO:83 is selected from G, Y, V, N, T, S, H, E, P, W, F and M.

Such HuCD3 CDR variant sequences have reduced binding affinity compared to huCD3 wildtype CDR sequences. The six CDR sequences may be inserted in any of the huCD3 VH and VL framework sequences VH1, VH2, VH3 and VH4, and VL1, VL2 and VL3, respectively, replacing the CDR sequences of huCD3. In one embodiment, the six CDR sequences are inserted in the huCD3 framework sequences VH1 and VL1. In a further embodiment, the six CDR sequences have been inserted in the huCD3 framework sequences VH1 and VL1, wherein the amino acid T in position 41 of VL1 (SEQ ID NO:10) has been mutated to K.

In yet a further embodiment, the CD3 binding arm comprises the six CDR sequences selected from the CDR sequences set forth in the below Table 3, wherein $X_2$ of SEQ ID NO:73 is selected from M and P;
$X_3$ of SEQ ID NO:74 is A;
$X_4$ of SEQ ID NO:75 is E;
$X_6$ of SEQ ID NO:77 is selected from F, G, I, K, L, and N;
$X_7$ of SEQ ID NO:78 is P;
$X_8$ of SEQ ID NO:79 is selected from A and G; and
$X_9$ of SEQ ID NO:80 is selected from M, R and V.

TABLE 3

| VH CDR1 (SEQ ID NO) | VH CDR2 (SEQ ID NO) | VH CDR3 (SEQ ID NO) | VL CDR1 (SEQ ID NO) | VL CDR2 | VL CDR3 (SEQ ID NO) |
|---|---|---|---|---|---|
| 73 | 2 | 3 | 4 | GTN | 5 |
| 74 | 2 | 3 | 4 | GTN | 5 |
| 1 | 75 | 3 | 4 | GTN | 5 |
| 1 | 2 | 77 | 4 | GTN | 5 |
| 1 | 2 | 78 | 4 | GTN | 5 |
| 1 | 2 | 79 | 4 | GTN | 5 |
| 1 | 2 | 80 | 4 | GTN | 5 |

Such HuCD3 CDR variant sequences have reduced binding affinity compared to huCD3 wildtype CDR sequences. The six CDR sequences may be inserted in any of the huCD3 VH and VL framework sequences VH1, VH2, VH3 and VH4, and VL1, VL2 and VL3, respectively, replacing the CDR sequences of huCD3. In one embodiment, the six CDR sequences are inserted in the huCD3 framework sequences VH1 and VL1. In a further embodiment, the six CDR sequences have been inserted in the huCD3 framework sequences VH1 and VL1, wherein the amino acid T in position 41 of VL1 (SEQ ID NO:10) has been mutated to K.

In a further embodiment of the bispecific antibody as defined in any of the embodiments disclosed herein, the first binding arm is derived from a CD3 antibody having a binding affinity value ($K_D$) to human CD3 epsilon higher than $3.4 \times 10^{-8}$ M as determined by Bio-Layer Interferometry, such as from $3.5 \times 10^{-8}$ M to $9.9 \times 10^{-8}$ M, or from $1.0 \times 10^{-7}$ M to $9.9 \times 10^{-7}$ M as determined by Bio-Layer Interferometry.

In a further embodiment of the invention, one or both of the antibodies forming part of the bispecific antibody have been engineered to reduce or increase the binding to the neonatal Fc receptor (FcRn) in order to manipulate the serum half-life of the bispecific antibody. Techniques for increasing or reducing the serum half-life are well-known in the art. See for example Dall'Acqua et al. 2006, J. Biol. Chem., 281:23514-24; Hinton et al. 2006, J. Immunol., 176:346-56; and Zalevsky et al. 2010 Nat. Biotechnol., 28:157-9.

In one aspect, the bispecific antibody as defined in any of the embodiments disclosed herein comprises a first constant heavy chain (HC) and a first constant light chain (LC), wherein the positions corresponding to positions L234, L235, and D265 in the human IgG1 heavy chain of SEQ ID NO:15 of both the first heavy chain and the second heavy chain are F, E, and A, respectively.

In one embodiment, the bispecific antibody as defined in any of the embodiments disclosed herein comprises a first and second constant heavy chain (HC) and a first and second constant light chain (LC), wherein the positions corresponding to positions L234 and L235 in the human IgG1 heavy chain of SEQ ID NO:15 of both the first heavy chain and the second heavy chain are F and E, respectively.

In one embodiment of the bispecific antibody as defined in any of the embodiments disclosed herein the first binding arm is a Fab arm derived from IgG1-huCD3-H1L1-FEAR, and the second binding arm is a Fab arm derived from IgG1-7D8-FEAL.

Herein, huCD3-H1L1 refers to the humanized SP34 anti-CD3 antibody having VH1 and VL1 which are set forth in table 1 as SEQ ID Nos: 6 and 10. FEAL refers to L234F, L235E and D265A and F405L mutations in the constant region of the antibody whereas FEAR refers to L234F, L235E and D265A and K409R mutations in the constant region of the antibody wherein the amino acid positions corresponds to the amino acid positions of human IgG1. "IgG1" refers to that the antibody constant regions are derived from the human IgG1 outside the specified mutations. 7D8 refers to the anti-CD20 antibody having the VH and VL sequence set forth in Table 1 as SEQ ID Nos: 27 and 28.

In one embodiment of the bispecific antibody as defined in any of the embodiments disclosed herein the first binding arm is a half-molecule antibody derived from IgG1-huCD3-H1L1-FEAR, and the second binding arm is a half-molecule antibody derived from IgG1-7D8-FEAL.

In one embodiment of the bispecific antibody as defined in any of the embodiments disclosed herein the first binding arm is a Fab arm derived from IgG1-huCD3-H1L1-FEAL, and the second binding arm is a Fab arm derived from IgG1-7D8-FEAR.

In one embodiment of the bispecific antibody as defined in any of the embodiments disclosed herein the first binding arm is a half-molecule antibody (i.e. comprising one heavy and one light chain) derived from IgG1-huCD3-H1L1-FEAL, and the second binding arm is a half-molecule antibody (Fab arm and Fc arm) derived from IgG1-7D8-FEAR.

In one embodiment, the bispecific antibody as defined in any of the embodiments disclosed herein comprises a first and second constant heavy chain (HC) and a first and second constant light chain (LC), wherein the positions corresponding to positions L234, L235, and D265 in the human IgG1 heavy chain of SEQ ID NO:15 of both the first constant heavy chain and the second constant heavy chain are F, E, and A, respectively, and wherein the position corresponding to F405 in the human IgG1 heavy chain of SEQ ID NO: 15 of the first constant heavy chain is L, and the position corresponding to K409 in the human IgG1 heavy chain of SEQ ID NO:15 of the second constant heavy chain is R, and wherein (i) the positions corresponding to positions F10, T41, K55, and L97 in the lambda light chain of SEQ ID NO:10 of the first constant light chain are L, K, N, and H, respectively, or (ii) the position corresponding to position T41 in the lambda light chain of SEQ ID NO: 10 of the first light constant chain is K.

Further Embodiments of the Bispecific Antibodies

The bispecific antibody of the invention can be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. The effector function of the antibodies of the present invention may be changed by isotype switching to, e.g., an IgG1, IgG2, IgG3, IgG4, IgD, IgA, IgE, or IgM antibody for various therapeutic uses. In one embodiment, both Fc-regions of an antibody of the present invention are of the IgG1 isotype, for instance an IgG1, κ. In one embodiment, the two Fc-regions of a bispecific antibody are of the IgG1 and IgG4 isotypes, respectively. Optionally, the Fc-region may be modified in the hinge and/or CH3 region as described elsewhere herein.

In one embodiment, the bispecific antibody of the invention is a full-length antibody, preferably an IgG1 antibody, in particular an IgG1, κ antibody or a variant thereof. In another embodiment, the bispecific antibody of the invention comprises an antibody fragment or a single-chain antibody. Antibody fragments may e.g. be obtained by fragmentation using conventional techniques, and the fragments screened for utility in the same manner as described herein for whole antibodies. For example, F(ab')$_2$ fragments may be generated by treating an antibody with pepsin. The resulting F(ab')$_2$ fragment may be treated to reduce disulfide bridges with a reducing agent, such as dithiothreitol, to produce Fab' fragments. Fab fragments may be obtained by treating an antibody with papain. A F(ab')$_2$ fragment may also be produced by binding Fab' fragments via a thioether bond or a disulfide bond. Antibody fragments may also be generated by expression of nucleic acids encoding such fragments in recombinant cells (see for instance Evans et al., J. Immunol. Meth. 184, 123-38 (1995)). For example, a chimeric gene encoding a portion of an F(ab')$_2$ fragment could include DNA sequences encoding the $C_H1$ domain and hinge region of the H chain, followed by a translational stop codon to yield such a truncated antibody fragment molecule.

The bispecific CD3×CD20 antibodies of the invention may also be prepared from single chain antibodies. Single chain antibodies are peptides in which the heavy and light chain Fv regions are connected. In one embodiment, the bispecific antibody of the present invention comprises a single-chain Fv (scFv) wherein the heavy and light chains in the Fv of a CD20 antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in 'The Pharmacology of Monoclonal Antibodies', vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). A bispecific antibody can then be formed from two VH and VL from a single-chain CD20 antibody and a single-chain CD3 antibody, or a polyvalent antibody formed from more than two $V_H$ and $V_L$ chains.

In one embodiment, one or both Fc-regions of the CD3 and CD20 monoclonal antibodies for producing a bispecific antibody of the invention are effector-function-deficient.

Conjugates

In a further aspect, the present invention provides a bispecific CD3×CD20 antibody linked or conjugated to one or more therapeutic moieties, such as a cytokine, an immune-suppressant, an immune-stimulatory molecule and/or a radioisotope. Such conjugates are referred to herein as "immunoconjugates" or "drug conjugates". Immunoconjugates which include one or more cytotoxins are referred to as "immunotoxins".

In one embodiment, the first and/or second Fc-region is conjugated to a drug or a prodrug or contains an acceptor group for the same. Such acceptor group may e.g. be an unnatural amino acid.

Compositions

In a further aspect, the invention relates to a composition comprising a bispecific antibody according to any one of the embodiments disclosed herein.

In a further aspect, the invention relates to a pharmaceutical composition comprising:

a bispecific CD3×CD20 antibody as defined in any of the embodiments disclosed herein, and a pharmaceutically acceptable carrier.

The pharmaceutical composition of the present invention may contain one bispecific antibody of the present invention or a combination of different bispecific antibodies of the present invention.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e. g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a bispecific antibody of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical bispecific antibodies of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical bispecific antibodies of the present invention may also comprise isotonicity agents, such as sugars, polyalcohols, such as mannitol, sorbitol, glycerol or sodium chloride in the compositions.

The pharmaceutical bispecific antibodies of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The bispecific antibodies of the present invention may be prepared with carriers that will protect the bispecific antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Uses

In one aspect, the invention relates to the bispecific antibody according to any one of the embodiments disclosed herein, the composition as disclosed herein, or the pharmaceutical composition as disclosed herein for use as a medicament.

In one aspect, the invention relates to the bispecific antibody according to any one of the embodiments disclosed herein, the composition as disclosed herein, or the pharmaceutical composition as disclosed herein for use in the treatment of a disease.

In one aspect, the invention relates to a method of treatment of a disease comprising administering the bispecific antibody according to any one of the embodiments disclosed herein, the composition as disclosed herein, or the pharmaceutical composition as disclosed herein to a subject in need thereof.

In one embodiment, the disease is mature B-cell malignancy.

In one embodiment, the disease is cancer, such as NHL or B cell leukemia.

The bispecific antibodies of the invention may be used for a number of purposes. In particular, the bispecific antibodies of the invention may be used for the treatment of various forms of cancer, including metastatic cancer and refractory cancer.

In particular, the bispecific antibodies according to the invention may be useful in therapeutic settings in which specific targeting and T cell-mediated killing of cells that express CD20 is desired, and they may be more efficient compared to a regular CD20 antibody in certain such indications and settings.

The bispecific antibodies of the invention also have additional utility in therapy and diagnosis of a variety of CD20-related diseases. For example, the bispecific antibodies can be used to elicit in vivo or in vitro one or more of the following biological activities: to inhibit the growth of and/or differentiation of a cell expressing CD20; to kill a cell expressing CD20; to mediate phagocytosis or ADCC of a cell expressing CD20 in the presence of human effector cells; to mediate CDC of a cell expressing CD20 in the presence of complement; to mediate apoptosis of a cell expressing CD20; and/or to induce translocation into lipid rafts upon binding CD20.

In another embodiment, the bispecific antibodies of the invention can be used to effect T cell-mediated immune responses, inflammation and microenvironment re-modelling.

In a particular embodiment, the bispecific antibodies are used in vivo to treat, prevent or diagnose a variety of CD20-related diseases. Examples of CD20-related diseases include, among others, B cell lymphoma, e.g., non-Hodgkin's lymphoma (NHL), B cell leukemia and immune diseases, e.g., autoimmune diseases, such as those listed below.

In one embodiment the bispecific antibodies according to the invention are used for the treatment of NHL or B cell leukemia.

In one embodiment, the bispecific antibodies according to the invention are used for the treatment of CD20 antibody-resistant NHL or B cell leukemia, such as rituximab- or ofatumumab-resistant NHL or B cell leukemia, e.g. rituximab-resistant non-aggressive B-cell lymphoma.

In one embodiment, the bispecific antibodies according to the invention are used for the treatment of Acute Lymphoblastic Leukemia (ALL), such as relapsed or refractory ALL.

In one embodiment, the bispecific antibodies according to the invention are used for the treatment of CLL, such as relapsed or refractory CLL.

In one embodiment, the bispecific antibodies according to the invention are used for the treatment of FL, such as or relapsed or refractory FL.

In one embodiment, the bispecific antibodies according to the invention are used for the treatment of Adult Grade III Lymphomatoid Granulomatosis; Adult Nasal Type Extranodal NK/T-cell Lymphoma; Anaplastic Large Cell Lymphoma; Angioimmunoblastic T-cell Lymphoma; Contiguous Stage II Adult Burkitt Lymphoma; Contiguous Stage II Adult Diffuse Large Cell Lymphoma; Contiguous Stage II Adult Diffuse Mixed Cell Lymphoma; Contiguous Stage II Adult Diffuse Small Cleaved Cell Lymphoma; Contiguous Stage II Adult Immunoblastic Large Cell Lymphoma; Contiguous Stage II Adult Lymphoblastic Lymphoma; Contiguous Stage II Grade 1 Follicular Lymphoma; Contiguous Stage II Grade 2 Follicular Lymphoma; Contiguous Stage II Grade 3 Follicular Lymphoma; Contiguous Stage II Mantle Cell Lymphoma; Contiguous Stage II Marginal Zone Lymphoma; Contiguous Stage II Small Lymphocytic Lymphoma; Cutaneous B-cell Non-Hodgkin Lymphoma; Epstein-Barr Virus Infection; Extranodal Marginal Zone B-cell Lymphoma of Mucosa-associated Lymphoid Tissue; Hepatosplenic T-cell Lymphoma; Intraocular Lymphoma; Nodal Marginal Zone B-cell Lymphoma; Noncontiguous Stage II Adult Burkitt Lymphoma; Noncontiguous Stage II Adult Diffuse Large Cell Lymphoma; Noncontiguous Stage II Adult Diffuse Mixed Cell Lymphoma; Noncontiguous Stage II Adult Diffuse Small Cleaved Cell Lymphoma; Noncontiguous Stage II Adult Immunoblastic Large Cell Lymphoma; Noncontiguous Stage II Adult Lymphoblastic Lymphoma; Noncontiguous Stage II Grade 1 Follicular Lymphoma; Noncontiguous Stage II Grade 2 Follicular Lymphoma; Noncontiguous Stage II Grade 3 Follicular Lymphoma; Noncontiguous Stage II Mantle Cell Lymphoma; Noncontiguous Stage II Marginal Zone Lymphoma; Noncontiguous Stage II Small Lymphocytic Lymphoma; Noncutaneous Extranodal Lymphoma; Peripheral T-cell Lymphoma; Post-transplant Lymphoproliferative Disorder; Progressive Hairy Cell Leukemia, Initial Treatment; Recurrent Adult Burkitt Lymphoma; Recurrent Adult Diffuse Mixed Cell Lymphoma; Recurrent Adult Diffuse Small Cleaved Cell Lymphoma; Recurrent Adult Grade III Lymphomatoid Granulomatosis; Recurrent Adult Hodgkin Lymphoma; Recurrent Adult Immunoblastic Large Cell Lymphoma; Recurrent Adult Lymphoblastic Lymphoma; Recurrent Adult T-cell Leukemia/Lymphoma; Recurrent Cutaneous T-cell Non-Hodgkin Lymphoma; Recurrent Grade 1 Follicular Lymphoma; Recurrent Grade 2 Follicular Lymphoma; Recurrent Grade 3 Follicular Lymphoma; Recurrent Mantle Cell Lymphoma; Recurrent Marginal Zone Lymphoma; Recurrent Mycosis Fungoides/Sezary Syndrome; Recurrent Small Lymphocytic Lymphoma; Refractory Hairy Cell Leukemia; Small Intestine Lymphoma; Splenic Marginal Zone Lymphoma; Stage I Adult Burkitt Lymphoma; Stage I Adult Diffuse Large Cell Lymphoma; Stage I Adult Diffuse Mixed Cell Lymphoma; Stage I Adult Diffuse Small Cleaved Cell Lymphoma; Stage I Adult Hodgkin Lymphoma; Stage I Adult Immunoblastic Large Cell Lymphoma; Stage I Adult Lymphoblastic Lymphoma; Stage I Adult T-cell Leukemia/Lymphoma; Stage I Cutaneous T-cell Non-Hodgkin Lymphoma; Stage I Grade 1 Follicular Lymphoma; Stage I Grade 2 Follicular Lymphoma; Stage I Grade 3 Follicular Lymphoma; Stage I Mantle Cell Lymphoma; Stage I Marginal Zone Lymphoma; Stage I Small Lymphocytic Lymphoma; Stage IA Mycosis Fungoides/Sezary Syndrome; Stage IB Mycosis Fungoides/Sezary Syndrome; Stage II Adult Hodgkin's Lymphoma; Stage II Adult T-cell Leukemia/Lymphoma; Stage II Cutaneous T-cell Non-Hodgkin Lymphoma; Stage IIA Mycosis Fungoides/Sezary Syndrome; Stage IIB Mycosis Fungoides/Sezary Syndrome; Stage III Adult Burkitt Lymphoma; Stage III Adult Diffuse Large Cell Lymphoma; Stage III Adult Diffuse Mixed Cell Lymphoma; Stage III Adult Diffuse Small Cleaved Cell Lymphoma; Stage III Adult Hodgkin Lymphoma; Stage III Adult Immunoblastic Large Cell Lymphoma; Stage III Adult Lymphoblastic Lymphoma; Stage III Adult T-cell Leukemia/Lymphoma; Stage III Cutaneous T-cell Non-Hodgkin Lymphoma; Stage III Grade 1 Follicular Lymphoma; Stage III Grade 2 Follicular Lymphoma; Stage III Grade 3 Follicular Lymphoma; Stage III Mantle Cell Lymphoma; Stage III Marginal Zone Lymphoma; Stage III Small Lymphocytic Lymphoma; Stage IIIA Mycosis Fungoides/Sezary Syndrome; Stage IIIB Mycosis Fungoides/Sezary Syndrome; Stage IV Adult Burkitt Lymphoma; Stage IV Adult Diffuse Large Cell Lymphoma; Stage IV Adult Diffuse Mixed Cell Lymphoma; Stage IV Adult Diffuse Small Cleaved Cell Lymphoma; Stage IV Adult Hodgkin Lymphoma; Stage IV Adult Immunoblastic Large Cell Lymphoma; Stage IV Adult Lymphoblastic Lymphoma; Stage IV Adult T-cell Leukemia/Lymphoma; Stage IV Cutaneous T-cell Non-Hodgkin Lymphoma; Stage IV Grade 1 Follicular Lymphoma; Stage IV Grade 2 Follicular Lymphoma; Stage IV Grade 3 Follicular Lymphoma; Stage IV Mantle Cell Lymphoma; Stage IV Marginal Zone Lymphoma; Stage IV Small Lymphocytic Lymphoma; Stage IVA Mycosis Fungoides/Sezary Syndrome; Stage IVB Mycosis Fungoides/Sezary Syndrome; T-cell Large Granular Lymphocyte Leukemia; Testicular Lymphoma; Untreated Hairy Cell Leukemia; or Waldenström Macroglobulinemia.

In a particular embodiment, the antibodies of the invention are used to treat or to prevent NHL, as the antibodies deplete the CD20 bearing tumor cells.

NHL is a type of B cell lymphoma. Lymphomas, e.g., B cell lymphomas, are a group of related cancers that arise when a lymphocyte (a blood cell) becomes malignant. The normal function of lymphocytes is to defend the body against invaders: germs, viruses, fungi, even cancer. There are many subtypes and maturation stages of lymphocytes and, therefore, there are many kinds of lymphomas. Like normal cells, malignant lymphocytes can move to many parts of the body. Typically, lymphoma cells form tumors in the lymphatic system: bone marrow, lymph nodes, spleen, and blood. However, these cells can migrate to other organs. Certain types of lymphoma will tend to grow in locations in which the normal version of the cell resides. For example, it is common for follicular NHL tumors to develop in the lymph nodes.

CD20 is usually expressed at elevated levels on neoplastic (i.e., tumorigenic) B cells associated with NHL. Accordingly, CD20 binding antibodies of the invention can be used to deplete CD20 bearing tumor cells which lead to NHL and, thus, can be used to prevent or treat this disease.

The bispecific antibodies of the present invention also can be used to block or inhibit other effects of CD20. For example, it is known that CD20 is expressed on B lymphocytes and is involved in the proliferation and/or differentiation of these cells. Since B lymphocytes function as immunomodulators, CD20 is an important target for antibody mediated therapy to target B lymphocytes, e.g., to inactivate or kill B lymphocytes, involved in autoimmune disorders. Such autoimmune disorders include, for example, the above listed diseases Similarly, the invention relates to a method for killing a tumor cell expressing CD20, comprising administration, to an individual in need thereof, of an effective amount of a bispecific antibody of the invention.

The present invention also relates to a method for inhibiting growth and/or proliferation of one or more tumor cells expressing CD20, comprising administration, to an indicidual in need thereof, of a bispecific antibody of the present invention.

The present invention alto relates to a method for treating cancer, comprising
 a) selecting a subject suffering from a cancer comprising tumor cells expressing CD20, and
 b) administering to the subject the bispecific antibody of the present invention or a pharmaceutical composition of the present invention.

Also, the invention relates to the use of a bispecific antibody that binds to human CD3 and human CD20 for the preparation of a medicament for the treatment of cancer, such as one of the specific cancer indications mentioned herein.

The invention further relates to a bispecific antibody for use in the treatment of cancer, such as one of the cancer indications mentioned above.

In one embodiment the bispecific antibody is for use in the treatment of mature B-cell malignancies. In one embodiment the bispecific antibody is for use in the treatment of tumors expressing CD20. In one embodiment the bispecific antibody is for use in the treatment of B cell lymphoma. In one embodiment the bispecific antibody is for use in the treatment of B cell lymphoma such as NHL. In one embodiment the bispecific antibody is for use in the treatment of precursor B cell lymphoblastic leukemia. In one embodiment the bispecific antibody is for use in the treatment of B cell chronic lymhocytic leukemia (CLL).
In one embodiment the bispecific antibody is for use in the treatment of small lymphocytic lymphoma (SLL).
In one embodiment the bispecific antibody is for use in the treatment of B cell prolymphocytic leukemia.
In one embodiment the bispecific antibody is for use in the treatment of lymphoplasmacytic lymphoma.
In one embodiment the bispecific antibody is for use in the treatment of mantle cell lymphoma (MCL).
In one embodiment the bispecific antibody is for use in the treatment of follicular lymphoma (FL), including low-grade, intermediate-grade and high-grade FL.
In one embodiment the bispecific antibody is for use in the treatment of B cell Hodgkin's lymphoma.
In one embodiment the bispecific antibody is for use in the treatment of immune disorders in which CD20 expressing B cells are involved.
In one embodiment the bispecific antibody is for use in the treatment of psoriasis.
In one embodiment the bispecific antibody is for use in the treatment of sclerosis.
In one embodiment the bispecific antibody is for use in the treatment of inflammatory bowel disease.

For the above mentioned uses it is preferred that the antibody is bsIgG1-huCD3-H1L1-FEALxCD20-7D8-FEAR, however it may be any of the bispecific CD3xCD20 antibodies disclosed herein.

The bispecific antibodies of the present invention have numerous in vitro and in vivo diagnostic and therapeutic utilities involving the diagnosis and treatment of disorders involving cells expressing CD20. For example, the antibodies can be administered to cells in culture, e.g., in vitro or ex vivo, or to human subjects, e.g., in vivo, to treat, prevent and to diagnose a variety of disorders. As used herein, the term "subject" is intended to include human and non-human animals which respond to the bispecific antibodies against CD3 and CD20. Preferred subjects include human patients having disorders that can be corrected or ameliorated by inhibiting or controlling B cells (normal or malignant).

In one aspect, the invention relates to a diagnostic composition comprising a bispecific antibody according to any one of the embodiments as disclosed herein.

In one embodiment, the diagnostic composition is a companion diagnostic which is used to screen and select those patients who will benefit from treatment with the bispecific antibody.

In one embodiment, the bispecific antibodies of the present invention can be used to treat a subject with a tumorigenic disorder, e.g., a disorder characterized by the presence of tumor cells expressing CD20 including, for example, B cell lymphoma, e.g., NHL. Examples of tumorigenic diseases which can be treated and/or prevented include B cell lymphoma, e.g., NHL, including precursor B cell lymphoblastic leukemia/lymphoma and mature B cell neoplasms, such as B cell chronic lymhocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma (DLBCL), Burkitt's lymphoma, plasmacytoma, plasma cell myeloma, post-transplant lymphoproliferative disorder, Waldenström's macroglobulinemia, malignant melanoma and anaplastic large-cell lymphoma (ALCL).

Further examples of B cell non-Hodgkin's lymphomas are lymphomatoid granulomatosis, primary effusion lymphoma, intravascular large B cell lymphoma, mediastinal large B cell lymphoma, heavy chain diseases (including γ, μ, and α disease), lymphomas induced by therapy with immunosuppressive agents, such as cyclosporine-induced lymphoma, and methotrexate-induced lymphoma.

In a further embodiment, the bispecific antibodies of the present invention can be used to treat B cell Hodgkin's lymphoma.

Examples of immune disorders in which CD20 expressing B cells are involved which can be treated and/or prevented include autoimmune disorders, such as psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis (incuding chronic fatigue syndrome/myalgic encephalitis (CFS/ME) and chronic fatigue syndrome/myalgic encephalitis (CFS/ME), uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HIV, and herpes virus associated diseases. Further examples are severe acute respiratory distress syndrome and choreoretinitis. Furthermore, other diseases and disorders include those caused by or mediated by infection of B-cells with virus, such as Epstein-Barr virus (EBV).

Further examples of inflammatory, immune and/or autoimmune disorders in which autoantibodies and/or excessive B lymphocyte activity are prominent and which can be treated and/or prevented, include the following:

vasculitides and other vessel disorders, such as microscopic polyangiitis, Churg-Strauss syndrome, and other ANCA-associated vasculitides, polyarteritis nodosa, essential cryoglobulinaemic vasculitis, cutaneous leukocytoclastic angiitis, Kawasaki disease, Takayasu arteritis, giant cell arthritis, Henoch-Schonlein purpura, primary or isolated cerebral angiitis, erythema nodosum, thrombangiitis obliterans, thrombotic thrombocytopenic purpura (including hemolytic uremic syndrome), and secondary vasculitides, including cutaneous leukocytoclastic vasculitis (e.g., secondary to hepatitis B, hepatitis C, Waldenström's macroglobulinemia, B-cell neoplasias, rheumatoid arthritis, Sjögren's syndrome, or systemic lupus erythematosus); further examples are erythema nodosum, allergic vasculitis, panniculitis, Weber-Christian disease, purpura hyperglobulin-aemica, and Buerger's disease;

skin disorders, such as contact dermatitis, linear IgA dermatosis, vitiligo, pyoderma gangrenosum, epidermolysis bullosa acquisita, pemphigus vulgaris (including cicatricial pemphigoid and bullous pemphigoid), alopecia areata (including alopecia universalis and alopecia totalis), dermatitis herpetiformis, erythema multiforme, and chronic autoimmune urticaria (including angioneurotic edema and urticarial vasculitis);

immune-mediated cytopenias, such as autoimmune neutropenia, and pure red cell aplasia;

connective tissue disorders, such as CNS lupus, discoid lupus erythematosus, CREST syndrome, mixed connective tissue disease, polymyositis/dermatomyositis, inclusion body myositis, secondary amyloidosis, cryoglobulinemia type I and type II, fibromyalgia, phospholipid antibody syndrome, secondary hemophilia, relapsing polychondritis, sarcoidosis, stiff man syndrome, and rheumatic fever; further examples are eosinophil fasciitis, myositis, and juvenile dermatomyositis;

arthritides, such as ankylosing spondylitis, juvenile chronic arthritis, adult Still's disease, and SAPHO syndrome; further examples are sacroileitis, reactive arthritis, Still's disease, and gout;

hematologic disorders, such as aplastic anemia, primary hemolytic anemia (including cold agglutinin syndrome), hemolytic anemia secondary to CLL or systemic lupus erythematosus; POEMS syndrome, pernicious anemia, and Waldenström's purpura hyperglobulinaemica; further examples are agranulocytosis, autoimmune neutropenia, Franklin's disease, Seligmann's disease, p-chain disease, paraneoplastic syndrome secondary to thymoma and lymphomas, and factor VIII inhibitor formation;

endocrinopathies, such as polyendocrinopathy, and Addison's disease; further examples are autoimmune hypoglycemia, autoimmune hypothyroidism, autoimmune insulin syndrome, de Quervain's thyroiditis, and insulin receptor antibody-mediated insulin resistance;

hepato-gastrointestinal disorders, such as celiac disease, Whipple's disease, primary biliary cirrhosis, chronic active hepatitis, and primary sclerosing cholangiitis; a further example is autoimmune gastritis;

nephropathies, such as rapid progressive glomerulonephritis, post-streptococcal nephritis, Goodpasture's syndrome, membranous glomerulonephritis, and cryoglobulinemic nephritis; a further example is minimal change disease;

neurological disorders, such as autoimmune neuropathies, mononeuritis multiplex, Lambert-Eaton's myasthenic syndrome, Sydenham's chorea, tabes dorsalis, and Guillain-Barre's syndrome; further examples are myelopathy/tropical spastic paraparesis, myasthenia gravis, acute inflammatory demyelinating polyneuropathy, and chronic inflammatory demyelinating polyneuropathy;

cardiac and pulmonary disorders, such as fibrosing alveolitis, bronchiolitis obliterans, allergic aspergillosis, cystic fibrosis, Loffler's syndrome, myocarditis, and pericarditis; further examples are hypersensitivity pneumonitis, and paraneoplastic syndrome secondary to lung cancer;

allergic disorders, such as bronchial asthma and hyper-IgE syndrome; a further example is amaurosis fugax;

ophthalmologic disorders, such as idiopathic chorioretinitis;

infectious diseases, such as parvovirus B infection (including hands-and-socks syndrome); and gynecological-obstretical disorders, such as recurrent abortion, recurrent fetal loss, and intrauterine growth retardation; a further example is paraneoplastic syndrome secondary to gynaecological neoplasms;

male reproductive disorders, such as paraneoplastic syndrome secondary to testicular neoplasms; and transplantation-derived disorders, such as allograft and xenograft rejection, and graft-versus-host disease (including chronic graft-versus-host disease).

In one embodiment, the disease is an inflammatory, immune and/or autoimmune disorder selected from ulcerative colitis, Crohn's disease, juvenile onset diabetes, multiple sclerosis, immune-mediated thrombocytopenias, such as acute idiopathic thrombocytopenic purpura and chronic idiopathic thrombocytopenic purpura, hemolytic anemia (including autoimmune hemolytic anemia), myasthenia gravis, systemic sclerosis, and pemphigus vulgaris.

In a further embodiment of the methods of treatment of the present invention, the efficacy of the treatment is being monitored during the therapy, e.g. at predefined points in time, by determining tumor burden or CD20 expression levels on the relevant tumor cells.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the bispecific antibodies depend on the disease or condition to be treated and may be determined by the persons skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg. Another exemplary, non-limiting range for a therapeutically effective amount of a bispecific antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician or veterinarian having ordinary skill in the art may readily determine and prescribe the effective amount of the pharmaceutical composition required. For example, the physician or veterinarian could start doses of the bispecific antibody employed in the pharmaceutical composition at levels lower than that required in order to achieve the desired therapeutic effect and gradually increase the dosage until the desired effect is achieved. In general, a suitable daily dose of a bispecific antibody of the present invention will be that amount of the compound which is the lowest dose effective to produce a therapeutic effect. Administration may e.g. be parenteral, such as intravenous, intramuscular or subcutaneous. In one embodiment, the bispecific antibodies may be administered by infusion in a weekly dosage of calculated by $mg/m^2$. Such dosages can, for example, be based on the mg/kg dosages provided above according to the following: dose (mg/kg)×70: 1.8. Such administration may be repeated, e.g., 1 to 8 times, such as 3 to 5 times. The administration may be performed by continuous infusion over a period of from 2 to 24 hours, such as of from 2 to 12 hours. In one embodiment, the bispecific antibodies may be administered by slow continuous infusion over a long period, such as more than 24 hours, in order to reduce toxic side effects.

In one embodiment the bispecific antibodies may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of bispecific antibody of the present invention in the blood upon administration by for instance taking out a biological sample and using anti-idiotypic antibodies which target the CD20 antigen antigen-binding region of the bispecific antibodies of the present invention.

In one embodiment, the bispecific antibodies may be administered as maintenance therapy, such as, e.g., once a week for a period of 6 months or more.

A bispecific antibody may also be administered prophylactically in order to reduce the risk of developing cancer, delay the onset of the occurrence of an event in cancer progression, and/or reduce the risk of recurrence when a cancer is in remission.

The bispecific antibodies of the invention may also be administered in combination therapy, i.e., combined with other therapeutic agents relevant for the disease or condition to be treated. Accordingly, in one embodiment, the bispecific antibody-containing medicament is for combination with one or more further therapeutic agents, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder involving cells expressing CD20 as described above, which methods comprise administration of a bispecific antibody of the present invention combined with one or more additional therapeutic agents as described below.

In one embodiment, the present invention provides a method for treating a disorder involving cells expressing CD20 in a subject, which method comprises administration of a therapeutically effective amount of a bispecific antibody of the present invention, and optionally at least one additional therapeutic agent, or an antibody binding to a different CD20 epitope than said antibody, to a subject in need thereof.

In one embodiment, the present invention provides a method for treating or preventing cancer, which method comprises administration of a therapeutically effective amount of a bispecific antibody of the present invention and at least one additional therapeutic agent to a subject in need thereof.

In one embodiment, such an additional therapeutic agent may be selected from a tyrosine kinase inhibitor (TKI), such as imatinib (Glivec, Gleevec STI571), ibrutinib (PCI-32765, Imbruvica) or lapatinib (PTK787/ZK222584).

In one embodiment, such an additional therapeutic agent may be selected from a Bruton tyrosine kinase (BTK) inhibitor, such as ibrutinib.

In one embodiment, such an additional therapeutic agent may be selected from a proteasome inhibitor (PI), such as carfilzomib.

In one embodiment, such an additional therapeutic agent may be selected from a immunomodulatory agent (IMID), such as pomalidomide, thalidomide, or lenalidomide.

In one embodiment, such an additional therapeutic agent may be selected from a phosphoinositide 3-kinase inhibitor, such as idelalisib or duvelisib.

In one embodiment, such an additional therapeutic agent may be selected from an aurora A kinase inhibitor, such as alisertib.

In one embodiment, such an additional therapeutic may be selected from a B-cell lymphoma-2 (Bcl-2) inhibitor, such as venetoclax.

In one embodiment, such an additional therapeutic may be selected from histone deacytelase (HDAC) inhibitors, such as panobinostat.

Pharmaceutical compositions of the invention also can be administered in combination therapy, i.e., combined with other agents. In one embodiment, such therapeutic agents include one or more chemotherapeutics, from the class of alkylating agents, antimetabolites, mitotic inhibitors, anti-tumor antibiotics, topoisomerase inhibitors or platinum analogs. Examples of such chemotherapeutic agents are doxorubicin (Adriamycin), cisplatin (Platinol), bleomycin (Blenoxane), carmustine (Gliadel), cyclophosphamide (Cytoxan, Procytox, Neosar), bendamustine, and chlorambucil (Leukeran).

In another embodiment, bispecific antibodies of the present invention may be administered in combination with chlorambucil; CHOP (cyclophosphamide, hydroxydaunorubicin, oncovin, prednisone or prednisolone); cyclophosphamide and prednisolone; cyclophosphamide, vincristine, and prednisone; cyclophosphamide, vincristine, doxorubicin, and prednisone; fludarabine and an alkylating agent; dose-adjusted EPOCH (etoposide, prednisolone, vincristine, cyclophosphamide and doxorubicin); GemOx (gemcitabine and oxaliplatin); GDP (gemcitabine, dexamethasone and cisplatin) or in combination with other common multi-drugs regimens for NHL, such as disclosed, e.g., in Non-Hodgkin's Lymphomas: Making sense of Diagnosis, Treatment, and Options, Lorraine Johnston, 1999, O'Reilly and Associates, Inc.

In one embodiment, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In another embodiment, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In another embodiment, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In another embodiment, such an additional therapeutic agent may be selected from a topoisomerase inhibitor, such as topotecan or irinotecan, or a cytostatic drug, such as etoposide and teniposide.

In another embodiment, the present invention provides a method for treating a disorder involving cells expressing CD20 in a subject, which method comprises administration of a therapeutically effective amount of a bispecific antibody of the present invention and at least one inhibitor of angiogenesis, neovascularization, and/or other vascularization to a subject in need thereof Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF (e.g. bevacizumab), bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2).

Other examples of such inhibitors of angiogenesis, neovascularization, and/or other vascularization are anti-angiogenic heparin derivatives (e.g., heperinase III), temozolomide, NK4, macrophage migration inhibitory factor, cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other targets, such as anti-alpha-v/beta-3 integrin and anti-kininostatin antibodies.

In one embodiment, a therapeutic agent for use in combination with a bispecific antibody for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines) or tumor-derived heat shock proteins, In one embodiment, a therapeutic agent for use in combination with a bispecific antibody for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C-C chemokine families. Suitable cytokines include cytokine derivatives, cytokine variants, cytokine fragments, and cytokine fusion proteins.

In one embodiment, a therapeutic agent for use in combination with a bispecific antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, interferon-y (IFN-γ) and anti-sense Bcl-2.

In one embodiment, a therapeutic agent for use in combination with a bispecific antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In one embodiment, a therapeutic agent for use in combination with a bispecific antibody for treating the disorders as described above may be an immune check-point inhibitor, such as molecules that block the activity of CTLA-4, e.g. ipilimumab, PD-1, e.g. pembrolizumab, PD-L1, TIM3, TIGIT, BTLA, VISTA or LAG-3.

In one embodiment, a therapeutic agent for use in combination with a bispecific antibody for treating the disorders as described above may be an anti-cancer nucleic acid or an anti-cancer inhibitory RNA molecule.

Examples of other anti-cancer agents, which may be relevant as therapeutic agents for use in combination with a bispecific antibody according to the invention for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, RON (such as an anti-RON antibody), Sea, Tie, Tie2, Eph, Ret, Ros, Alk, LTK, PTK7 and similar agents.

Examples of other anti-cancer agents, which may be relevant as therapeutic agents for use in combination with a bispecific antibody according to the invention for treating the disorders as described above are estramustine and epirubicin.

Examples of other anti-cancer agents, which may be relevant as therapeutic agents for use in combination with a bispecific antibody according to the invention for treating the disorders as described above are a HSP90 inhibitor like 17-allyl amino geld-anamycin, antibodies directed against a tumor antigen such as PSA, CA125, KSA, integrins, e.g. integrin 131, or inhibitors of VCAM.

Examples of other anti-cancer agents, which may be relevant as therapeutic agents for use in combination with a bispecific antibody for treating the disorders as described above are calcineurin-inhibitors (such as valspodar, PSC 833 and other MDR-1 or p-glycoprotein inhibitors), TOR-inhibitors (such as sirolimus, everolimus and rapamcyin), and inhibitors of "lymphocyte homing" mechanisms (such as FTY720), and agents with effects on cell signaling such as adhesion molecule inhibitors (for instance anti-LFA).

In yet another embodiment, the bispecific antibodies may be administered in conjunction with radiotherapy and/or autologous or allogeneic peripheral stem cell or bone marrow transplantation.

In still another embodiment, the bispecific antibodies may be administered in combination with one or more antibodies selected from anti-CD25 antibodies, anti-CD19 antibodies, anti-CD20 antibodies (e.g. ofatumumab or rituximab), anti-CD21 antibodies, anti-CD22 antibodies, anti-CD37 antibodies, anti-CD38 antibodies, anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g., natalizumab), and CTLA4-Ig.

In a further embodiment, the bispecific antibodies may be administered in combination with one or more antibodies that block immune checkpoints, such as anti-CTLA-4 (CD152) antibodies, anti-PD-1 (CD279) antibodies, anti-PD-L1 (CD274) antibodies, anti-LAG-3 (CD223) antibodies, anti-TIM3 antibodies, anti-CEACAM1 (CD66a) antibodies, anti-VISTA antibodies, anti-TIGIT antibodies, anti-BTLA (CD272) antibodies.

In a further embodiment, the bispecific antibodies may be administered in combination with one or more agonistic antibodies which are specific for costimulatory receptors on immune cells, such as anti-4-1BB (CD137) antibodies (e.g. urelumab), anti-OX40 (CD134) antibodies, anti-CD40 antibodies, anti-CD27 antibodies.

In a further embodiment, the bispecific antibodies may be administered in combination with one or more type II macrophage depleting or polarizing antibodies, such as anti-CSF-1R (CD115) antibodies.

In a further embodiment, the bispecific antibodies may be administered in combination with one or more antibodies that bind to molecules involved in regulation of the innate immune system, such as anti-CD47 antibodies, anti-CD200 antibodies, anti-CD200R antibodies, antibodies against killer cell inhibitory receptors (KIRs), antibodies against CD94/NKG2 receptors, anti-CD305 (LAIR1).

In another particular embodiment, the bispecifc antibodies are administered in combination with one or more antibodies selected from anti-CD19 antibodies, anti-CD21 antibodies, anti-CD22 antibodies, anti-CD37 antibodies, and anti-CD38 antibodies for the treatment of malignant diseases.

In another particular embodiment, the bispecific antibodies are administered in combination with an anti-CD20 antibody, such as ofatumumab.

In still another particular embodiment, the bispecific antibodies are administered in combination with one or more antibodies selected from anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g natalizumab), and CTLA4-Ig for the treatment of inflammatory diseases.

In one embodiment, the bispecific antibody of the invention is for use in combination with one or more other therapeutic antibodies, such as zanolimumab, daratumumab (Darzalex), ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), and/or efalizumab (Raptiva).

In another embodiment the bispecific antibody of the invention is for use in combination with one or more antibody-drug conjugates (ADCs), for example brentuximab-vedotin (Adcetris), inotuzumab ozogamicin (CMC-544), polatuzumab vedotin (RG7593), coltuximab ravtansine (SAR3419), indatuximab ravtansine (BT-062), inotuzumab ozogamicin (CMC-544), denintuzumab mafodotin (SGN-CD19), polatuzumab vedotin (RG7596) or a CD37-specific antibody drug conjugated (for example IMGN529 or AGS67E).

In another embodiment, the bispecific antibody of the invention can be used in combination with an anti-inflammatory or an immunosuppressive agent. For example, the combination therapy can include a composition of the present invention with at least one anti-inflammatory agent or at least one immunosuppressive agent. In one embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In another embodiment, such therapeutic agents include one or more DMARDs, such as methotrexate (Rheumatrex), hydroxychloroquine (Plaquenil), sulfasalazine (Asulfidine), pyrimidine synthesis inhibitors, e.g., leflunomide (Arava), IL-1 receptor blocking agents, e.g., anakinra (Kineret), and TNF-α blocking agents, e.g., etanercept (Enbrel), infliximab (Remicade) and adalimumab.

In another embodiment, such therapeutic agents include one or more immunosuppressive agents, such as cyclosporine (Sandimmune, Neoral) and azathioprine (Imural).

In a particular embodiment, the bispecific antibodies are administered in combination with an anti-CD25 antibody for the treatment of bullous pemphigoid, e.g., in patients with graft-versus-host disease.

Radiotherapy—Surgery

In one embodiment, the present invention provides a method for treating a disorder involving cells expressing CD20 in a subject, which method comprises administration of a therapeutically effective amount of a CD3×CD20 bispecifc antibody of the present invention, and radiotherapy to a subject in need thereof.

In one embodiment, the present invention provides a method for treating or preventing cancer, which method comprises administration of a therapeutically effective amount of a CD3×CD20 bispecific antibody of the present invention, and radiotherapy to a subject in need thereof.

In one embodiment, the present invention provides the use of a bispecific antibody of the present invention, for the preparation of a pharmaceutical composition for treating cancer to be administered in combination with radiotherapy.

Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of a bispecific antibody of the present invention, in combination with surgery.

Diagnostic Uses

Thus, in one aspect, the invention relates to a diagnostic composition comprising a bispecific CD3×CD20 antibody as defined herein, and to its use.

In another aspect, the invention relates to a kit for detecting cross-linking between CD3- and CD20-expressing cells, in a sample derived from a patient such as a blood sample, lymph node sample or bone marrow sample, comprising i) a bispecific antibody according to any one of the embodiments as disclosed herein; and ii) instructions for use of said kit.

In one embodiment, the present invention provides a kit for diagnosis of cancer comprising a container comprising a bispecific CD3×CD20 antibody, and one or more reagents for detecting cross-linking of CD20 expressing cells and CD3 expressing cells.

Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

In a further aspect, the invention relates to a method for detecting whether cross-linking between CD3- and CD20-expressing cells occurs in a sample derived from a patient, such as a blood sample, lymph node sample or bone marrow sample, upon administration of a bispecific antibody according to any one of the embodiments as disclosed herein, comprising the steps of:

(i) contacting the sample with a bispecific antibody according to any one of the embodiments as disclosed herein under conditions that allow for formation of a complex between said bispecific antibody and the CD3- and CD20-expressing cells; and (ii) analyzing whether a complex has been formed.

Detection of the complex can be done by methods known in the art, such as by the method disclosed in Example 5.

In a further aspect, the invention relates to an anti-idiotypic antibody which binds to the first antigen-binding region as defined in any one of the embodiments disclosed herein, or which binds to the second antigen-binding region as defined in any one of the embodiments disclosed herein.

The present invention is further illustrated by the following examples, which should not be construed as limiting the scope of the invention.

EXAMPLES

Example 1—Generation of Humanized CD3 Antibodies and Non-Activating Antibody Variants Humanization of CD3 Antibodies Humanization of a murine CD3 antibody SP34 (U.S. Pat. No. 8,236,308, described herein as IgG1-CD3) was performed by Antitope (Cambridge, UK) using their improved version of the germline humanization (CDR-grafting) technology (EP0629240). Using this technology, 4 different VH chains (SEQ ID NOs:6, 7, 8, and 9) and 3 different VL chains (SEQ ID NOs:10, 11, and 12) were designed. By combining these 4 VH with the 3 VL chains, 12 different antibodies were generated. The humanized variants are described herein as huCD3. Thus, humanized variants comprising a VH and a VL according to the invention, are described as, e.g., IgG1-huCD3-H1L1 meaning that said specific variant is of the IgG1 isotype, is a humanized SP34 CD3-specific antibody and comprises the VH amino acid sequence termed "H1" and is defined according to SEQ ID NO:6, and the VL amino acid sequence termed "L1" and is defined according to SEQ ID NO:10. Thus, H1 refers to the variable heavy chain region VH1, L1 refers to the variable light chain region VL1, and so forth.

In particular, the variants IgG1-huCD3-H1L1 (humanized CD3 comprising the VH1 sequence set forth in SEQ ID NO:6 and the VL1 sequence set forth in SEQ ID NO:10), IgG1-huCD3-H1L2 (humanized CD3 comprising the VH1 sequence set forth in SEQ ID NO:6 and the VL2 sequence set forth in SEQ ID NO:11), IgG1-huCD3-H1L3 (humanized CD3 comprising the VH1 sequence set forth in SEQ ID NO:6 and the VL3 sequence set forth in SEQ ID NO:12), IgG1-huCD3-H3L3 (humanized CD3 comprising the VH3 sequence set forth in SEQ ID NO:8 and the VL3 sequence set forth in SEQ ID NO:12), IgG1-huCD3-H4L1 (humanized CD3 comprising the VH4 sequence set forth in SEQ ID NO:9 and the VL1 sequence set forth in SEQ ID NO:10), IgG1-huCD3-H3L1 (humanized CD3 comprising the VH3 sequence set forth in SEQ ID NO:8 and the VL1 sequence set forth in SEQ ID NO:10), IgG1-huCD3-H3L3 (humanized CD3 comprising the VH3 sequence set forth in SEQ ID NO:8 and the VL3 sequence set forth in SEQ ID NO:12), and IgG1-huCD3-H4L3 (humanized CD3 comprising the VH4 sequence set forth in SEQ ID NO:9 and the VL3 sequence set forth in SEQ ID NO:12) have been used as the first antigen-binding region of the bispecific antibodies according to the invention. Herein, "IgG1-huCD3", if not further defined refers to IgG1-huCD3-H1L1.

In some examples the CD3 antibody comprising the heavy and light chain variable region sequences of huCLB-T3/4 (SEQ ID NOs:17 and 18, respectively) were used as the first antigen-binding region of the bispecific antibodies according to the invention. huCLB-T3/4 is a humanized version of the murine CD3 antibody CLB-T3/4 (Parren et al., Res Immunol. 1991, 142(9):749-63). Both sequences (SEQ ID NOs:17 and 18) were cloned into the relevant pcDNA3.3 (Invitrogen) expression vectors and expressed by cotransfection in HEK293F cells. The resulting CD3 antibody is described as IgG1-huCLB-T3/4.

The humanized CD3 antibodies are further disclosed in WO2015001085.

CD20 Antibodies

The CD20 antibodies used as the second binding arm of the present bispecific antibodies are further disclosed in WO2004035607 (Genmab) and WO2005103081 (Genmab).

Control Antibodies

The following antibodies were used as control antibodies in the examples: CD3 antibodies IgG1-CD3 (the parental CD3 antibody SP34 having the VH and VL sequences set forth in SEQ ID NO:25 and SEQ ID NO:26, respectively)

IgG1-huCD3 (H1L1) (having the VH and VL sequences set forth in SEQ ID NO:6 and SEQ ID NO:10, respectively)

IgG1-huCLB-T3/4 bsIgG1-huCD3-H1L1-FEAL×b12-FEAR (bispecific antibody using as the second arm the antibody b12 which is a gp120 specific antibody (Barbas, C F. J Mol Biol. 1993 Apr. 5; 230(3):812-23).

IgG1-huCD3-H1L1-FEAL

IgG1-huCLB-T3/4-FEAL

CD20 Antibodies

IgG1-7D8 (having the VH and VL sequences set forth in SEQ ID NO:27 and SEQ ID NO:28, respectively)

IgG1-11B8 (having the VH and VL sequences set forth in SEQ ID NO:40 and SEQ ID NO:41, respectively)

IgG1-2F2 (having the VH and VL sequences set forth in SEQ ID NO:37 and SEQ ID NO:28, respectively)

IgG1-RTX (having the VH and VL sequences of rituximab)

IgG1-GA101 (having the VH and VL sequences of obinutuzumab, CHEMBL1743048, U.S. Pat. No. 8,883,980, with a wild type human IgG1 Fc domain)

IgG1-2C6 (having the VH and VL sequences set forth in SEQ ID NO:47 and SEQ ID NO:48, respectively).

IgG1-7D8-FEAR

IgG1-11B8-FEAR

IgG1-2F2-FEAR

IgG1-GA101-FEAR

IgG1-2C6-FEAR

TABLE 4

Quantification of 7D8 CD20 antibody binding on different B cell lines

| Lymphoma type | Cell line | 50,000-100,000 ABC*/cell | 100,000-200,000 ABC/cell | >200,000 ABC/cell |
|---|---|---|---|---|
| Burkitt's lymphoma | Daudi | | X | |
| Burkitt's lymphoma | Raji | | X | |
| B-ALL | Nalm-16 | X | | |
| ABC-DLBCL | OCl-Ly7 | | | X |
| GC-DLBCL | SU-DHL-4 | | | X |
| FL | WSU-NHL | | | X |

*ABC: antibody-binding capacity
Quantitative flow cytometry (QIFIKIT ®, Dako; cat. no K0078) was performed as described (Poncelet and Carayon, 1985, J. Immunol. Meth. 85: 65-74), to quantify the binding of 7D8 CD20 antibody on different human B-cell lines used in the examples, as an indication of CD20 expression. To this end, human B-cell lines were incubated with a saturating concentration of 7D8, and the number of bound 7D8 molecules was determined using quantitative flow cytometry.
The anti-human CD20 antibody 7D8, that was engineered to express a murine Fc domain (10 µg/mL, mmIgG1-7D8 (Overdijk et al. 2012, J. Immunol. 189: 3430-3438), was used in this assay. B-ALL: B cell acute lymphoblastic leukemia, ABC-DLBCL: activated B cell diffuse large B-cell lymphoma, GC-DLBCL: germinal center diffuse large B-cell-lymphoma, FL: follicular lymphoma.

Example 2—Generation of Bispecific Antibodies by 2-MEA-Induced Fab-Arm Exchange

An in vitro method for producing bispecific antibodies is described in WO2008119353 (Genmab) and reported by van der Neut-Kolfschoten et al. (Science. 2007 Sep. 14; 317 (5844):1554-7). Herein, the bispecific antibodies were formed by "Fab-arm" or "half-molecule" exchange (swapping of a heavy chain and attached light chain) between two monospecific IgG4- or IgG4-like antibodies upon incubation under mildly reducing conditions. Without being limited to theory, this Fab-arm exchange reaction was the result of a disulfide-bond isomerization reaction wherein the inter heavy-chain disulfide bonds in the hinge regions of monospecific antibodies were reduced and the resulting free cysteines form a new inter heavy-chain disulfide bond with cysteine residues of another antibody molecule with a different specificity. The resulting products were bispecific antibodies having two Fab arms with different sequences.

The knowledge of this natural IgG4 Fab-arm exchange was adapted to generate a method to produce stable IgG1-based bispecific antibodies (WO2011131746 (Genmab)). The bispecific antibody product generated by this method described below will no longer participate in IgG4 Fab-arm exchange. The basis for this method was the use of complimentary CH3 domains, which promote the formation of heterodimers under specific assay conditions. To enable the production of bispecific antibodies by this method, IgG1 molecules carrying certain mutations in the CH3 domain were generated: in one of the parental IgG1 antibody T350I, K370T and F405L mutations (or minimally F405L) in the other parental IgG1 antibody the K409R mutation.

To generate bispecific antibodies, these two parental antibodies, each antibody at a final concentration of 0.5 mg/mL (equimolar concentration), were incubated with 25 mM 2-mercaptoethylamine-HCl (2-MEA) in a total volume of 100 µL Tris-EDTA (TE) at 37° C. for 90 min. The reduction reaction is stopped when the reducing agent 2-MEA is removed by using spin columns (Microcon centrifugal filters, 30 k, Millipore) according to the manufacturer's protocol.

Example 3—Generation of Mutants to Optimize the Production of the Humanized CD3 Antibodies Generation of huCD3-L1 Mutant Plasmids Several IgG1-huCD3-H1L1 variants with mutations in the L1 light chainwere generated in order to improve the expression levels of IgG1-huCD3-H1L1 in transient transfection assays, cf. Table 5. The selection of residues was based on comparisons with germline sequences or screening for the presence of rare residues in the huCD3-L1 sequence in combination with crystal structures from homologous antibodies. The selected sequences were synthesized at GeneArt (Life Technologies, Germany). p33L encodes the constant domain of the human IgLC2/IgLC3 lambda light chain of SEQ ID NO:29. p33G1f encodes the IgG1m(f) heavy chain constant region of SEQ ID NO: 15.

TABLE 5

| LC constructs | LC Mutants | Antibody name after co-expression with HC VH1 encoding plasmid |
|---|---|---|
| p33L-huCD3-VL1 | — | IgG1-huCD3-H1L1 |
| p33L-huCD3-VL1-F10L | F10L | IgG1-huCD3-H1L1-LF10L |
| p33L-huCD3-VL1-R23A | R23A | IgG1-huCD3-H1L1-LR23A |
| p33L-huCD3-VL1-A35P | A35P | IgG1-huCD3-H1L1-LA35P |
| p33L-huCD3-VL1-T41K | T41K | IgG1-huCD3-H1L1-LT41K |
| p33L-huCD3-VL1-K55N | K55N | IgG1-huCD3-H1L1-LK55N |
| p33L-huCD3-VL1-L97H | L97H | IgG1-huCD3-H1L1-LL97H |
| p33L-huCD3-VL1-LKNH | F10L, T41K, K55N, L97H | IgG1-huCD3-H1L1-LLKNH |
| p33L-huCD3-VL1-LTGPEAEY | F10L, R47T, D71G, A82P, D83E, S86A, I87E, F89Y | IgG1-huCD3-H1L1-LLTGPEAEY |
| p33L-huCD3-VL1-LAPTGPEAEY | F10L, R23A, A35P, R47T, D71G, A82P, D83E, S86A, I87E, F89Y | IgG1-huCD3-H1L1-LLAPTGPEAEY |

Transient Expression in Expi293F Cells

For a single antibody, the plasmids encoding heavy chain (HC) and light chain (LC) were transiently transfected in Freestyle Expi293F cells (Life technologies, USA) using ExpiFectamine 293 (Life technologies). In total 1.5 µg HC encoding plasmid and 1.5 µg LC encoding plasmid (Table 5) were diluted in 150 µL Opti-MEM (Gibco, USA). To prepare the transfection mix, 8 µL ExpiFectamine 293 was diluted in 150 µL Opti-MEM and incubated for 5 minutes at room temperature. Next, the DNA/Opti-MEM and ExpiFectamine 293/Opti-MEM solutions were mixed, incubated for 20 minutes at room temperature and added to 2.55 mL Expi293 Expression Medium containing 7.5×106 Expi293F cells and 50 U/mL Pen-Strep. The cells were incubated at 37° C., 8% C02 and shaken at 200 rpm. To enhance expression, 21 hours after transfection, 15 µL enhancer mix 1 and 150 µL enhancer mix 2 were added. The cells were incubated for 4 days followed by the harvest of the supernatant. Supernatants were spun at 3,000×g and filter sterilized over a 0.2 µm filter. The IgG expression levels were measured on the Octet RED (ForteBio, US) using anti-human IgG sensors (ForteBio, USA).

IgG Concentration Analysis

The IgG1-huCD3-H1L1 antibody expressed at 72 µg/mL. A 4-fold increase in IgG expression was observed for the IgG1-huCD3-H1L1-LT41K mutant (295 µg/mL). Similar expression levels were observed for IgG1-huCD3-H1L1-LLKNH mutant (311 µg/mL), including the T41K mutation amongst other mutations. The other mutations in these constructs did not show expression enhancement when tested individually (IgG1-huCD3-H1L1-LF10L, IgG1-huCD3-H1L1-LK55N, IgG1-huCD3-H1L1-LL97H) compared to IgG1-huCD3-H1L1.

A second set of expression enhancing mutations was observed for the combination of R23A and A35P. While IgG1-huCD3-H1L1-LLTGPEAEY variant lacking R23A and A35P did not show enhanced expression (83 µg/mL), IgG1-huCD3-H1L1-LLAPTGPEAEY containing the additional R23A and A35P mutations did show a 3-fold increase in expression (237 µg/mL). Individually, R23A or A35P did not show enhanced expression levels (56 and 81 µg/mL, respectively).

Example 4—Binding of Bispecific CD3×CD20 Antibodies to Daudi and Jurkat Cells

Binding of bsIgG1-huCD3-H1L1-FEAL×CD20-7D8-FEAR to the human CD3-negative CD20-positive Daudi (American Type Culture Collection, ATCC® CCL-213™, derived from human Burkitt's lymphoma) and the human CD3-positive CD20-negative Jurkat (Deutsche Sammlung von Mikroorgansimen und Zellkulturen, DSMZ® ACC 282™, derived from acute T-cell leukemia) cell lines was analyzed by flow cytometry. In addition to the non-activating mutations, L234F, L235E, D265A, on both arms, the bispecific antibody contained an F405L mutation on one arm and a K409R mutation on the other arm.

Cells ($1 \times 10^5$ cells/well) were incubated in polystyrene 96-well round-bottom plates (Greiner bio-one, cat. no. 650101) with serial dilutions of antibodies (range 0.041 to 30 µg/mL in 3-fold dilution steps [A-E] and 0.00061 to 10 µg/mL in 4-fold dilution steps [F-I]) in 100 µL PBS/0.1% BSA/0.02% azide (from here designated as staining buffer) at 4° C. for 30 min.

After washing twice in staining buffer, cells were incubated in 50 µL secondary antibody at 4° C. for 30 min. As a secondary antibody, R-Phycoerythrin (PE)-conjugated goat-anti-human IgG F(ab')$_2$ (cat. no. 109-116-098, Jackson ImmunoResearch Laboratories, Inc., West Grove, Pa.) diluted 1:200 in staining buffer, was used for all experiments. Next, cells were washed twice in staining buffer, re-suspended in 30 µL staining buffer and analyzed on an iQue screener (Intellicyt Corporation, USA) (for FIG. 1A-E) or re-suspended in 100 µL staining buffer and analyzed on a FACSCANTOII (BD Biosciences) (FIG. 1F-I). Binding curves were analyzed using non-linear regression (sigmoidal dose-response with variable slope) using GraphPad Prism V75.04 software (GraphPad Software, San Diego, Calif., USA).

FIG. 1 A-F show that bsIgG1-huCD3-H1L1-FEAL×CD20-7D8-FEAR and bsIgG1-huCD3-H1L1-FEAL×CD20-2F2-FEAR showed dose-dependent binding to Daudi cells, with higher maximum binding than monospecific, bivalent CD20 antibodies IgG1-7D8 and IgG1-2F2. For bsIgG1-huCD3-H1L1-FEAL×CD20-11B8-FEAR, bsIgG1-huCD3-H1L1-FEAL×CD20-RTX-FEAR and bsIgG1-huCD3-H1L1-FEAL×CD20-GA101-FEAR, the maximum binding was similar to that of the bivalent, monospecific CD20 antibodies IgG1-11B8, IgG1-RTX and IgG1-GA101. Maximum binding of bsIgG1-huCD3-H1L1-FEAL×CD20-11B8-FEAR, bsIgG1-huCD3-H1L1-FEAL×CD20-RTX-FEAR, bsIgG1-huCD3-H1L1-FEAL×CD20-GA101-FEAR, and of the bivalent, monospecific CD20 antibodies IgG1-11B8, IgG1-RTX and IgG1-GA101 was lower than that of bsIgG1-huCD3-H1L1-FEAL×CD20-7D8-FEAR, bsIgG1-huCD3-H1L1-FEAL×CD20-2F2-FEAR and bivalent, monospecific CD20 antibodies IgG1-7D8 and IgG1-2F2. Maximum binding of huCD3-H1L1-FEAL×CD20-2C6-FEAR was comparable to that of monospecific CD20 antibody IgG1-7D8.

Figure 1G:
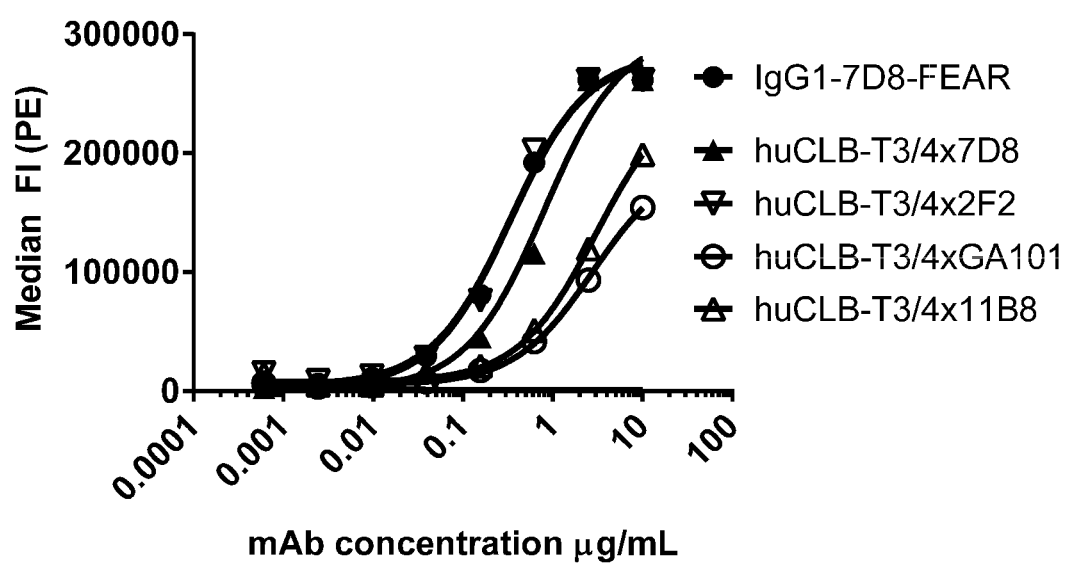

FIG. 1G shows binding to Daudi cells of CD3×CD20 bispecific antibodies containing the CD3-specific huCLB-T3/4 Fab-arm. BsIgG1-huCLB-T3/4-FEAL×CD20-7D8-FEAR, bsIgG1-huCLB-T3/4-FEAL×CD20-2F2-FEAR showed binding comparable to the monospecific CD20 antibody IgG1-7D8. As for the CD3×CD20 bispecifics containing the CD3-specific huCD3-H1L1 Fab-arm, the binding for bsIgG1-huCLB-T3/4-FEAL×CD20-11B8-FEAR and bsIgG1-huCLB-T3/4-FEAL×CD20-GA101-FEAR was lower than that of the monospecific CD20 antibody IgG1-7D8 and the CD3×CD20 bispecific antibodies containing a CD20-specific 7D8- or a 2F2-Fab-arm.

Figure 1H:
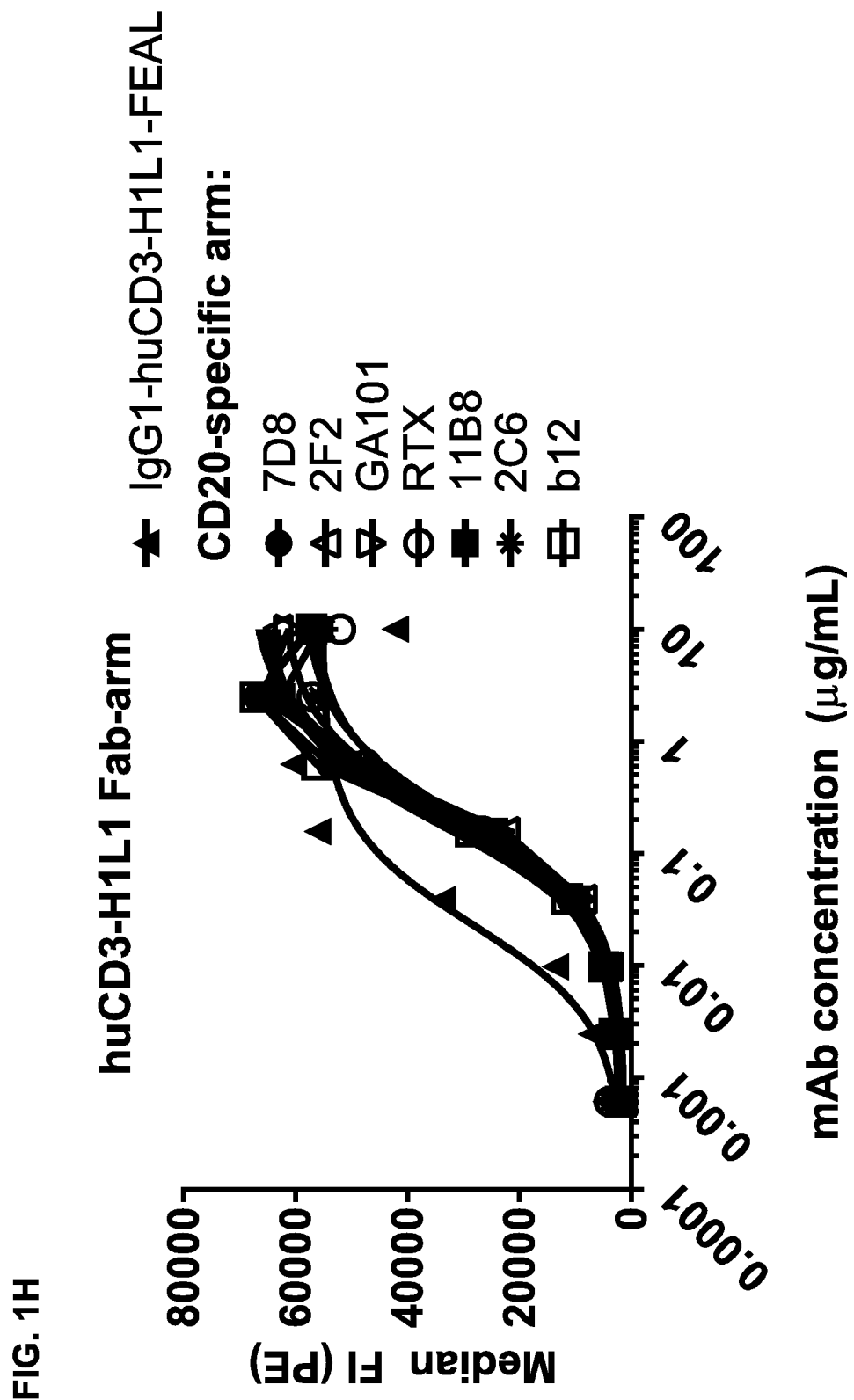
Figure 1I:
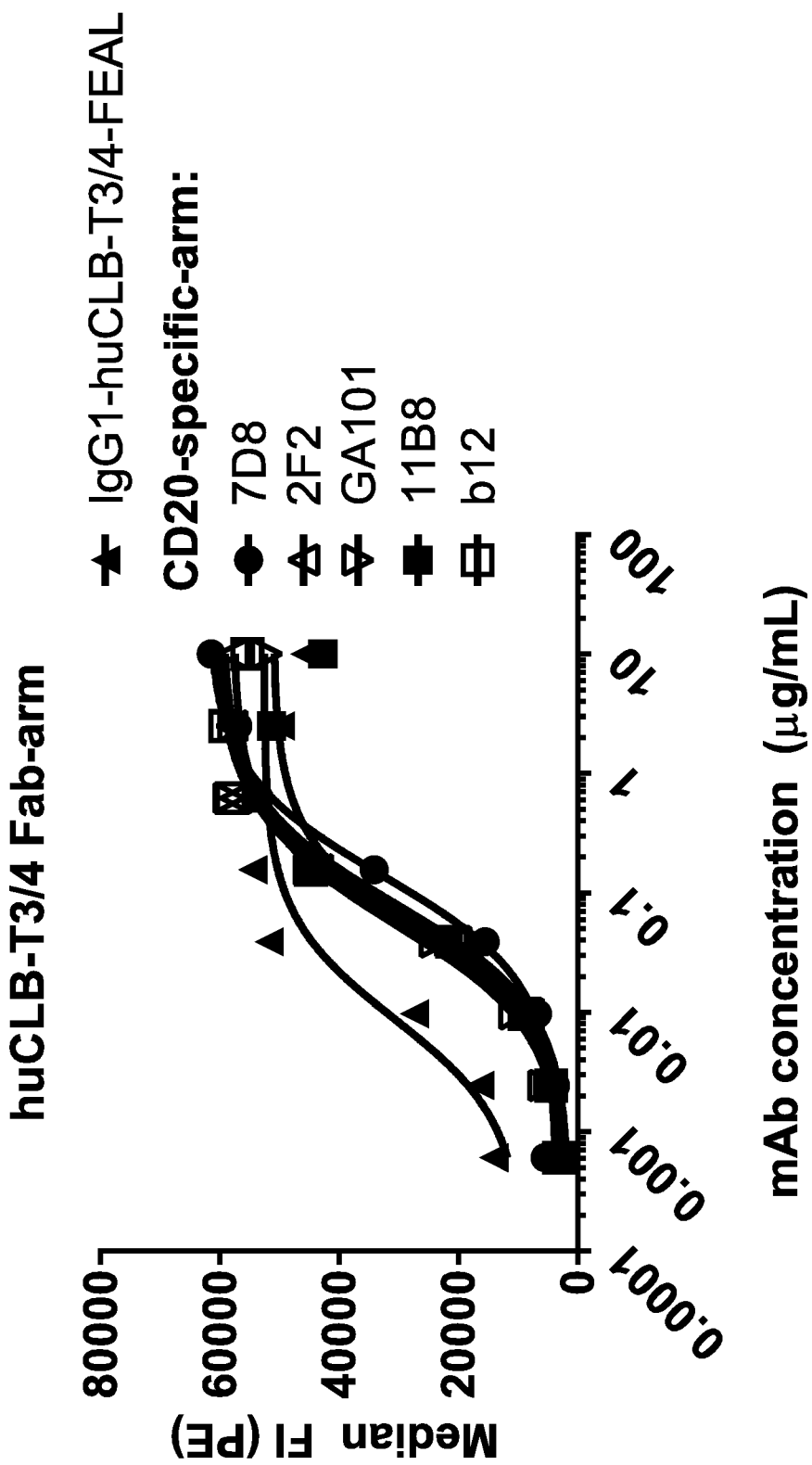

FIGS. 1H and I show binding to Jurkat cells of CD3×CD20 bispecific antibodies containing a CD3-specific huCD3-H1L1- or a huCLB-T3/4-Fab-arm, respectively. All CD3×CD20 bispecific antibodies with a CD3-specific Fab-arm originating from IgG1-huCD3-H1L1-FEAL showed comparable binding to Jurkat cells, irrespective of the origin of the CD20-specific Fab-arm (FIG. 1H). Similarly, all CD3×CD20 bispecific antibodies with a CD3 Fab-arm obtained from IgG1-huCLB-T3/4-FEAL showed comparable binding (FIG. 1G). The monospecific, bivalent parental CD3-specific antibodies, IgG1-huCD3-H1L1 and IgG1-huCLB-T3/4, bound to Jurkat cells with lower EC5so values than the CD3×CD20 bispecific antibodies.

Example 5—Concentration-Dependent Simultaneous Binding of bsIgG1-huCD3-H1L1-FEAL×CD20-7D8-FEAR to T Cells and B Cells Human B cells express the surface antigen CD20, but lack expression of CD3. In contrast, human T cells express the surface antigen CD3, but lack expression of CD20. The bispecific antibody bsIgG1-huCD3-H1L1-FEAL×CD20-7D8-FEAR recognizes both CD3 and CD20 and is therefore able to bind both human B and T cells. Simultaneous binding of the bispecific antibody bsIgG1-huCD3-H1L1-FEAL×CD20-7D8-FEAR to B and T cells was shown by incubating 100 µL heparinized whole blood from a healthy donor in the presence of a concentration range of antibodies (range 0.001 to 100 µg/mL in 10-fold dilution steps, obtained by adding different volumes of undiluted antibody to the blood sample) at 37° C. for 2 hours. The CD20 antibody 2F2 and bsIgG1-huCD3-H1L1-FEAL×b12-FEAR, that exclusively recognize CD20 or CD3 respectively, and thus are unable to simultaneously bind B and T cells, were used as negative control antibodies. Cells were washed twice in staining buffer (1200 RPM, 3 min.) and incubated with antibodies specific for CD4 (CD4-PE; Becton Dickinson, cat. no. 555347) or CD8 (CD8-PE; Miltenyi, cat. no. BW135/80) (to identify the different T cell subsets) and CD19 (CD19-APC; DAKO, cat. no. C7224) (to identify B cells) for 30 min at 4° C. Before analysis, erythrocytes were lysed by addition of 100 µL erythrocyte lysis buffer (10 mM KHCO3/0.01 mM EDTA/155 mM NH4CI dissolved in $dH_2O$) (KHCO3: Sigma, cat. no. P9144; EDTA: FLUKA, cat. no. 036; NH4CI: Sigma, cat. no. A-5666). Samples were analyzed by flow cytometry, using a FACSCANTOII equipped with an automated plate loader (Becton Dickinson). The number of $CD4^+$ $CD19^+$ or $CD8^+$ $CD19^+$ double-positive events, indicative of simultaneous binding of bsIgG1-huCD3-H1L1-FEAL×CD20-7D8-FEAR to human T and B cells, was quantified by CD4/CD19 and CD8/CD19 quadrant analysis.

Figure 2A:
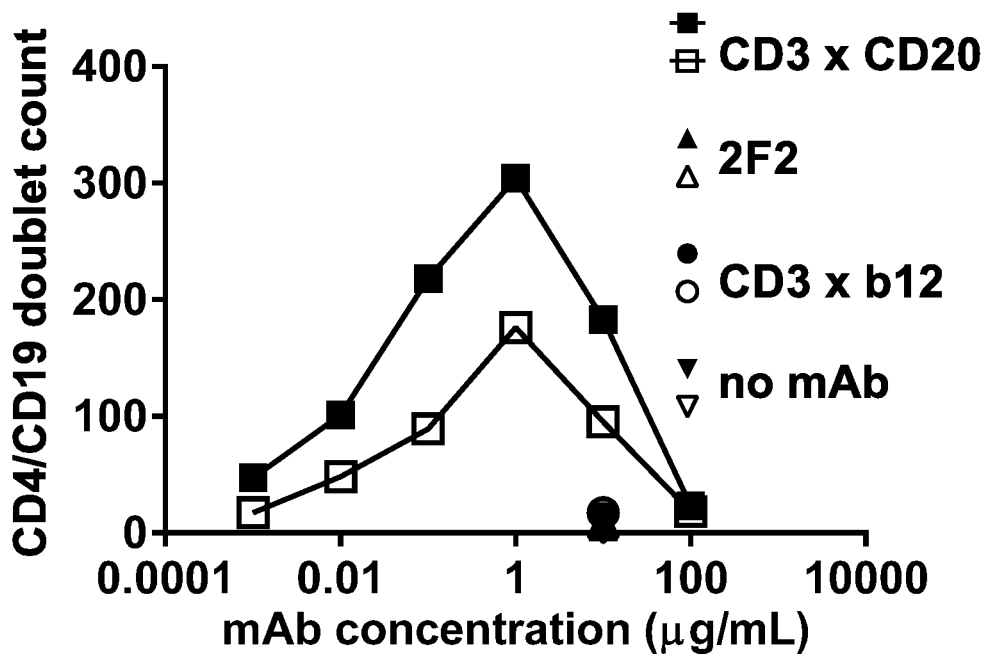
FIGS. 2A and 2B: Concentration-dependent simultaneous binding of bsIgG1-huCD3-H1L1-FEAL×CD20-7D8-FEAR (CD3×CD20) to T cells and B cells. Simultaneous binding of the bispecific antibody bsIgG1-huCD3-H1L1-FEAL×CD20-7D8-FEAR (CD3×CD20) to B and T cells in blood was analyzed by flow cytometry. Data shown are from one representative experiment. Data shown are the number of double-positive (CD19 and CD4 [FIG. 2A] or CD19 and CD8 [FIG. 2B]) events, as determined by the number of events in the upper right quadrant of the CD4/CD19 or the CD8/CD19 flow cytometry dot-plot. Closed and open symbols indicate data from different healthy donors. IgG1-2F2 (2F2, CD20-specific) and bsIgG1-huCD3-H1L1-FEAL×b12-FEAR (CD3×b12, CD3-specific) were included as negative control antibodies.
Figure 2B:
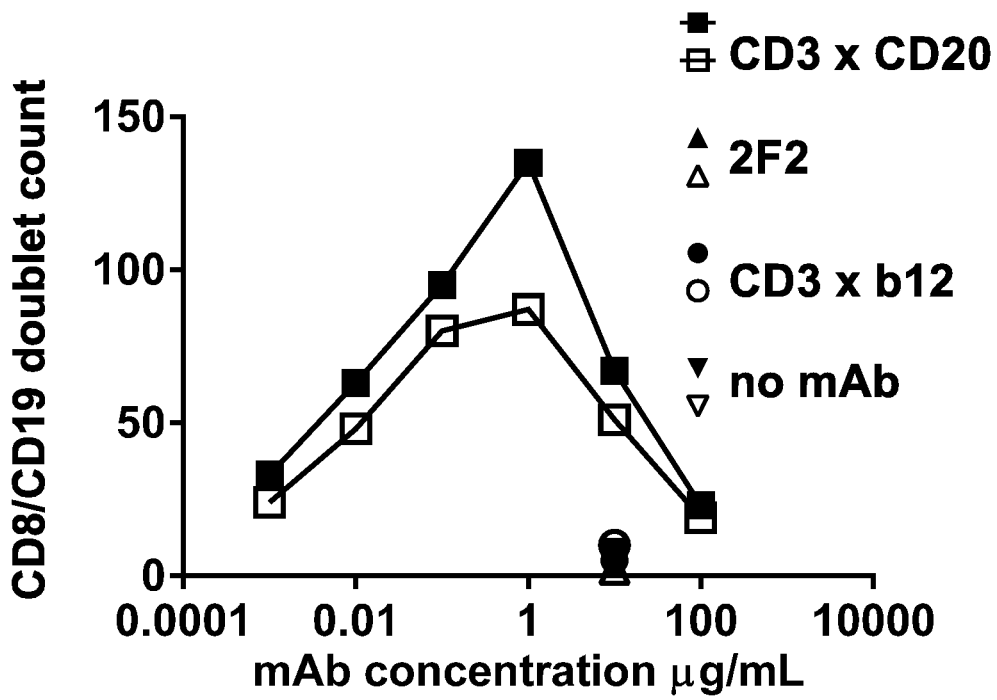
Figure 3A:
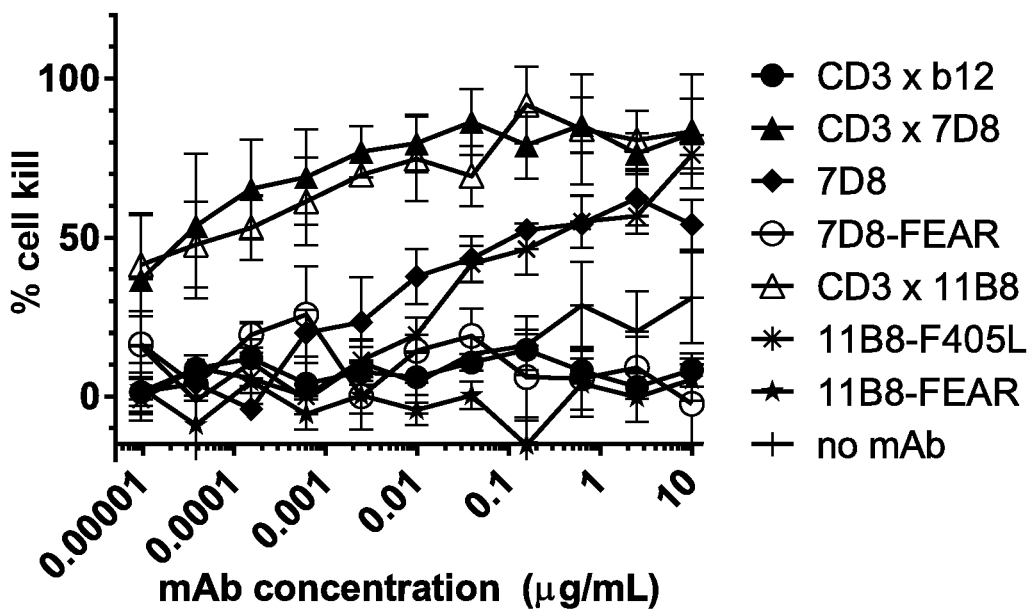
FIGS. 3A-3N: Induction of cytotoxicity in vitro by CD3×CD20 bispecific antibodies in human B-cell lymphoma and B cell leukemia cell lines.
Figure 3B:
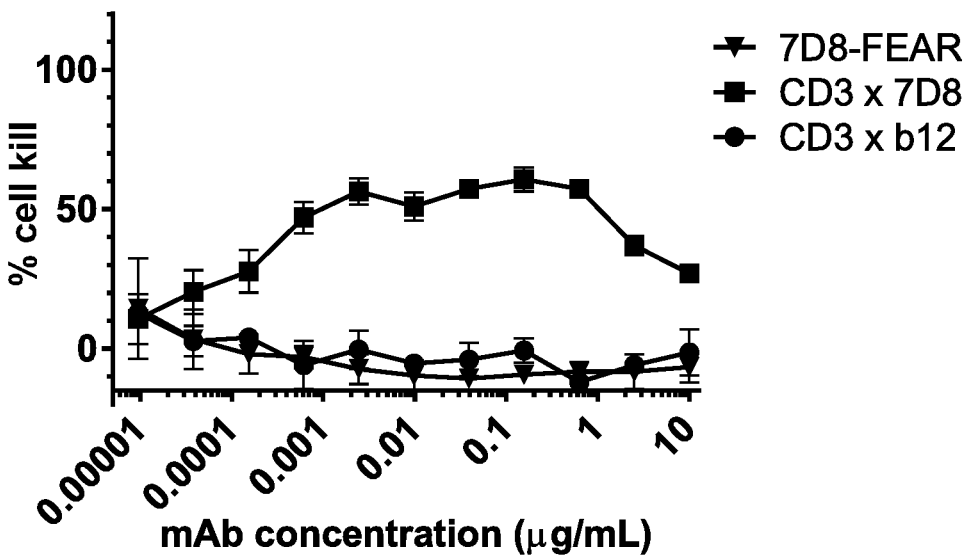
(FIG. 3B) Daudi cells were incubated with BsIgG1-huCD3-H1L1-FEAL×CD20-7D8-FEAR (CD3×7D8), the monospecific CD20 antibody IgG1-7D8-FEAR (7D8-FEAR; with inactive Fc region) and bsIgG1-huCD3-H1L1-FEAL×b12-FEAR (CD3×b12), purified T cells were used as effector cells.
Figure 3C:
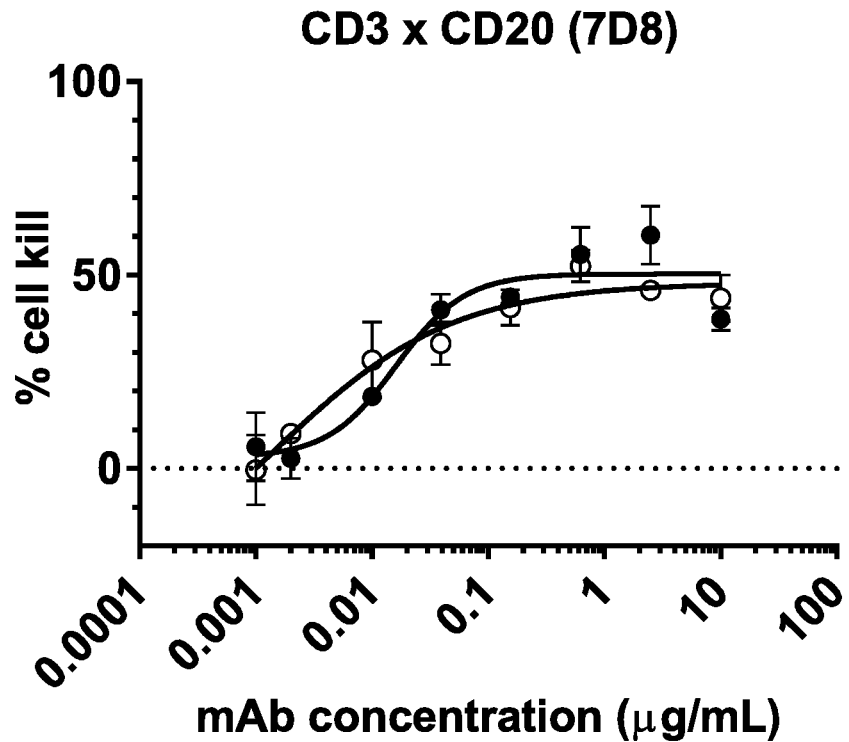
(FIGS. 3C-3F) Daudi cells were incubated with CD3×CD20 bispecific antibodies based on two different CD3 arms (huCD3-H1L1-FEAL and huCLB-T3/4-FEAL Fab arm, represented by open and closed symbols, respectively) and four different CD20 arms: 7D8 (BsIgG1-huCD3-H1L1-FEAL×CD20-7D8-FEAR and BsIgG1-huCLB-T3/4-FEAL×CD20-7D8-FEAR.
Figure 3D:
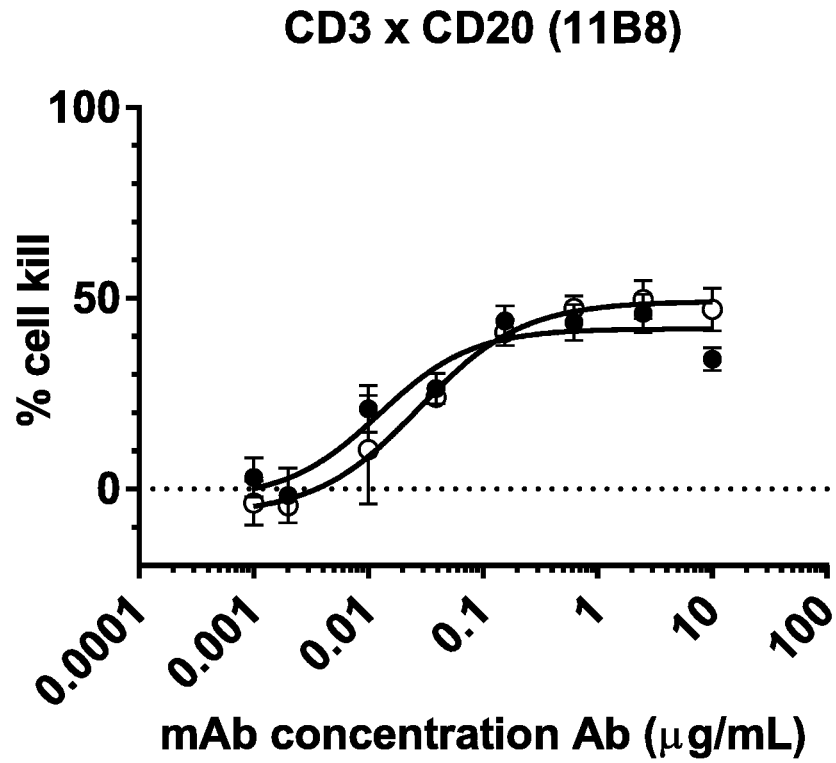
Figure 3E:
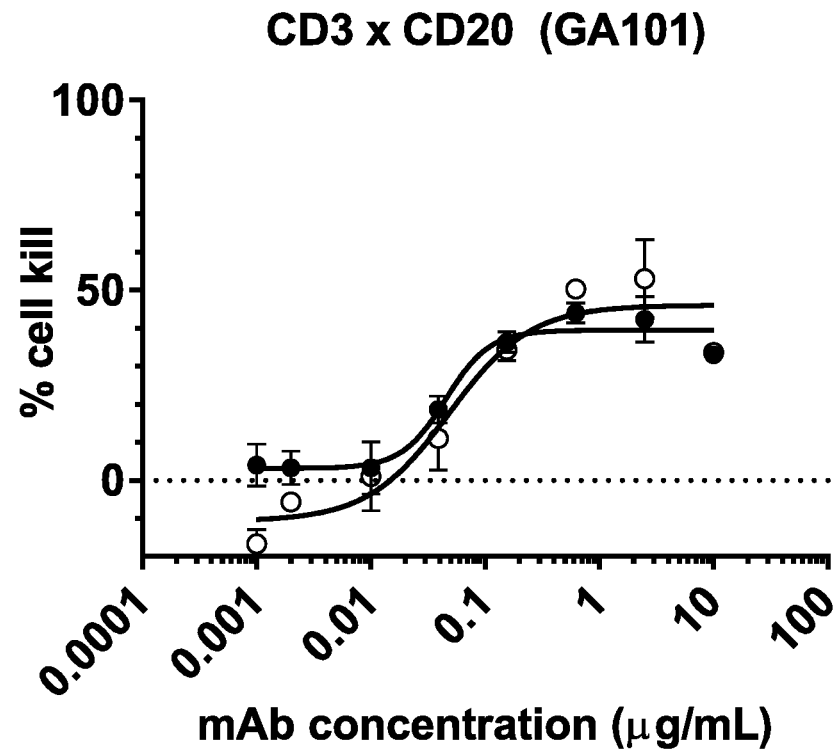
Figure 3F:
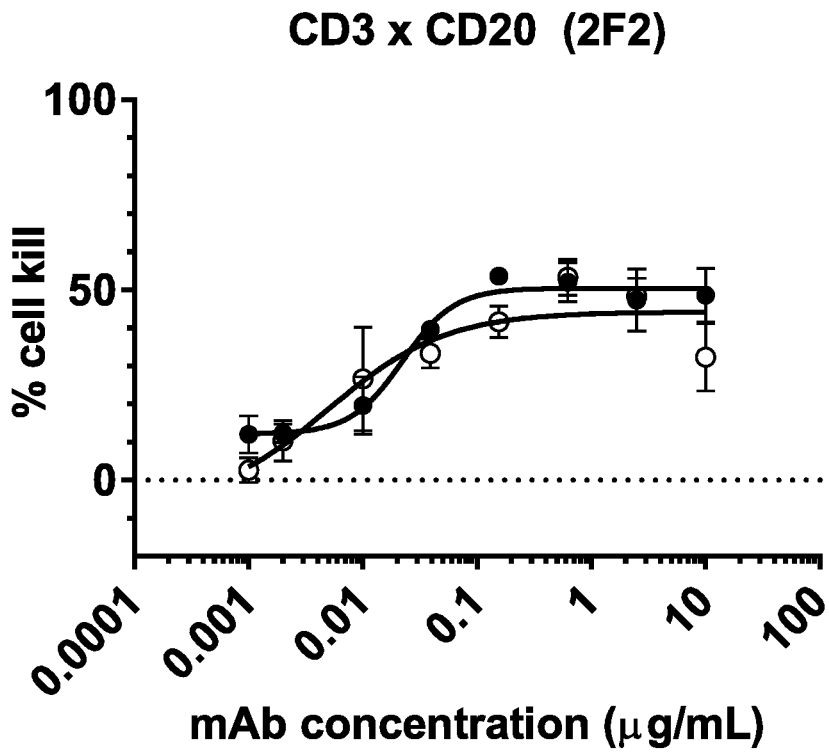
Figure 3G:
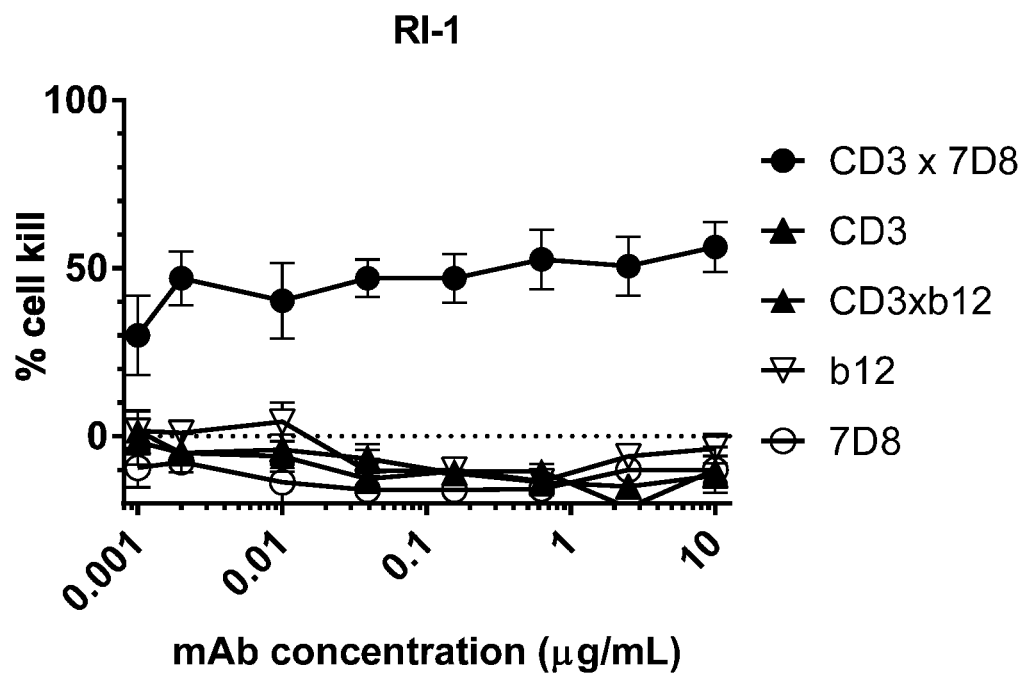
(FIGS. 3G-3M) Different B-cell lines were used as target cells and incubated with antibodies as indicated. CD3×CD20 bispecific antibodies contained the huCD3-H1L1-FEAL Fab arm and different CD20 Fab arms (7D8, 11B8, 2F2, GA101 or RTX) as indicated. CD3 antibody alone was IgG1-huCD3-H1L1. Purified T cells were used as effector cells.
Figure 3H:
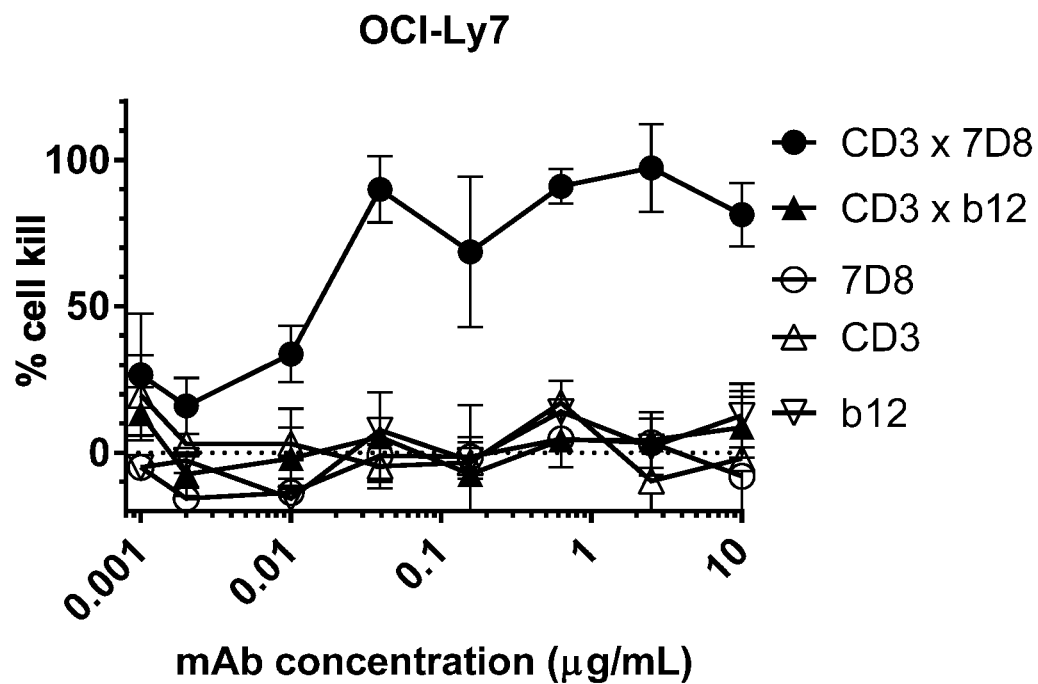
Figure 3I:
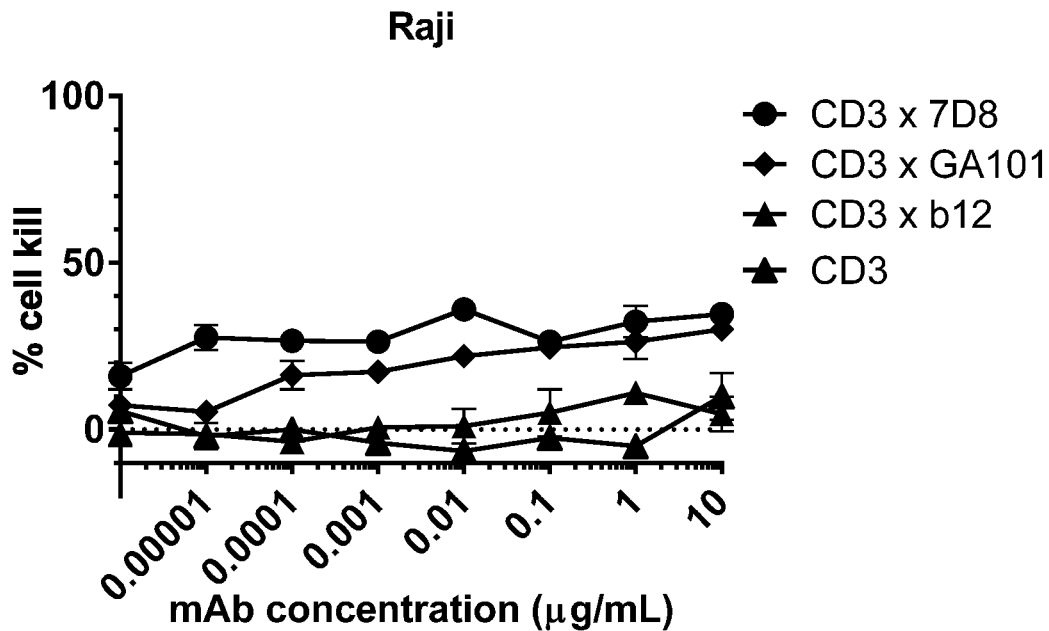
Figure 3J:
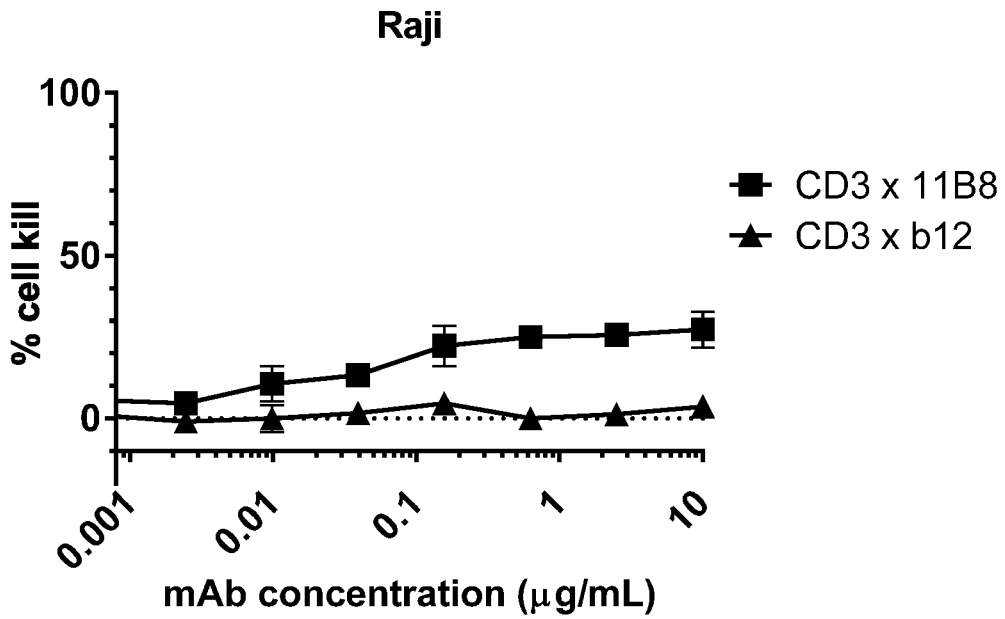
Figure 3K:
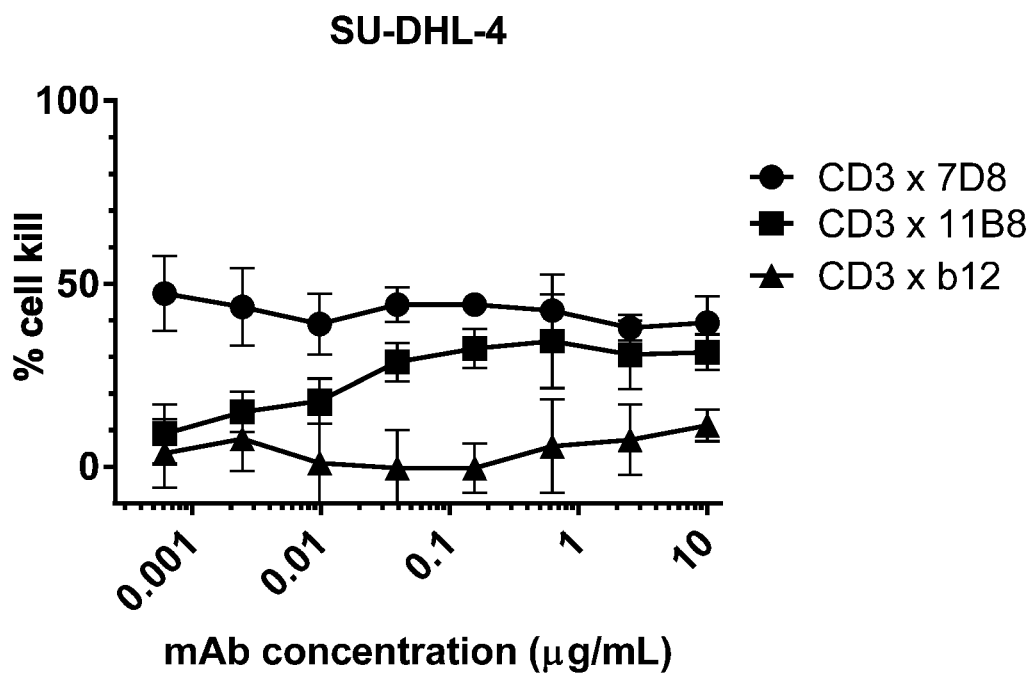
Figure 3L:
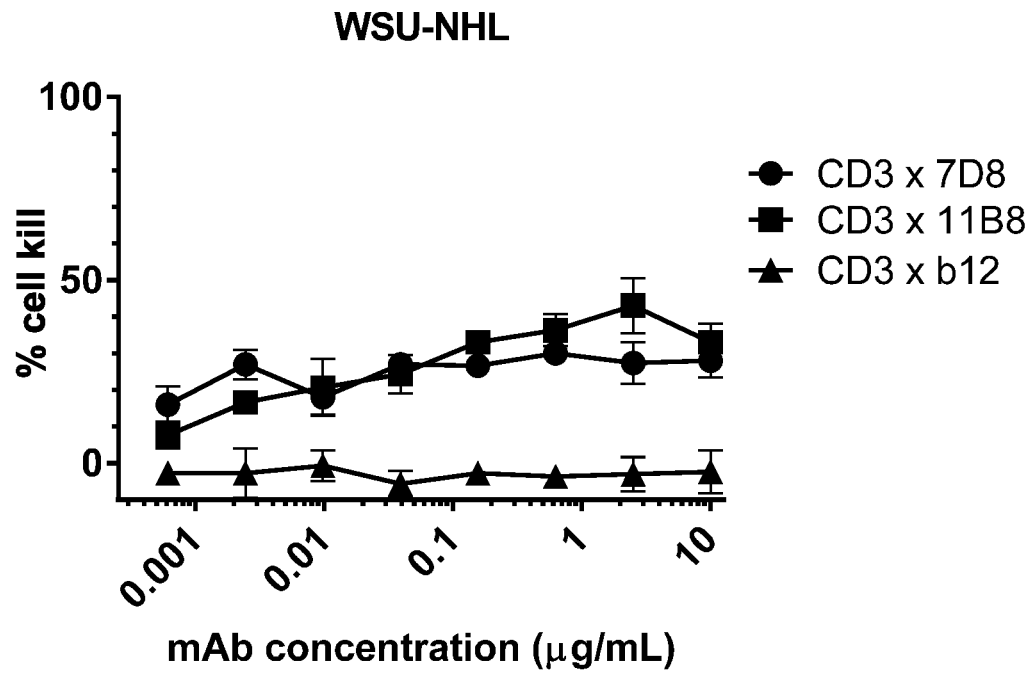
Figure 3M:
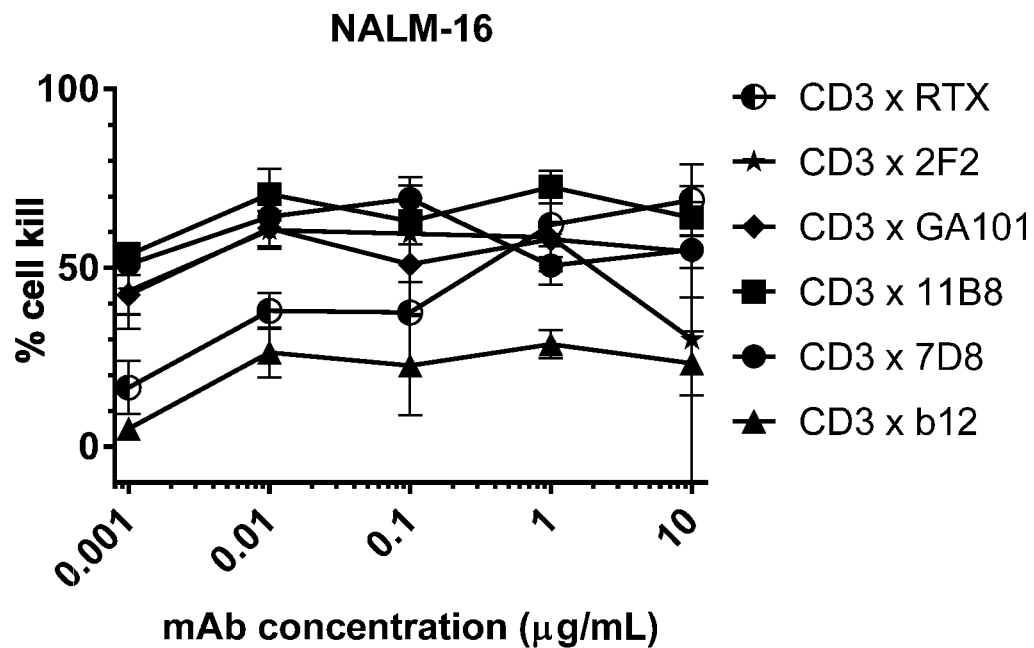
Figure 3N:
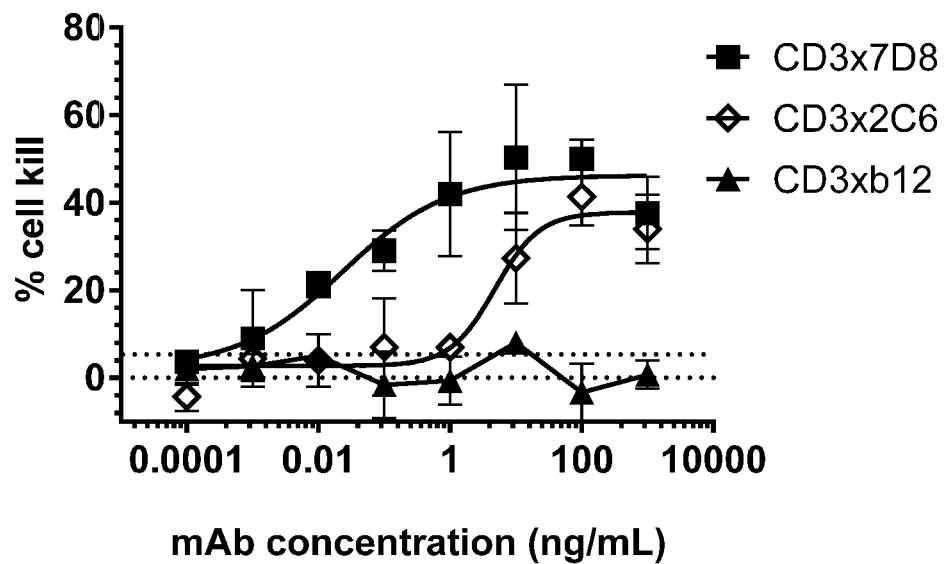

FIGS. 2A and 2B show that only in the presence of the CD3×CD20 bispecific antibody, a population of $CD4^+$ $CD1^9$ and $CD8^+$ $CD19^+$ double-positive events, representing T cell-B cell doublets, was observed, indicating that these bispecific antibodies can bind two cell types simultaneously. The appearance of doublets was antibody concentration-dependent and occurred for both $CD4^+$ (A) and $CD8^+$ T cells (B).

Example 6—Induction of Cytotoxicity In Vitro by CD3×CD20 Bispecific Antibodies

Different CD3×CD20 bispecific antibodies were tested in an in vitro cytotoxicity assay using tumor cell lines as target cells and peripheral blood mononuclear cells (PBMCs) or purified T cells as effector cells.

Target Cells:

The following tumor cell lines were used: Daudi and Raji (described supra), OCI-Ly7 (DSMZ; cat. no. ACC 688; derived from DLBCL), SU-DHL-4 (DSMZ; cat. no. ACC 495; derived from DLBCL), RI-1 (DSMZ; cat. no. ACC 585, derived DLBCL]), NALM-16 (DSMZ; cat. no. ACC 680; derived from B-ALL) and WSU-NHL (DSMZ, cat. no. ACC 58; derived from NHL). Cells were collected ($5\times10^6$ cells) in RPMI++(RPMI-1640 [with 25 mM HEPES and L-glutamin; Lonza, cat. no. BE12-115F], supplemented with 10% bovine serum [Gibco; cat. no. 10371-029] and 25,000 units penicillin/25,000 µg streptomycin [Lonza; cat. no. 17-603E]), spun down (1,200 RPM, 5 min.), re-suspended in 1 mL RPMI++, 100 µCi $^{51}Cr$ (Chromium-51; Perkin Elmer, cat. no. NEZ030002MC) was added and incubated (37° C. water bath, shaking; 1 hour). After washing the cells twice in PBS (1,200 RPM, 5 min.), cells were re-suspended in RPMI++ and counted by trypan blue exclusion. A cell suspension of $1\times10^5$ cells/mL was prepared.

Effector Cells:

Fresh PBMCs were isolated from 40 mL of buffy coat (Sanquin) using a Ficoll gradient (Lonza; lymphocyte separation medium, cat. no. 17-829E) according to the manufacturer's instructions. After re-suspension of cells in RPMI++, cells were counted using Turk solution to exclude erythrocytes and adjusted to a concentration of $10\times10^6$ cells/mL. Purified T cells were obtained from a buffy coat, using the RosetteSep™ Human T Cell Enrichment Cocktail (Stemcell Technologies, cat. no. 15061) or from PBMCs using the Dynabeads® Untouched™ Human T cells isolation kit (Invitrogen; cat. no. 11344D), according to the manufacturer's instructions. Cells were washed twice in PBS and counted using Turk solution and adjusted to a concentration of $1\times10^6$ cells/mL.

Cytotoxicity Assay:

50 µL $^{51}Cr$-labeled target cells were added to a 96-wells round-bottom plate. After addition of 50 µL antibody (final concentrations ranging from 10 µg/mL to 10 µg/mL) in RPMI++, cells were incubated at room temperature for 10 min.

50 µL effector cells (effector to target ratio as indicated), Triton-X-100 (1.7% final concentration; to determine maximum lysis), or RPMI++(to determine background lysis), were added. Cells were incubated at 37° C., 5% $CO_2$, for 24-48 hours. After spinning down the cells (1,200 RPM, 3 min.), 75 µL of supernatant was harvested into 1.4-mL tubes (Micronic; cat. no. MP226RN), and counted in a gamma counter (Perkin Elmer). The percentage specific lysis was calculated as follows: % specific lysis=(cpm sample−cpm target cells only)/(cpm maximal lysis−cpm target cells only)×100. Cpm=counts per minute.

FIG. 3 shows that all bispecific antibodies containing a CD3-specific Fab arm (half-molecule) (derived from IgG1- huCD3-H1L1-FEAL or IgG1-huCLB-T3/4-FEAL) and a CD20-specific Fab arm (i.e. half-molecule) (derived from IgG1-CD20-7D8-FEAR, IgG1-CD20-11B8-FEAR, IgG1-CD20-2F2-FEAR, IgG1-CD20-RTX-FEAR, IgG1-CD20-2C6-FEAR or IgG1-CD20-GA101-FEAR) are capable of inducing cytotoxicity in the B cell lines tested, both when using PBMCs (FIG. 3A, 3M) and purified T cells (FIG. 3B-3L, 3N) as effector cells. The monospecific bivalent antibodies with inert Fc domains (IgG1-7D8-FEAR, IgG1-11B8-FEAR, IgG1-huCD3-H1L1-FEAL, IgG1-huCLB-T3/4-FEAL) were not capable of inducing T cell- or PBMC-mediated cytotoxicity in the B cell lines. This indicates that for the CD3×CD20 bispecific antibodies cytotoxicity was dependent on both CD3 and CD20 binding by the bispecific antibodies. As previously disclosed, the monospecific bivalent CD20 antibodies with active Fc (IgG1-7D8 and IgG1-11B8-F405L) were capable of inducing antibody-dependent cell-mediated cytotoxicity by PBMCs in Daudi cells (FIG. 3A, 3M). In this case, the dominant effector cells are natural killer (NK) cells. The CD3×C20 bispecific antibodies were active at lower concentrations than the monospecific bivalent CD20 antibodies. FIGS. 3C-3F show that both the IgG1-huCLB-T3/4- and the IgG1-huCD3-H1L1-derived CD3 arms induced cytotoxicity with similar efficacy. FIGS. 3G-3M furthermore show that similar results were obtained using tumor cell lines obtained from a wide range of B cell lines. These cell lines were derived from different B cell tumors as indicated in Table 4. This table also shows CD20 expression levels on these cell lines.

Example 7—Induction of Cytotoxicity In Vitro by bsIgG1-huCD3-H1L1-FEALxCD20-7D8-FEAR Using Purified Human Peripheral Blood CD4+ and CD8+ T Cells as Effector Cells To determine whether bsIgG1-huCD3-H1L1-FEAL× CD20-7D8-FEAR could induce cytotoxic activity of both CD4 and CD8 T cells, a cytotoxicity assay was performed using the different T cell subsets as effector cells. Daudi cells were prepared as target cells as described supra.

PBMCs were isolated from a buffycoat from a healthy donor using lymphocyte separation medium, as described supra.

T cells (total T cell population, CD4+ or CD8+ T cell populations) were isolated from the PBMCs using Dynabeads® Untouched™ Human T cells, Dynabeads® Untouched™ Human CD4 T cells or Dynabeads® Untouched™ Human CD8 T cells cell isolation kits (Invitrogen, cat. no. 11344D, 11352D and 11348D, respectively). After isolation, the purity of each fraction was determined by flow cytometry. Cells were incubated with CD3 (CD3-PER-CP; Becton Dickinson, cat. no. 345766) and CD8 (CD8-APC; Becton Dickinson, cat. no. 555369) antibodies, to identify the different T cell subsets, at 4° C. for 30 min. Samples were analyzed by flow cytometry, using a FACSCANTOII equipped with an automated plate loader (Becton Dickinson). A CD3/CD8 quadrant analysis was performed to quantify the frequency of CD3+ events (total T cell population), the CD3+CD8+ double-positive events (CD8+ T cell population) and the CD3+CD8− events (CD4+ T cell population).

Total T cells were added to Daudi cells in a 10:1 effector to target ratio, CD4+ T cells were added in a 8:1 effector to target ratio and CD8+ T cells were added in a 4:1 or 8:1 effector to target (E/T) ratio (as indicated) (FIG. 4A), and a cytotoxicity assay was performed as described supra. To test whether CD4+ T cells inhibited the activity of CD8+ T cells, when added as effector cells, a cytotoxicity assay was performed using either only CD8+ T cells (E/T ratio 4:1) or CD8+ T cells (E/T ratio 4:1) together with CD4+ T cells (E/T ratio 8:1) as effector cells (FIG. 4B).

Figure 4A:
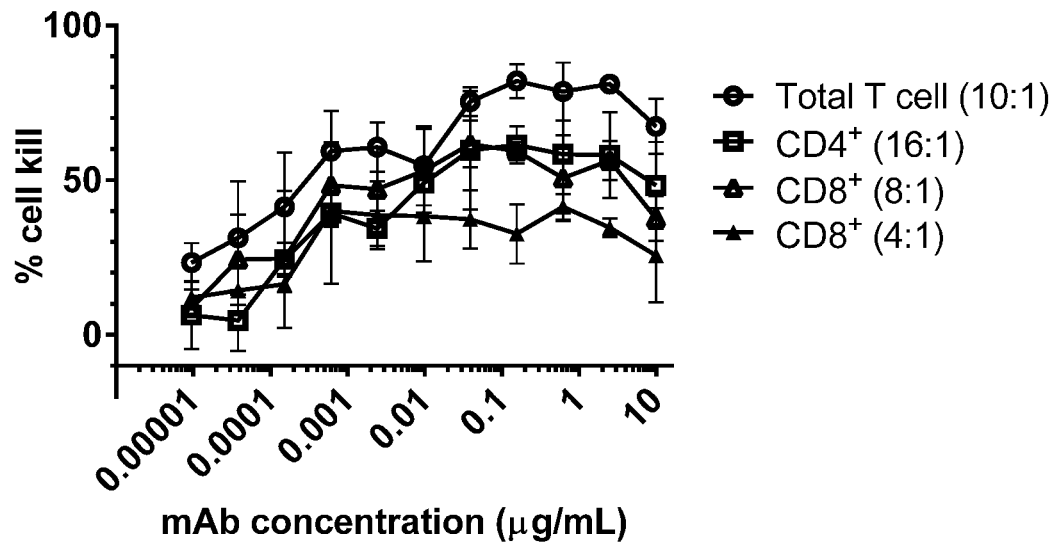
FIGS. 4A and 4B: Dose-dependent induction of cytotoxicity in vitro by bsIgG1-huCD3-H1L1-FEAL×CD20-7D8-FEAR using purified total T cells (CD3$^+$), CD4$^+$ T cells (CD3$^+$ CD8$^-$) and CD8$^+$ T cells (CD3+CD8$^+$) as effector cells. Daudi cells were incubated with the different T-cell subsets, as indicated, and a dilution series of bsIgG1-huCD3-H1L1-FEALxCD20-7D8-FEAR or the control antibodies IgG1-huCD3-H1L1-FEALxb12-FEAR and IgG1-7D8-FEAR (data not shown). Data shown are mean percentages of tumor cell lysis±S.E.M. of triplicate wells (FIG. 4A, FIG. 4B).
Figure 4B:
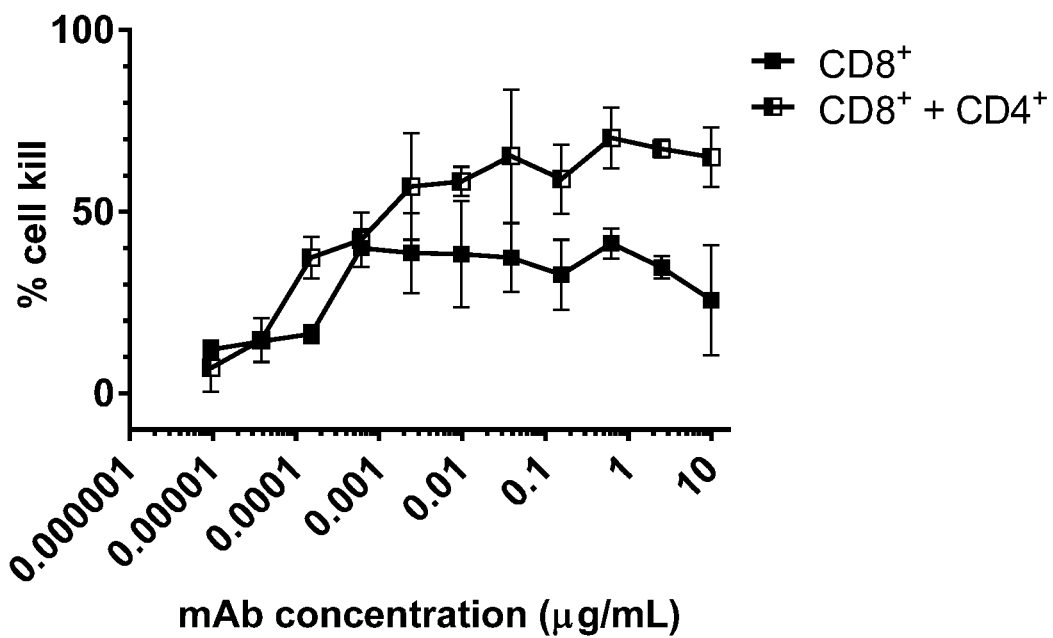

FIG. 4A shows that bsIgG1-huCD3-H1L1-FEAL×CD20-7D8-FEAR induced T-cell-dependent cytotoxicity in Daudi cells, using total T cells, CD4+ T cells or CD8+ T cells as effector cells. The antibodies bsIgG1-huCD3-H1L1-FEAL× b12-FEAR and IgG1-7D8-FEAR, used as negative controls here, did not induce cytotoxicity of Daudi cells (data not shown), indicating that cytotoxicity was dependent on recognition of both CD3 and CD20 by the bispecific molecule. FIG. 4B shows that the addition of CD4+ T cells to CD8+ T cells, as effector cells, did not reduce the efficacy of bsIgG1-huCD3-H1L1-FEAL×CD20-7D8-FEAR.

Table 6 shows that the purity of the isolated cell fractions was ~90% or higher.

TABLE 6

The purity of T-cell subsets, as determined by flow cytometry.

|  | All T cells (CD3+) | CD4+ T cells (CD3+ CD8−) | CD8+ T cells (CD3+ CD8+) |
| --- | --- | --- | --- |
| Total T cells isolated | 95 | 55 | 43 |
| CD4 isolated | 92 | 95 | 0.6 |
| CD8 isolated | 90 | 9.0 | 86 |

Example 8—Kinetics of Cytotoxicity Induction In Vitro by bsIgG1-huCLB-T3/4-FEALxCD20-7D8-FEAR Using Purified T Cells as Effector Cells To determine the kinetics of bsIgG1-huCLB-T3/4-FEAL×CD20-7D8-FEAR-induced cytotoxicity in vitro, Daudi cells were incubated with bsIgG1-huCLB-T3/4-FEAL×CD20-7D8-FEAR in presence of purified T cells, and cytotoxicity was assessed at different timepoints.

The cytotoxicity assay was performed as described supra, with the exception that supernatants were harvested not only after 24 hours, but at different time points ranging from 3-24 hours after incubation.

Figure 5A:
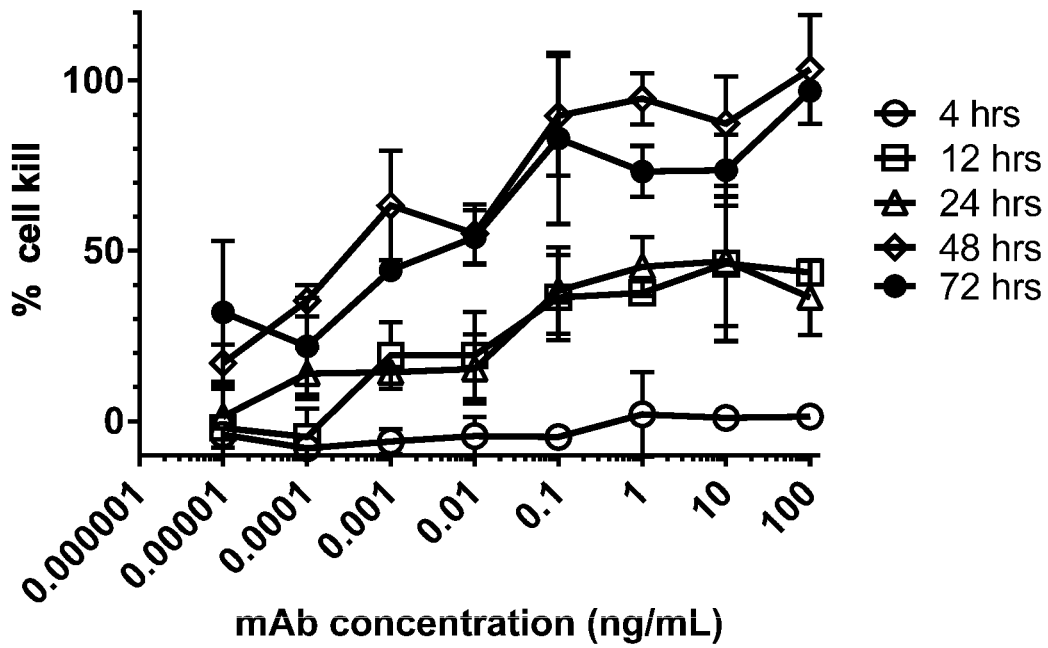
FIGS. 5A and 5B: Kinetics of bsIgG1-huCLB-T3/4-FEALxCD20-7D8-FEAR-dependent cytoxicity in Daudi cells. Daudi cells were incubated with bsIgG1-huCLB-T3/4-FEALxCD20-7D8-FEAR in presence of purified T cells isolated from two different donors (FIG. 5A and FIG. 5B). Cytotoxicity was assessed after 4, 12, 24, 48 and 72 hours of incubation (FIG. 5A) or after 3, 16 and 24 hours of incubation (FIG. 5B). Data shown are percentages cell kill±S.D. of triplicate wells of cells incubated with bsIgG1-huCLB-T3/4-FEALxCD20-7D8-FEAR for different incubation times. Data shown in FIG. 5A and FIG. 5B are from two independent experiments, using purified T cells isolated from two different donors.
Figure 5B:
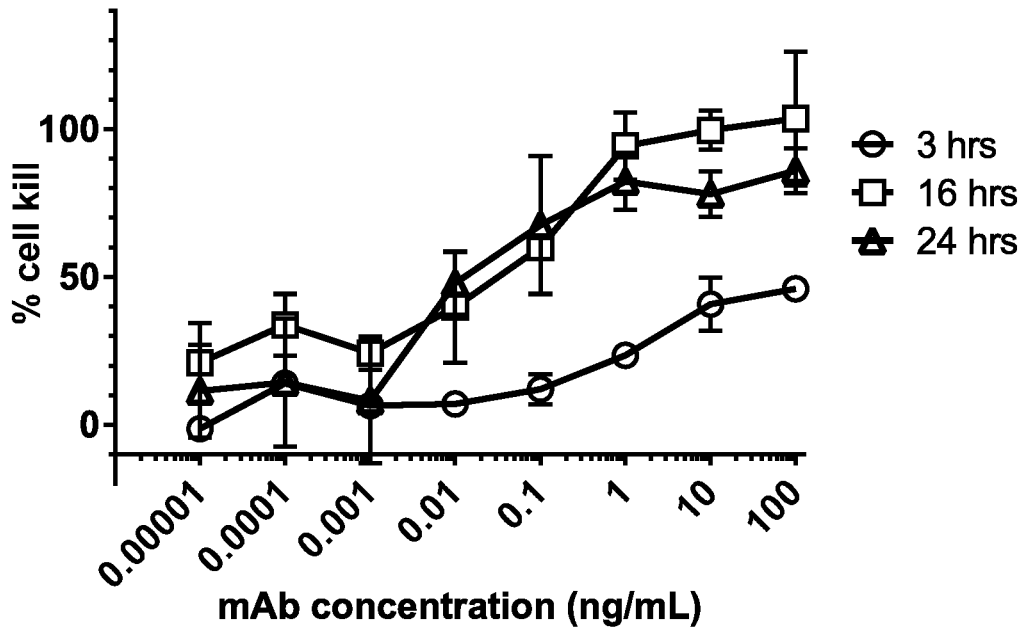
Figure 6A:
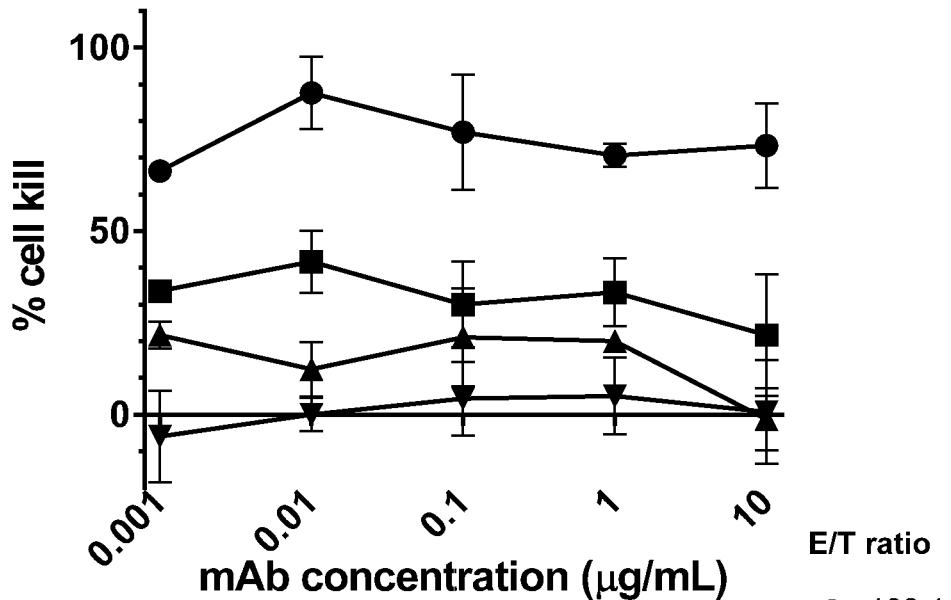
FIGS. 6A-6E: Efficacy of induction of cytotoxicity in vitro by CD3xCD20 bispecific antibodies at different effector to target ratios. A cytotoxicity assay was performed using different CD3xCD20 bispecific antibodies and different E/T ratios. CD3xCD20 bispecific antibodies included bsIgG1-huCD3-H1L1-FEALxCD20-7D8-FEAR (FIG. 6A), bsIgG1-huCD3-H1L1-FEALxCD20-11B8-FEAR (FIG. 6B), bsIgG1-huCD3-H1L1-FEALxCD20-GA101-FEAR (FIG. 6C), bsIgG1-huCD3-H1L1-FEALxCD20-RTX-FEAR (FIG. 6D) and bsIgG1-huCD3-H1L1-FEALxCD20-2F2-FEAR (FIG. 6E). As a negative control, bsIG1-huCLB-T3/4-FEALxb12-FEAR was included at an E/T ratio of 10:1. Data shown are mean percentages lysis±S.D. of triplicate wells as determined in a cytotoxicity assay for one representative experiment. Each line represents a different E/T ratio (as indicated).
Figure 6B:
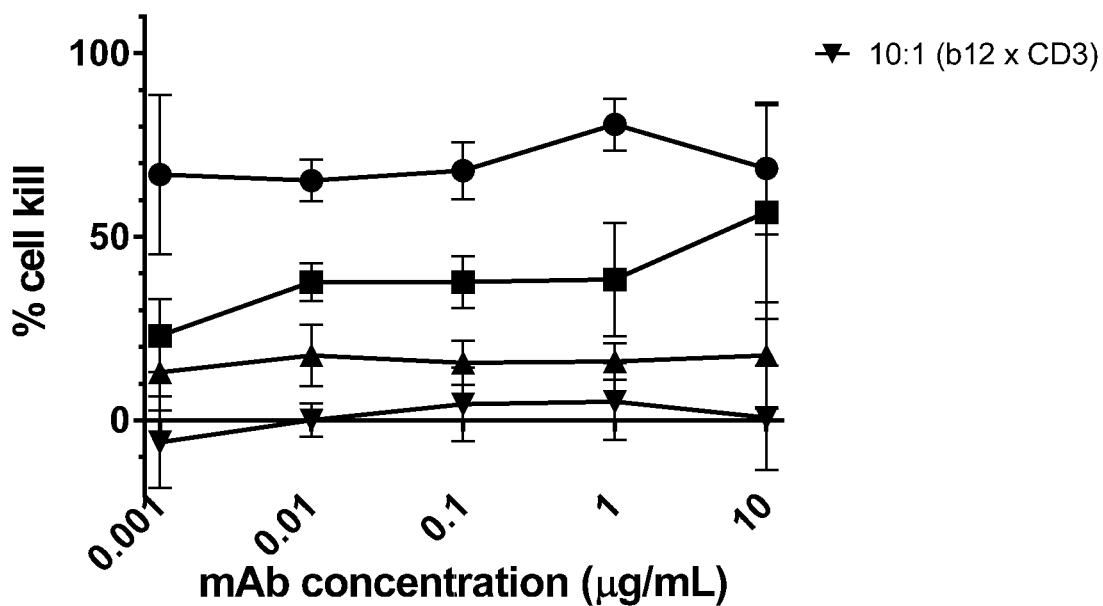
Figure 6C:
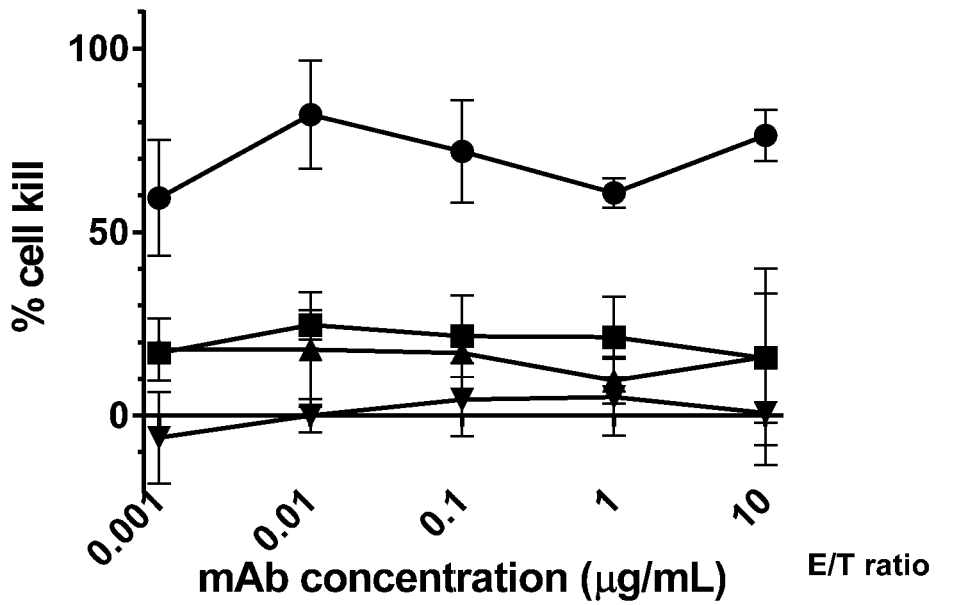
Figure 6D:
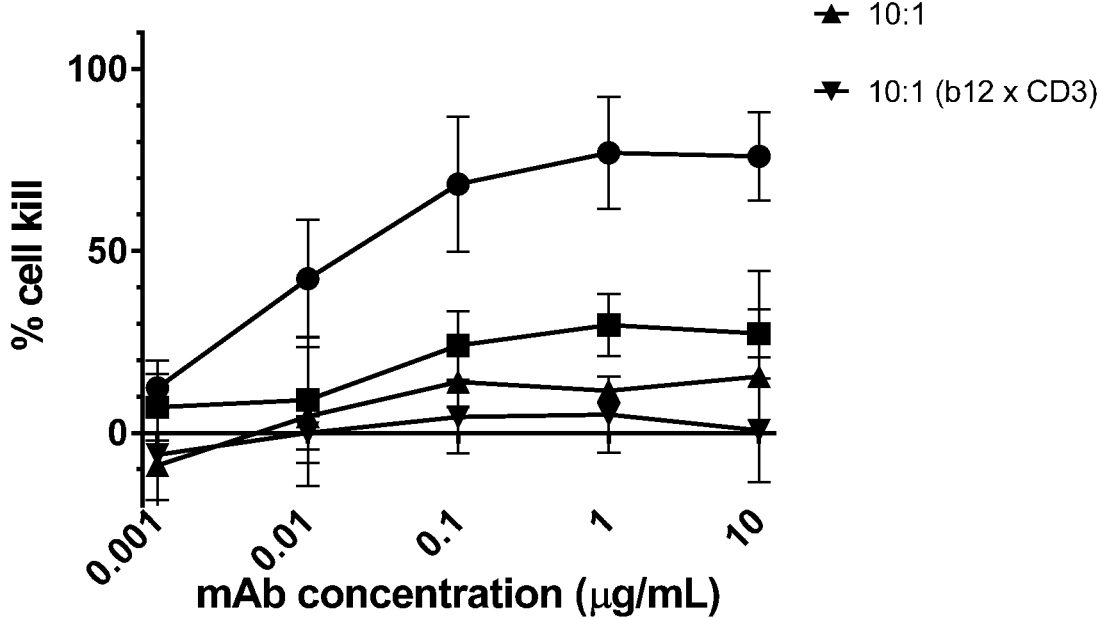
Figure 6E:
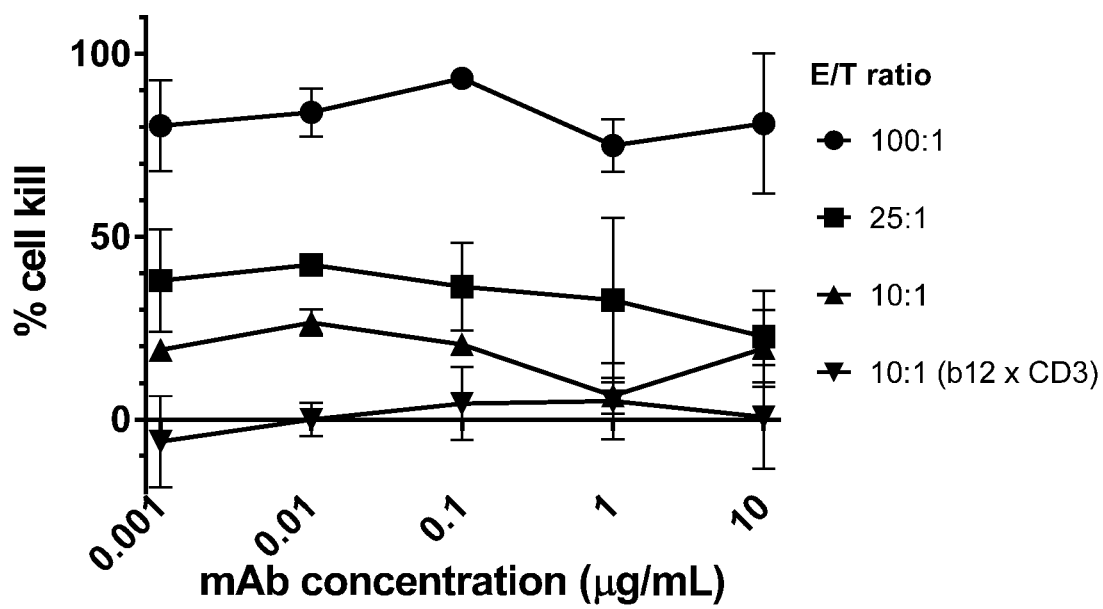

FIG. 5 shows the results of two independent experiments, performed with purified T cells derived from two different donors. Using purified T cells from the first donor, dose-dependent cytotoxicity was observed after 12 hours, and cytotoxicity was even more efficient after 48-72 hours (FIG. 5A). In presence of purified T cells from the second donor, bsIgG1-huCLB-T3/4-FEAL×CD20-7D8-FEAR was able to induce cytotoxicity as early as 3 hrs after incubation, and the efficiency increased upon 16-24 hours incubation (FIG. 5B).

Example 9—Efficacy of Induction of Cytotoxicity In Vitro by CD3×CD20 Bispecific Antibodies at Different Effector to Target Ratios To determine the efficiency of cytotoxicity induction by CD3×CD20 bispecific antibodies containing CD20 Fab-arms originating from different CD20 antibodies, a cytotoxicity assay was performed as described supra, using different effector to target ratios. PBMC were used as effector cells, and Daudi cells were used as target cells. As shown in FIG. 6, even at an E/T ratio between 10:1 and 25:1, cell kill was observed for the CD3×CD20 bispecific antibodies.

Figure 7A:
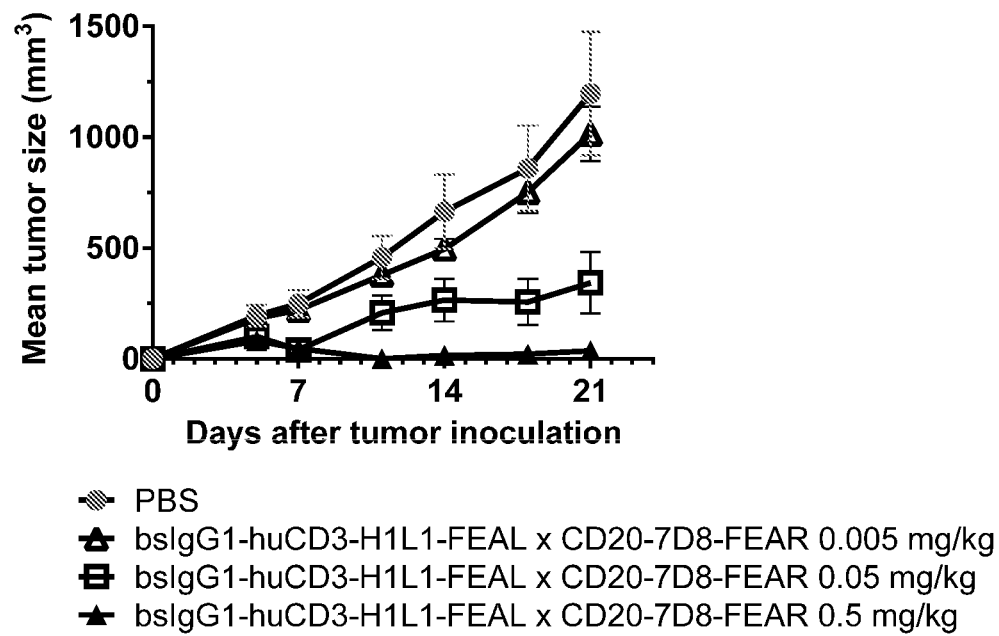
FIGS. 7A-7I: Cytotoxic activity of CD3xCD20 bispecific antibodies in the Raji-luc co-engraftment model in NOD-SCID mice.
Figure 7B:
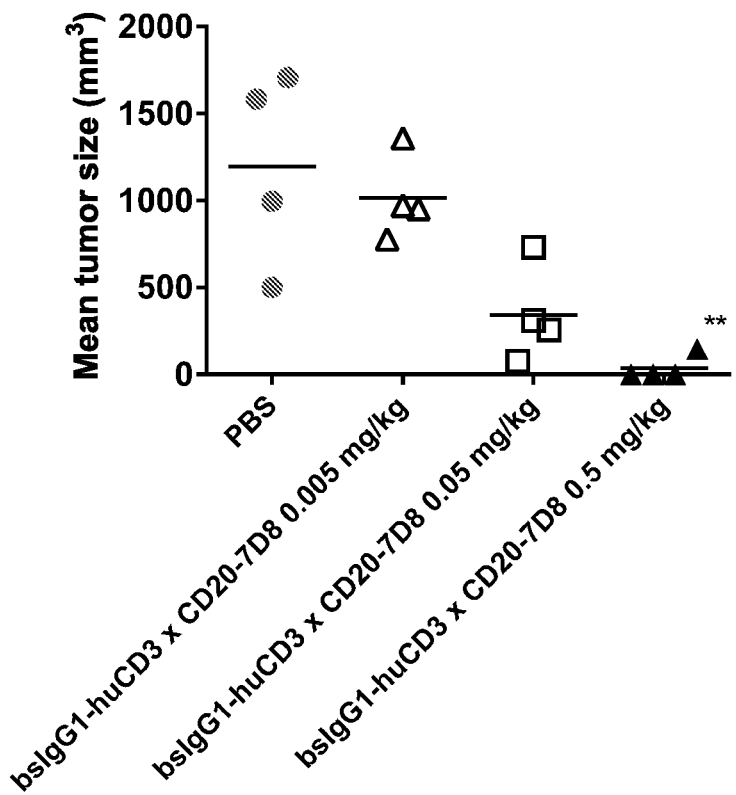
Figure 7C:
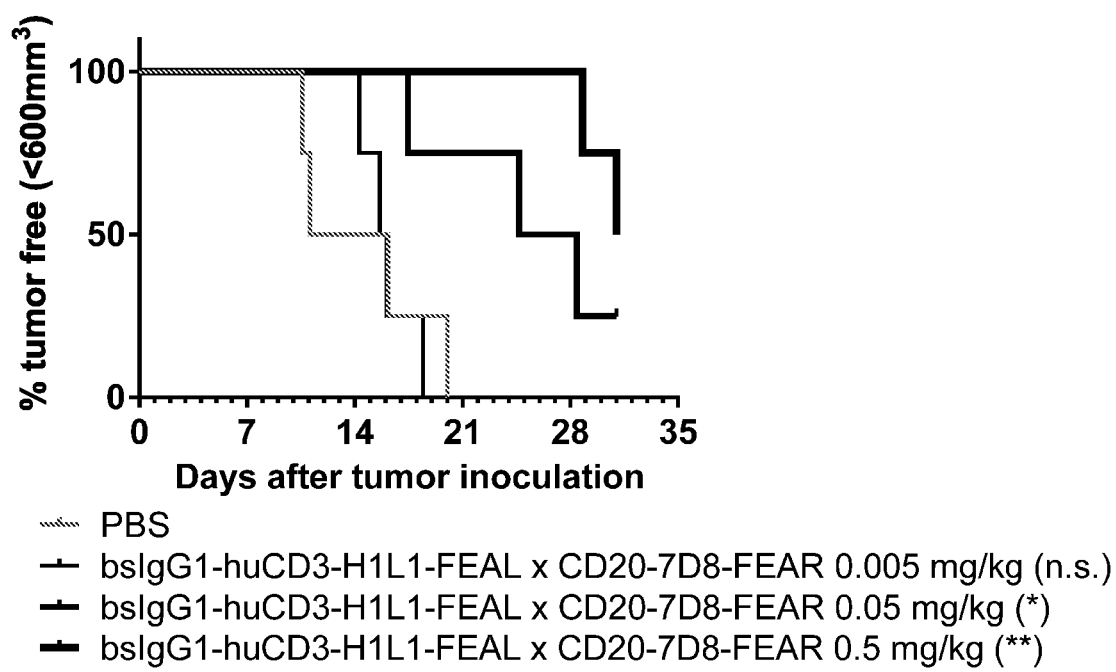

Example 10—Cytotoxicity of CD3×CD20 Bispecific Antibodies in the Raji-Luc Co-Engraftment Model in NOD-SCID Mice The in vivo anti-tumor efficacy of bsIgG1-huCD3-H1L1-FEALxCD20-7D8-FEAR, bsIgG1-huCD3-H1L1-FEALx CD20-11B8-FEAR and bsIgG1-huCLB-T3/4-FEALx CD20-7D8-FEAR was evaluated in a subcutaneous Raji-luc co-engraftment model. In this model, human unstimulated PBMCs, as a source of human T cells, were co-inoculated with tumor cells, analogous to the model described by Brischwein et al. (Mol. Immunol. 43 (2006), 1129-1143). At day 0, a mixture containing $5 \times 10^6$ PBMCs and $5 \times 10^6$ Raji-luc cells in 200 µL PBS/0.1% BSA were inoculated subcutaneously (s.c.) in the right flank of each mouse (female NOD-SCID mice; NOD.C.B-17-Prkdcscid/J, Charles-River, 6-11 week old). Within one hour of injection, mice were sorted into treatment groups (4-5 mice per treatment group [experiments shown in FIG. 7A-F] or 10 mice per treatment group [experiment shown in FIG. 7G-I]) and each group was injected intravenously (i.v.) with a single dose of 100-150 µL (bispecific) antibody in PBS. Treatment groups are shown in Table 7 (for the experiment shown in FIG. 7A, B, C), Table 8 (for the experiment shown in FIG. 7D, E, F) and Table 8.1 (for the experiment shown in FIG. 7G, H, I). Tumor volumes were determined at least two times per week. Tumor volumes (mm³) were calculated from caliper (PLEXX) measurements as: $0.52 \times (\text{length}) \times (\text{width})^2$.

Raji-luc cells were generated by transfecting gWIZ luciferase (GTS, San Diego, USA). Cells were thawed, cultured in RPMI (Lonza, BE12-115F) supplemented with 10% donor bovine serum with iron (Gibco, cat. no. 10371-029), penicillin/streptomycin and sodium pyruvate and 1 µg/mL puromycin (Sigma, Zwijndrecht, The Netherlands; cat. no. P-8833). Cells were harvested in log-phase and counted by trypan blue exclusion.

For each study, human PBMCs were isolated from a healthy donor buffy coat as described supra, frozen and thawed before use. All cells were washed in PBS/0.1% BSA, filtered through a cell strainer and resuspended to a concentration of $50 \times 10^6$ cells/mL in PBS/0.1% BSA.

The results are shown in FIG. 7. BsIgG1-huCD3-H1L1-FEALxCD20-7D8-FEAR efficiently reduced Raji-luc tumor size at dosages of 0.05 and 0.5 mg/kg. At 0.005 mg/kg, bsIgG1-huCD3-H1L1-FEALxCD20-7D8-FEAR did not affect tumor growth (FIG. 7A). On day 21 after tumor inoculation (the last day all treatment groups were complete), the average tumor size in mice that had been treated with 0.5 mg/kg bsIgG1-huCD3-H1L1-FEALxCD20-7D8-FEAR was significantly smaller than in mice that had been treated with the vehicle control PBS (FIG. 7B) ($p<0.01$, Kruskal Wallis test followed by Dunn's multiple comparison post-test). Kaplan-Meier analysis demonstrated that the tumor-free survival after treatment with bsIgG1-huCD3-H1L1-FEALxCD20-7D8-FEAR (0.5 and 0.05 mg/kg) was significantly better than after treatment with PBS ($p<0.01$ and $p<0.05$ for the 0.5 and 0.05 mg/kg treatment groups, respectively, Mantel Cox analysis) (FIG. 7C).

Figure 7D:
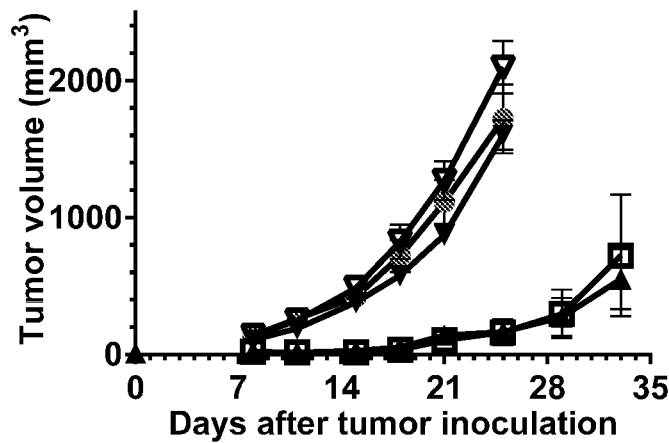
Figure 7E:
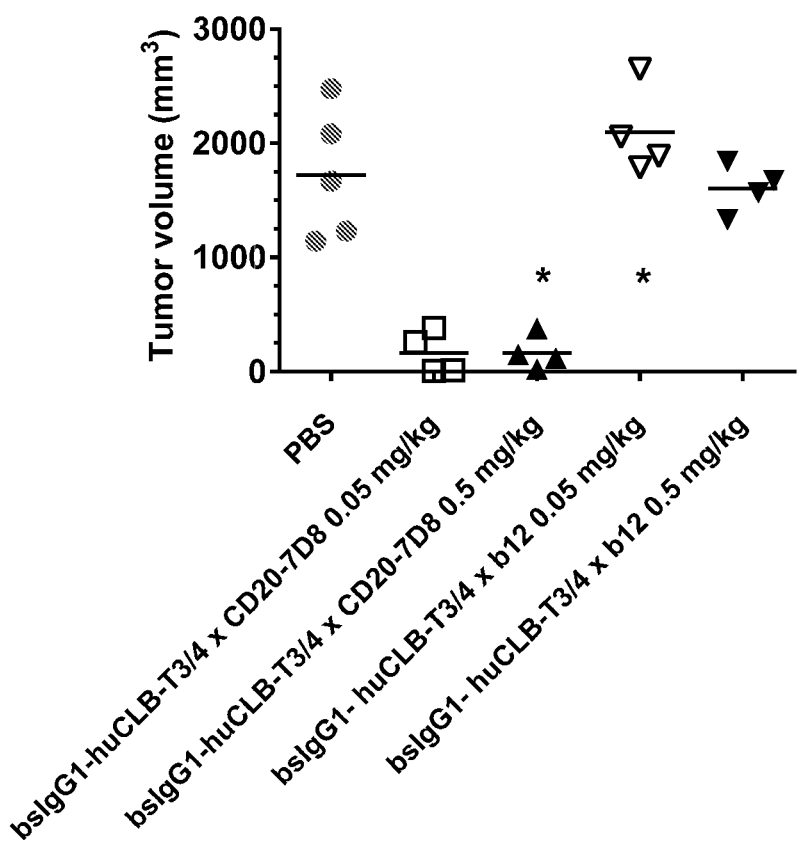
Figure 7F:
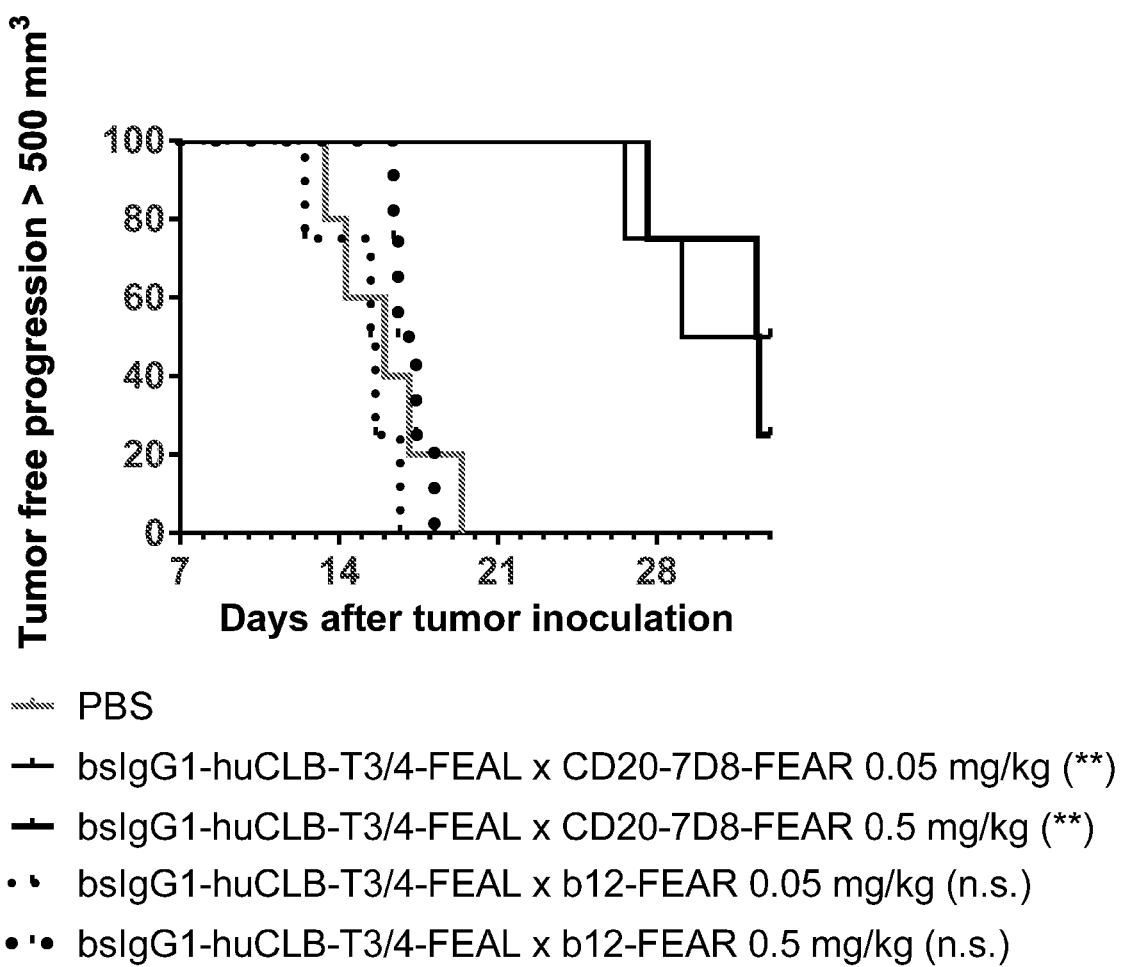

Similarly, treatment with bsIgG1-huCLB-T3/4-FEALx CD20-7D8-FEAR significantly inhibited tumor growth at doses of 0.05 and 0.5 mg/kg (FIG. 7D). On day 25 after tumor inoculation (the last day all treatment groups were complete), the average tumor size in mice that had been treated with 0.05 and 0.5 mg/kg bsIgG1-huCLB-T3/4-FEALxCD20-7D8-FEAR was significantly smaller than in mice that had been treated with the vehicle control (PBS) ($p<0.05$, Kruskal Wallis test followed by Dunn's multiple comparison post-test) (FIG. 7E). Kaplan-Meier analysis demonstrated that the tumor-free survival after treatment with bsIgG1-huCLB-T3/4-FEALxCD20-7D8-FEAR (0.5 and 0.05 mg/kg) was significantly better than after treatment with the vehicle control (PBS) ($p<0.01$, Mantel Cox analysis) (FIG. 7F).

Figure 7G:
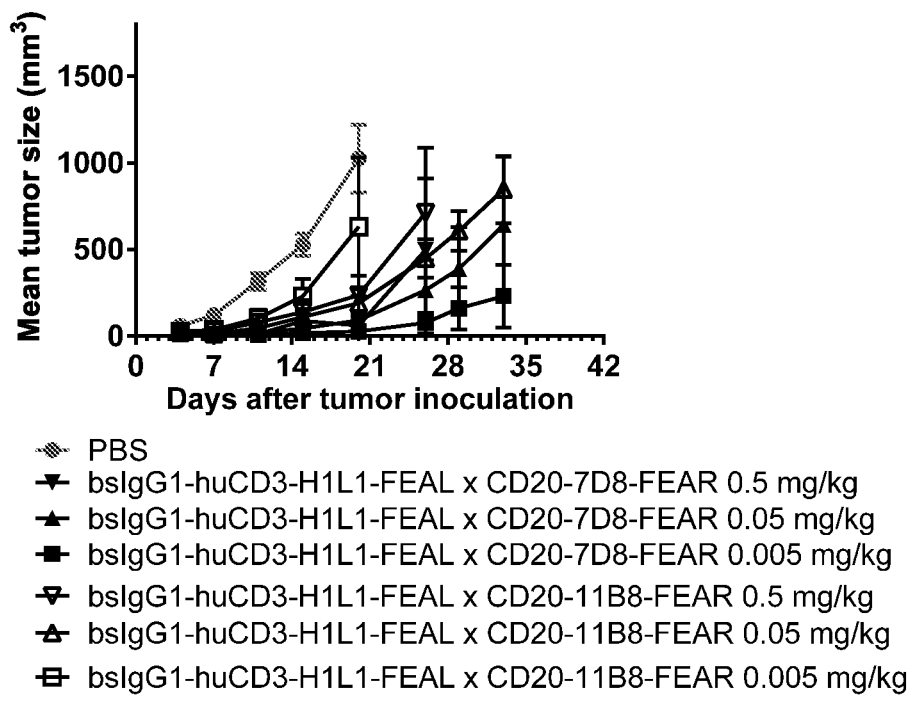
Figure 7H:
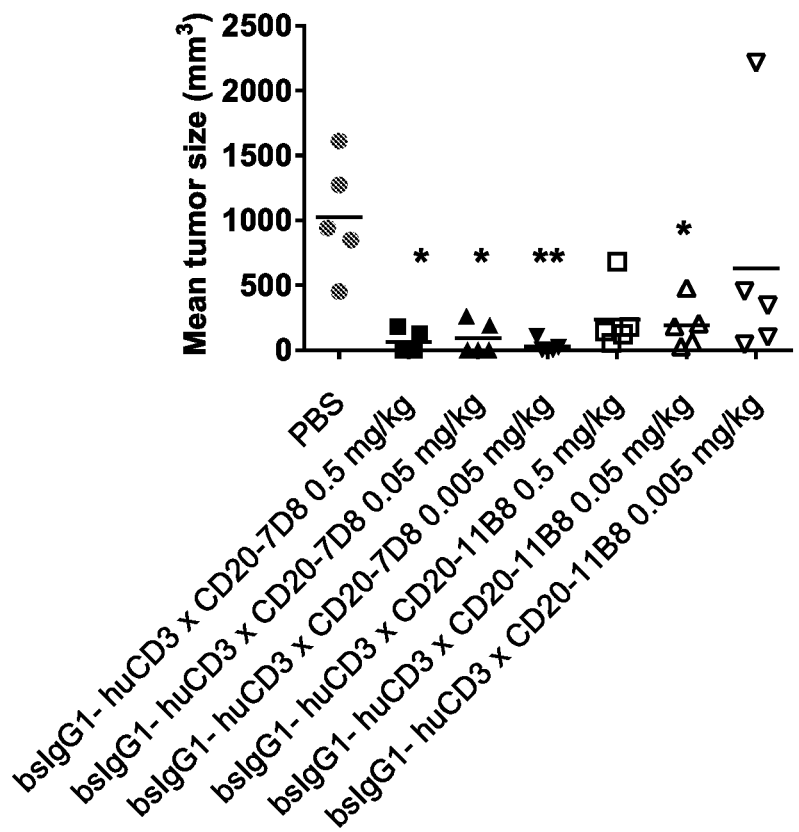
Figure 7I:
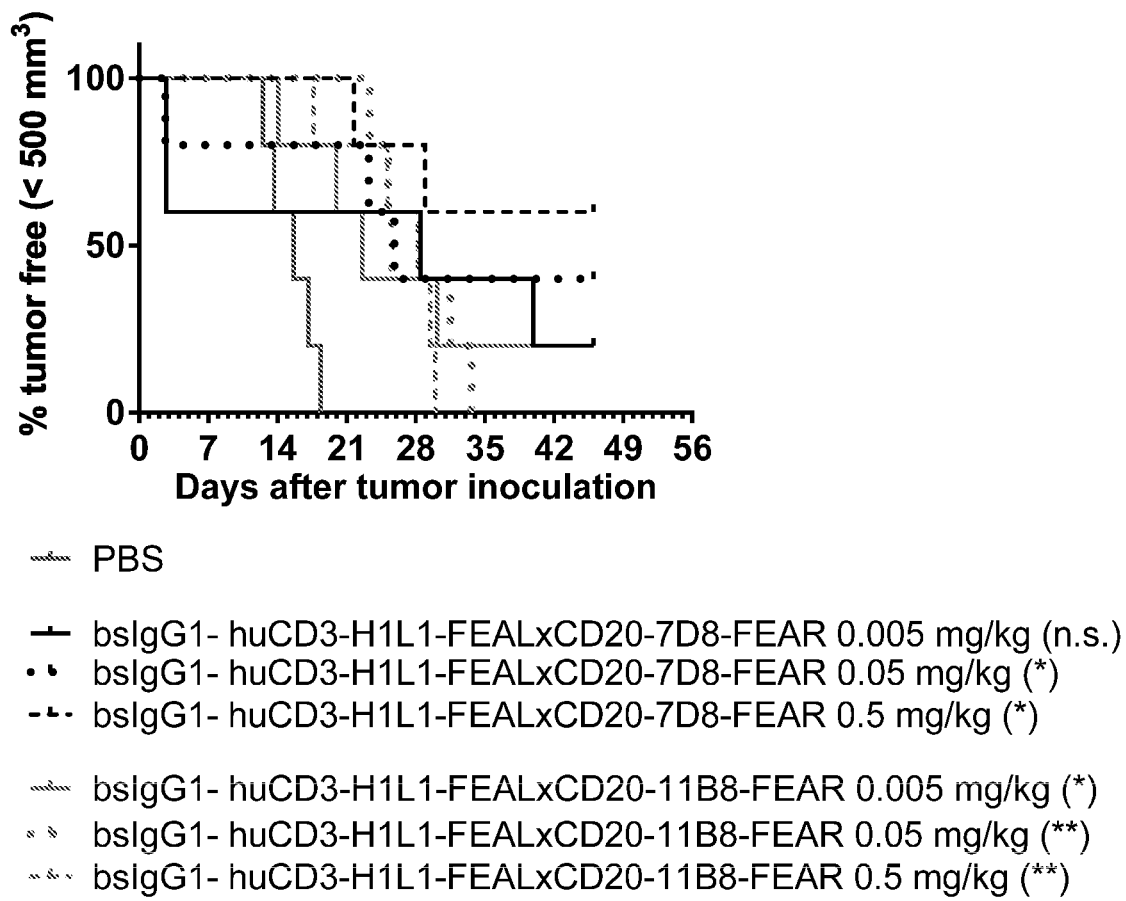

FIG. 7G shows that both bsIgG1-huCD3-H1L1-FEALx CD20-7D8-FEAR (all doses tested) and bsIgG1-huCD3-H1L1-FEALxCD20-11B8-FEAR (0.05 mg/kg) induced a delay in tumor growth. On day 20 after tumor inoculation (the last day all treatment groups were complete), the average tumor size in mice that had been treated with bsIgG1-huCD3-H1L1-FEALxCD20-7D8-FEAR (0.005, 0.05 and 0.5 mg/kg) and in mice that had been treated with 0.05 mg/kg bsIgG1-huCD3-H1L1-FEALxCD20-11B8-FEAR was significantly smaller than in mice that had been treated with vehicle control (PBS) ($p<0.05$ for all groups, except for the bsIgG1-huCD3-H1L1-FEALxCD20-7D8-FEAR 0.005 µg/kg group where $p<0.01$; one-way ANOVA, followed by Tukey's multiple comparison post-test) (FIG. 7H). Kaplan-Meier analysis demonstrated that the tumor-free survival in all treatment groups, except for the bsIgG1-huCD3-H1L1-FEALxCD20-7D8-FEAR at 0.005 mg/kg, was significantly better than in mice treated with vehicle control (PBS) ($p<0.05$, Mantel Cox analysis) (FIG. 7I).

TABLE 7

| Group | Antibody | Dose |
| --- | --- | --- |
| 1 | PBS | |
| 2 | bsIgG1-huCD3-H1L1-FEALxCD20-7D8-FEAR | 0.1 µg (~0.005 mg/kg) |
| 3 | bsIgG1-huCD3-H1L1-FEALxCD20-7D8-FEAR | 1 µg (~0.05 mg/kg) |
| 4 | bsIgG1-huCD3-H1L1-FEALxCD20-7D8-FEAR | 10 µg (~0.5 mg/kg) |

TABLE 8

| Group | Antibody | Dose |
| --- | --- | --- |
| 1 | PBS | |
| 2 | bsIgG1-huCLB-T3/4-FEALxCD20-7D8-FEAR | 1 µg (~0.05 mg/kg) |
| 3 | bsIgG1-huCLB-T3/4-FEALxCD20-7D8-FEAR | 10 µg (~0.5 mg/kg) |
| 4 | bsIgG1-huCLB-T3/4-FEALxb12-FEAR | 1 µg (~0.05 mg/kg) |
| 5 | bsIgG1-huCLB-T3/4-FEALxb12-FEAR | 10 µg (~0.5 mg/kg) |

TABLE 8.1

| Group | Antibody | Dose |
|---|---|---|
| 1 | PBS | |
| 2 | bsIgG1-huCD3-H1L1-FEALxCD20-7D8-FEAR | 1 µg (~0.05 mg/kg) |
| 3 | bsIgG1-huCD3-H1L1-FEALxCD20-7D8-FEAR | 10 µg (~0.5 mg/kg) |
| 4 | bsIgG1-huCD3-H1L1-FEALxCD20-7D8-FEAR | 1 µg (~0.05 mg/kg) |
| 5 | bsIgG1-huCD3-H1L1-FEALxCD20-11B8-FEAR | 10 µg (~0.5 mg/kg) |
| 6 | bsIgG1-huCD3-H1L1-FEALxCD20-11B8-FEAR | 1 µg (~0.05 mg/kg) |
| 7 | bsIgG1-huCD3-H1L1-FEALxCD20-11B8-FEAR | 10 µg (~0.5 mg/kg) |

Example 11—Anti-Tumor Activity of bsIgG1-huCD3-H1L1-FEALxCD20-7D8-FEAR in a Humanized Immune System Mouse Xenograft Model The in vivo anti-tumor efficacy of bsIgG1-huCD3-H1L1-FEALxCD20-7D8-FEAR was evaluated in humanized immune system (HIS) mice that were inoculated with human Daudi-luc tumor cells (BRGS-HIS-Daudi-luc) (experiments performed at Axenis, Paris, France). In this model, human hematopoietic CD34$^+$ progenitor cells (~1×10$^5$ cells) were obtained from cord blood, and injected intrahepatically into neonatal BALB/c Rag2tm1Fwa IL-2Rγc tm1Cgn SIR-PaNOD (BRGS) mice as described by Legrand et al. (PNAS. 108 (2011), 13224-13229). After 14 weeks, humanization of the BRGS mice was confirmed by flow cytometry. Subsequently, mice were divided in three groups (7 mice per group), based on the percentage of human CD3$^+$ T cells in the human CD45$^+$ population (29.5±7.5, 28.4±9.4 and 28.3±11.6 for the PBS-, bsIgG1-huCD3-H1L1-FEALxb12-FEAR- and bsIgG1-huCD3-H1L1-FEALxCD20-7D8-FEAR-treated groups, respectively). At week 15, 5×10$^6$ Daudi-luc cells in 100 µL PBS, were injected intravenously (i.v.) in the BRGS-HIS mice and this was indicated as day 0 in the study. At day 3 and 7, the BRGS-HIS mice with Daudi-luc cells were injected i.v. with 1 mg/kg (bispecific) antibody. Treatment groups are shown in Table 9. Tumor growth was evaluated weekly (starting at day 2) by bioluminescence imaging (BLI). Mice were injected intraperitoneally (i.p) with 100 µL firefly D-luciferin (30 mg/mL; Caliper LifeSciences) and bioluminescence was measured using a Biospace Bioluminescence Imaging System (PerkinElmer). In addition, a blood sample was taken of each individual mouse at day 9, and flow cytometry was performed to determine the percentage of the different leukocyte populations (total human leukocytes: hCD45$^+$mCD45$^-$ population; B cells: hCD3-hCD19$^+$ population; T cells: hCD3$^+$hCD19$^-$ population and activated T cells: hCD3$^+$ hCD19-FSC$^{hi}$ population. The following antibodies were used for staining: anti-hCD45 clone HI30, labeled with Alexa Fluor® 700 (BioLegend, cat. no. 304023; final dilution 1:50; anti-mCD45 clone 30-F11, labeled with allophycocyanin (APC)-eFluor® 780 (eBioscience, cat. no. 47-0451-80; final dilution 1:200); anti-hCD3 clone UCHT1, labeled with eFluor® 450 (eBioscience, cat. no. 48-0038-80; final dilution 1:50), anti-hCD19 clone HIB19 labeled with phycoerythrin (PE) (Becton Dickinson, cat. no. 561741; final dilution 1:25).

Figure 8A:
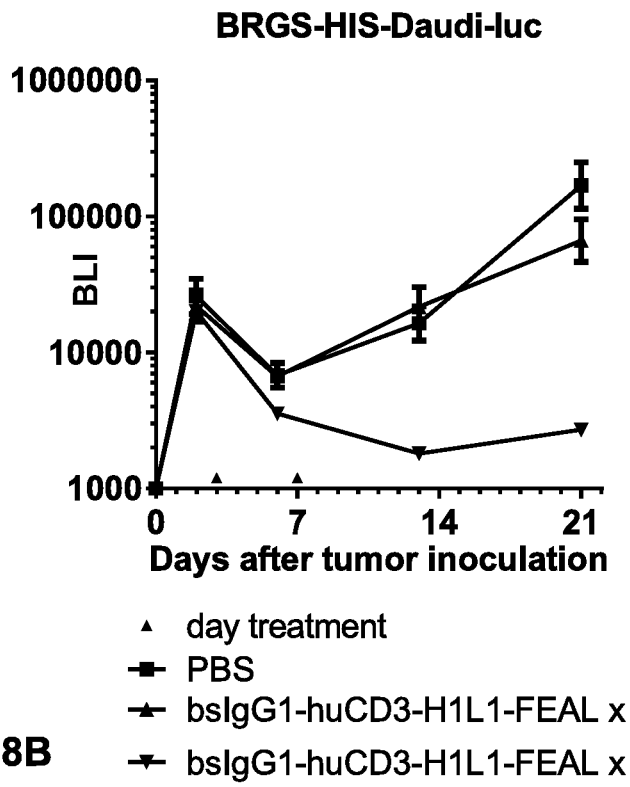
FIGS. 8A-8C: Anti-tumor activity of bsIgG1-huCD3-H1L1-FEALxCD20-7D8-FEAR in a Daudi-luc xenograft model in HIS mice.
Figure 8B:
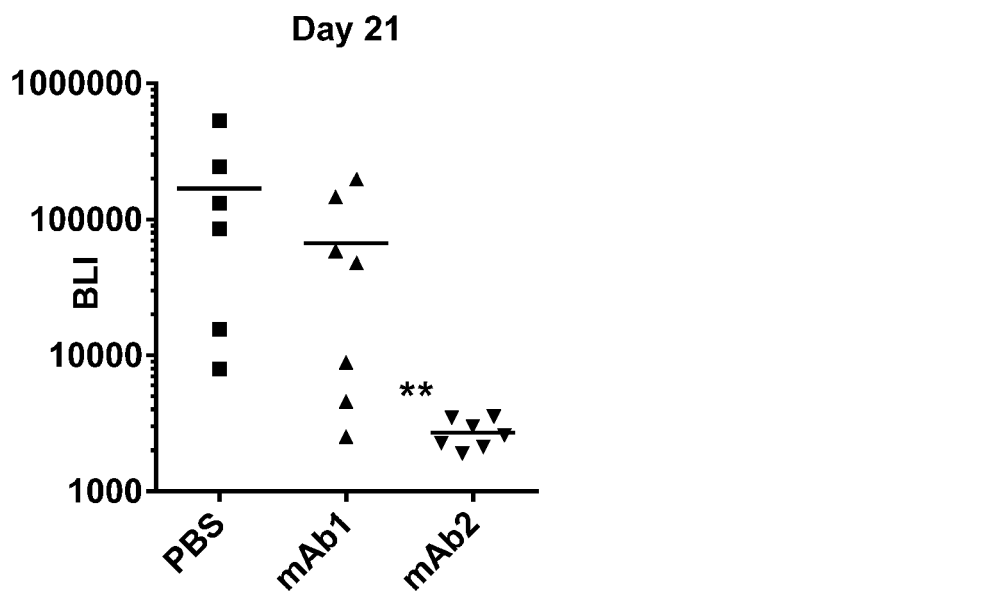

The results are shown in FIG. 8. As can be seen from FIG. 8A, bsIgG1-huCD3-H1L1-FEALxCD20-7D8-FEAR efficiently reduced tumor burden at a dose of 1 mg/kg. The control bispecific antibody bsIgG1-huCD3-H1L1-FEALx b12-FEAR did not inhibit tumor growth. Statistical comparison of tumor burden at day 21 (Kruskal Wallis test followed by Dunn's multiple comparison post-test) demonstrated that the tumor burden in the bsIgG1-huCD3-H1L1-FEALxCD20-7D8-FEAR treatment group was significantly lower than in the vehicle (PBS)-treated animals (p<0.01). The difference between the bsIgG1-huCD3-H1L1-FEALx b12-FEAR and vehicle treatment groups was not significant (FIG. 8B).

Figure 8C:
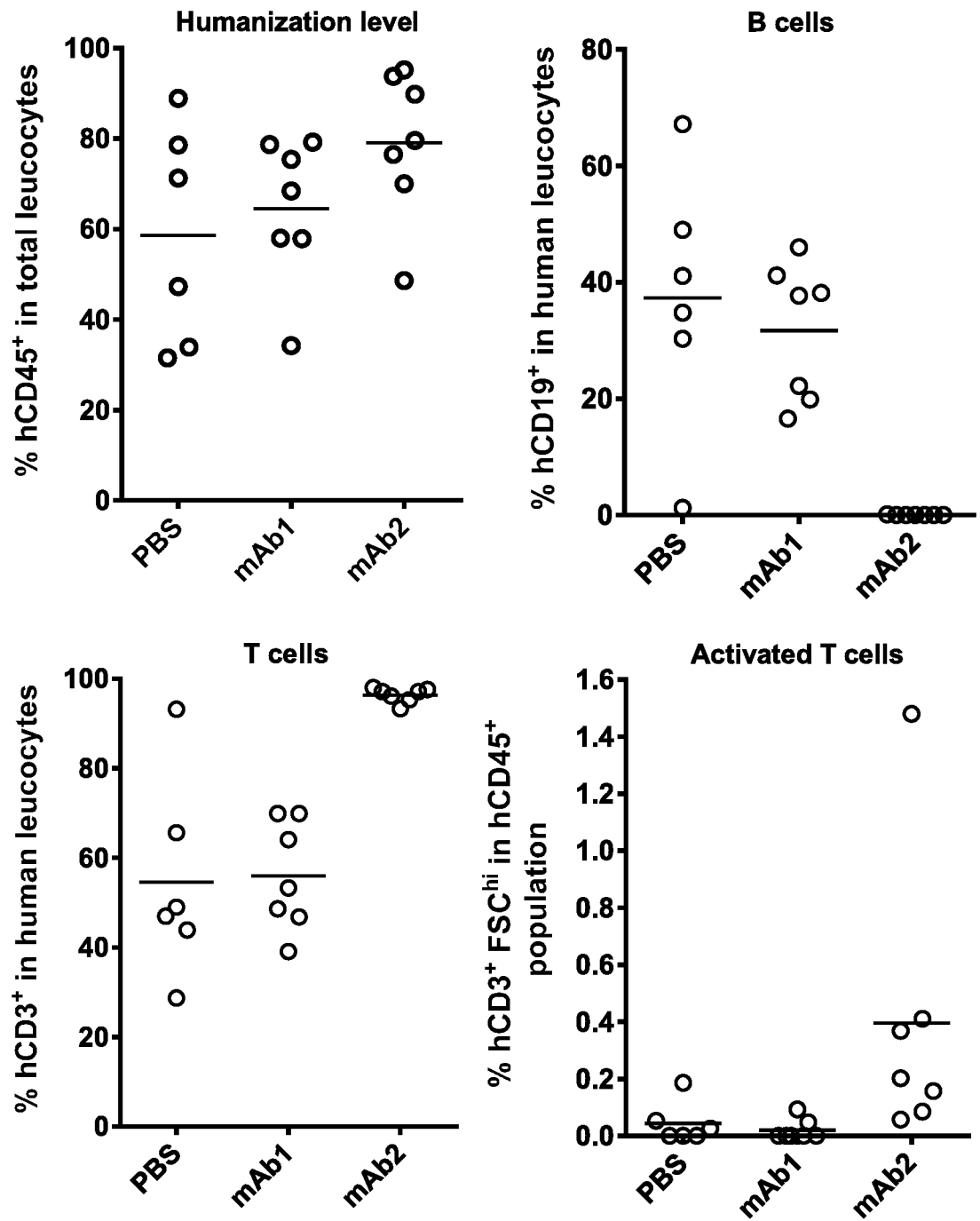

In FIG. 8C, the percentages of different human leukocyte populations, as determined by flow cytometry, are indicated. The percentage of circulating human leukocytes (hCD45$^+$ cells) was comparable in all groups. However, the percentage of human B cells in mice treated with bsIgG1-huCD3-H1L1-FEALxCD20-7D8-FEAR was strongly reduced (p=0.0012, compared to the vehicle control group, according to the Mann Whitney test). Treatment with the control bispecific antibody bsIgG1-huCD3-H1L1-FEALxb12-FEAR did not affect the percentage of human B cells. The percentage of activated T cells (hCD3$^+$ FSC$^{hi}$ population) was enhanced in mice treated with bsIgG1-huCD3-H1L1-FEALxCD20-7D8-FEAR, (p=0.0093 compared to the vehicle control group, according to the Mann Whitney test). Treatment with the control bispecific antibody bsIgG1-huCD3-H1L1-FEALxb12-FEAR did not significantly change the number of activated T cells. This indicates that T cell activation after treatment with the CD3xCD20 bispecific antibody was dependent on both CD3 and CD20 binding and not on CD3 binding alone.

TABLE 9

| Group | Antibody | Dose |
|---|---|---|
| 1 | PBS | |
| 2 | bsIgG1-huCD3-H1L1-FEALxb12-FEAR | 1 mg/kg (~20 µg) |
| 3 | bsIgG1-huCD3-H1L1-FEALxCD20-7D8-FEAR | 1 mg/kg (~20 µg) |

Example 12—Pilot Study to Determine the Pharmacology and Pharmacokinetics of CD3xCD20 Bispecific Antibodies in Cynomolgus Monkeys The safety profile, pharmacokinetics and induction of B cell depletion in cynomolgus monkeys by one of the CD3x CD20 bispecific antibodies according to the invention, bsIgG1-huCD3-H1L1-FEALxCD20-7D8-FEAR, was tested according to the study described below.

The objective of this study was to determine the pharmacokinetic characteristics, toxicological and pharmacological effects of bsIgG1-huCD3-H1L1-FEALxCD20-7D8-FEAR in female cynomolgus monkeys (*Macaca fascicularis*, originating from Mauritius, approximately 2-3 years old; weight range of 2.5-3 kg) following a single intravenous infusion via the tail vein. The study was performed at Charles River Laboratories, Tranent, UK. The parental IgG1 antibodies, IgG1-huCD3-H1L1 and IgG1-7D8, that were engineered to make the bispecific molecule, have been shown to be cross-reactive with cynomolgus monkey CD3 and CD20, respectively. Eight female cynomolgus monkeys were assigned to four dose groups that received bsIgG1-huCD3-H1L1-FEALxCD20-7D8-FEAR at a dose of 0.01, 0.1, 1 or 10 mg/kg at a constant dose volume of 10 mL/kg. One animal of each dose group was sacrificed 28 days after the administered dose, whereas the second animal of each dose group was sacrificed when B-cell counts in that animal had recovered to a level that was comparable to the pre-dose values, as assessed by flow cytometry (recovery animals). The practices and procedures adopted during this study were consistent with the OECD Principles of Good Laboratory Practice as set forth by the United Kingdom Department of Health.

Figure 9A:
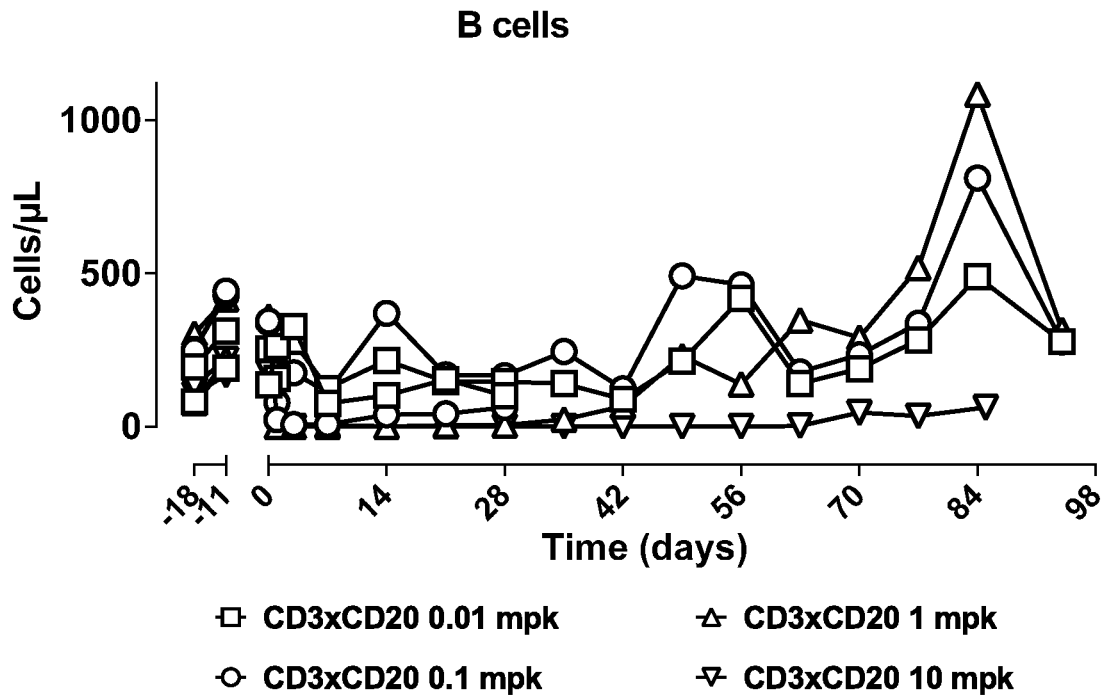
FIGS. 9A-9F: Study of effects of a single dose of bsIgG1-huCD3-H1L1-FEALxCD20-7D8-FEAR in cynomolgus monkeys. B-cell counts (CD19$^+$ CD21$^+$ cells) (FIG. 9A) and T-cell counts (CD4$^+$ plus CD8$^+$ cells) (FIG. 9B) over time in peripheral blood of cynomolgus monkeys treated with different doses of bsIgG1-huCD3-H1L1-FEALxCD20-7D8-FEAR (0.01, 0.1, 1 or 10 mg/kg). Days −18 and −11 show pre-dose B- and T-cell counts. B cells (FIG. 9C) and T cells (FIG. 9D) as percentage of the total lymphocyte population over time in lymph node samples from cynomolgus monkeys treated with different doses of bsIgG1-huCD3-H1L1-FEALxCD20-7D8-FEAR (0.01, 0.1, 1 or 10 mg/kg). Plasma levels of IL-2, IL-6, IL-8, IL-10, IFN-γ and TNF-α in cynomolgus monkeys treated with different doses of bsIgG1-huCD3-H1L1-FEALxCD20-7D8-FEAR (0.01, 0.1, 1 or 10 mg/kg) (FIG. 9E). Pharmacokinetic profile of bsIgG1-huCD3-H1L1-FEALxCD20-7D8-FEAR in blood samples at pre-dose and at various time-points after dosing up to 70 days (FIG. 9F). The dotted line shows the predicted pharmacokinetic profile of IgG1, using a two-compartment model, with $k_{10}$ (clearance constant) at 0.006 h$^{-1}$, Vc (plasma volume) 40 mL·kg$^{-1}$ and 3.5 kg bodyweight.
Figure 9B:
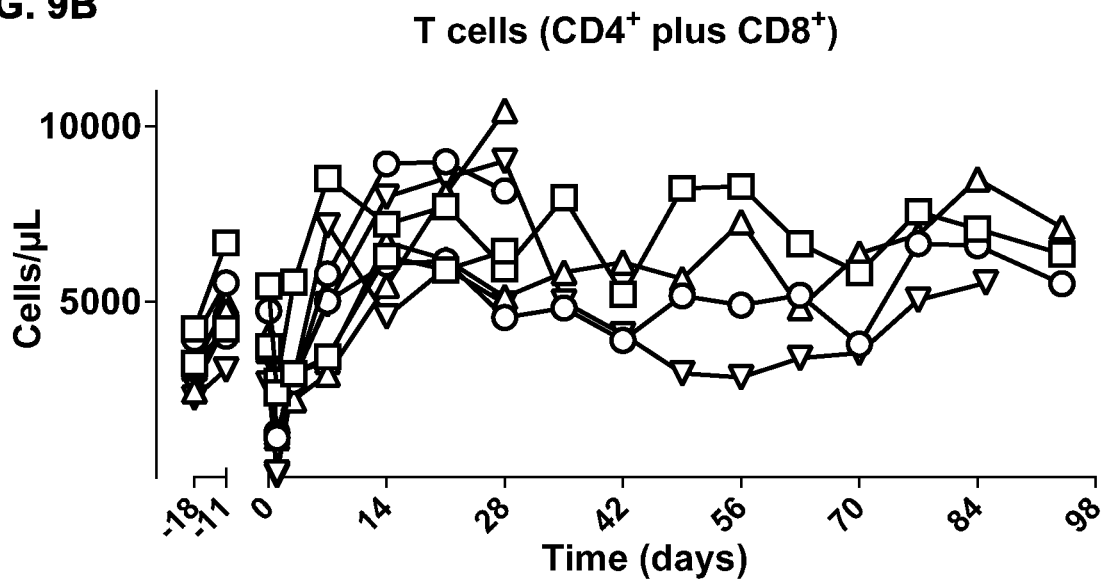

B and T cell populations in the peripheral blood were analyzed by flow cytometry, at different timepoints after dosing. B cells were identified using the cell surface markers CD19 and CD21 ($CD19^+CD21^+$ cells); total T cells were assessed as the sum of $CD4^+$ and $CD8^+$ cells. As shown in FIG. 9A, administration of bsIgG1-huCD3-H1L1-FEALx CD20-7D8-FEAR at dose levels of 1 and 10 mg/kg resulted in depletion of circulating B cells to undetectable levels by the first time point measured (1 day post-dose). Dose levels of 0.01 and 0.1 mg/kg showed only partial depletion or no depletion. The B-cell depletion was maintained until four to six weeks (28-42 days) after dosing in the 1 mg/kg dose group, followed by a recovery of B-cell levels reaching pre-dose levels at 9 weeks (63 days) post dosing. In the 10 mg/kg dose group recovery of B-cell levels only started at week 9-10 (70 days) after dosing. A transient decrease in circulating T cell numbers was observed at 1 day post-dose in all dose groups (FIG. 9B). T-cell levels had returned to pre-dose levels at the next measurement on day 3 and remained constant until the end of the experiment.

Figure 9C:
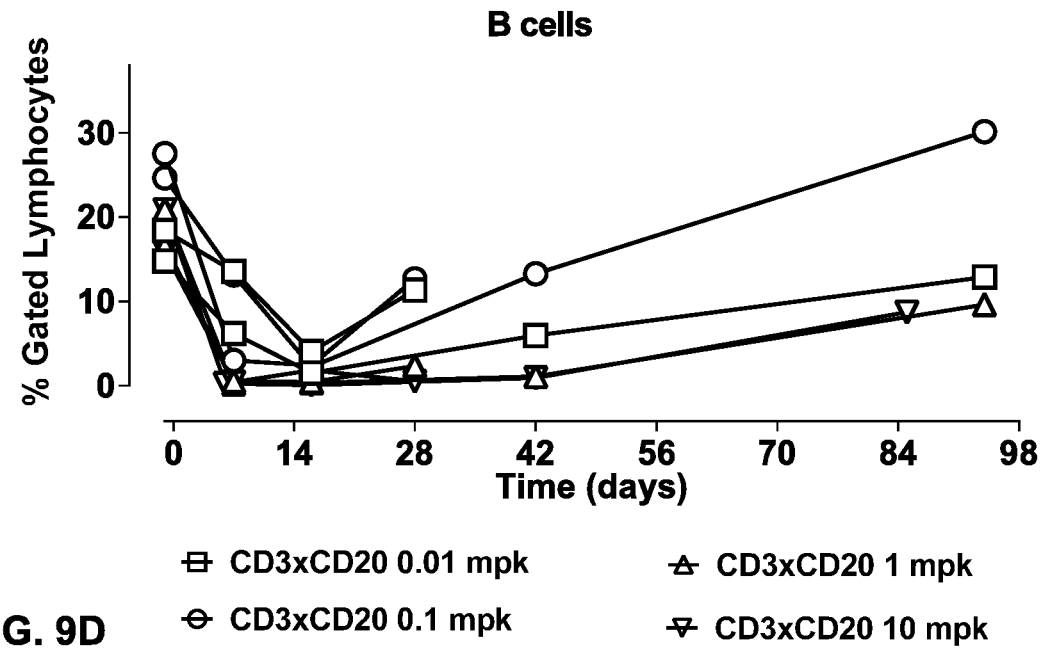
Figure 9D:
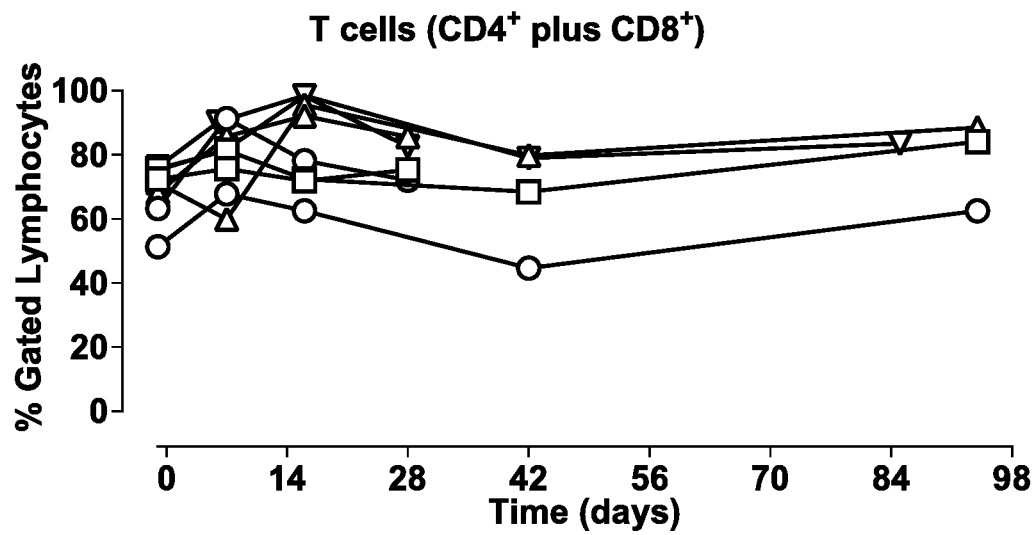

Biopsies (approximately 20 mg) were taken from superficial lymph nodes (left and right inguinal and axillary) from all animals, at different timepoints after dosing. Biopsies were homogenized and the frequency of B and T cells, as a percentage of the total lymphocyte population (identified based on forward scatter-side scatter (FSC-SSC), was assessed by flow cytometry. B cells were identified using the cell surface markers CD19 and CD21 ($CD19^+CD21^+$ cells); total T cells were assessed as the sum of $CD4^+$ and $CD8^+$ cells. As shown in FIG. 9C, administration of bsIgG1-huCD3-H1L1-FEALxCD20-7D8-FEAR resulted in depletion of B cells to undetectable levels at the first time point measured (7 days post-dose) at dose levels of 1 and 10 mg/kg. B-cell depletion was maintained until 7 weeks after dosing in these dose groups followed by a recovery of B-cell levels, that was not yet complete at 13-14 weeks (84-95 days) post dosing. Dose levels of 0.01 and 0.1 mg/kg induced maximal B-cell depletion at 16 days post-dosing with complete recovery observed at 28 days after dosing (0.01 mg/kg) or partial recovery at 14 weeks (95 days) post-dose (0.1 mg/kg). No major changes in T cell frequencies were observed in the lymph nodes at any dose level (FIG. 9D).

Figure 9E:
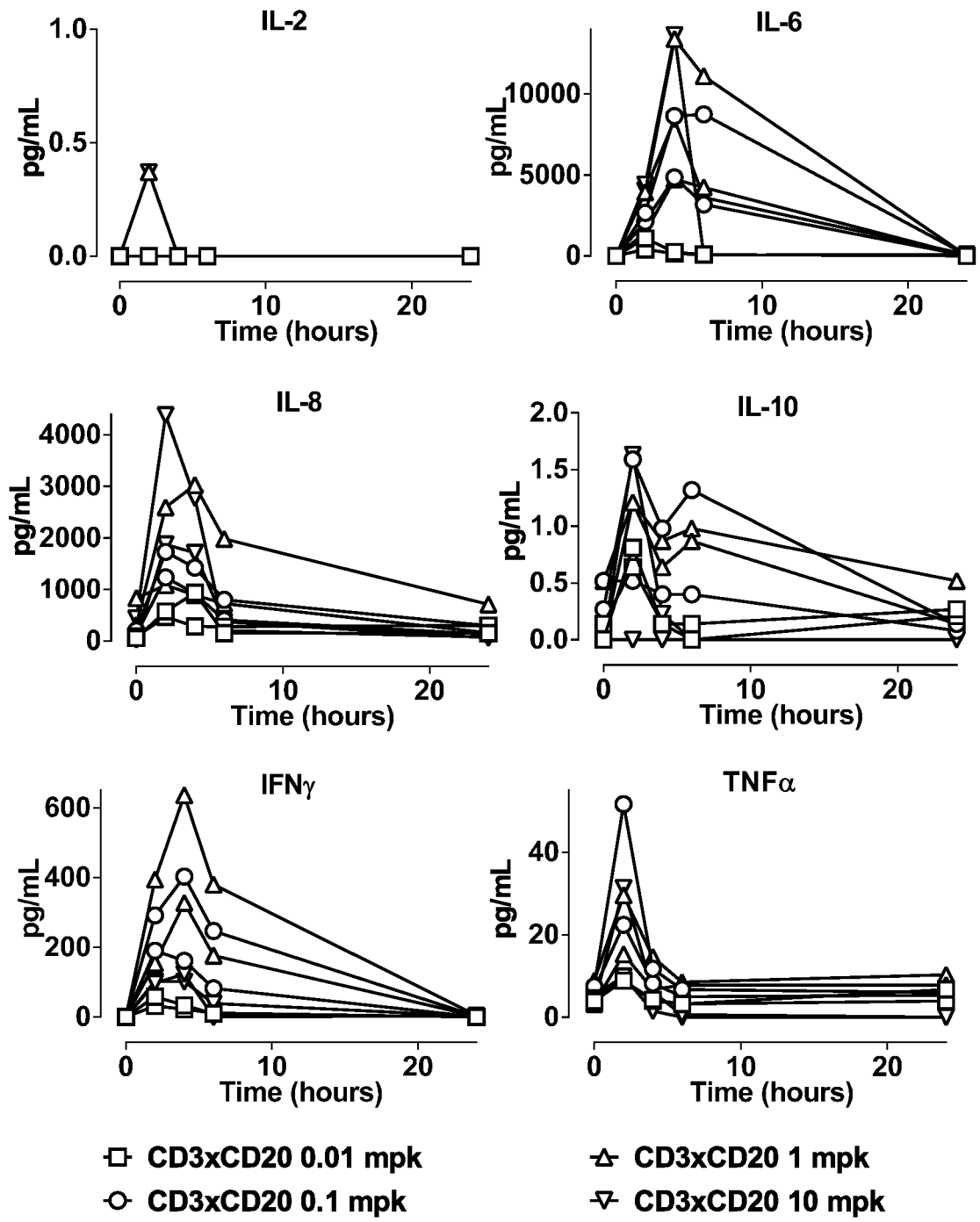

Plasma samples were analyzed for cytokine levels (IL-2, IL-6, IL-8, IL-10, IFN-γ and TNF-α) using standard analytical methods. Administration of bsIgG1-huCD3-H1L1-FEALxCD20-7D8-FEAR induced a transient increase in plasma cytokine levels, which appeared to be dose-dependent (FIG. 9E). All cytokine levels had returned to pre-dose levels at 24 hours post dosing.

Figure 9F:
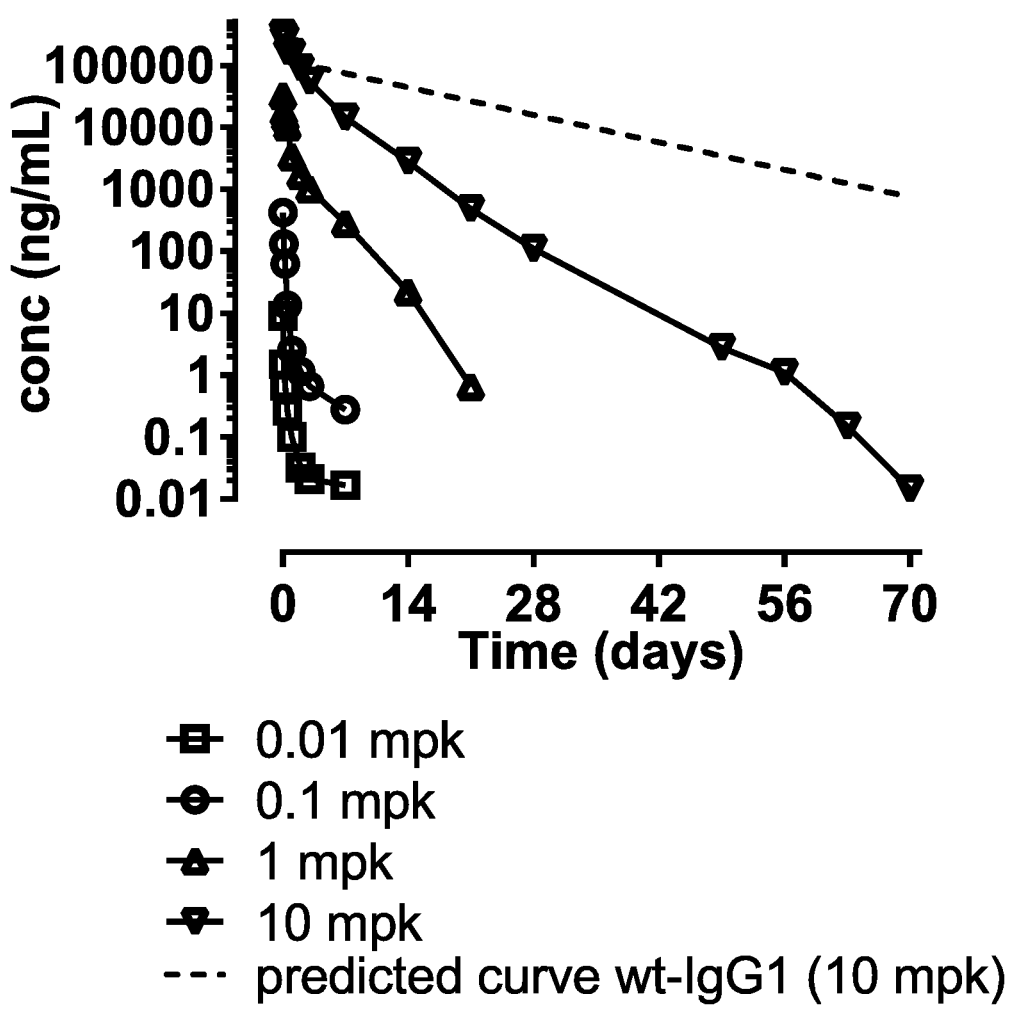

The pharmacokinetic profile of bsIgG1-huCD3-H1L1-FEALxCD20-7D8-FEAR was evaluated by analyzing plasma samples obtained pre-dose and at various time-points after dosing up to 70 days. The total concentration of bispecific antibody was determined by an immune PCR. Pharmacokinetic parameters were calculated by Non-Compartmental Analysis (Phoenix WinNonLin). Results are shown in Table 10. Dose-normalized $AUC_{0-\infty}$ values ($AUC_{0-\infty}/Dose$) indicate a non-linear increase in plasma exposure. The greater than proportional increase in these $AUC_{0-\infty}$ values indicate target-mediated clearance of bsIgG1-huCD3-H1L1-FEALxCD20-7D8-FEAR. In addition, the pharmacokinetic profile of bsIgG1-huCD3-H1L1-FEALxCD20-7D8-FEAR shows a faster initial distribution and clearance as compared to typical IgG1-type monoclonal antibodies dosed in cynomolgus monkeys (FIG. 9F).

In addition, anti-drug antibody (ADA) responses to bsIgG1-huCD3-H1L1-FEALxCD20-7D8-FEAR in cynomolgus serum were measured (data not shown). ADA responses were observed in all animals except for the 10 mg/kg animals from day 15 onwards.

TABLE 10

Pharmacokinetic characteristics of bsIgG1-huCD3-H1L1-FEALxCD20-7D8-FEAR in cynomolgus monkeys

| Parameter | Units | Treatment dose (# indicates individual animal identifier) | | | | | | | |
|---|---|---|---|---|---|---|---|---|---|
| | | 0.01 mg/kg | | 0.1 mg/kg | | 1 mg/kg | | 10 mg/kg | |
| | | # 151 | # 157 | # 152 | # 158 | # 153 | # 159 | # 154 | # 160 |
| $C_{max}$ | ng/mL | 7.26 | 10.73 | 478.5 | 364.6 | 36249 | 29154 | 364508 | 286869 |
| $C_{max}$/Dose | kg*ng/mL/mg | 725.8 | 1074 | 4785 | 3646 | 36249 | 29154 | 36451 | 28687 |
| $t_{max}$ | day | 0.042 | 0.042 | 0.042 | 0.042 | 0.042 | 0.042 | 0.042 | 0.042 |
| $AUC_{0-\infty}$ | ng*day/mL | 0.991 | 1.385 | 82.43 | 43.31 | 22559 | 14837 | 756967 | 471203 |
| $AUC_{0-\infty}$/Dose | kg*ng*day/mL/mg | 99.06 | 138.52 | 824.4 | 433.1 | 22559 | 14837 | 75697 | 47120 |
| Vd | mL | 30787 | 15797 | 4232 | 5078 | 114.5 | 136.3 | 42.2 | 100.9 |

Data for each monkey per dose group are shown separately (monkey number indicated above the column).

Example 13—Identification of CD20 Amino Acids Involved in Binding of CD3xCD20 Bispecific Antibodies Previous studies have indicated that the alanine residue at position 170 (A170) and particularly the proline residue at position 172 (P172) in the extracellular loop of CD20 are critical for recognition CD20 by rituximab (Polyak et al. 2002, Blood 99: 3256-3262; Perosa et al. 2005, Blood 107: 1070-1077). Rituximab completely lost binding to CD20 expressed in HEK293F upon introduction of the A170S and P172S mutations ("AxP mutation") in the CD20 extracellular domain. The mouse mAb B1 also showed strongly reduced binding to the AxP mutant, although residual binding was observed. In contrast, binding of IgG1-2F2, IgG1-7D8 and IgG1-2C6 to CD20 was unaffected by the A×P mutation. However, changing the asparagine residues at position 163 or 166 into aspartic acid (N163D or N166D, respectively) completely abrogated the binding of IgG1-2C6 and reduced that of IgG1-2F2 and IgG1-7D8 by up to 75%. A triple mutant with a threonine-to-lysine mutation at position 159 (T159K), in addition to the N163D and N166D mutations (T159K/N163D/N166D, "KDD mutation") abrogated the binding of 2F2, 7D8 and 2C6. The KDD mutation only had a modest effect on the binding of rituximab and B1 (Teeling et al. 2006, The Journal of Immunology 177: 362-371).

To examine the binding of CD3×CD20 bispecific antibodies to wild type (wt) CD20, the A×P mutant and the KDD mutant, a CD20 expression vector was constructed by amplifying the CD20 coding sequence using suitable primers introducing restriction sites and an ideal Kozak sequence for optimal expression. The amplified fragment was digested and ligated in the expression vector pEE12.4 (Lonza, Slough, UK). After transformation in $E.\ coli$, colonies were screened for inserts and two clones were selected for sequencing to confirm the correct sequence. The construct was named pEE12.4CD20HS-GA. Mutagenesis was performed to introduce the A×P or KDD mutations in the extracellular loop regions of human CD20. Mutagenesis was checked by restriction enzyme digestion and sequencing. The constructs were transiently expressed in HEK293F cells and analyzed 24 hours post-transfection using flow cytometry.

Oligonucleotide PCR Primers: Oligonucleotide primers were synthesized and quantified by Isogen BV (Maarssen, The Netherlands). Primers were reconstituted in water in a concentration of 100 pmol/μL and stored at −20° C. until use. A summary of PCR and sequencing primers is shown in Table 11.

Optical density determination of nucleic acids: Optical density was determined using an Ultrospec 2100 pro Classic (Amersham Biosciences, Uppsala, Sweden), according to the manufacturer's instructions. The DNA concentration was measured by analysis of the OD260 nm, where one OD260 nm unit=50 μg/mL. The reference solution was identical to the solution used to dissolve the nucleic acids.

Plasmid DNA isolation from $E.\ coli$ culture: Plasmid DNA was isolated from $E.\ coli$ cultures using kits from Qiagen (Westburg B V, Leusden, The Netherlands), according to the manufacturer's instructions. For 'bulk' plasmid preparation either a Hi-Speed plasmid Maxi kit or a Hi-Speed plasmid Midi kit were used (Qiagen). For a small scale plasmid preparation (i.e., 2 mL of $E.\ coli$ culture) a Qiaprep Spin Miniprep Kit (Qiagen) was used and the DNA eluted in 50 μL TE (Tris-HCl 10 mM pH 8.0, EDTA 1 mM).

PCR amplification: PCR reactions were performed according to the manufacturer's instructions for the Pfu-Turbo© Hotstart DNA polymerase (Stratagene, Amsterdam, The Netherlands). Each 20 mL-reaction contained 1×PCR reaction buffer, 200 mM mixed dNTPs, 6.7 pmol of each forward and reverse primer, approximately 1 ng template DNA and 1 unit of Pfu-Turbo© Hotstart DNA polymerase. PCR reactions were performed on a T-gradient Thermocycler 96 (Biometra GmbH, Goettingen, Germany) using a 30 cycle program of: +95° C. for 2 min, followed by 30 cycles of: +95° C. for 30 sec; anneal: a gradient of 45-65° C. for 30 sec and extension: +72° C. for 2 min, followed by a final extension step at 72° C. for 10 min and subsequent storage at 4° C. The completed reactions were analyzed by agarose gel electrophoresis.

Agarose gel electrophoresis: Agarose gel electrophoresis was performed according to Sambrook (Molecular Cloning Laboratory Manual, 3rd edition) using gels of 50 mL, in 1×Tris/acetic acid/EDTA (TAE) buffer. DNA was visualized by the inclusion of ethidium bromide in the gel and observation under UV light. Gel images were recorded by a CCD camera and an image analysis system (GeneGnome; Syngene, Cambridge, UK).

Restriction enzyme digestions: Restriction enzymes were supplied by New England Biolabs (Beverly, Mass.) and used according to the supplier's recommendations. In general, 100 ng was digested with 5 units of enzyme(s) in appropriate buffer in a final volume of 10 mL.

Reaction volumes were scaled up as appropriate. Digestions were incubated at the manufacturer's recommended temperature for a minimum of 60 min.

For fragments requiring double digestions with restriction enzymes which have incompatible buffer or temperature requirements, digestions were performed sequentially so as to offer favorable conditions for each enzyme in turn.

Alkaline phosphatase treatment: Shrimp alkaline phosphatase (USB, Cleveland, Ohio) was used according to the supplier's recommendations. Alkaline phosphatase removes 5'-phosphate groups from the ends of DNA fragments thereby preventing self-ligation. This is of particular relevance when self-re-ligation of a DNA fragment could result in a replication-competent vector. The enzyme is active in most restriction enzyme buffers and was added as appropriate. After the digestion, the enzyme was inactivated by raising the temperature to 70° C. for 15 min.

Purification of PCR and restriction enzyme reaction products: Purification was carried out using the mini-elute PCR Purification kit (supplied by Qiagen), according to the manufacturer's instructions. Briefly, DNA samples were diluted in 5 volumes of binding buffer I (Qiagen) and loaded onto a mini-elute column within an Eppendorf centrifuge tube. The assembly was centrifuged in a bench-top microcentrifuge. The column was washed twice with buffer II (Qiagen): Following buffer application, the assembly was centrifuged and the flow-through was discarded. The column was dried by centrifugation in the absence of added buffer. DNA was eluted by adding elution buffer to the column and the eluate collected by centrifugation. Isolated DNA was quantified by UV spectroscopy and quality assessed by agarose gel electrophoresis.

Isolation of DNA fragments from agarose gel: Where appropriate (i.e., when multiple fragments were present), digested DNA samples were separated by gel electrophoresis and the desired fragment excised from the gel and recovered using the QIAEX II gel extraction kit (Qiagen), according to the manufacturer's instructions. Briefly, DNA bands were excised from the agarose gel and melted in an appropriate buffer at +55° C. QIAEX II resin was added and incubated for 5 min. QIAEX II resin was pelleted by a short centrifugation step (1 min, 14000 g, room temperature) and washed twice with 500 μL of wash buffer PE (cat. no. 19065, Qiagen). The final pellet was dried in a hood and DNA was eluted with the appropriate volume of TE and at the appropriate temperature (depending on the size of the DNA).

Ligation of DNA fragments: Ligations were performed with the Quick Ligation Kit (New England Biolabs) according to the manufacturer's instructions. For each ligation, the vector DNA was mixed with approximately three-fold molar excess of insert DNA such that the total amount of DNA was lower than 200 ng in 10 μL, with volume adjusted with water as appropriate. To this was added 10 μL 2×Quick Ligation Buffer and 1 µL Quick T4 DNA ligase and the ligation mix was incubated at room temperature for 5-30 min.

Transformation of DNA into bacteria: Samples of DNA were used to transform One Shot DH5a-T1R competent E. coli cells (Invitrogen, Breda, The Netherlands) using the heat-shock method according to the manufacturer's instructions. Briefly, 1-5 µL of DNA solution (typically 2 µL of DNA ligation mix) was added to an aliquot of transformation competent bacterial cells and the mixture incubated on ice for 30 min. The cells were then heat-shocked by transferring to a water bath at 42° C. for 30 sec followed by a further incubation on ice for 5 min. Cells were left to recover by incubation in a non-selective culture medium (SOC) with agitation at 37° C. for 1 hour and were subsequently spread onto agar plates containing appropriate selective agent (ampicillin at 50 µg/ml). Plates were incubated at +37° C. for 16-18 hours or until colonies of bacteria became evident.

Screening of bacterial colonies by PCR: Bacterial colonies were screened for the presence of vectors containing the desired sequences using the PCR colony screening technique. 20 µL of PCR reaction mix containing 0.5 volumes of HotStarTaq Master Mix (Qiagen), 4 pmol of the forward and reverse primers and completed with water was added to a PCR tube. A colony was lightly touched with a 20 µL pipette tip, once touched in 2 mL LB in a culture tube (for growing bacteria containing the corresponding plasmid) and resuspended in the 20 µL PCR mix. PCR was performed on a Tgradient Thermocycler 96 (Biometra) using a 35 cycle program of: +95° C. for 15 min, followed by 35 cycles of: +94° C. for 30 sec, anneal: 55° C. for 30 sec and extension: +72° C. for 2 min, followed by a final extension step at 72° C. for 10 min and subsequent storage at 4° C. The completed reactions were analyzed by agarose gel electrophoresis. See Table 11 for details of primer pairs used for colony PCR.

DNA sequencing: Plasmid DNA samples were send to AGOWA (Berlin, Germany) for sequence analysis. Sequences were analyzed using the VectorNTI software package (Informax, Frederick, Md., USA).

TABLE 11

| Name | Length | Oligo Sequence |
|---|---|---|
| CD20hs-GA-A170S-P172S R | 42 | GGGAGTTCTTCTCGCTGCTGTTGCTGGGCT CGCAGTTGTAGA |
| CD20hs-GA-A170S-P172S F | 42 | TCTACAACTGCGAGCCCAGCAACAGCAGCG AGAAGAACTCCC |
| CD20hs-GA-T159K-N163D-N166D R | 43 | CTCGCAGTCGTAGATGTCGATGTAGGGCTT GTGGGCCCGGATG |
| CD20hs-GA-T159K-N163D-N166D F | 43 | CATCCGGGCCCACAAGCCCTACATCGACAT CTACGACTGCGAG |

Mutagenesis: The mutagenesis was performed, using the QuikChange® XL Site-Directed Mutagenesis kit (Cat 200517-5, Lot 1120630, Stratagene Europe) according to the manufacturer's instructions.

Mutagenesis reactions were concentrated using ethanol precipitation and transformed into either oneshot DH5α-TIR competent E. coli cells or electroporated into ElectroTen-Blue® Electroporation-Competent Cells. Colonies were checked by colony PCR and restriction digestion prior to transfection.

HEK293F cell transfection: HEK293F cells were obtained from Invitrogen and transfected according to the manufacturer's instructions, using 293fectin.

Anti-CD20 Antibody binding: HEK293F cells were taken up in staining buffer (PBS supplemented with 0.1% BSA and 0.02% $NaN_3$) and added to round bottom plates (1-3×$10^5$/ well in 100 µL). Then, 50 µL CD3×CD20 bispecific antibody was added, in serial dilutions (0.0015-10 µg/mL, three-fold dilutions) (4° C., 30 min).

After washing twice in staining buffer, cells were incubated in 50 µL secondary antibody at 4° C. for 30 min. As a secondary antibody, R-Phycoerythrin (PE)-conjugated goat-anti-human IgG F(ab')$_2$ was used, as described supra. Next, cells were washed once in staining buffer, re-suspended in 150 µL staining buffer and analyzed on a flow cytometer (FACSCanto-720, Becton Dickinson, San Diego, Calif., USA) and 10,000 events per sample were acquired at high flow rate. Binding curves were analyzed using non-linear regression (sigmoidal dose-response with variable slope) using GraphPad Prism V75.04 software (GraphPad Software, San Diego, Calif., USA).

Figure 10A:
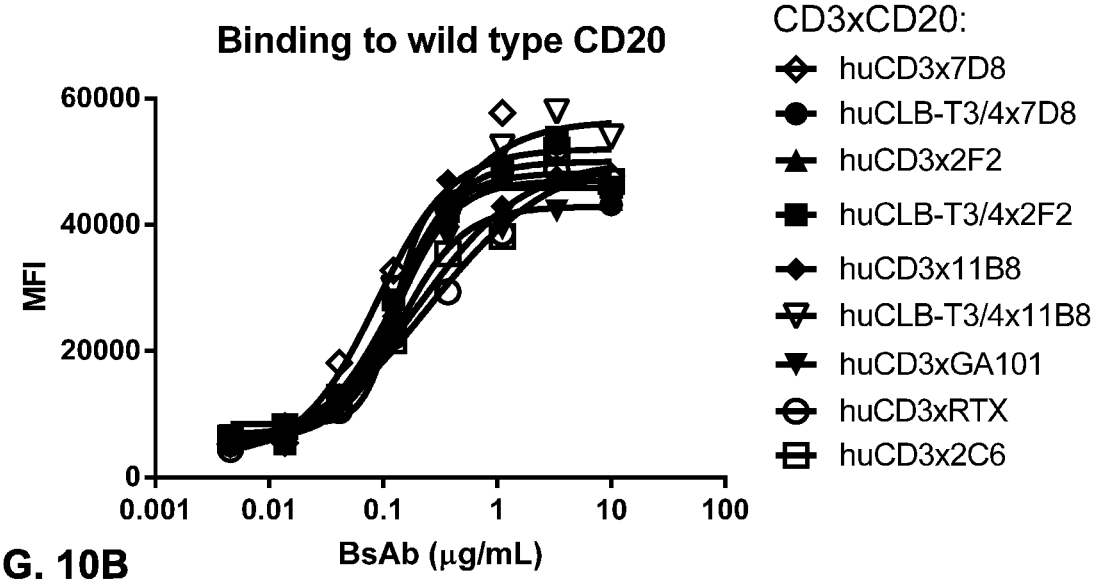
FIGS. 10A and 10B: Binding of bispecific CD3xCD20 antibodies to wild type CD20 and CD20-AxP expressed in HEK293F cells. Binding of CD3xCD20 bispecific antibodies (bsIgG1-huCD3-H1L1-FEALxCD20-7D8-FEAR [huCD3x7D8], bsIgG1-huCLB-T3/4-FEALxCD20-7D8-FEAR [huCLB-T3/4x7D8], bsIgG1-huCD3-H1L1-FEALxCD20-2F2-FEAR [huCD3x2F2], bsIgG1-huCLB-T3/4-FEALxCD20-2F2-FEAR [huCLB-T3/4x2F2], bsIgG1-huCD3-H1L1-FEALxCD20-11B8-FEAR [huCD3x11B8], bsIgG1-huCLB-T3/4-FEALxCD20-11B8-FEAR [huCLB-T3/4x11B8], bsIgG1-huCD3-H1L1-FEALxCD20-GA101-FEAR [huCD3xGA101], bsIgG1-huCD3-H1L1-FEALx CD20-RTX-FEAR [huCD3×RTX], bsIgG1-huCD3-H1L1-FEAL×CD20-2C6-FEAR [huCD3×2C6]) to wild type CD20 (FIG. 10A) and CD20 mutant (CD20-A×P) (FIG. 10B) expressed in HEK293F cells was measured by flow cytometry. Data shown are mean fluorescence intensities of one representative experiment.
Figure 10B:
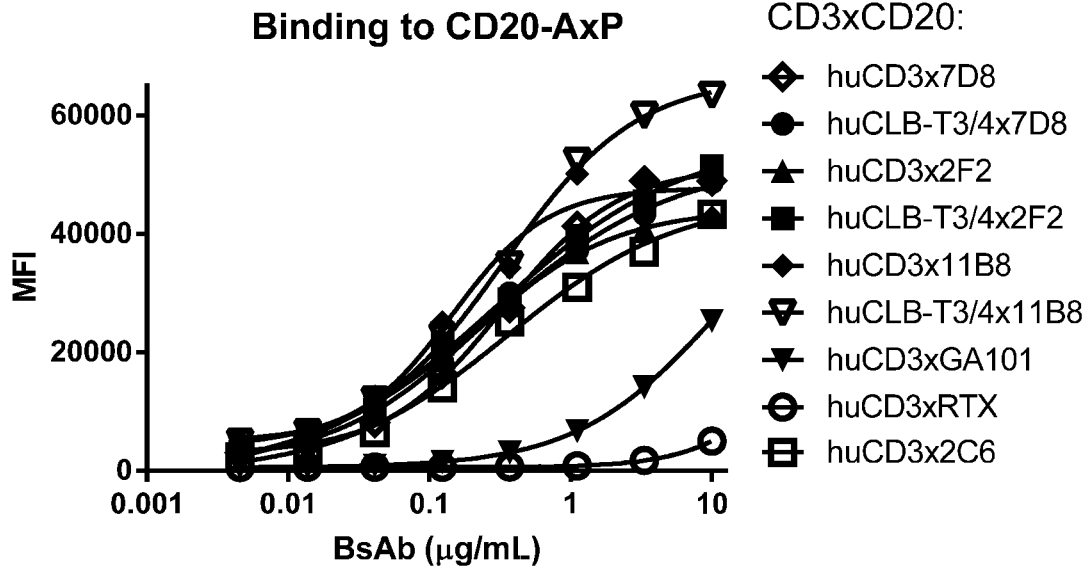

All CD3×CD20 bispecific antibodies bound efficiently to HEK293F cells expressing WT CD20 (FIG. 10A). As shown in FIG. 10B and Table 12, bsIgG1-huCD3-H1L1-FEALx CD20-7D8-FEAR, bsIgG1-huCD3-H1L1-FEALxCD20-2F2-FEAR, bsIgG1-huCD3-H1L1-FEALxCD20-11B8-FEAR and bsIgG1-huCD3-H1L1-FEALxCD20-2C6-FEAR bound efficiently to the AxP mutant. Similarly, bsIgG1-huCLB-3/4-FEALxCD20-7D8-FEAR, bsIgG1-huCLB-3/4-FEALxCD20-2F2-FEAR and bsIgG1-huCLB-3/4-FEALx CD20-11B8-FEAR showed efficient binding to CD20-AxP. As expected, bsIgG1-huCD3-H1L1-FEALxCD20-RTX-FEAR completely lost binding to the AxP mutant, as was shown previously for the parental antibody IgG1-RTX. BsIgG1-huCD3-H1L1-FEALxCD20-GA101-FEAR showed greatly reduced binding to CD20-AxP.

BsIgG1-huCD3-H1L1-FEALxCD20-7D8-FEAR, bsIgG1-huCD3-H1L1-FEALxCD20-2F2-FEAR and bsIgG1-huCD3-H1L1-FEALxCD20-2C6-FEAR, as well as bsIgG1-huCLB-3/4-FEALxCD20-7D8-FEAR and bsIgG1-huCLB-3/4-FEALxCD20-2F2-FEAR lost binding to CD20 upon introduction of the KDD mutations (Table 12), confirming that these bispecific antibodies that monovalently bind CD20, showed comparable binding characteristics as the parental antibodies IgG1-7D8, IgG1-2F2 and IgG1-2C6, respectively. BsIgG1-huCD3-H1L1-FEALxCD20-11B8-FEAR and bsIgG1-huCLB-3/4-FEALxCD20-11B8-FEAR partially lost binding to CD20 when the KDD mutation was present.

TABLE 12

Binding of CD3×CD20 bispecific antibodiesto CD20 mutants.

| CD3 x CD20 bispecific antibody | Binding to CD20 mutants (% of wt CD20 binding) | |
|---|---|---|
| | KDD | AxP |
| BsIgG1-huCD3-H1L1-FEALxCD20-7D8-FEAR | 4 | 103 |
| BsIgG1-huCD3-H1L1-FEALxCD20-2F2-FEAR | 4 | 98 |
| BsIgG1-huCD3-H1L1-FEALxCD20-11B8-FEAR | 67 | 95 |
| BsIgG1-huCD3-H1L1-FEALxCD20-2C6-FEAR | 3 | 92 |
| BsIgG1-huCD3-H1L1-FEALxCD20-RTX-FEAR | 87 | 11 |
| BsIgG1-huCD3-H1L1-FEALxCD20-GA101-FEAR | 108 | 57 |
| BsIgG1-huCLB-T3/4-FEALxCD20-7D8-FEAR | 3 | 113 |

TABLE 12-continued

Binding of CD3xCD20 bispecific antibodiesto CD20 mutants.

| CD3 x CD20 bispecific antibody | Binding to CD20 mutants (% of wt CD20 binding) | |
|---|---|---|
| | KDD | AxP |
| BsIgG1-huCLB-T3/4-FEALxCD20-2F2-FEAR | 5 | 112 |
| BsIgG1-huCLB-T3/4-FEALxCD20-11B8-FEAR | 54 | 118 |

Binding of CD3xCD20 bispecific antibodies to CD20 mutants expressed in HEK293F cells was determined by flow cytometry. Numbers indicate the percentage of binding to the CD20 mutants, relative to binding to wild type CD20, at 10 µg/mL. The percentage of binding was calculated by the following formula: (MFI binding to CD20 mutant)/(MFI binding CD20 wt) × 100%

Example 14—Determination of the CD3 Binding Affinity Using Bio-Layer Interferometry To determine the affinity of the CD3×CD20 bispecific antibodies for CD3, Bio-Layer Interferometry was performed on a ForteBio Octet HTX. Anti-human Fc Capture (AHC) biosensors (ForteBio, Portsmouth, UK; cat no. 18-5060) were loaded for 600 s with the CD3×CD20 bispecific antibodies (1 µg/mL), aiming at a loading response of 1 nm. After a baseline (200 s), the association (1000 s) and dissociation (2000 s) of soluble CD3E27-GSKa was determined using concentrations ranging between 1 nM and 1000 nM. The CD3ε27-GSKa protein consists of the human CD3ε peptide (aa1-27) fused to the N-terminus of a kappa LC (SEQ ID NO: 402). For calculations, the theoretical molecular mass of CD3ε27-GSKa based on the amino acid sequence was used, i.e. 27.1 kDa. Experiments were carried out under shaking conditions (1000 rpm) at 30° C.

Data was analyzed with ForteBio Data Analysis Software v8.1, using the 1:1 model and a global full fit with 1000 s association time and 200 s dissociation time. Data traces were corrected by subtraction of a reference curve (CD3×CD20 bispecific antibodies without CD3ε27-GSKa), the Y-axis was aligned to the last 10 s of the baseline, and interstep correction as well as Savitzky-Golay filtering was applied. Data traces with a response lower than 0.05 nm were excluded from analysis.

The equilibrium dissociation constants ($K_D$) of the CD3×CD20 bispecific antibodies were all within 2-fold of the $K_D$ of the parental IgG1-huCD3-H1L1-FEAL molecule.

Example 15—BsIgG1-huCD3-H1L1-FEALxCD20-7D8-FEAR Induces T Cell Activation in the Presence of B Cells The capacity of CD3×CD20 bispecific antibodies to induce activation of T cells, in the presence of B cells, was tested by incubating PBMC with bsIgG1-huCD3-H1L1-FEALxCD20-7D8-FEAR. T cell activation was assessed by measuring CD69 expression.

PBMC, isolated from healthy donors as described supra, were added to 96-well round bottom culture plates (Greiner bio-one, cat 650180; 100,000 cells/well) and incubated with bsIgG1-huCD3-H1L1-FEALxCD20-7D8-FEAR diluted in RPMI++(final antibody concentration 0.1-1000 ng/mL). The final volume in each well was 100 µL. IgG1-huCD3-H1L1-FEAL and IgG1-huCLB-T3/4-FEAL, both of which are bivalent CD3-specific IgG1 antibodies with inactive Fc domains, as well as the isotype control antibody IgG1-b12-FEAL were included as negative control antibodies. IgE-huCLB-T3/4, a bivalent CD3-specific IgE antibody that is known to induce activation of T cells, and IgG1-huCLB-T3/4-F405L, a bivalent CD3 specific IgG1 antibody with an active Fc domain, were included as positive control antibodies. PBMC were incubated with antibodies (37° C., 5% $CO_2$) for 16-24 hours.

To assess T cell activation, PBMC were washed twice in staining buffer and resuspended in staining buffer (final volume 50 µL) containing APC-labeled mouse anti-human CD69 antibody (BD Pharmingen, cat 340560; final dilution 1:100) and PE-labeled mouse anti-human CD28 antibody (Milteny Biotech, cat 130-092-921; final dilution 1:40). After 30 minutes at 4° C., cells were washed twice. Cells were resuspended in 150 µL staining buffer and analyzed using a FACS Canto II (BD). The median fluorescence intensity of APC (CD69) was assessed within the population of CD28-positive cells. CD28 was used as a marker to identify T cells.

Figure 11:
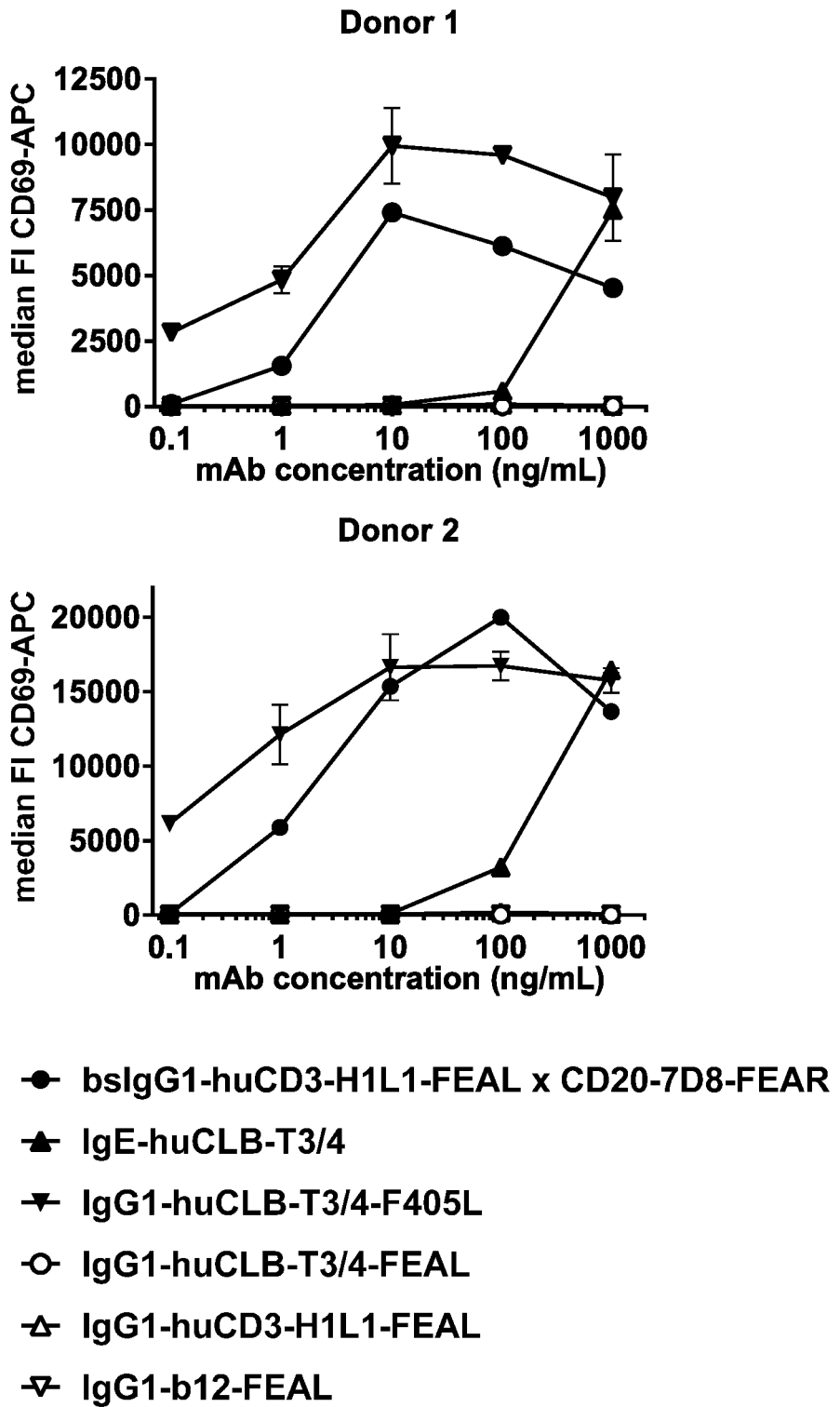
FIG. 11: T cell activation upon incubation of PBMC with bsIgG1-huCD3-H1L1-FEAL×CD20-7D8-FEAR.

As shown in FIG. 11, bsIgG1-huCD3-H1L1-FEALxCD20-7D8-FEAR induced dose-dependent activation of T cells, as indicated by an increase in CD69 expression in peripheral blood T cells. T cell activation was also observed after incubation with the positive control antibodies IgE-huCLB-T3/4 and IgG1-hu-CLB3/4-F405L. In contrast, the negative control antibodies IgG1-huCD3-H1L1-FEAL, IgG1-hu-CLB-T3/4-FEAL and IgG1-b12-FEAL did not induce CD69 expression.

TABLE 13

Equilibrium dissociation constants ($K_D$), association rates ($k_{on}$) and dissociation rates ($k_{dis}$) for selected CD3 x CD20 bispecific antibodies

| Antibody I D | $K_D$ (M) | $k_{on}$ (1/Ms) | $k_{dis}$ (1/s) |
|---|---|---|---|
| IgG1-huCD3-H1L1-FEAL | 1.4E−08 | 3.2E+05 | 4.5E−03 |
| BsIgG1-huCD3-H1L1-FEALxCD20-2F2-FEAR | 1.5E−08 | 2.7E+05 | 4.1E−03 |
| BsIgG1-huCD3-H1L1-FEALxCD20-GA101-FEAR | 1.5E−08 | 2.7E+05 | 4.0E−03 |
| BsIgG1-huCD3-H1L1-FEALxCD20-11B8-FEAR | 1.2E−08 | 4.1E+05 | 4.8E−03 |
| BsIgG1-huCD3-H1L1-FEALxCD20-2C6-FEAR | 0.81E−08 | 3.3E+05 | 2.7E−03 |
| BsIgG1-huCD3-H1L1-FEALxCD20-RTX-FEAR | 1.1E−08 | 3.9E+05 | 4.3E−03 |
| BsIgG1-huCD3-H1L1-FEALxCD20-7D8-FEAR | 1.1E−08 | 3.8E+05 | 4.3E−03 |
| BsIqG1-huCD3-H1L1-FEALxCD20-b12-FEAR | 2.1E−08 | 1.7E+05 | 3.7E−03 |

The invention claimed is:

1. A bispecific antibody comprising (i) a first binding arm comprising a first antigen-binding region which binds to human CD3ε (epsilon), wherein said first antigen-binding region comprises the VH sequence set forth in SEQ ID NO:6, and the VL sequence set forth in SEQ ID NO: 10, and (ii) a second binding arm comprising a second antigen-binding region which binds to human CD20.

2. The bispecific antibody according to claim 1, wherein the second antigen-binding region which binds to human CD20 comprises:

(i) the VH CDR1 region of SEQ ID NO:32, the VH CDR2 region of SEQ ID NO:33, the VH CDR3 region of SEQ ID NO:34, the VL CDR1 region of SEQ ID NO:35, the VL CDR2 region of DAS, and the VL CDR3 region of SEQ ID NO:36, (ii) the VH CDR1 region of SEQ ID NO:38, the VH CDR2 region of SEQ ID NO:39, the VH CDR3 region of SEQ ID NO:34, the VL CDR1 region of SEQ ID NO:35, the VL CDR2 region of DAS, and the VL CDR3 region of SEQ ID NO:36, (iii) the VH CDR1 region of SEQ ID NO:42, the VH CDR2 region of SEQ ID NO:43, the VH CDR3 region of SEQ ID NO:44, the VL CDR1 region of SEQ ID NO:45, the VL CDR2 region of DAS, and the VL CDR3 region of SEQ ID NO:46, (iv) the VH CDR1 region of SEQ ID NO:49, the VH CDR2 region of SEQ ID NO:50, the VH CDR3 region of SEQ ID NO:51, the VL CDR1 region of SEQ ID NO:52, the VL CDR2 region of DAS, and the VL CDR3 region of SEQ ID NO:53, (v) the VH CDR1 region of SEQ ID NO:32, the VH CDR2 region of SEQ ID NO:33, the VH CDR3 region of SEQ ID NO:34, the VL CDR1 region of SEQ ID NO:45, the VL CDR2 region of DAS, and the VL CDR3 region of SEQ ID NO:46, (vi) the VH CDR1 region of SEQ ID NO:32, the VH CDR2 region of SEQ ID NO:33, the VH CDR3 region of SEQ ID NO:34, the VL CDR1 region of SEQ ID NO:52, the VL CDR2 region of DAS, and the VL CDR3 region of SEQ ID NO:53, (vii) the VH CDR1 region of SEQ ID NO:38, the VH CDR2 region of SEQ ID NO:39, the VH CDR3 region of SEQ ID NO:34, the VL CDR1 region of SEQ ID NO:45, the VL CDR2 region of DAS, and the VL CDR3 region of SEQ ID NO:46, (viii) the VH CDR1 region of SEQ ID NO:38, the VH CDR2 region of SEQ ID NO:39, the VH CDR3 region of SEQ ID NO:34, the VL CDR1 region of SEQ ID NO:52, the VL CDR2 region of DAS, and the VL CDR3 region of SEQ ID NO:53, (ix) the VH CDR1 region of SEQ ID NO:42, the VH CDR2 region of SEQ ID NO:43, the VH CDR3 region of SEQ ID NO:44, the VL CDR1 region of SEQ ID NO:35, the VL CDR2 region of DAS, and the VL CDR3 region of SEQ ID NO:36, (x) the VH CDR1 region of SEQ ID NO:42, the VH CDR2 region of SEQ ID NO:43, the VH CDR3 region of SEQ ID NO:44, the VL CDR1 region of SEQ ID NO:52, the VL CDR2 region of DAS, and the VL CDR3 region of SEQ ID NO:53, (xi) the VH CDR1 region of SEQ ID NO:49, the VH CDR2 region of SEQ ID NO:50, the VH CDR3 region of SEQ ID NO:51, the VL CDR1 region of SEQ ID NO:35, the VL CDR2 region of DAS, and the VL CDR3 region of SEQ ID NO:36, or (xii) the VH CDR1 region of SEQ ID NO:49, the VH CDR2 region of SEQ ID NO:50, the VH CDR3 region of SEQ ID NO:51, the VL CDR1 region of SEQ ID NO:45, the VL CDR2 region of DAS, and the VL CDR3 region of SEQ ID NO:46.

3. The bispecific antibody according to claim 1, wherein the second antigen-binding region which binds to human CD20 comprises:

(i) the VH sequence of SEQ ID NO:27, and the VL sequence of SEQ ID NO:28,
(ii) the VH sequence of SEQ ID NO:37, and the VL sequence of SEQ ID NO:28,
(iii) the VH sequence of SEQ ID NO:40, and the VL sequence of SEQ ID NO:41,
(iv) the VH sequence of SEQ ID NO:47, and the VL sequence of SEQ ID NO:48,
(v) the VH sequence of SEQ ID NO:27, and the VL sequence of SEQ ID NO:41,
(vi) the VH sequence of SEQ ID NO:27, and the VL sequence of SEQ ID NO:48,
(vii) the VH sequence of SEQ ID NO:37, and the VL sequence of SEQ ID NO:41,
(viii) the VH sequence of SEQ ID NO:37, and the VL sequence of SEQ ID NO:48,
(ix) the VH sequence of SEQ ID NO:40, and the VL sequence of SEQ ID NO:28,
(x) the VH sequence of SEQ ID NO:40, and the VL sequence of SEQ ID NO:48,
(xi) the VH sequence of SEQ ID NO:47, and the VL sequence of SEQ ID NO:28, or
(xii) the VH sequence of SEQ ID NO:47, and the VL sequence of SEQ ID NO:41.

4. A bispecific antibody comprising (a) a first binding arm comprising a first antigen-binding region which binds to human CD3ε (epsilon), wherein the first antigen-binding region comprises the VH sequence set forth in SEQ ID NO:6, and a VL sequence set forth in SEQ ID NO: 10, and (b) a second binding arm comprising a second antigen-binding region which binds to human CD20, wherein the second antigen-binding region comprises the VH sequence set forth in SEQ ID NO:27, and the VL sequence set forth in SEQ ID NO:28.

5. The bispecific antibody according to claim 4, wherein the bispecific antibody comprises a first and second constant heavy chain (HC) and a first and second constant light chain (LC), wherein each of said first and second heavy chain comprises at least a hinge region, a CH2 and CH3 region, wherein in said first heavy chain at least one of the amino acids in the positions corresponding to a positions selected from the group consisting of T366, L368, K370, D399, F405, Y407, and K409 in a human IgG heavy chain has been substituted, and in said second heavy chain at least one of the amino acids in the positions corresponding to a position selected from the group consisting of T366, L368, K370, D399, F405, Y407, and K409 in a human IgG heavy chain has been substituted, and wherein said first and said second heavy chains are not substituted in the same positions.

6. The bispecific antibody according to claim 4, wherein (i) the amino acid in the position corresponding to F405 in a human IgG heavy chain is L in said first heavy chain, and the amino acid in the position corresponding to K409 in a human IgG heavy chain is R in said second heavy chain, or (ii) the amino acid in the position corresponding to K409 in a human IgG heavy chain is R in said first heavy chain, and the amino acid in the position corresponding to F405 in a human IgG heavy chain is L in said second heavy chain.

7. The bispecific antibody according to claim 4, wherein the bispecific antibody comprises a first constant heavy chain (HC) and a first constant light chain (LC), wherein the positions corresponding to positions L234, L235, and D265 in the human IgG1 heavy chain of SEQ ID NO: 15 of both the first heavy chain and the second heavy chain are F, E, and A, respectively.

8. The bispecific antibody according to claim 4, wherein the bispecific antibody comprises a first and second constant heavy chain (HC) and a first and second constant light chain (LC), wherein the positions corresponding to positions L234, L235, and D265 in the human IgG1 heavy chain of SEQ ID NO: 15 of both the first constant heavy chain and the second constant heavy chain are F, E, and A, respectively, and wherein the position corresponding to F405 in the human IgG1 heavy chain of SEQ ID NO: 15 of the first constant heavy chain is L, and the position corresponding to K409 in the human IgG heavy chain of SEQ ID NO: 15 of the second constant heavy chain is R.

9. A composition comprising a bispecific antibody according to claim 1, and a carrier.

10. A kit for detecting cross-linking between CD3- and CD20-expressing cells, in a sample derived from a patient comprising:

i) the bispecific antibody according to claim 1; and
ii) instructions for use of said kit.

11. A composition comprising a bispecific antibody according to claim 4 and a carrier.

12. A bispecific antibody comprising (i) a first binding arm comprising a first antigen-binding region which binds to human CD3ε (epsilon), wherein said first antigen-binding region comprises the VH sequence set forth in SEQ ID NO:6 and the VL sequence set forth in SEQ ID NO: 10, and (ii) a second binding arm comprising a second antigen-binding region which binds to human CD20, wherein the second antigen-binding region which binds to human CD20 comprises the VH CDR1 region of SEQ ID NO:32, the VH CDR2 region of SEQ ID NO:33, the VH CDR3 region of SEQ ID NO:34, the VL CDR1 region of SEQ ID NO:35, the VL CDR2 region of DAS, and the VL CDR3 region of SEQ ID NO:36.

* * * * *

UNITED STATES PATENT AND TRADEMARK OFFICE
CERTIFICATE OF CORRECTION

PATENT NO. : 10,544,220 B2  
APPLICATION NO. : 15/541594  
DATED : January 28, 2020  
INVENTOR(S) : Patrick Engelberts et al.

Page 1 of 2

It is certified that error appears in the above-identified patent and that said Letters Patent is hereby corrected as shown below:

On the Title Page

At Column 1, item (30), Line 2 of the "Foreign Application Priority Data" section, delete "2015 00412" and insert --PA 2015 00412--.

At Column 1, item (30), Line 3 of the "Foreign Application Priority Data" section, delete "2015 00413" and insert --PA 2015 00413--.

At Column 1, item (30), Line 4 of the "Foreign Application Priority Data" section, delete "2015 00415" and insert --PA 2015 00415--.

At Column 1, item (30), Line 5 of the "Foreign Application Priority Data" section, delete "2015 00416" and insert --PA 2015 00416--.

In the Claims

At Column 170, Claim number 4, Line number 11, delete "a VL sequence" and insert --the VL sequence--.

At Column 170, Claim number 5, Line numbers 18-20, delete "a first and second constant heavy chain (HC) and a first and second constant light chain (LC)" and insert --first and second heavy chains (HC) and first and second light chains (LC)--.

At Column 170, Claim number 5, Line number 23, delete "acids in the positions corresponding to a positions selected" and insert --acids in the positions corresponding to a position selected--.

At Column 170, Claim number 6, Line number 32, delete "claim 4" and insert --claim 5--.

Signed and Sealed this  
Eighteenth Day of August, 2020

Andrei Iancu  
*Director of the United States Patent and Trademark Office*

CERTIFICATE OF CORRECTION (continued)
U.S. Pat. No. 10,544,220 B2

At Column 170, Claim number 7, Line numbers 42-43, delete "first constant heavy chain (HC) and a first constant light chain (LC)" and insert --first heavy chain and a second heavy chain (HC) and a first light chain and a second light chain (LC)--.

At Column 170, Claim number 8, Line number 49, delete "constant".

At Column 170, Claim number 8, Line number 50, delete "constant".

At Column 170, Claim number 8, Line number 53, delete "constant".

At Column 170, Claim number 8, Line number 54, delete "constant".

At Column 170, Claim number 8, Line number 57, delete "constant".

At Column 170, Claim number 8, Line number 59, delete "constant".

SEQUENCE LISTING

<160> NUMBER OF SEQ ID NOS: 87

<210> SEQ ID NO 1
<211> LENGTH: 8
<212> TYPE: PRT
<213> ORGANISM: Mus Musculus

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: Mus Musculus

<400> SEQUENCE: 2

Ile Arg Ser Lys Tyr Asn Asn Tyr Ala Thr
1               5                   10

<210> SEQ ID NO 3
<211> LENGTH: 16
<212> TYPE: PRT
<213> ORGANISM: Mus Musculus

<400> SEQUENCE: 3

Val Arg His Gly Asn Phe Gly Asn Ser Tyr Val Ser Trp Phe Ala Tyr
1               5                   10                  15

<210> SEQ ID NO 4
<211> LENGTH: 9
<212> TYPE: PRT
<213> ORGANISM: Mus Musculus

<400> SEQUENCE: 4

Thr Gly Ala Val Thr Thr Ser Asn Tyr
1               5

<210> SEQ ID NO 5
<211> LENGTH: 9
<212> TYPE: PRT
<213> ORGANISM: Mus Musculus

<400> SEQUENCE: 5

Ala Leu Trp Tyr Ser Asn Leu Trp Val
1               5

<210> SEQ ID NO 6
<211> LENGTH: 125
<212> TYPE: PRT
<213> ORGANISM: Mus Musculus

<400> SEQUENCE: 6

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

```
Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 7
<211> LENGTH: 125
<212> TYPE: PRT
<213> ORGANISM: Mus Musculus

<400> SEQUENCE: 7

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 8
<211> LENGTH: 125
<212> TYPE: PRT
<213> ORGANISM: Mus Musculus

<400> SEQUENCE: 8

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 9
<211> LENGTH: 125
<212> TYPE: PRT
<213> ORGANISM: Mus Musculus
```

<400> SEQUENCE: 9

```
Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125
```

<210> SEQ ID NO 10
<211> LENGTH: 109
<212> TYPE: PRT
<213> ORGANISM: Mus Musculus

<400> SEQUENCE: 10

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 11
<211> LENGTH: 109
<212> TYPE: PRT
<213> ORGANISM: Mus Musculus

<400> SEQUENCE: 11

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80
```

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 12
<211> LENGTH: 109
<212> TYPE: PRT
<213> ORGANISM: Mus Musculus

<400> SEQUENCE: 12

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 13
<211> LENGTH: 186
<212> TYPE: PRT
<213> ORGANISM: homo sapiens

<400> SEQUENCE: 13

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
                100                 105                 110

Val Ile Val Asp Ile Cys Ile Thr Gly Gly Leu Leu Leu Leu Val Tyr
            115                 120                 125

Tyr Trp Ser Lys Asn Arg Lys Ala Lys Ala Lys Pro Val Thr Arg Gly
        130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
            180                 185

<210> SEQ ID NO 14
<211> LENGTH: 150
<212> TYPE: PRT
<213> ORGANISM: homo sapiens

<400> SEQUENCE: 14

```
Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
50                  55                  60

Val Gln Val His Tyr Arg Met Cys Gln Ser Cys Val Glu Leu Asp Pro
65                  70                  75                  80

Ala Thr Val Ala Gly Ile Ile Val Thr Asp Val Ile Ala Thr Leu Leu
                85                  90                  95

Leu Ala Leu Gly Val Phe Cys Phe Ala Gly His Glu Thr Gly Arg Leu
            100                 105                 110

Ser Gly Ala Ala Asp Thr Gln Ala Leu Leu Arg Asn Asp Gln Val Tyr
        115                 120                 125

Gln Pro Leu Arg Asp Arg Asp Asp Ala Gln Tyr Ser His Leu Gly Gly
    130                 135                 140

Asn Trp Ala Arg Asn Lys
145                 150
```

<210> SEQ ID NO 15
<211> LENGTH: 330
<212> TYPE: PRT
<213> ORGANISM: homo sapiens

<400> SEQUENCE: 15

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 330
<212> TYPE: PRT
<213> ORGANISM: homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220
```

-continued

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 17
<211> LENGTH: 119
<212> TYPE: PRT
<213> ORGANISM: Mus Musculus

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Phe Trp Val Arg Gln Ala Pro Gly Lys Gly Leu Glu Trp Val
        35                  40                  45

Ala Thr Ile Ser Arg Tyr Ser Arg Tyr Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Leu Tyr Gly Ser Ser Pro Asp Tyr Trp Gly Gln Gly
            100                 105                 110

Thr Leu Val Thr Val Ser Ser
        115

<210> SEQ ID NO 18
<211> LENGTH: 106
<212> TYPE: PRT
<213> ORGANISM: Mus Musculus

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Ser Gly Thr Lys Leu Glu Met Arg
            100                 105

<210> SEQ ID NO 19
<211> LENGTH: 177
<212> TYPE: PRT
<213> ORGANISM: Macaca Fascicularis

<400> SEQUENCE: 19

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

Val Met Ala Val Ala Thr Ile Val Ile Val Asp Ile Cys Ile Thr Leu
            100                 105                 110

Gly Leu Leu Leu Leu Val Tyr Tyr Trp Ser Lys Asn Arg Lys Ala Lys
        115                 120                 125

Ala Lys Pro Val Thr Arg Gly Ala Gly Ala Gly Gly Arg Gln Arg Gly
    130                 135                 140

Gln Asn Lys Glu Arg Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 20
<211> LENGTH: 177
<212> TYPE: PRT
<213> ORGANISM: Macaca Mulatta

<400> SEQUENCE: 20

Gln Asp Gly Asn Glu Glu Met Gly Ser Ile Thr Gln Thr Pro Tyr His
1               5                   10                  15

Val Ser Ile Ser Gly Thr Thr Val Ile Leu Thr Cys Ser Gln His Leu
            20                  25                  30

Gly Ser Glu Val Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

Val Met Ala Val Ala Thr Ile Val Ile Val Asp Ile Cys Ile Thr Leu
            100                 105                 110

Gly Leu Leu Leu Leu Val Tyr Tyr Trp Ser Lys Asn Arg Lys Ala Lys
        115                 120                 125

```
Ala Lys Pro Val Thr Arg Gly Ala Gly Gly Arg Gln Arg Gly
    130                 135                 140

Gln Asn Lys Glu Arg Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                    165                 170                 175

Ile

<210> SEQ ID NO 21
<211> LENGTH: 330
<212> TYPE: PRT
<213> ORGANISM: homo sapiens

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320
```

-continued

Gln Lys Ser Leu Ser Leu Ser Pro Gly Lys
            325                 330

<210> SEQ ID NO 22
<211> LENGTH: 330
<212> TYPE: PRT
<213> ORGANISM: homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 23
<211> LENGTH: 330
<212> TYPE: PRT
<213> ORGANISM: homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 24
<211> LENGTH: 330
<212> TYPE: PRT
<213> ORGANISM: homo sapiens

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 125
<212> TYPE: PRT
<213> ORGANISM: Mus Musculus

<400> SEQUENCE: 25

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile

```
            65                  70                  75                  80
Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
            115                 120                 125

<210> SEQ ID NO 26
<211> LENGTH: 109
<212> TYPE: PRT
<213> ORGANISM: Mus Musculus

<400> SEQUENCE: 26

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 27
<211> LENGTH: 122
<212> TYPE: PRT
<213> ORGANISM: homo sapiens

<400> SEQUENCE: 27

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
            35                  40                  45

Ser Thr Ile Ser Trp Asn Ser Gly Thr Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
            115                 120

<210> SEQ ID NO 28
<211> LENGTH: 107
<212> TYPE: PRT
<213> ORGANISM: homo sapiens

<400> SEQUENCE: 28
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 29
<211> LENGTH: 106
<212> TYPE: PRT
<213> ORGANISM: homo sapiens

<400> SEQUENCE: 29

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65              70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 30
<211> LENGTH: 109
<212> TYPE: PRT
<213> ORGANISM: Mus Musculus

<400> SEQUENCE: 30

Gln Ala Val Val Thr Gln Glu Pro Ser Leu Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65              70                  75                  80

Gln Ala Asp Asp Glu Ser Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 31
<211> LENGTH: 109
<212> TYPE: PRT
<213> ORGANISM: Mus Musculus

<400> SEQUENCE: 31

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 32
<211> LENGTH: 8
<212> TYPE: PRT
<213> ORGANISM: homo sapiens

<400> SEQUENCE: 32

Gly Phe Thr Phe His Asp Tyr Ala
1               5

<210> SEQ ID NO 33
<211> LENGTH: 8
<212> TYPE: PRT
<213> ORGANISM: homo sapiens

<400> SEQUENCE: 33

Ile Ser Trp Asn Ser Gly Thr Ile
1               5

<210> SEQ ID NO 34
<211> LENGTH: 15
<212> TYPE: PRT
<213> ORGANISM: homo sapiens

<400> SEQUENCE: 34

Ala Lys Asp Ile Gln Tyr Gly Asn Tyr Tyr Gly Met Asp Val
1               5                   10                  15

<210> SEQ ID NO 35
<211> LENGTH: 6
<212> TYPE: PRT
<213> ORGANISM: homo sapiens

<400> SEQUENCE: 35

Gln Ser Val Ser Ser Tyr
1               5

<210> SEQ ID NO 36
<211> LENGTH: 9
<212> TYPE: PRT
<213> ORGANISM: homo sapiens

<400> SEQUENCE: 36

Gln Gln Arg Ser Asn Trp Pro Ile Thr
1               5

<210> SEQ ID NO 37
<211> LENGTH: 122
<212> TYPE: PRT
<213> ORGANISM: homo sapiens

<400> SEQUENCE: 37

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 38
<211> LENGTH: 8
<212> TYPE: PRT
<213> ORGANISM: homo sapiens

<400> SEQUENCE: 38

Gly Phe Thr Phe Asn Asp Tyr Ala
1               5

<210> SEQ ID NO 39
<211> LENGTH: 8
<212> TYPE: PRT
<213> ORGANISM: homo sapiens

<400> SEQUENCE: 39

Ile Ser Trp Asn Ser Gly Ser Ile
1               5

<210> SEQ ID NO 40
<211> LENGTH: 125
<212> TYPE: PRT
<213> ORGANISM: homo sapiens

<400> SEQUENCE: 40

Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
                20                  25                  30

Ala Met His Trp Val Arg Gln Ala Pro Gly Lys Gly Leu Glu Trp Val
            35                  40                  45

Ser Ile Ile Gly Thr Gly Gly Val Thr Tyr Tyr Ala Asp Ser Val Lys
        50                  55                  60

-continued

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
            85                  90                  95

Arg Asp Tyr Tyr Gly Ala Gly Ser Phe Tyr Asp Gly Leu Tyr Gly Met
        100                 105                 110

Asp Val Trp Gly Gln Gly Thr Thr Val Thr Val Ser Ser
        115                 120             125

<210> SEQ ID NO 41
<211> LENGTH: 107
<212> TYPE: PRT
<213> ORGANISM: homo sapiens

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
            85                  90                  95

Thr Phe Gly Gly Gly Thr Lys Val Glu Ile Lys
        100                 105

<210> SEQ ID NO 42
<211> LENGTH: 8
<212> TYPE: PRT
<213> ORGANISM: homo sapiens

<400> SEQUENCE: 42

Gly Phe Thr Phe Ser Tyr His Ala
1               5

<210> SEQ ID NO 43
<211> LENGTH: 7
<212> TYPE: PRT
<213> ORGANISM: homo sapiens

<400> SEQUENCE: 43

Ile Gly Thr Gly Gly Val Thr
1               5

<210> SEQ ID NO 44
<211> LENGTH: 19
<212> TYPE: PRT
<213> ORGANISM: homo sapiens

<400> SEQUENCE: 44

Ala Arg Asp Tyr Tyr Gly Ala Gly Ser Phe Tyr Asp Gly Leu Tyr Gly
1               5                   10                  15

Met Asp Val

<210> SEQ ID NO 45

```
<211> LENGTH: 6
<212> TYPE: PRT
<213> ORGANISM: homo sapiens

<400> SEQUENCE: 45

Gln Ser Val Ser Ser Tyr
1               5

<210> SEQ ID NO 46
<211> LENGTH: 9
<212> TYPE: PRT
<213> ORGANISM: homo sapiens

<400> SEQUENCE: 46

Gln Gln Arg Ser Asp Trp Pro Leu Thr
1               5

<210> SEQ ID NO 47
<211> LENGTH: 123
<212> TYPE: PRT
<213> ORGANISM: homo sapiens

<400> SEQUENCE: 47

Ala Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
                20                  25                  30

Thr Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Asn Gln Tyr Gly Ser Gly Ser Thr Tyr Gly Leu Gly Val
                100                 105                 110

Trp Gly Gln Gly Thr Leu Val Thr Val Ser Ser
            115                 120

<210> SEQ ID NO 48
<211> LENGTH: 107
<212> TYPE: PRT
<213> ORGANISM: homo sapiens

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
```

-continued

```
<210> SEQ ID NO 49
<211> LENGTH: 8
<212> TYPE: PRT
<213> ORGANISM: homo sapiens

<400> SEQUENCE: 49

Gly Phe Thr Phe Gly Asp Tyr Thr
1               5

<210> SEQ ID NO 50
<211> LENGTH: 8
<212> TYPE: PRT
<213> ORGANISM: homo sapiens

<400> SEQUENCE: 50

Ile Ser Trp Asn Ser Gly Ser Ile
1               5

<210> SEQ ID NO 51
<211> LENGTH: 16
<212> TYPE: PRT
<213> ORGANISM: homo sapiens

<400> SEQUENCE: 51

Thr Lys Asp Asn Gln Tyr Gly Ser Gly Ser Thr Tyr Gly Leu Gly Val
1               5                   10                  15

<210> SEQ ID NO 52
<211> LENGTH: 6
<212> TYPE: PRT
<213> ORGANISM: homo sapiens

<400> SEQUENCE: 52

Gln Ser Val Ser Ser Tyr
1               5

<210> SEQ ID NO 53
<211> LENGTH: 9
<212> TYPE: PRT
<213> ORGANISM: homo sapiens

<400> SEQUENCE: 53

Gln Gln Arg Ser Asn Trp Pro Leu Thr
1               5

<210> SEQ ID NO 54
<211> LENGTH: 9
<212> TYPE: PRT
<213> ORGANISM: Mus Musculus

<400> SEQUENCE: 54

Ala Leu Trp Tyr Ser Asn His Trp Val
1               5

<210> SEQ ID NO 55
<211> LENGTH: 8
<212> TYPE: PRT
<213> ORGANISM: Mus Musculus

<400> SEQUENCE: 55

Gly Phe Thr Phe Ser Ser Tyr Gly
1               5
```

```
<210> SEQ ID NO 56
<211> LENGTH: 8
<212> TYPE: PRT
<213> ORGANISM: Mus Musculus

<400> SEQUENCE: 56

Ile Ser Arg Tyr Ser Arg Tyr Ile
1               5

<210> SEQ ID NO 57
<211> LENGTH: 12
<212> TYPE: PRT
<213> ORGANISM: Mus Musculus

<400> SEQUENCE: 57

Ala Arg Arg Pro Leu Tyr Gly Ser Ser Pro Asp Tyr
1               5                   10

<210> SEQ ID NO 58
<211> LENGTH: 5
<212> TYPE: PRT
<213> ORGANISM: Mus Musculus

<400> SEQUENCE: 58

Ser Ser Val Thr Tyr
1               5

<210> SEQ ID NO 59
<211> LENGTH: 9
<212> TYPE: PRT
<213> ORGANISM: Mus Musculus

<400> SEQUENCE: 59

Phe Gln Gly Ser Gly Tyr Pro Leu Thr
1               5

<210> SEQ ID NO 60
<211> LENGTH: 107
<212> TYPE: PRT
<213> ORGANISM: homo sapiens

<400> SEQUENCE: 60

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 61
<211> LENGTH: 107
<212> TYPE: PRT
<213> ORGANISM: homo sapiens
```

-continued

<400> SEQUENCE: 61

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 62
<211> LENGTH: 107
<212> TYPE: PRT
<213> ORGANISM: homo sapiens

<400> SEQUENCE: 62

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Gly Leu His Asn His Tyr
                85                  90                  95

Thr Gln Lys Ser Leu Ser Leu Ser Pro Gly Lys
            100                 105

<210> SEQ ID NO 63
<211> LENGTH: 330
<212> TYPE: PRT
<213> ORGANISM: homo sapiens

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys

```
            100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 64
<211> LENGTH: 330
<212> TYPE: PRT
<213> ORGANISM: homo sapiens

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Leu
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 65
<211> LENGTH: 330
<212> TYPE: PRT
<213> ORGANISM: homo sapiens

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 330
<212> TYPE: PRT
<213> ORGANISM: homo sapiens

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
```

```
            225                 230                 235                 240
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 67
<211> LENGTH: 330
<212> TYPE: PRT
<213> ORGANISM: homo sapiens

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Ser Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 330
<212> TYPE: PRT
<213> ORGANISM: homo sapiens

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
                325                 330

<210> SEQ ID NO 69
<211> LENGTH: 330
<212> TYPE: PRT
<213> ORGANISM: homo sapiens

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 70
<211> LENGTH: 330
<212> TYPE: PRT

<213> ORGANISM: homo sapiens

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 71
<211> LENGTH: 330
<212> TYPE: PRT
<213> ORGANISM: homo sapiens

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 72
<211> LENGTH: 8
<212> TYPE: PRT
<213> ORGANISM: Mus Musculus
<220> FEATURE:
<221> NAME/KEY: misc
<222> LOCATION: (5)..(5)
<223> OTHER INFORMATION: wherein X is selected from V, H, F, T, P, L, Q,
      D, K, W, S, G, A, C and R

<400> SEQUENCE: 72

Gly Phe Thr Phe Xaa Thr Tyr Ala
1               5

<210> SEQ ID NO 73
<211> LENGTH: 8
<212> TYPE: PRT
```

```
<213> ORGANISM: Mus Musculus
<220> FEATURE:
<221> NAME/KEY: MISC_FEATURE
<222> LOCATION: (6)..(6)
<223> OTHER INFORMATION: wherein X is selected from S, N, G, A, K, V, R,
      H, Q, P, I, F, M, Y, L, W, D, E and C

<400> SEQUENCE: 73

Gly Phe Thr Phe Asn Xaa Tyr Ala
1               5

<210> SEQ ID NO 74
<211> LENGTH: 8
<212> TYPE: PRT
<213> ORGANISM: Mus Musculus
<220> FEATURE:
<221> NAME/KEY: MISC_FEATURE
<222> LOCATION: (7)..(7)
<223> OTHER INFORMATION: wherein X is selected from F, H, N, M, W, G, Q,
      V, T, S, L, P, I, A, K, R and C

<400> SEQUENCE: 74

Gly Phe Thr Phe Asn Thr Xaa Ala
1               5

<210> SEQ ID NO 75
<211> LENGTH: 10
<212> TYPE: PRT
<213> ORGANISM: Mus Musculus
<220> FEATURE:
<221> NAME/KEY: MISC_FEATURE
<222> LOCATION: (7)..(7)
<223> OTHER INFORMATION: wherein X is selected from S, Y, Q, W, L, A, I,
      M, D, T, K, R, G, F, E, V, C and P

<400> SEQUENCE: 75

Ile Arg Ser Lys Tyr Asn Xaa Tyr Ala Thr
1               5                   10

<210> SEQ ID NO 76
<211> LENGTH: 10
<212> TYPE: PRT
<213> ORGANISM: Mus Musculus
<220> FEATURE:
<221> NAME/KEY: MISC_FEATURE
<222> LOCATION: (9)..(9)
<223> OTHER INFORMATION: wherein X is selected from N, L, Y, W, H, M, G,
      F, K, S, V, R, Q, D, C, E, P and T

<400> SEQUENCE: 76

Ile Arg Ser Lys Tyr Asn Asn Tyr Xaa Thr
1               5                   10

<210> SEQ ID NO 77
<211> LENGTH: 16
<212> TYPE: PRT
<213> ORGANISM: Mus Musculus
<220> FEATURE:
<221> NAME/KEY: MISC_FEATURE
<222> LOCATION: (3)..(3)
<223> OTHER INFORMATION: wherein X is selected from A, S, V, N, K, L, T,
      I, P, Q, C, G, Y, W, F, and R

<400> SEQUENCE: 77

Val Arg Xaa Gly Asn Phe Gly Asn Ser Tyr Val Ser Trp Phe Ala Tyr
1               5                   10                  15

<210> SEQ ID NO 78
<211> LENGTH: 16
```

-continued

```
<212> TYPE: PRT
<213> ORGANISM: Mus Musculus
<220> FEATURE:
<221> NAME/KEY: MISC_FEATURE
<222> LOCATION: (7)..(7)
<223> OTHER INFORMATION: wherein X is selected from P, Q, A, Y, H, I, N,
      V, E, L, F, W, M, R, C,  S and T

<400> SEQUENCE: 78

Val Arg His Gly Asn Phe Xaa Asn Ser Tyr Val Ser Trp Phe Ala Tyr
1               5                   10                  15

<210> SEQ ID NO 79
<211> LENGTH: 16
<212> TYPE: PRT
<213> ORGANISM: Mus Musculus
<220> FEATURE:
<221> NAME/KEY: MISC_FEATURE
<222> LOCATION: (12)..(12)
<223> OTHER INFORMATION: wherein X is selected from A, T, G, L, N, C, P,
      F, Q, H, R, K, E, W, and Y

<400> SEQUENCE: 79

Val Arg His Gly Asn Phe Gly Asn Ser Tyr Val Xaa Trp Phe Ala Tyr
1               5                   10                  15

<210> SEQ ID NO 80
<211> LENGTH: 16
<212> TYPE: PRT
<213> ORGANISM: Mus Musculus
<220> FEATURE:
<221> NAME/KEY: MISC_FEATURE
<222> LOCATION: (16)..(16)
<223> OTHER INFORMATION: wherein X is selected from H, S, F, N, W, T, C,
      A, I, L, Q, V, E, M, K, R, G and P

<400> SEQUENCE: 80

Val Arg His Gly Asn Phe Gly Asn Ser Tyr Val Ser Trp Phe Ala Xaa
1               5                   10                  15

<210> SEQ ID NO 81
<211> LENGTH: 9
<212> TYPE: PRT
<213> ORGANISM: Mus Musculus
<220> FEATURE:
<221> NAME/KEY: MISC_FEATURE
<222> LOCATION: (6)..(6)
<223> OTHER INFORMATION: wherein X is selected from S, A, G, R, V, F, I,
      E, M, H, N, Y, P, Q, D, K and L

<400> SEQUENCE: 81

Thr Gly Ala Val Thr Xaa Ser Asn Tyr
1               5

<210> SEQ ID NO 82
<211> LENGTH: 9
<212> TYPE: PRT
<213> ORGANISM: Mus Musculus
<220> FEATURE:
<221> NAME/KEY: MISC_FEATURE
<222> LOCATION: (2)..(2)
<223> OTHER INFORMATION: wherein X is selected from C, F, Y, I, T, V, M,
      A, S, N, G, W, E, K, P, R and D

<400> SEQUENCE: 82

Ala Xaa Trp Tyr Ser Asn Leu Trp Val
1               5

<210> SEQ ID NO 83
```

```
<211> LENGTH: 9
<212> TYPE: PRT
<213> ORGANISM: Mus Musculus
<220> FEATURE:
<221> NAME/KEY: MISC_FEATURE
<222> LOCATION: (7)..(7)
<223> OTHER INFORMATION: wherein X is selected from D, K, Q, R, G, V, E,
      T, N, Y, S, P, W, F and M

<400> SEQUENCE: 83

Ala Leu Trp Tyr Ser Asn Xaa Trp Val
1               5

<210> SEQ ID NO 84
<211> LENGTH: 42
<212> TYPE: DNA
<213> ORGANISM: Artificial Sequence
<220> FEATURE:
<223> OTHER INFORMATION: Primer

<400> SEQUENCE: 84
gggagttctt ctcgctgctg ttgctgggct cgcagttgta ga                    42

<210> SEQ ID NO 85
<211> LENGTH: 42
<212> TYPE: DNA
<213> ORGANISM: Artificial Sequence
<220> FEATURE:
<223> OTHER INFORMATION: Primer

<400> SEQUENCE: 85
tctacaactg cgagcccagc aacagcagcg agaagaactc cc                    42

<210> SEQ ID NO 86
<211> LENGTH: 43
<212> TYPE: DNA
<213> ORGANISM: Artificial Sequence
<220> FEATURE:
<223> OTHER INFORMATION: Primer

<400> SEQUENCE: 86
ctcgcagtcg tagatgtcga tgtagggctt gtgggcccgg atg                   43

<210> SEQ ID NO 87
<211> LENGTH: 43
<212> TYPE: DNA
<213> ORGANISM: Artificial Sequence
<220> FEATURE:
<223> OTHER INFORMATION: Primer

<400> SEQUENCE: 87
catccgggcc cacaagccct acatcgacat ctacgactgc gag                   43
```